United States Patent
Feder et al.

(10) Patent No.: US 7,122,358 B2
(45) Date of Patent: Oct. 17, 2006

(54) TESTIS-SPECIFIC TUBULIN TYROSINE-LIGASE-LIKE PROTEIN, BGS42

(75) Inventors: John N. Feder, Belle Mead, NJ (US); Thomas C. Nelson, Lawrenceville, NJ (US); Shujian Wu, Langhorne, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 413 days.

(21) Appl. No.: 10/635,977

(22) Filed: Aug. 7, 2003

(65) Prior Publication Data
US 2004/0171131 A1 Sep. 2, 2004

Related U.S. Application Data

(63) Continuation-in-part of application No. 10/615,659, filed on Jul. 9, 2003.

(60) Provisional application No. 60/394,725, filed on Jul. 9, 2002.

(51) Int. Cl.
*C12N 9/00* (2006.01)
*C12N 1/20* (2006.01)
*C12N 15/00* (2006.01)
*C07K 1/00* (2006.01)

(52) U.S. Cl. .................. 435/183; 530/350; 435/252.3; 435/320.1

(58) Field of Classification Search ................ 530/350; 435/183, 320.1, 252.3
See application file for complete search history.

(56) References Cited

FOREIGN PATENT DOCUMENTS

| WO | WO00/55173 | 9/2000 |
|---|---|---|
| WO | WO00/58473 | 10/2000 |

OTHER PUBLICATIONS

Altschul, et al., "Gapped Blast and PSI-BLAST: a new generation of protein database search programs", Nucleic Acids Res., vol. 25 (17), pp. 3389-3402 (1997).
Bateman, et al., "The Pfam Protein Families Database", Nucleic Acids Res., vol. 28(1), pp. 263-266 (2000).
Birney, et al., "Using GeneWise in the *Drosophila* Annotation Experiment", Genome Res., vol. 10, pp. 547-548 (2000).
Bonaldo, et al., "Normalization and Subtraction: Two Approaches to Facilitate Gene Discovery", Genome Res., vol. 6, pp. 791-806 (1996).
Carninci, et al., "[2] High-Efficiency Full-Length cDNA Cloning", Methods Enzy., vol. 303, pp. 19-44 (1999).
Dunham, et al., "The DNA sequence of human chromosome 22", Nature, vol. 402, pp. 489-495 (1999).
Elgar, et al., "Generation and Analysis of 25 Mb of Genomic DNA from the Pufferfish *Fugu rubripes* by Sequence Scanning", Genome Res., vol. 9, pp. 960-971 (1999).
Ersfeld, et al., "Characterization of the Tubulin-Tyrosine Ligase", J. Cell Biol., vol. 120(3), pp. 725-732 (1993).
Herman, et al., "Methylation-specific PCR: A novel PCR assay for methylation status of GpG islands", PNAS, vol. 93, pp. 9821-9826 (1996).
Idriss, H.T., "Suppression of tubulin tyrosine ligase activity through reversible phosphorylation: a mechanism for inhibition of α-tubulin tyrosinylation", Medical Hypotheses, vol. 56(2), pp. 129-133 (2001).
Mialhe, et al., "Tubulin Detyrosination Is a Frequent Occurence in Breast Cancers of Poor Prognosis", Cancer Res., vol. 61, pp. 5024-5027 (2001).
Needleman, et al., "A General Method Applicable to the Search for Similarities in the Amino Acid Sequence of Two Proteins", J. Mol. Biol., vol. 48, pp. 443-453 (1970).
Raybin, et al., "Enzyme Which Specifically Adds Tyrosine to the α Chain of Tubulin", Biochem., vol. 16(10), pp. 2189-2194 (1977).
Takai, et al., "Comprehensive analysis of CpG islands in human chromosomes 21 and 22", PNAS, vol. 99(6), pp. 3740-3745 (2002).
Trichet, et al., Characterization of the human tubulin tyrosine ligase-like 1 gene (TTLL1) mapping to 22q13.1, Gene, vol. 257, pp. 109-117 (2000).
Wiemann, et al., "Toward a Catalog of Human Genes and Proteins: Sequencing and Analysis of 500 Novel Complete Protein Coding Human cDNAs", Genome Res., vol. 11, pp. 422-435 (2001).
NCBI Entrez Accession No. A45443 (gi:423218), Ersfeld, et al., Jun. 3, 2002.
NCBI Entrez Accession No. AAF23353 (gi:6683745), Yu, et al., Jan. 9, 2000.
NCBI Entrez Accession No. AA061487 (gi:1555346), Marra, et al., Feb. 3, 1997.
NCBI Entrez Accession No. AA144756 (gi:1714179), Marra, et al., Feb. 11, 1997.
NCBI Entrez Accession No. AF078842 (gi:6683744), Yu, et al., Jan. 9, 2000.
NCBI Entrez Accession No. AI026623 (gi:3246111), NCI-CGAP, Aug. 27, 1998.
NCBI Entrez Accession No. AL022327 (gi:5304851), Cobley, V., May 18, 2005.
NCBI Entrez Accession No. AL026623 (gi:3263966), Elgar, et al., Feb. 25, 2004.
NCBI Entrez Accession No. AL096725 (gi:5419858), Wambutt, et al., Feb. 18, 2000.
NCBI Entrez Accession No. BB004438 (gi:8093886), Konno, et al., Jun. 22, 2000.
NCBI Entrez Accession No. BE102364 (gi:8494463), Bonaldo, et al., Jun. 13, 2000.
NCBI Entrez Accession No. BM808516 (gi:19125339), NIH-MGC, Mar. 5, 2002.

(Continued)

*Primary Examiner*—Maryam Monshipouri
(74) *Attorney, Agent, or Firm*—Stephen C. D'Amico

(57) ABSTRACT

The present invention provides novel polynucleotides encoding BGS-42 polypeptides, fragments and homologues thereof Also provided are vectors, host cells, antibodies, and recombinant and synthetic methods for producing said polypeptides. The invention further relates to diagnostic and therapeutic methods for applying these novel BGS-42 polypeptides to the diagnosis, treatment, and/or prevention of various diseases and/or disorders related to these polypeptides. The invention further relates to screening methods for identifying agonists and antagonists of the polynucleotides and polypeptides of the present invention.

19 Claims, 24 Drawing Sheets

OTHER PUBLICATIONS

NCBI Entrez Accession No. BM808637 (gi:19125460), NIH-MGC., Mar. 5, 2002.
NCBI Entrez Accession No. BU937372 (gi:24126191), NIH-MGC, Oct. 18, 2002.
NCBI Entrez Accession No. CAB46375 (gi:5419859), Wambutt, et al., Feb. 18, 2000.
NCBI Entrez Accession No. CAI42686 (gi:57208207), Cobley, V., May 18, 2005.
NCBI Entrez Accession No. CK604006 (gi:41117345), NIH-MGC, Jan. 22, 2004.
NCBI Entrez Accession No. CK653583 (gi:41389106), NIH-MGC, Jan. 29, 2004.
NCBI Entrez Accession No. CR745100 (gi:51667573), Ebert, et al., Dec. 21, 2004.
NCBI Entrez Accession No. CX205198 (gi:56860370), Williams, C., Dec. 29, 2004.
NCBI Entrez Accession No. DN831611 (gi:62640254), Stevens, et al., Apr. 27, 2005.
NCBI Entrez Accession No. DN831612 (gi:62640255), Stevens, et al., Apr. 27, 2005.
NCBI Entrez Accession No. DN831950 (gi:62640634), Stevens, et al., Apr. 27, 2005.
NCBI Entrez Accession No. DN831951 (gi:62640635), Stevens, et al., Apr. 27, 2005.
NCBI Entrez Accession No. DR008133 (gi:66272229), Stevens, et al., May 18, 2005.
NCBI Entrez Accession No. DR008134 (gi:66272231), Stevens, et al., May 18, 2005.
NCBI Entrez Accession No. Q9Y4R7 (gi:20455371), Yu, et al., Sep. 13, 2005.
NCBI Entrez Accession No. T12515 (gi:597202), Liew, et al., Nov. 28, 1994.
NCBI Entrez Accession No. XP_104657 (gi:37564887), NCBI Annotation Process, Feb. 19, 2004.
NCBI Entrez Accession No. XP_104657 (gi:51476104), NCBI Annotation Process, Aug. 20, 2004.
NCBI Entrez Accession No. XP_515212 (gi:55661552), NCBI Annotation Process,, Nov. 9, 2004.
Baylin, et al., "Aberrant patterns of DNA methylation, chromatin formation and gene expression in cancer", Human Molecular Genetics, vol. 10(7), pp. 687-692 (2001).
ENSEMBL:ENSP00000266182 Jan. 14, 2004.
NCBI Entrez Accession No. gi|NP_766406, Okazaki, Y. et al., Dec. 22, 2003.
Carninci, P. et al., "Normalization and Subtraction of Cap-Trapper-Selected cDNAs to Prepare Full-Length cDNA Libraries for Rapid Discovery of New Genes", Genome Research, vol. 10, pp. 1617-1630 (2000).
Shibata, K. et al., "RIKEN Integrated Sequence Analysis (RISA) System—384-Format Sequencing Pipeline with 384 Multicapillary Sequencer", Genome Research, vol. 10, pp. 1757-1771 (2000).
The FANTOM Consortium and the RIKEN Genome Exploration Research Group Phase I & II Team, "Analysis of the mouse transcriptome bases on functional annotation of 60,770 full-length cDNAs", Nature, vol. 420, pp. 563-573 (2002).
The RIKEN Genome Exploration Research Group Phase II Team and the FANTOM Consortium, "Functional annotation of a full-length mouse cDNA collection", Nature, vol. 409, pp. 685-690 (2001).

FIG. 1A

```
  1 TGGGAGCAGGCCTGGGCCCCATCGGCTATGAGGGCGGGAAGTGGGGCGGGTTGGGGAGCC   60

61 TCCGTGGCCCTGGCCCCATCTCCAGTCCCCAGTCCTGGCTCGGACAGATAGGGCGAGGCT  120

121 GTGCTGTCCTTTCAGAAGACTTCCGGCGCACCATGGCATCCAGCATCCTCAAGTGGGTGG  180
  1                                   M  A  S  S  I  L  K  W  V  V   10

181 TCAGCCACCAGAGCTGCAGCAGGAGCAGCAGAAGCAAGCCCAGGGACCAGAGGGAGGAGG  240
 11  S  H  Q  S  C  S  R  S  S  R  S  K  P  R  D  Q  R  E  E  A   30

241 CCGGGAGCAGCGACCTGAGCAGCAGGCAAGATGCTGAAAATGCTGAGGCAAAGCTCAGGG  300
 31  G  S  S  D  L  S  S  R  Q  D  A  E  N  A  E  A  K  L  R  G   50

301 GCCTCCCGGGGCAGCTTGTGGACATCGCGTGCAAGGTGTGCCAGGCCTACCTGGGGCAGC  360
 51  L  P  G  Q  L  V  D  I  A  C  K  V  C  Q  A  Y  L  G  Q  L   70

361 TGGAGCATGAGGACATCGACACGTCAGCAGATGCCGTGGAGGACCTCACTGAGGCCGAGT  420
 71  E  H  E  D  I  D  T  S  A  D  A  V  E  D  L  T  E  A  E  W   90

421 GGGAGGACCTGACCCAGCAGTACTACTCCCTCGTTCATGGCGATGCTTTCATCTCCAATT  480
 91  E  D  L  T  Q  Q  Y  Y  S  L  V  H  G  D  A  F  I  S  N  S  110

481 CAAGAAATTACTTTTCGCAGTGCCAGGCTCTGCTGAATAGAATCACGTCTGTGAACCCTC  540
111  R  N  Y  F  S  Q  C  Q  A  L  L  N  R  I  T  S  V  N  P  Q  130

541 AGACGGACATTGACGGGCTCCGGAACATCTGGATTATAAAGCCCGCGGCCAAGTCCCGGG  600
131  T  D  I  D  G  L  R  N  I  W  I  I  K  P  A  A  K  S  R  G  150

601 GCCGAGACATAGTGTGCATGGACCGTGTGGAGGAGATCCTGGAGCTGGCAGCTGCAGACC  660
151  R  D  I  V  C  M  D  R  V  E  E  I  L  E  L  A  A  A  D  H  170

661 ACCCTCTTTCCAGGGACAACAAGTGGGTGGTCCAGAAGTACATCGAGACGCCGCTGCTCA  720
171  P  L  S  R  D  N  K  W  V  V  Q  K  Y  I  E  T  P  L  L  I  190

721 TCTGTGACACCAAGTTCGACATCAGACAGTGGTTCCTCGTCACGGACTGGAACCCCCTGA  780
191  C  D  T  K  F  D  I  R  Q  W  F  L  V  T  D  W  N  P  L  T  210

781 CCATCTGGTTCTACAAGGAGAGTTACTTGCGGTTCTCAACTCAGCGCTTCTCCCTGGACA  840
211  I  W  F  Y  K  E  S  Y  L  R  F  S  T  Q  R  F  S  L  D  K  230
```

FIG. 1B

```
 841  AGCTGGACAGCGCCATCCACCTGTGCAACAACGCCGTCCAGAAGTACCTGAAGAATGATG   900
 231    L   D   S   A   I   H   L   C   N   N   A   V   Q   K   Y   L   K   N   D   V    250

901  TGGGCCGCAGCCCCCTGCTGCCCGCACACAACATGTGGACCAGCACCAGGTTCCAGGAGT   960
 251    G   R   S   P   L   L   P   A   H   N   M   W   T   S   T   R   F   Q   E   Y    270

961  ACCTGCAGCGCCAGGGCCGTGGCGCCGTGTGGGGCAGCGTCATCTACCCGTCCATGAAGA  1020
 271    L   Q   R   Q   G   R   G   A   V   W   G   S   V   I   Y   P   S   M   K   K    290

1021  AGGCCATCGCCCACGCCATGAAGGTGGCCCAGGACCACGTGGAGCCTCGCAAGAACAGCT  1080
 291    A   I   A   H   A   M   K   V   A   Q   D   H   V   E   P   R   K   N   S   F    310

1081  TTGAGCTCTACGGGGCTGACTTCGTCCTTGGGAGGGACTTCAGGCCCTGGCTGATCGAGA  1140
 311    E   L   Y   G   A   D   F   V   L   G   R   D   F   R   P   W   L   I   E   I    330

1141  TCAATTCCAGCCCCACCATGCACCCGTCCACGCCGGTCACGGCCCAGCTGTGTGCACAGG  1200
 331    N   S   S   P   T   M   H   P   S   T   P   V   T   A   Q   L   C   A   Q   V    350

1201  TGCAGGAGGACACCATCAAGGTGGCCGTGGACCGCAGCTGTGACATCGGCAACTTCGAGC  1260
 351    Q   E   D   T   I   K   V   A   V   D   R   S   C   D   I   G   N   F   E   L    370

1261  TCCTGTGGAGGCAGCCGGTGGTTGAGCCGCCCCCATTCAGCGGGTCCGACCTCTGCGTGG  1320
 371    L   W   R   Q   P   V   V   E   P   P   P   F   S   G   S   D   L   C   V   A    390

1321  CGGGCGTCAGTGTGAGGAGAGCCAGGAGGCAGGTGCTGCCCGTCTGCAACCTCAAGGCCT  1380
 391    G   V   S   V   R   R   A   R   R   Q   V   L   P   V   C   N   L   K   A   S    410

1381  CGGCCTCGCTGTTGGACGCGCAGCCGCTGAAGGCACGGGGCCCCTCGGCCATGCCAGACC  1440
 411    A   S   L   L   D   A   Q   P   L   K   A   R   G   P   S   A   M   P   D   P    430

1441  CTGCCCAGGGACCCCCATCACCAGCTCTCCAGCGGGACTTGGGACTGAAGGAAGAGAAGG  1500
 431    A   Q   G   P   P   S   P   A   L   Q   R   D   L   G   L   K   E   E   K   G    450

1501  GGCTCCCCCTGGCCTTGCTGGCACCCTTAAGGGGGGCAGCCGAGAGCGGTGGAGCCGCAC  1560
 451    L   P   L   A   L   L   A   P   L   R   G   A   A   E   S   G   G   A   A   Q    470

1561  AGCCCACCCGCACCAAAGCTGCTGGGAAGGTGGAGCTCCCGGCCTGCCCCTGTCGCCACG  1620
 471    P   T   R   T   K   A   A   G   K   V   E   L   P   A   C   P   C   R   H   V    490

1621  TGGACAGTCAGGCCCCAAACACCGGTGTCCCCGTAGCCCAGCCCGCCAAAAGCTGGGATC  1680
 491    D   S   Q   A   P   N   T   G   V   P   V   A   Q   P   A   K   S   W   D   P    510
```

FIG. 1C

```
1681  CAAACCAGCTAAATGCGCACCCGCTGGAGCCTGTGCTGCGGGGCCTGAAGACAGCAGAGG  1740
 511   N  Q  L  N  A  H  P  L  E  P  V  L  R  G  L  K  T  A  E  G   530

1741  GCGCGCTGCGTCCGCCGCCCCGGAGGAAAAGGTTCATGACAGCGTCAGATTCTCTGCAGCA  1800
 531   A  L  R  P  P  P  G  G  K  G  S                                541

1801  GGAGTACAGGTTGCAGCCACTCTCCCAAGGGCGAATTC  1838
```

FIG. 2

```
  1 ATTGACGGGCTCCGGAACATCTGGATTATAAAGCCCGCGGCCAAGTCCCGGGGCCGAGAC   60
  1  I  D  G  L  R  N  I  W  I  I  K  P  A  A  K  S  R  G  R  D   20

61 ATAGTGTGCATGGACCGTGTGGAGGAGATCCTGGAGCTGGCAGCTGCAGACCACCCTCTT  120
 21  I  V  C  M  D  R  V  E  E  I  L  E  L  A  A  A  D  H  P  L   40

121 TCCAGGGACAACAAGTGGGTGGTCCAGAAGTACATCGAGACGCCGCTGCTCATCTGTGAC  180
 41  S  R  D  N  K  W  V  V  Q  K  Y  I  E  T  P  L  L  I  C  D   60

181 ACCAAGTTCGACATCAGACAGTGGTTCCTCGTCACGGACTGGAACCCCCTGACCATCTGG  240
 61  T  K  F  D  I  R  Q  W  F  L  V  T  D  W  N  P  L  T  I  W   80

241 TTCTACAAGGAGAGTTACTTGCGGTTCTCAACTCAGCGCTTCTCCCTGGACAAGCTGGAC  300
 81  F  Y  K  E  S  Y  L  R  F  S  T  Q  R  F  S  L  D  K  L  D  100

301 AGCGCCATCCACCTGTGCAACAACGCCGTCCAGAAGTACCTGAAGAATGATGTGGGCCGC  360
101  S  A  I  H  L  C  N  N  A  V  Q  K  Y  L  K  N  D  V  G  R  120

361 AGCCCCCTGCTGCCCGCACACAACATGTGGACCAGCACCAGGTTCCAGGAGTACCTGCAG  420
121  S  P  L  L  P  A  H  N  M  W  T  S  T  R  F  Q  E  Y  L  Q  140

421 CGCCAGGGCCGTGGCGCCGTGTGGGGCAGCGTCATCTACCCGTCCATGAAGAAGGCCATC  480
141  R  Q  G  R  G  A  V  W  G  S  V  I  Y  P  S  M  K  K  A  I  160

481 GCCCACGCCATGAAGGTGGCCCAGGACCACGTGGAGCCTCGCAAGAACAGCTTTGAGCTC  540
161  A  H  A  M  K  V  A  Q  D  H  V  E  P  R  K  N  S  F  E  L  180

541 TACGGGGCTGACTTCGTCCTTGGGAGGGACTTCAGGCCCTGGCTGATCGAGATCAATTCC  600
181  Y  G  A  D  F  V  L  G  R  D  F  R  P  W  L  I  E  I  N  S  200

601 AGCCCCACCATGCACCCGTCCACGCCGGTCACGGCCCAGCTGTGTGCACAGGTGCAGGAG  660
201  S  P  T  M  H  P  S  T  P  V  T  A  Q  L  C  A  Q  V  Q  E  220

661 GACACCATCAAGGTGGCCGTGGACCGCAGCTGTGACATCGGCAACTTCGAGCTCCTGTGG  720
221  D  T  I  K  V  A  V  D  R  S  C  D  I  G  N  F  E  L  L  W  240

721 AGGCAG  726
241  R  Q   242
```

FIG. 3A

```
              1                                                  50
BGS-42   (1)  --------MASSILKWVVSHQSCSRSSRSKPRDQREEAGSSDLSSRQDAE
TTL_PIG  (1)  MYTFVVRDENSSVYAEVSRLLLATGHWKRLRRDNPRFNLMLGERNRLPFG
TTLL_Hu  (1)  --------MAGKVKWVTDIEKSVLINNFEKRGWVQVTENEDWNFYWMSV
TTLH_Hu  (1)  --------------------------------------------------
HOTTL    (1)  --------------------------------------------------

51                                                 100
BGS-42   (43) NAEAKLRGLPGQLVDIACKVCQAYLGQLEHEDIDTSADAVEDLTEAEWED
TTL_PIG  (51) RLGHEPGLMQLVNYYRGADKLCRKASLVKLIKTSPELAESCTWFPESYVI
TTLL_Hu  (42) QTIRNVFSVEAGYRLSDDQIVNHFP--NHYELTRKDLMVKN--IKRYRKE
TTLH_Hu  (1)  ------------------------------MDIDKDLEAPLYLTPEGWSL
HOTTL    (1)  --------------------------------------------------

101                                                150
BGS-42   (93) LTQQYYSLVHGDAFISNSRNYFSQCQALLNRLTSVNPQTDIDGLRNIWIL
TTL_PIG  (101) YPTNLKTPVAPAQNGIHPPIHSSRTDEREFFLTSYNKKKE-DGEGNWIA
TTLL_Hu  (88) LEKEGSPLAEKDENGKYLYLDFVPVTYMLPADYNLFVEEFRKSPSSIWIM
TTLH_Hu  (21) FLQRYYQVVHEGAELRHLDTQVQRCEDTLQQLQAVVPQIDMEGDRNIWIV
HOTTL    (1)  ---------------------------------------MEGDRNIWIV 151                                                200
BGS-42   (143) KPAAKSRGRDIVCMDRVEEILELAAADHPLSRDN-----KWVVQKYIETP
TTL_PIG  (150) KSSAGAKGEGILISSEATELLDFIDN------QGQ----VHVIQKYLERP
TTLL_Hu  (138) KPCCKAQGKGIFLINKLSQIKKWSRDSKTSSFVSQSNKEAYVISLYINNP
TTLH_Hu  (71) KPGAKSRGRGIMCMDHLEEMLKLVNGNPVVMKDG-----KWVVQKYIERP
HOTTL    (11) KPGAKSRGRGIMCMDHLEEMLKLVNGNPVVMKDG-----KWVVQKYIERP 201                                                250
BGS-42   (188) LLICD--TKFDIRQWFLVTDWNPLTIWFYKESYLRFSTQRFSLDKLDSA-
TTL_PIG  (190) LLLEPGHRKFDIRSWVLVD--HQYNLYLYREGVLRTASEPYHTDNEQDKT
TTLL_Hu  (188) LLIGG--RKFDLRLYVLVSTYRPLRCYMYKLGFCRFCTVKYTPSISELDN
TTLH_Hu  (116) LLIFG--TKFDLRQWFLVTDWNPLTVWFYRDSYIRFSTQPFSLKNLDNS-
HOTTL    (56) LLIFG--TKFDLRQWFLVTDWNPLTVWFYRDSYIRFSTQPFSLKNLDNS- 251                                                300
BGS-42   (235) --IHLCNNAVQKYLKNDVGRSPLLPAHNMWTSTRFQEYLQRQGRGAVWGS
TTL_PIG  (238) --CHLTNHCIQKEYSKNYGKYE--E-GNEMFFEEFNQYITSAL-NITLES
TTLL_Hu  (236) MFVHLTNVAIQKHGEDYNHIH---G--GKWTVSNLRLYIESTR-GKEVTS
TTLH_Hu  (163) --VHLCNNSIQKHLENSCRHPLLPPDNMWSSQRFQAHLQEMGAPNAWST
HOTTL    (103) --VHLCNNSIQKHLENSCRHPLLPPDNMWSSQRFQAHLQEMGAPNAWST 301                                                350
BGS-42   (283) VIYPSMKKAIAHAMKVAQDHVEPRKN---SFELYGADFVLGRDFRPWLIE
TTL_PIG  (282) SILLQIKHITRSCLLSVEPATSTRHLPYQSFQLFGFDEMVDEDLKVWLIE
TTLL_Hu  (280) KLFDEIHWIIVQSLKAVAPVMNNDKH---CFECYGYDITTDDKLKPWLIE
TTLH_Hu  (211) IIVPGMKDAVIHALQTSQDTVQCRKA---SFELYGADFVFGEDFCPWLIE
HOTTL    (151) IIVPGMKDAVIHALQTSQDTVQCRKA---SFELYGADFVFGEDFCPWLIE
```

FIG. 3B

```
              351                                                    400
BGS-42  (330) INSSPTMHPSTPVTAQLCAQVQEDTKKVAVD------------RSCDIG
TTL_PIG (332) VNG------APACAQKLYAELCQGIEDAIAS---------------
TTLL_Hu (327) VNASPSLTSSTANDRILKYNLINDTLEAVPNGEIPDCKWNKSPPKEVLG
TTLH_Hu (258) INASPTMAPSTAVTARLCAGVQADTLRVVIDR---------MLDRNCDTG
HOTTL   (198) INASPTMAPSTAVTARLCAGVQADTLRVVIDR---------MLDRNCDTG 401                                                    450
BGS-42  (367) NFELLWRQPVVEPPPFSGSDLCVAGVSVRRARRQVLPVCNLKASASLLDA
TTL_PIG (358) VEPPPDAEQQQQ----QPPEAARIKL------------------------
TTLL_Hu (377) NYEELYDEELAQGDGADRELRSRQGQSLGPRAGR-----SRDSGRAVLTT
TTLH_Hu (299) AFELIYKQPVTTSPASTPRESCLLPMYSDTRAR--------SSDDSTASW
HOTTL   (239) AFELIYKQPVTTSPASTPRESCLLPMYSDTRAR--------SSDDSTASW 451                                                    500
BGS-42  (417) QPTKARGESAMPDPAQGPPSPALQRDLGLKEEKGLPLALLAPLRGAAESG
TTL_PIG (380) -------------------------------------------------
TTLL_Hu (422) WK-----------------------------------------------
TTLH_Hu (341) WALRPCRPQARP-------------------------------------
HOTTL   (281) WALRPCRPQARP-------------------------------------

501                                                    550
BGS-42  (467) GAAQPTRTKAAGKVELPACPCRHVDSQAPNTGVPVAQPAKSWDPNQLNAH
TTL_PIG (380) -------------------------------------------------
TTLL_Hu (424) -------------------------------------------------
TTLH_Hu (353) -------------------------------------------------
HOTTL   (293) -------------------------------------------------

551             575
BGS-42  (517) PLEPVLRGLKTAEGALRPPPGGKGS
TTL_PIG (380) -------------------------
TTLL_Hu (424) -------------------------
TTLH_Hu (353) -------------------------
HOTTL   (293) -------------------------
```

FIG. 4

```
Model     Description                                    Score    E-value   N
-------   -----------                                    -----    -------   ---
TTL       Tubulin-tyrosine ligase family                 293.0    3.7e-84   1

Q      73  EDIDTS----ADAVEDLTEAEWEDLTQQYYSLVHGDAFISNSR-------NYFSQCQALL
           ++ID +      +++ ++ +   W   ++ ++   ++ + +         ++  +++++
T       1  MRIDMHYRMMHQMINHFPGSYWITRKDRLWMNIKRMMCDFHWKHDHFDWMPRTFILPTDY

Q     122  NRITSVNPQTDIDGLRNIWIIKPAAKSRGRDIVCMDRVEEILELAA-----ADHPLSRDN
           +++ +   ++ +  +G++N+WI+KP++++RGR+I++M+  ++I+ ++       +P++ ++
T      61  QEFVDYWQKHEWWGQDNHWIVKPWNSCRGRGIWIMNDWKQIPRWVNDFMDNPFVPQHQRR

Q     177  KWVVQKYIETPLLICD-----TKFDIRQWFLVTDWNPLTIWFYKESYLRFSTQRFS--LD
           +WVVQKYIE PLLI       +KFDIR+++LVT++NPL+I++Y+E+++RF+++  ++   +
T     121  PWVVQKYIERPLLIDGMDVGHHKFDIRCYVLVTSFNPLRIYVYREGWCRFCSVKYHPMDN

Q     230  KLDSAIHLCNNAVQKYLKN--DVGRSPLLPAHNMWTSTRFQEYLQR--QGRGAVWGSVIY
              +  +HL+N+++QK+ +N      +R ++++ ++MWT  +F++Y+++   +  ++W +++
T     181  FDNYCMHLTNYCIQKHYSNYSRCNRDYNECGHMWTLQNFWNYYENMGIDWDNIWSQICD

Q     286  PSMKKAIAHA-MKVAQDHVEPRKNSFELYGADFVL----GRDFRPWLIEINSSPTMHPST
           +  +K+++A++ +++++++++PR+N+FELYG+DF +      +++ PWL+E+N+SP+MH+++
T     241  IIIKTIVAAWCVEACRMNMQPRYNCFELYGFDFMIQWDDDENLKPWLLEVNWSPDMHCTC

Q     341  PVTAQLCAQVQEDTIK-----VAVDRSCDI
           P+++ LC+Q+++D+++      V +D++ D+
T     301  PYDMHLCHQLIRDVLNCAGCHVPPDCMKDC
```

FIG. 5A

BGS-42 – Clone A
TGGGAGCAGGCCTGGGCCCCATCGGCTATGAGGGCGGGAAGTGGGGCGGGTTGG
GGAGCCTCCGTGGCCCTGGCCCCATCTCCAGTCCCCAGTCCTGGCTCGGACAGAT
AGGGCGAGGCTGTGCTGTCCTTTCAGAAGACTTCCGGCGCACCATGGCATCCAGC
ATCCTCAAGTGGGTGGTCAGCCACCAGAGCTGCAGCAGGAGCAGCAGAAGCAAG
CCCAGGGACCAGAGGGAGGAGGCCGGGAGCAGCGACCTGAGCAGCAGGCAAGA
TGCTGAAAATGCTGAGGCAAAGCTCAGGGGCCTCCCGGGGCAGCTTGTGGACAT
CGCGTGCAAGGTGTGCCAGGCCTACCTGGGGCAGCTGGAGCATGAGGACATCGA
CACGTCAGCAGATGCCGTGGAGGACCTCACTGAGGCCGAGTGGGAGGACCTGAC
CCAGCAGTACTACTCCCTCGTTCATGGCGATGCTTTCATCTCCAATTCAAGAAATT
ACTTTTCGCAGTGCCAGGCTCTGCTGAATAGAATCACGTCTGTGAACCCTCAGAC
GGACATTGACGGGCTCCGGAACATCTGGATTATAAAGCCCGCGGCCAAGTCCCG
GGGCCGAGGGACAACAAGTGGGTGGTCCAGAAGTACATCGAGACGCCGCTGCTC
ATCTGTGACACCAAGTTCGACATCAGACAGTGGTTCCTCGTCACGGACTGGAACC
CCCTGACCATCTGGTTCTACAAGGAGAGTTACTTGCGGTTCTCAACTCAGCGCTT
CTCCCTGGACAAGCTGGACAGCGCCATCCACCTGTGCAACAACACCGTCCAGAA
GTACCTGAAGAATGATGTGGGCCGCAGCCCCTGCTGCCCGCACACAACATGTG
GACCAGCACCAGGTTCCAGGAGTACCTGCAGCGCCAGGGCCGTGGCGCCGTGTG
GGGCAGCGTCATCTACCCGTCCATGAAGAAGGCCATCGCCCACGCCATGAAGGT
GGCCCAGGACCACGTGGAGCCTCGCAAGAACAGCTTTGAGCTCTACGGGCTGA
CTTCGTCCTTGGGAGGGACTTCAGGCCCTGGCTGATCGAGATCAATTCCAGCCCC
ACCATGCACCCGTCCACGCCGGTCACGGCCCAGCTGTGTGCACAGGTGCAGGAG
GACACCATCAAGGTGGCCGTGGACCGCAGCTGTGACATCGGCAACTTCGAGCTC
CTGTGGAGGCAGCCGGTGGTTGAGCCGCCCCATTCAGCGGGTCCGACCTCTGCG
TGGCGGGCGTCAGTGTGAGGAGAGCCAGGAGGCAGGTGCTGCCCGTCTGCAACC
TCAAGGCCTCGGCCTCGCTGTTGGACGCGCAGCCGCTGAAGGCACGGGGCCCCT
CGGCCATGCCAGACCCTGCCCAGGGACCCCATCACCAGCTCTCCAGCGGGACTT
GGGACTGAAGGAAGAGAAGGGGCTCCCCCTGGCCTTGCTGGCACCCTTAAGGGG
GGCAGCCGAGAGCGGTGGAGCCGCACAGCCCACCCGCACCAAAGCTGCTGGGAA
GGTGGAGCTCCCGGCCTGCCCCTGTCGCCACGTGGACAGTCAGGCCCCAAACAC
CGGTGTCCCCGTAGCCCAGCCCGCCAAAAGCTGGGATCCAAACCAGCTAAATGA
GCACCCGCTGGAGCCTGTGCTGCGGAGCCTGAAGACAGCAGAGGGCGCGCTGCG
TCCGCCGCCCGGAGGAAAAGGTTCATGACAGCGTCAGATTCTCTGCAGCAGGAG
TACAGGTTGCAGCCACTCTCCCGCCGAACATTGAATACGTCTTTCCACCATCTTGT
CTTTGCTGTGGCTCTGGGAAAATCAGCAGAGTCAGCCATCACTCTCCAAGGGGAG
CTGTCAGTTCTATCTGCCAGCTTTTGAGTGTTCAATTTGATTTTTACTTATTCAACC
TGGAATTTGAATGTCAAAAAAAAAAAAAAAAAAAA (SEQ ID NO:9)

FIG. 5B

BGS-42 – Clone B
GTAGCAGCGTGGGAAGAAGGAGTTCCTGGAAGACTTCCGGCGCACCATGGCATC
CAGCATCCTCAAGTGGGTGGTCAGCCACCAGAGCTGCAGCAGGAGCAGCAGAAG
CAAGCCCAGGGACCAGAGGGAGGAGGCCGGGAGCAGCGACCTGAGCAGCAGGC
AAGATGCTGAAAATGCTGAGGCAAAGCTCAGGGGCCTCCCGGGGCAGCTTGTGG
ACATCGCGTGCAAGGTGTGCCAGGCCTACCTGGGGCAGCTGGAGCATGAGGACA
TCGACACGTCAGCAGATGCCGTGGAGGACCTCACTGAGGCCGAGTGGGAGGACC
TGACCCAGCAGTACTACTCCCTCGTTCATGCCAGGCTCTGCTGAATAGAATCACG
TCTGTGAACCCTCAGACGGACATTGACGGGCTCCGGAACATCTGGATTATAAAGC
CCGCGGCCAAGTCCCGGGGCCGAGACATAGTGTGCATGGACCGTGTGGAGGAGA
TCCTGGAGCTGGCAGCTGCAGACCACCCTCTTTCCAGGGACAACAAGTGGGTGGT
CCAGAAGTACATCGAGACGCCGCTGCTCATCTGTGACACCAAGTTCGACATCAG
ACAGTGGTTCCTCGTCACGGACTGGAACCCCCTGACCATCTGGTTCTACAAGGAG
AGTTACTTGCGGTTCTCAACTCAGCGCTTCTCCCTGGACAAGCTGGACAGCGCCA
TCCACCTGTGCAACAACGCCGTCCAGAAGTACCTGAAGAATGATGTGGGCCGCA
GCCCCCTGCTGCCCGCACACAACATGTGGACCAGCACCAGGTTCCAGGAGTACCT
GCAGCGCCAGGGCCGTGGCGCCGTGTGGGGCAGCGTCATCTACCCGTCCATGAA
GAAGGCCATCGCCCACGCCATGAAGGTGGCCCAGGACCACGTGGAGCCTCGCAA
GAACAGCTTTGAGCTCTACGGGGCTGACTTCGTCCTTGGGAGGGACTTCAGGCCC
TGGCTGATCGAGATCAATTCCAGCCCCACCATGCACCCGTCCACGCCGGTCACGG
CCCAGCTGTGTGCACAGGTGCAGGAGGACACCATCAAGGTGGCCGTGGACCGCA
GCTGTGACATCGGCAACTTCGAGCTCCTGTGGAGCCGGTGGTTGAGCCGCCCCA
TTCAGCGGGTCCGACCTCTGCGTGGCGGGCGTCAGTGTGAGGAGAGCCAGGAGG
CAGGTGCTGCCCGTCTGCAACCTCAAGGCCTCGGCCTCGCTGTTGGACGCGCAGC
CGCTGAAGGCACGGGGCCCCTCGGCCATGCCAGACCCTGCCCAGGGACCCCCAT
CACCAGCTCTCCAGCGGGACTTGGGACTGAAGGAAGAGAAGGGGCTCCCCCTGG
CCTTGCTGGCACCCTTAAGGGGGGCAGCCGAGAGCGGTGGAGCCGCACAGCCCA
CCCGCACCAAAGCTGCTGGGAAGGTGGAGCTCCCGGCCTGCCCCTGTCGCCACGT
GGACAGTCAGGCCCCAAACACCGGTGTCCCCGTAGCCCAGCCCGCCAAAAGCTG
GGATCCAAACCAGCTAAATGAGCACCCGCTGGAGCCTGTGCTGCGGAGCCTGAA
GACAGCAGAGGGCGCGCTGCGTCCGCCGCCCGGAGGAAAAGGTTCATGACAGCG
TCAGATTCTCTGCAGCAGGAGTACAGGTTGCAGCCACTCTCCCGCCGAACATTGA
ATACGTCTTTCCACCATCTTGTCTTTGCTGTGGCTCTGGGAAAATCAGCAGAGTC
AGCCATCACTCTCCAAGGGGAGCTGTCAGTTCTATCTGCCAGCTTTTGAGTGTTC
AATTTGATTTTTACTTATTCAACCTGGAATTTGAATGTCAAAAAAAAAAAAAAAA
AAAAAAAA (SEQ ID NO:10)

FIG. 5C

BGS-42 – Clone C
CCCAGGACTCCTGGTCTAAGGCCGTGGCCAGAATCACTCGGTGCCCACCCCACCC
CCAGCACCCCTGTGCCCTTTGCTCTGTGTCTCTGGGTGAATCCGGGGCCCCAGAA
GCTCCCTCCTCAGGGCACAGAGGCCAAAGATGGGGCTGACTGGGGGCTGCCACC
GGGCTTTGGGTGCTGAGGGGGCTGTGGGACCCCAGGGGAAGAGGTGCCGCTCCC
CCCAGCACCGGGCACTCCCCCGCCTCCCCGGCCTCCAGCCCTGCACAAAGCAGC
TTGCCACACCCTTCCCACCAAGGCCCAGGGCTGAGGCCTGCCCAGGACGCAGGG
TGTGGGGACCCTGCTGAGGGAGGGGTCCCGGAAGAGGGGCTTCCCTGGCACAGA
GGTCCCTCTCAGCAGGCCAGGTGCGGCTGCCTCAGCACAGTGTGGGGCGGAGGT
GCAGGACAAGGTTCCCTTCCGCACCTAATACCCCAGGGTCAGGCCAGCGCCAGC
GCTGCTAGTGGCAACATGGCCCCTTCAAAGACCCCGTGTGCAGAGCCAGTCAGC
GTGCGCTGTGTTTCTGGGGGCCAGCCACTTTTTTCCTTAACGGGGTGACAAACC
AGACATCGGGGTGCGGGACTTCACGATATGCCTCTCTAATGGCGCGTGCTACCT
CGCGTGTGGTGGGCAGTGCTGGGCATGTGGCTGCGTTCCGGGCCCTGCAGCCGCT
CCTCCCTCTCCTGGGGTCTGAGGTGTGGGACACCCTGTGGCCCGTTTGGGGGCCT
GGAGGGAGCCCCAGTGCCCACCGCCCTCGGTGCCCTCAGCTGCAGCCTCCCCATT
CCCTGGGGCCTGCCACGCCCTCCACTGCCTCAAGGATGCGTCTGAGCCTGGCCTG
CACATCCATGCTCCCACCGGCTGGAGGGGGTGTTCTGGGGCCCTGGGGGACCGT
ATATCTGGGGAGGGGGAGGGATCCGCCCTAGGGGTGCTGTGTGGTGCCCCATAG
CCAGGCAAGTCTGAGGTGGACGGCCCGTCCTCGCCTTGTGAGCGAGGCAGAGCT
GAGCTGAGCTGCCCCTCCTGCCTAACACGCCACTGTCTCTGGAGATCGGGCTGTG
CGTGAACATGCGGAGCCTGCCCTGGTACGTCCGGCCAACCCCGACTCCTTCTTC
CCACGCTGCTACAGCCTCTGCACCGAGAGTGAGCAGCAGGAGTTCCTGGGTAAG
TGAGGAGACGGCAGAGGGCCCCAGTGCTGTCAGCAGAGAGGCTTCTAGAAAGAT
CCCCCTGGTGCTGAGACAGACTGATGGGGCAGGGTCTGAGGATAGAGGACCGGG
GAGAGGCCTCCCATGGTCATGGTCATGGCAGTACAGAGGCCAGGGGCCCCGGGA
GGGAGGGCGGGCAGTCAAGGAGTGTGTGGTTCTGTGCTAGGCTTGTGGACAGCG
CGGCGAGCAGCTGGGGCAAGGCCGGCTCCGTGGTCGGAGGCCGAGGGGTGCAGC
TGGACGGCCGCAGTCACAGAGACACTGCAGGGAGAAGGGCAGGCAGACTGGGG
GTGTGGGAGCAGGCCTGGGCCCATCGGCTATGAGGGCGGGAAGTGGGGCGGGT
TGGGGAGCCTCCGTGGCCCTGGCCCCATCTCCAGTCCCCAGTCCTGGCTCGGACA
GATAGGGCGAGGCTGTGCTGTCCTTTCAGAAGACTTCCGGCGCACCATGGCATCC
AGCATCCTCAAGTGGGTGGTCAGCCACCAGAGCTGCAGCAGGAGCAGCAGAAGC
AAGCCCAGGGACCAGAGGGAGGAGGCCGGGAGCAGCGACCTGAGCAGCAGGCA
AGATGCTGAAAATGCTGAGGCAAAGCTCAGGGGCCTCCCGGGGCAGCTTGTGGA
CATCGCGTGCAAGGTGTGCCAGGCCTACCTGGGGCAGCTGGAGCATGAGGACAT
CGACACGTCAGCAGATGCCGTGGAGGACCTCACTGAGGCCGAGTGGGAGGACCT
GACCCAGCAGTACTACTCCCTCGTTCATGGCGATGCTTTCATCTCCAATTCAAGA
AATTACTTTTCGCAGTGCCAGGCTCTGCTGAATAGAATCACGTCTGTGAACCCTC
AGACGGACATTGACGGGCTCCGGAACATCTGGATTATAAAGCCCGCGGCCAAGT
CCCGGGGCCGAGGGACAACAAGTGGGTGGTCCAGAAGTACATCGAGACGCCGCT
GCTCATCTGTGACACCAAGTTCGACATCAGACAGTGGTTCCTCGTCACGGACTGG
AACCCCCTGACCATCTGGTTCTACAAGGAGAGTTACTTGCGGTTCTCAACTCAGC
GCTTCTCCCTGGACAAG

FIG. 5C (CONT.)

CTGGACAGCGCCATCCACCTGTGCAACAACGCCGTCCAGAAGTACCTGAA
GAATGATGTGGGCCGCAGCCCCCTGCTGCCCGCACACAACATGTGGACCAGCAC
CAGGTTCCAGGAGTACCTGCAGCGCCAGGGCCGTGGCGCCGTGTGGGGCAGCGT
CATCTACCCGTCCATGAAGAAGGCCATCGCCCACGCCATGAAGGTGGCCCAGGA
CCACGTGGAGCCTCGCAAGAACAGCTTTGAGCTCTACGGGGCTGACTTCGTCCTT
GGGAGGGACTTCAGGCCCTGGCTGATCGAGATCAATTCCAGCCCCACCATGCAC
CCGTCCACGCCGGTCACGGCCCAGCTGTGTGCACAGGTGCAGGAGGACACCATC
AAGGTGGCCGTGGACCGCAGCTGTGACATCGGCAACTTCGAGCTCCTGTGGAGG
CAGCCGGTGGTTGAGCCGCCCCATTCAGCGGGTCCGACCTCTGCGTGGCGGGCG
TCAGTGTGAGGAGAGCCAGGAGGCAGGTGCTGCCCGTCTGCAACCTCAAGGCCT
CGGCCTCGCTGTTGGACGCGCAGCCGCTGAAGGCACGGGGCCCCTCGGCCATGC
CAGACCCTGCCCAGGGACCCCCATCACCAGCTCTCCAGCGGGACTTGGGACTGA
AGGAAGAGAAGGGGCTCCCCCTGGCCTTGCTGGCACCCTTAAGGGGGGCAGCCG
AGAGCGGTGGAGCCGCACAGCCCACCCGCACCAAAGCTGCTGGGAAGGTGGAGC
TCCCGGCCTGCCCCTGTCGCCACGTGGACAGTCAGGCCCCAAACACCGGTGTCCC
CGTAGCCCAGCCCGCCAAAAGCTGGGATCCAAACCAGCTAAATGAGCACCCGCT
GGAGCCTGTGCTGCGGAGCCTGAAGACAGCAGAGGGCGCGCTGCGTCCGCCGCC
CGGAGGAAAAGGTTCATGACAGCGTCAGATTCTCTGCAGCAGGAGTACAGGTTG
CAGCCACTCTCCCGCCGAACATTGAATACGTCTTTCCACCATCTTGTCTTTGCTGT
GGCTCTGGGAAAATCAGCAGAGTCAGCCATCACTCCAAGGGGAGCTGTCAGT
TCTATCTGCCAGCTTTTGAGTGTTCAATTTGATTTTTACTTATTCAACCTGGAATTT
GAATGTCAAAAAAAAAAAAAAAAAAAAA (SEQ ID NO:11)

FIG. 6A

```
   1  GTCTAAGGCCGTGGCCAGAATCACTCGGTGCCCACCCCACCCCCAGCACCCCTGTGCCCT    60

61  TTGCTCTGTGTCTCTGGGTGAATCCGGGGCCCCAGAAGCTCCCTCCTCAGGGCACAGAGG   120

121  CCAAAGATGGGGCTGACTGGGGGCTGCCACCGGGCTTTGGGTGCTGAGGGGGCTGTGGGA   180

181  CCCCAGGGGAAGAGGTGCCGCTCCCCCCAGCACCGGGCACTCCCCCGCCTCCCCCGGCCT   240

241  CCAGCCCTGCACAAAGCAGCTTGCCACACCCTTCCCACCAAGGCCCAGGGCTGAGGCCTG   300

301  CCCAGGACGCAGGGTGTGGGGACCCTGCTGAGGGAGGGGTCCCGGAAGAGGGGCTTCCCT   360

361  GGCACAGAGGTCCCTCTCAGCAGGCCAGGTGCGGCTGCCTCAGCACAGTGTGGGGCGGAG   420

421  GTGCAGGACAAGGTTCCCTTCCGCACCTAATACCCCAGGGTCAGGCCAGCGCCAGCGCTG   480

481  CTAGTGGCAACATGGCCCCTTCAAAGACCCCGTGTGCAGAGCCAGTCAGCGTGCGCTGTG   540

541  TTTTCTGGGGGCCAGCCACTTTTTTCCTTAACGGGGTGACAAACCAGACATCGGGGTGCG   600

601  GGGACTTCACGATATGCCTCTCTAATGGCGCGTGCTACCTCGCGTGTGGTGGGCAGTGCT   660

661  GGGCATGTGGCTGCGTTCCGGGCCCTGCAGCCGCTCCTCCCTCTCCTGGGGTCTGAGGTG   720

721  TGGGACACCCTGTGGCCCGTTTGGGGGCCTGGAGGGAGCCCCAGTGCCCACCGCCCTCGG   780

781  TGCCCTCAGCTGCAGCCTCCCCATTCCCTGGGGCCTGCCACGCCCTCCACTGCCTCAAGG   840

841  ATGCGTCTGAGCCTGGCCTGCACATCCATGCTCCCACCGGCTGGAGGGGGTGTTCTGGGG   900

901  CCCTGGGGGACCGTATATCTGGGGAGGGGGAGGGATCCGCCCTAGGGGTGCTGTGTGGTG   960

961  CCCCATAGCCAGGCAAGTCTGAGGTGGACGGCCCGTCCTCGCCTTGTGAGCGAGGCAGAG  1020

1021  CTGAGCTGAGCTGCCCCTCCTGCCTAACACGCCACTGTCTCTGGAGATCGGGCTGTGCGT  1080

1081  GAACATGCGGAGCCTGCCCTGGTACGTCCCGGCCAACCCCGACTCCTTCTTCCCACGCTG  1140
```

FIG. 6B

```
1141 CTACAGCCTCTGCACCGAGAGTGAGCAGCAGGAGTTCCTGGGTAAGTGAGGAGACGGCAG 1200

1201 AGGGCCCCAGTGCTGTCAGCAGAGAGGCTTCTAGAAAGATCCCCCTGGTGCTGAGACAGA 1260

1261 CTGATGGGGCAGGGTCTGAGGATAGAGGACCGGGGAGAGGCCTCCCATGGTCATGGTCAT 1320

1321 GGCAGTACAGAGGCCAGGGGCCCCGGGAGGGAGGGCGGGCAGTCAAGGAGTGTGTGGTTC 1380

1381 TGTGCTAGGCTTGTGGACAGCGCGGCGAGCAGCTGGGGCAAGGCCGGCTCCGTGGTCGGA 1440

1441 GGCCGAGGGGTGCAGCTGGACGGCCGCAGTCACAGAGACACTGCAGGGAGAAGGGCAGGC 1500

1501 AGACTGGGGGTGTGGGAGCAGGCCTGGGCCCCATCGGCTATGAGGGCGGGAAGTGGGGCG 1560

1561 GGTTGGGGAGCCTCCGTGGCCCTGGCCCCATCTCCAGTCCCCAGTCCTGGCTCGGACAGA 1620

1621 TAGGGCGAGGCTGTGCTGTCCTTTCAGAGTAGCAGCGTGGGAAGAAGGAGTTCCTGGAAG 1680

1681 ACTTCCGGCGCACCATGGCATCCAGCATCCTCAAGTGGGTGGTCAGCCACCAGAGCTGCA 1740
   1              M   A   S   S   I   L   K   W   V   V   S   H   Q   S   C   S   16

1741 GCAGGAGCAGCAGAAGCAAGCCCAGGGACCAGAGGGAGGAGGCCGGGAGCAGCGACCTGA 1800
  17    R   S   S   R   S   K   P   R   D   Q   R   E   E   A   G   S   S   D   L   S   36

1801 GCAGCAGGCAAGATGCTGAAAATGCTGAGGCAAAGCTCAGGGGCCTCCCGGGGCAGCTTG 1860
  37    S   R   Q   D   A   E   N   A   E   A   K   L   R   G   L   P   G   Q   L   V   56

1861 TGGACATCGCGTGCAAGGTGTGCCAGGCCTACCTGGGGCAGCTGGAGCATGAGGACATCG 1920
  57    D   I   A   C   K   V   C   Q   A   Y   L   G   Q   L   E   H   E   D   I   D   76

1921 ACACGTCAGCAGATGCCGTGGAGGACCTCACTGAGGCCGAGTGGGAGGACCTGACCCAGC 1980
  77    T   S   A   D   A   V   E   D   L   T   E   A   E   W   E   D   L   T   Q   Q   96

1981 AGTACTACTCCCTCGTTCATGGCGATGCTTTCATCTCCAATTCAAGAAATTACTTTTCGC 2040
  97    Y   Y   S   L   V   H   G   D   A   F   I   S   N   S   R   N   Y   F   S   Q   116

2041 AGTGCCAGGCTCTGCTGAATAGAATCACGTCTGTGAACCCTCAGACGGACATTGACGGGC 2100
 117    C   Q   A   L   L   N   R   I   T   S   V   N   P   Q   T   D   I   D   G   L   136
```

FIG. 6C

```
2101  TCCGGAACATCTGGATTATAAAGCCCGCGGCCAAGTCCCGGGGCCGAGACATAGTGTGCA  2160
 137    R  N  I  W  I  I  K  P  A  A  K  S  R  G  R  D  I  V  C  M   156

2161  TGGACCGTGTGGAGGAGATCCTGGAGCTGGCAGCTGCAGACCACCCTCTTTCCAGGGACA  2220
 157    D  R  V  E  E  I  L  E  L  A  A  A  D  H  P  L  S  R  D  N   176

2221  ACAAGTGGGTGGTCCAGAAGTACATCGAGACGCCGCTGCTCATCTGTGACACCAAGTTCG  2280
 177    K  W  V  V  Q  K  Y  I  E  T  P  L  L  I  C  D  T  K  F  D   196

2281  ACATCAGACAGTGGTTCCTCGTCACGGACTGGAACCCCCTGACCATCTGGTTCTACAAGG  2340
 197    I  R  Q  W  F  L  V  T  D  W  N  P  L  T  I  W  F  Y  K  E   216

2341  AGAGTTACTTGCGGTTCTCAACTCAGCGCTTCTCCCTGGACAAGCTGGACAGCGCCATCC  2400
 217    S  Y  L  R  F  S  T  Q  R  F  S  L  D  K  L  D  S  A  I  H   236

2401  ACCTGTGCAACAACGCCGTCCAGAAGTACCTGAAGAATGATGTGGGCCGCAGCCCCCTGC  2460
 237    L  C  N  N  A  V  Q  K  Y  L  K  N  D  V  G  R  S  P  L  L   256

2461  TGCCCGCACACAACATGTGGACCAGCACCAGGTTCCAGGAGTACCTGCAGCGCCAGGGCC  2520
 257    P  A  H  N  M  W  T  S  T  R  F  Q  E  Y  L  Q  R  Q  G  R   276

2521  GTGGCGCCGTGTGGGGCAGCGTCATCTACCCCGTCCATGAAGAAGGCCATCGCCCACGCCA  2580
 277    G  A  V  W  G  S  V  I  Y  P  S  M  K  K  A  I  A  H  A  M   296

2581  TGAAGGTGGCCCAGGACCACGTGGAGCCTCGCAAGAACAGCTTTGAGCTCTACGGGGCTG  2640
 297    K  V  A  Q  D  H  V  E  P  R  K  N  S  F  E  L  Y  G  A  D   316

2641  ACTTCGTCCTTGGGAGGGACTTCAGGCCCTGGCTGATCGAGATCAATTCCAGCCCCACCA  2700
 317    F  V  L  G  R  D  F  R  P  W  L  I  E  I  N  S  S  P  T  M   336

2701  TGCACCCGTCCACGCCGGTCACGGCCCAGCTGTGTGCACAGGTGCAGGAGGACACCATCA  2760
 337    H  P  S  T  P  V  T  A  Q  L  C  A  Q  V  Q  E  D  T  I  K   356

2761  AGGTGGCCGTGGACCGCAGCTGTGACATCGGCAACTTCGAGCTCCTGTGGAGGCAGCCGG  2820
 357    V  A  V  D  R  S  C  D  I  G  N  F  E  L  L  W  R  Q  P  V   376

2821  TGGTTGAGCCGCCCCCATTCAGCGGGTCCGACCTCTGCGTGGCGGGCGTCAGTGTGAGGA  2880
 377    V  E  P  P  P  F  S  G  S  D  L  C  V  A  G  V  S  V  R  R   396

2881  GAGCCAGGAGGCAGGTGCTGCCCGTCTGCAACCTCAAGGCCTCGGCCTCGCTGTTGGACG  2940
 397    A  R  R  Q  V  L  P  V  C  N  L  K  A  S  A  S  L  L  D  A   416
```

FIG. 6D

```
2941  CGCAGCCGCTGAAGGCACGGGGCCCCTCGGCCATGCCAGACCCTGCCCAGGGACCCCCAT  3000
417     Q   P   L   K   A   R   G   P   S   A   M   P   D   P   A   Q   G   P   P   S    436

3001  CACCAGCTCTCCAGCGGGACTTGGGACTGAAGGAAGAGAAGGGGCTCCCCCTGGCCTTGC  3060
437     P   A   L   Q   R   D   L   G   L   K   E   E   K   G   L   P   L   A   L   L    456

3061  TGGCACCCTTAAGGGGGGCAGCCGAGAGCGGTGGAGCCGCACAGCCCACCCGCACCAAAG  3120
457     A   P   L   R   G   A   A   E   S   G   G   A   A   Q   P   T   R   T   K   A    476

3121  CTGCTGGGAAGGTGGAGCTCCCGGCCTGCCCCTGTCGCCACGTGGACAGTCAGGCCCCAA  3180
477     A   G   K   V   E   L   P   A   C   P   C   R   H   V   D   S   Q   A   P   N    496

3181  ACACCGGTGTCCCCGTAGCCCAGCCCGCCAAAAGCTGGGATCCAAACCAGCTAAATGAGC  3240
497     T   G   V   P   V   A   Q   P   A   K   S   W   D   P   N   Q   L   N   E   H    516

3241  ACCCGCTGGAGCCTGTGCTGCGGAGCCTGAAGACAGCAGAGGGCGCGCTGCGTCCGCCGC  3300
517     P   L   E   P   V   L   R   S   L   K   T   A   E   G   A   L   R   P   P   P    536

3301  CCGGAGGAAAAGGTTCATGACAGCGTCAGATTCTCTGCAGCAGGAGTACAGGTTGCAGCC  3360
537     G   G   K   G   S                                                                541

3361  ACTCTCCCGCCGAACATTGAATACGTCTTTCCACCATCTTGTCTTTGCTGTGGCTCTGGG  3420

3421  AAAATCAGCAGAGTCAGCCATCACTCTCCAAGGGGAGCTGTCAGTTCTATCTGCCAGCTT  3480

3481  TTGAGTGTTCAATTTGATTTTTACTTATTCAACCTGGAATTTGAATGTCAAAAAAAAAAA  3540

3541  AAAAAAAAAAAAAA  3554
```

FIG. 7A

```
-2057   tgcctgcagcagagcccggctgggatcctcacgctgcacgccatttgtcctctgatggtt   -1998

-1997   gcctcactccatcccatcctggctggtgtgaaccttgaatgctgggcatcaataaagact   -1938

-1937   tttttcttgccagtctagcttggtaaaaaatgagatgccgtacctcctctggaccatcaa   -1878

-1877   gagggacatcattgactatcacagcctgacctacgaccagatgctgaaccactacgcaaa   -1818

-1817   gacagcctccttcaccaccaaggtgagccggccgcgcttgagcgtggcgggagccggcaa   -1758

-1757   gggtggtggggaggagcttctgcagccattagggaccctcggtggctggtcagtggccac   -1698

-1697   cagtcacctcctgggtgcatcccaggactcctggtctaaggccgtggccagaatcactcg   -1638

-1637   gtgcccaccccaccccagcacccctgtgccctttgctctgtgtctctgggtgaatccgg   -1578

-1577   ggccccagaagctccctcctcagggcacagaggccaaagatggggctgactgggggctgc   -1518

-1517   caccgggctttgggtgctgagggggctgtgggaccccaggggaagaggtgccgctccccc   -1458

-1457   cagcaccgggcactcccccgcctcccccggcctccagccctgcacaaagcagcttgccac   -1398

-1397   acccttcccaccaaggcccagggctgaggcctgcccaggacgcagggtgtggggaccctg   -1338

-1337   ctgagggaggggtcccggaagaggggcttccctggcacagaggtccctctcagcaggcca   -1278

-1277   ggtgcggctgcctcagcacagtgtggggcggaggtgcaggacaaggttcccttccgcacc   -1218

-1217   taatacccccagggtcaggccagcgccagcgctgctagtggcaacatggccccttcaaaga   -1158

-1157   ccccgtgtgcagagccagtcagcgtgcgctgtgttttctggggccagccacttttttcc   -1098

-1097   ttaacagggtgacaaaccagacatcggggtgcggggacttcacgatatgcctctctaatg   -1038

-1037   gcgcgtgctacctcgcgtgtggtgggcagtgctgggcatgtggctgcgttccggccctg   -978

-977    cagccgctcctccctctcctggggtctgaggtgtgggacaccctgtggcccgtttggggg   -918

-917    cctggagggagcccagtgcccaccgccctcggtgccctcagctgcagcctccccattcc   -858
```

FIG. 7B

```
-857  ctggggcctgccacgccctccactgcctcaaggatgcgtctgagcctggcctgcacatcc   -798

-797  atgctcccaccggctggagggggtgttctggggccctgggggaccgtatatctggggagg   -738

-737  gggagggatccgccctagggggtgctgtgtggtgccccatagccaggcaagtctgaggtgg   -678

-677  acggcccgtcctcgccttgtgagcgaggcagagctgagctgagctgcccctcctgcctaa   -618

-617  cacgccactgtctctggagatcgggctgtgcgtgaacatgcggagcctgccctggtacgt   -558

-557  cccggccaaccccgactccttcttcccacgctgctacagcctctgcaccgagagtgagca   -498

-497  gcaggagttcctgggtaagtgaggagacggcagagggccccagtgctgtcagcagagagg   -438

-437  cttctagaaagatcccccctggtgctgagacagactgatggggcagggtctgaggatagag   -378

-377  gaccggggagaggcctcccatggtcatggtcatggcagtacagaggccaggggccccggg   -318

-317  agggagggcgggcagtcaaggagtgtgtggttctgtgctaggcttgtggacagcgcggcg   -258

-257  agcagctggggcaaggccggctccgtggtcggaggccgaggggtgcagctggacggccgc   -198

-197  agtcacagagacactgcagggagaagggcaggcagactgggggtgtgggagcaggcctgg   -138

-137  gccccatcggctatgagggcgggaagtggggcgggttggggagcctccgtggccctggcc   -78

-77   ccatctccagtccccagtcctggctcggacagatagggcgaggctgtgctgtcctttcag   -18

-17   aagacttccggcgcaccatggcatccagcatcctcaagtgggtggtcagccaccagagct   42
1                  M   A   S   S   I   L   K   W   V   V   S   H   Q   S   C   15

43    gcagcaggagcagcagaagcaagcccagggaccagagggaggaggccgggagcagcgacc   102
16    S   R   S   S   R   S   K   P   R   D   Q   R   E   E   A   G   S   S   D   L   35

103   tgagcagcaggcaaggtgcgctgggccgggcagggcagtgccaggccaccagagctcgg   162
36    S   S   R   Q   G   A   L   G   R   G   R   A   V   P   G   H   Q   S   S   G   55

163   ggcctccacaggggccctccc   183
56    P   P   Q   G   P       61
```

FIG. 12

| Protein | Genbank ID | Identities | Similarities |
|---|---|---|---|
| Human HOTTL protein | gi\|6683745 | 57.5% | 65.5% |
| Pig tubulin--tyrosine ligase protein (TTL) | gi\|423218 | 29.4% | 40.0% |
| Human tubulin tyrosine ligase-like protein (TTLH_HUMAN) | gi\|20455371 | 53.3% | 61.4% |
| Human tubulin tyrosine ligase-like protein (TTLL_HUMAN) | gi\|20455347 | 27.4% | 38.4% |

FIG. 13

```
1gsaA    MIKLGIVMDP  IANINIKKDS  SFAMLLEAQR  RGYELHYMEM  GDLYLINGEA
BGS42    ..........  .......MAS  SILKWVVSHQ  SCSRSSRSKP  RDQREEAGSS 1gsaA    RAHTRTLNVK  QNYEEWFSFV  GEQDLPLADL  DVILMRKDPP  FDTEFIYATY
BGS42    DLSSRQDA..  ENAEAKLRGL  PGQLVDIACK  VCQAYLGQLE  HEDIDTSADA 1gsaA    ILERAEEKGT  LIVNKPQSLR  DCNEKLFTAW  FSDLTPETLV  TRNKAQLKAF
BGS42    VEDLTEAEWE  DLTQQYYSLV  HGDAFISNSR  NYFSQCQALL  NRITSVNPQT
                     ^*        ^*           *            *                                     ^^*
1gsaA    WEKHS..DII  LKPLDGMGGA  SIFRVKEGDP  NLGVIAETLT  EHGTRYCMAQ
BGS42    DIDGLRNIWI  IKPAAKSRGR  DIVCMDRVEE  ILELAAADHP  LSRDNKWVVQ
         **                  *          ^  ^
1gsaA    NYLPAIKDG.  ....DKRVLV  VDGEPVPYCL  ARIP......  ..........
BGS42    KYIETPLLIC  DTKFDIRQWF  LVTDWNPLTI  WFYKESYLRF  STQRFSLDKL 1gsaA    ..........  ..........  ..........  .QGGETRGNL  AAGGRGEPRP
BGS42    DSAIHLCNNA  VQKYLKNDVG  RSPLLPAHNM  WTSTRFQEYL  QRQGRGAVWG
                                       ^           *^^  ^*          ^*
1gsaA    L.........  ..TESDWKIA  RQIGPTLKEK  GLIFVGLDII  GDR.....LT
BGS42    SVIYPSMKKA  IAHAMKVAQD  HVEPRKNSFE  LYGA...DFV  LGRDFRPWLI
         *^*
1gsaA    EINVTSPTCI  REIEAEFPVS  ITGMLMDAIE  ARLQ......  ..........
BGS42    EINSSPTMHP  STPVTAQLCA  QVQEDTIKV.  AVDRSCDIGN  FELLWRQPVV 1gsaA    ..........  ..........  ..........  ..........  ..........
BGS42    EPPPFSGSDL  CVAGVSVRRA  RRQVLPVCNL  KASASLLDAQ  PLKARGPSAM 1gsaA    ..........  ..........  ..........  ..........  ..........
BGS42    PDPAQGPPSP  ALQRDLGLKE  EKGLPLALLA  PLRGAAESGG  AAQPTRTKAA 1gsaA    ..........  ..........  ..........  ..........  ..........
BGS42    GKVELPACPC  RHVDSQAPNT  GVPVAQPAKS  WDPNQLNAHP  LEPVLRGLKT 1gsaA    ..........  ........
BGS42    AEGALRPPPG  GKGS....
```

SEQUENCE LISTING

<160> NUMBER OF SEQ ID NOS: 103

<210> SEQ ID NO 1
<211> LENGTH: 1838
<212> TYPE: DNA
<213> ORGANISM: Homo sapiens
<220> FEATURE:
<221> NAME/KEY: CDS
<222> LOCATION: (153)..(1775)

<400> SEQUENCE: 1

```
tgggagcagg cctgggcccc atcggctatg agggcgggaa gtggggcggg ttggggagcc          60
tccgtggccc tggccccatc tccagtcccc agtcctggct cggacagata gggcgaggct         120
gtgctgtcct ttcagaagac ttccggcgca cc atg gca tcc agc atc ctc aag          173
                                    Met Ala Ser Ser Ile Leu Lys
                                    1               5 tgg gtg gtc agc cac cag agc tgc agc agg agc agc aga agc aag ccc          221
Trp Val Val Ser His Gln Ser Cys Ser Arg Ser Ser Arg Ser Lys Pro
        10                  15                  20 agg gac cag agg gag gag gcc ggg agc agc gac ctg agc agc agg caa          269
Arg Asp Gln Arg Glu Glu Ala Gly Ser Ser Asp Leu Ser Ser Arg Gln
    25                  30                  35 gat gct gaa aat gct gag gca aag ctc agg ggc ctc ccg ggg cag ctt          317
Asp Ala Glu Asn Ala Glu Ala Lys Leu Arg Gly Leu Pro Gly Gln Leu
40                  45                  50                  55 gtg gac atc gcg tgc aag gtg tgc cag gcc tac ctg ggg cag ctg gag          365
Val Asp Ile Ala Cys Lys Val Cys Gln Ala Tyr Leu Gly Gln Leu Glu
                60                  65                  70 cat gag gac atc gac acg tca gca gat gcc gtg gag gac ctc act gag          413
His Glu Asp Ile Asp Thr Ser Ala Asp Ala Val Glu Asp Leu Thr Glu
            75                  80                  85 gcc gag tgg gag gac ctg acc cag cag tac tac tcc ctc gtt cat ggc          461
Ala Glu Trp Glu Asp Leu Thr Gln Gln Tyr Tyr Ser Leu Val His Gly
        90                  95                 100 gat gct ttc atc tcc aat tca aga aat tac ttt tcg cag tgc cag gct          509
Asp Ala Phe Ile Ser Asn Ser Arg Asn Tyr Phe Ser Gln Cys Gln Ala
    105                 110                 115 ctg ctg aat aga atc acg tct gtg aac cct cag acg gac att gac ggg          557
Leu Leu Asn Arg Ile Thr Ser Val Asn Pro Gln Thr Asp Ile Asp Gly
120                 125                 130                 135 ctc cgg aac atc tgg att ata aag ccc gcg gcc aag tcc cgg ggc cga          605
Leu Arg Asn Ile Trp Ile Ile Lys Pro Ala Ala Lys Ser Arg Gly Arg
                140                 145                 150 gac ata gtg tgc atg gac cgt gtg gag gag atc ctg gag ctg gca gct          653
Asp Ile Val Cys Met Asp Arg Val Glu Glu Ile Leu Glu Leu Ala Ala
            155                 160                 165 gca gac cac cct ctt tcc agg gac aac aag tgg gtg gtc cag aag tac          701
Ala Asp His Pro Leu Ser Arg Asp Asn Lys Trp Val Val Gln Lys Tyr
        170                 175                 180 atc gag acg ccg ctg ctc atc tgt gac acc aag ttc gac atc aga cag          749
Ile Glu Thr Pro Leu Leu Ile Cys Asp Thr Lys Phe Asp Ile Arg Gln
    185                 190                 195 tgg ttc ctc gtc acg gac tgg aac ccc ctg acc atc tgg ttc tac aag          797
Trp Phe Leu Val Thr Asp Trp Asn Pro Leu Thr Ile Trp Phe Tyr Lys
200                 205                 210                 215 gag agt tac ttg cgg ttc tca act cag cgc ttc tcc ctg gac aag ctg          845
Glu Ser Tyr Leu Arg Phe Ser Thr Gln Arg Phe Ser Leu Asp Lys Leu
                220                 225                 230
```

```
gac agc gcc atc cac ctg tgc aac aac gcc gtc cag aag tac ctg aag      893
Asp Ser Ala Ile His Leu Cys Asn Asn Ala Val Gln Lys Tyr Leu Lys
            235                 240                 245 aat gat gtg ggc cgc agc ccc ctg ctg ccc gca cac aac atg tgg acc      941
Asn Asp Val Gly Arg Ser Pro Leu Leu Pro Ala His Asn Met Trp Thr
        250                 255                 260 agc acc agg ttc cag gag tac ctg cag cgc cag ggc cgt ggc gcc gtg      989
Ser Thr Arg Phe Gln Glu Tyr Leu Gln Arg Gln Gly Arg Gly Ala Val
    265                 270                 275 tgg ggc agc gtc atc tac ccg tcc atg aag aag gcc atc gcc cac gcc     1037
Trp Gly Ser Val Ile Tyr Pro Ser Met Lys Lys Ala Ile Ala His Ala
280                 285                 290                 295 atg aag gtg gcc cag gac cac gtg gag cct cgc aag aac agc ttt gag     1085
Met Lys Val Ala Gln Asp His Val Glu Pro Arg Lys Asn Ser Phe Glu
                300                 305                 310 ctc tac ggg gct gac ttc gtc ctt ggg agg gac ttc agg ccc tgg ctg     1133
Leu Tyr Gly Ala Asp Phe Val Leu Gly Arg Asp Phe Arg Pro Trp Leu
            315                 320                 325 atc gag atc aat tcc agc ccc acc atg cac ccg tcc acg ccg gtc acg     1181
Ile Glu Ile Asn Ser Ser Pro Thr Met His Pro Ser Thr Pro Val Thr
        330                 335                 340 gcc cag ctg tgt gca cag gtg cag gag gac acc atc aag gtg gcc gtg     1229
Ala Gln Leu Cys Ala Gln Val Gln Glu Asp Thr Ile Lys Val Ala Val
    345                 350                 355 gac cgc agc tgt gac atc ggc aac ttc gag ctc ctg tgg agg cag ccg     1277
Asp Arg Ser Cys Asp Ile Gly Asn Phe Glu Leu Leu Trp Arg Gln Pro
360                 365                 370                 375 gtg gtt gag ccg ccc cca ttc agc ggg tcc gac ctc tgc gtg gcg ggc     1325
Val Val Glu Pro Pro Pro Phe Ser Gly Ser Asp Leu Cys Val Ala Gly
                380                 385                 390 gtc agt gtg agg aga gcc agg agg cag gtg ctg ccc gtc tgc aac ctc     1373
Val Ser Val Arg Arg Ala Arg Arg Gln Val Leu Pro Val Cys Asn Leu
            395                 400                 405 aag gcc tcg gcc tcg ctg ttg gac gcg cag ccg ctg aag gca cgg ggc     1421
Lys Ala Ser Ala Ser Leu Leu Asp Ala Gln Pro Leu Lys Ala Arg Gly
        410                 415                 420 ccc tcg gcc atg cca gac cct gcc cag gga ccc cca tca cca gct ctc     1469
Pro Ser Ala Met Pro Asp Pro Ala Gln Gly Pro Pro Ser Pro Ala Leu
    425                 430                 435 cag cgg gac ttg gga ctg aag gaa gag aag ggg ctc ccc ctg gcc ttg     1517
Gln Arg Asp Leu Gly Leu Lys Glu Glu Lys Gly Leu Pro Leu Ala Leu
440                 445                 450                 455 ctg gca ccc tta agg ggg gca gcc gag agc ggt gga gcc gca cag ccc     1565
Leu Ala Pro Leu Arg Gly Ala Ala Glu Ser Gly Gly Ala Ala Gln Pro
                460                 465                 470 acc cgc acc aaa gct gct ggg aag gtg gag ctc ccg gcc tgc ccc tgt     1613
Thr Arg Thr Lys Ala Ala Gly Lys Val Glu Leu Pro Ala Cys Pro Cys
            475                 480                 485 cgc cac gtg gac agt cag gcc cca aac acc ggt gtc ccc gta gcc cag     1661
Arg His Val Asp Ser Gln Ala Pro Asn Thr Gly Val Pro Val Ala Gln
        490                 495                 500 ccc gcc aaa agc tgg gat cca aac cag cta aat gcg cac ccg ctg gag     1709
Pro Ala Lys Ser Trp Asp Pro Asn Gln Leu Asn Ala His Pro Leu Glu
    505                 510                 515 cct gtg ctg cgg ggc ctg aag aca gca gag ggc gcg ctg cgt ccg ccg     1757
Pro Val Leu Arg Gly Leu Lys Thr Ala Glu Gly Ala Leu Arg Pro Pro
520                 525                 530                 535
```

```
ccc gga gga aaa ggt tca tgacagcgtc agattctctg cagcaggagt         1805
Pro Gly Gly Lys Gly Ser
                540 acaggttgca gccactctcc caagggcgaa ttc                              1838
```

<210> SEQ ID NO 2
<211> LENGTH: 541
<212> TYPE: PRT
<213> ORGANISM: Homo sapiens

<400> SEQUENCE: 2

```
Met Ala Ser Ser Ile Leu Lys Trp Val Val His Gln Ser Cys Ser
1               5                   10                  15

Arg Ser Ser Arg Ser Lys Pro Arg Asp Gln Arg Glu Glu Ala Gly Ser
                20                  25                  30

Ser Asp Leu Ser Ser Arg Gln Asp Ala Glu Asn Ala Glu Ala Lys Leu
            35                  40                  45

Arg Gly Leu Pro Gly Gln Leu Val Asp Ile Ala Cys Lys Val Cys Gln
50                  55                  60

Ala Tyr Leu Gly Gln Leu Glu His Glu Asp Ile Asp Thr Ser Ala Asp
65                  70                  75                  80

Ala Val Glu Asp Leu Thr Glu Ala Glu Trp Glu Asp Leu Thr Gln Gln
                85                  90                  95

Tyr Tyr Ser Leu Val His Gly Asp Ala Phe Ile Ser Asn Ser Arg Asn
            100                 105                 110

Tyr Phe Ser Gln Cys Gln Ala Leu Leu Asn Arg Ile Thr Ser Val Asn
        115                 120                 125

Pro Gln Thr Asp Ile Asp Gly Leu Arg Asn Ile Trp Ile Lys Pro
130                 135                 140

Ala Ala Lys Ser Arg Gly Arg Asp Ile Val Cys Met Asp Arg Val Glu
145                 150                 155                 160

Glu Ile Leu Glu Leu Ala Ala Asp His Pro Leu Ser Arg Asp Asn
                165                 170                 175

Lys Trp Val Val Gln Lys Tyr Ile Glu Thr Pro Leu Leu Ile Cys Asp
            180                 185                 190

Thr Lys Phe Asp Ile Arg Gln Trp Phe Leu Val Thr Asp Trp Asn Pro
        195                 200                 205

Leu Thr Ile Trp Phe Tyr Lys Glu Ser Tyr Leu Arg Phe Ser Thr Gln
210                 215                 220

Arg Phe Ser Leu Asp Lys Leu Asp Ser Ala Ile His Leu Cys Asn Asn
225                 230                 235                 240

Ala Val Gln Lys Tyr Leu Lys Asn Asp Val Gly Arg Ser Pro Leu Leu
                245                 250                 255

Pro Ala His Asn Met Trp Thr Ser Thr Arg Phe Gln Glu Tyr Leu Gln
            260                 265                 270

Arg Gln Gly Arg Gly Ala Val Trp Gly Ser Val Ile Tyr Pro Ser Met
        275                 280                 285

Lys Lys Ala Ile Ala His Ala Met Lys Val Ala Gln Asp His Val Glu
290                 295                 300

Pro Arg Lys Asn Ser Phe Glu Leu Tyr Gly Ala Asp Phe Val Leu Gly
305                 310                 315                 320

Arg Asp Phe Arg Pro Trp Leu Ile Glu Ile Asn Ser Ser Pro Thr Met
                325                 330                 335

His Pro Ser Thr Pro Val Thr Ala Gln Leu Cys Ala Gln Val Gln Glu
            340                 345                 350
```

```
Asp Thr Ile Lys Val Ala Val Asp Arg Ser Cys Asp Ile Gly Asn Phe
        355                 360                 365

Glu Leu Leu Trp Arg Gln Pro Val Glu Pro Pro Phe Ser Gly
370                 375                 380

Ser Asp Leu Cys Val Ala Gly Val Ser Val Arg Arg Ala Arg Arg Gln
385                 390                 395                 400

Val Leu Pro Val Cys Asn Leu Lys Ala Ser Ala Ser Leu Leu Asp Ala
                405                 410                 415

Gln Pro Leu Lys Ala Arg Gly Pro Ser Ala Met Pro Asp Pro Ala Gln
                420                 425                 430

Gly Pro Pro Ser Pro Ala Leu Gln Arg Asp Leu Gly Leu Lys Glu Glu
            435                 440                 445

Lys Gly Leu Pro Leu Ala Leu Leu Ala Pro Leu Arg Gly Ala Ala Glu
450                 455                 460

Ser Gly Gly Ala Ala Gln Pro Thr Arg Thr Lys Ala Ala Gly Lys Val
465                 470                 475                 480

Glu Leu Pro Ala Cys Pro Cys Arg His Val Asp Ser Gln Ala Pro Asn
                485                 490                 495

Thr Gly Val Pro Val Ala Gln Pro Ala Lys Ser Trp Asp Pro Asn Gln
                500                 505                 510

Leu Asn Ala His Pro Leu Glu Pro Val Leu Arg Gly Leu Lys Thr Ala
                515                 520                 525

Glu Gly Ala Leu Arg Pro Pro Gly Gly Lys Gly Ser
530                 535                 540

<210> SEQ ID NO 3
<211> LENGTH: 726
<212> TYPE: DNA
<213> ORGANISM: Homo sapiens
<220> FEATURE:
<221> NAME/KEY: CDS
<222> LOCATION: (1)..(726)

<400> SEQUENCE: 3 att gac ggg ctc cgg aac atc tgg att ata aag ccc gcg gcc aag tcc      48
Ile Asp Gly Leu Arg Asn Ile Trp Ile Ile Lys Pro Ala Ala Lys Ser
1               5                   10                  15 cgg ggc cga gac ata gtg tgc atg gac cgt gtg gag gag atc ctg gag      96
Arg Gly Arg Asp Ile Val Cys Met Asp Arg Val Glu Glu Ile Leu Glu
                20                  25                  30 ctg gca gct gca gac cac cct ctt tcc agg gac aac aag tgg gtg gtc     144
Leu Ala Ala Ala Asp His Pro Leu Ser Arg Asp Asn Lys Trp Val Val
            35                  40                  45 cag aag tac atc gag acg ccg ctg ctc atc tgt gac acc aag ttc gac     192
Gln Lys Tyr Ile Glu Thr Pro Leu Leu Ile Cys Asp Thr Lys Phe Asp
        50                  55                  60 atc aga cag tgg ttc ctc gtc acg gac tgg aac ccc ctg acc atc tgg     240
Ile Arg Gln Trp Phe Leu Val Thr Asp Trp Asn Pro Leu Thr Ile Trp
65                  70                  75                  80 ttc tac aag gag agt tac ttg cgg ttc tca act cag cgc ttc tcc ctg     288
Phe Tyr Lys Glu Ser Tyr Leu Arg Phe Ser Thr Gln Arg Phe Ser Leu
                85                  90                  95 gac aag ctg gac agc gcc atc cac ctg tgc aac aac gcc gtc cag aag     336
Asp Lys Leu Asp Ser Ala Ile His Leu Cys Asn Asn Ala Val Gln Lys
                100                 105                 110 tac ctg aag aat gat gtg ggc cgc agc ccc ctg ctg ccc gca cac aac     384
Tyr Leu Lys Asn Asp Val Gly Arg Ser Pro Leu Leu Pro Ala His Asn
            115                 120                 125
```

-continued

```
atg tgg acc agc acc agg ttc cag gag tac ctg cag cgc cag ggc cgt      432
Met Trp Thr Ser Thr Arg Phe Gln Glu Tyr Leu Gln Arg Gln Gly Arg
130                 135                 140 ggc gcc gtg tgg ggc agc gtc atc tac ccg tcc atg aag aag gcc atc      480
Gly Ala Val Trp Gly Ser Val Ile Tyr Pro Ser Met Lys Lys Ala Ile
145                 150                 155                 160 gcc cac gcc atg aag gtg gcc cag gac cac gtg gag cct cgc aag aac      528
Ala His Ala Met Lys Val Ala Gln Asp His Val Glu Pro Arg Lys Asn
                165                 170                 175 agc ttt gag ctc tac ggg gct gac ttc gtc ctt ggg agg gac ttc agg      576
Ser Phe Glu Leu Tyr Gly Ala Asp Phe Val Leu Gly Arg Asp Phe Arg
            180                 185                 190 ccc tgg ctg atc gag atc aat tcc agc ccc acc atg cac ccg tcc acg      624
Pro Trp Leu Ile Glu Ile Asn Ser Ser Pro Thr Met His Pro Ser Thr
        195                 200                 205 ccg gtc acg gcc cag ctg tgt gca cag gtg cag gag gac acc atc aag      672
Pro Val Thr Ala Gln Leu Cys Ala Gln Val Gln Glu Asp Thr Ile Lys
    210                 215                 220 gtg gcc gtg gac cgc agc tgt gac atc ggc aac ttc gag ctc ctg tgg      720
Val Ala Val Asp Arg Ser Cys Asp Ile Gly Asn Phe Glu Leu Leu Trp
225                 230                 235                 240 agg cag                                                              726
Arg Gln
```

<210> SEQ ID NO 4
<211> LENGTH: 242
<212> TYPE: PRT
<213> ORGANISM: Homo sapiens

<400> SEQUENCE: 4

```
Ile Asp Gly Leu Arg Asn Ile Trp Ile Ile Lys Pro Ala Ala Lys Ser
1               5                   10                  15

Arg Gly Arg Asp Ile Val Cys Met Asp Arg Val Glu Glu Ile Leu Glu
                20                  25                  30

Leu Ala Ala Ala Asp His Pro Leu Ser Arg Asp Asn Lys Trp Val Val
            35                  40                  45

Gln Lys Tyr Ile Glu Thr Pro Leu Leu Ile Cys Asp Thr Lys Phe Asp
        50                  55                  60

Ile Arg Gln Trp Phe Leu Val Thr Asp Trp Asn Pro Leu Thr Ile Trp
65                  70                  75                  80

Phe Tyr Lys Glu Ser Tyr Leu Arg Phe Ser Thr Gln Arg Phe Ser Leu
                85                  90                  95

Asp Lys Leu Asp Ser Ala Ile His Leu Cys Asn Asn Ala Val Gln Lys
                100                 105                 110

Tyr Leu Lys Asn Asp Val Gly Arg Ser Pro Leu Leu Pro Ala His Asn
            115                 120                 125

Met Trp Thr Ser Thr Arg Phe Gln Glu Tyr Leu Gln Arg Gln Gly Arg
        130                 135                 140

Gly Ala Val Trp Gly Ser Val Ile Tyr Pro Ser Met Lys Lys Ala Ile
145                 150                 155                 160

Ala His Ala Met Lys Val Ala Gln Asp His Val Glu Pro Arg Lys Asn
                165                 170                 175

Ser Phe Glu Leu Tyr Gly Ala Asp Phe Val Leu Gly Arg Asp Phe Arg
            180                 185                 190

Pro Trp Leu Ile Glu Ile Asn Ser Ser Pro Thr Met His Pro Ser Thr
        195                 200                 205
```

-continued

Pro Val Thr Ala Gln Leu Cys Ala Gln Val Gln Glu Asp Thr Ile Lys
    210                 215                 220

Val Ala Val Asp Arg Ser Cys Asp Ile Gly Asn Phe Glu Leu Leu Trp
225                 230                 235                 240

Arg Gln

<210> SEQ ID NO 5
<211> LENGTH: 292
<212> TYPE: PRT
<213> ORGANISM: Homo sapiens

<400> SEQUENCE: 5

Met Glu Gly Asp Arg Asn Phe Trp Ile Val Lys Pro Gly Ala Lys Ser
1               5                   10                  15

Arg Gly Arg Gly Ile Met Cys Met Asp His Leu Glu Glu Met Leu Lys
            20                  25                  30

Leu Val Asn Gly Asn Pro Val Val Met Lys Asp Gly Lys Trp Val Val
        35                  40                  45

Gln Lys Tyr Ile Glu Arg Pro Leu Leu Ile Phe Gly Thr Lys Phe Asp
    50                  55                  60

Leu Arg Gln Trp Phe Leu Val Thr Asp Trp Asn Pro Leu Thr Val Trp
65                  70                  75                  80

Phe Tyr Arg Asp Ser Tyr Ile Arg Phe Ser Thr Gln Pro Phe Ser Leu
                85                  90                  95

Lys Asn Leu Asp Asn Ser Val His Leu Cys Asn Asn Ser Ile Gln Lys
            100                 105                 110

His Leu Glu Asn Ser Cys His Arg His Pro Leu Leu Pro Pro Asp Asn
        115                 120                 125

Met Trp Ser Ser Gln Arg Phe Gln Ala His Leu Gln Glu Met Gly Ala
130                 135                 140

Pro Asn Ala Trp Ser Thr Ile Ile Val Pro Gly Met Lys Asp Ala Val
145                 150                 155                 160

Ile His Ala Leu Gln Thr Ser Gln Asp Thr Val Gln Cys Arg Lys Ala
                165                 170                 175

Ser Phe Glu Leu Tyr Gly Ala Asp Phe Val Phe Gly Glu Asp Phe Gln
            180                 185                 190

Pro Trp Leu Ile Glu Ile Asn Ala Ser Pro Thr Met Ala Pro Ser Thr
        195                 200                 205

Ala Val Thr Ala Arg Leu Cys Ala Gly Val Gln Ala Asp Thr Leu Arg
    210                 215                 220

Val Val Ile Asp Arg Met Leu Asp Arg Asn Cys Asp Thr Gly Ala Phe
225                 230                 235                 240

Glu Leu Ile Tyr Lys Gln Pro Val Thr Thr Ser Pro Ala Ser Thr Pro
                245                 250                 255

Arg Pro Ser Cys Leu Leu Pro Met Tyr Ser Asp Thr Arg Ala Arg Ser
            260                 265                 270

Ser Asp Asp Ser Thr Ala Ser Trp Trp Ala Leu Arg Pro Cys Arg Pro
        275                 280                 285

Gln Ala Arg Pro
    290

<210> SEQ ID NO 6
<211> LENGTH: 379
<212> TYPE: PRT
<213> ORGANISM: Homo sapiens

<400> SEQUENCE: 6

```
Met Tyr Thr Phe Val Val Arg Asp Glu Asn Ser Ser Val Tyr Ala Glu
1               5                   10                  15

Val Ser Arg Leu Leu Leu Ala Thr Gly His Trp Lys Arg Leu Arg Arg
            20                  25                  30

Asp Asn Pro Arg Phe Asn Leu Met Leu Gly Glu Arg Asn Arg Leu Pro
        35                  40                  45

Phe Gly Arg Leu Gly His Glu Pro Gly Leu Met Gln Leu Val Asn Tyr
    50                  55                  60

Tyr Arg Gly Ala Asp Lys Leu Cys Arg Lys Ala Ser Leu Val Lys Leu
65                  70                  75                  80

Ile Lys Thr Ser Pro Glu Leu Ala Glu Ser Cys Thr Trp Phe Pro Glu
                85                  90                  95

Ser Tyr Val Ile Tyr Pro Thr Asn Leu Lys Thr Pro Val Ala Pro Ala
                100                 105                 110

Gln Asn Gly Ile His Pro Pro Ile His Ser Ser Arg Thr Asp Glu Arg
            115                 120                 125

Glu Phe Phe Leu Thr Ser Tyr Asn Lys Lys Glu Asp Gly Glu Gly
130                 135                 140

Asn Val Trp Ile Ala Lys Ser Ser Ala Gly Ala Lys Gly Glu Gly Ile
145                 150                 155                 160

Leu Ile Ser Ser Glu Ala Thr Glu Leu Leu Asp Phe Ile Asp Asn Gln
                165                 170                 175

Gly Gln Val His Val Ile Gln Lys Tyr Leu Glu Arg Pro Leu Leu Leu
            180                 185                 190

Glu Pro Gly His Arg Lys Phe Asp Ile Arg Ser Trp Val Leu Val Asp
            195                 200                 205

His Gln Tyr Asn Ile Tyr Leu Tyr Arg Glu Gly Val Leu Arg Thr Ala
210                 215                 220

Ser Glu Pro Tyr His Thr Asp Asn Phe Gln Asp Lys Thr Cys His Leu
225                 230                 235                 240

Thr Asn His Cys Ile Gln Lys Glu Tyr Ser Lys Asn Tyr Gly Lys Tyr
                245                 250                 255

Glu Glu Gly Asn Glu Met Phe Phe Glu Glu Phe Asn Gln Tyr Leu Thr
            260                 265                 270

Ser Ala Leu Asn Ile Thr Leu Glu Ser Ser Ile Leu Leu Gln Ile Lys
        275                 280                 285

His Ile Ile Arg Ser Cys Leu Leu Ser Val Glu Pro Ala Ile Ser Thr
290                 295                 300

Arg His Leu Pro Tyr Gln Ser Phe Gln Leu Phe Gly Phe Asp Phe Met
305                 310                 315                 320

Val Asp Glu Asp Leu Lys Val Trp Leu Ile Glu Val Asn Gly Ala Pro
                325                 330                 335

Ala Cys Ala Gln Lys Leu Tyr Ala Glu Leu Cys Gln Gly Ile Val Asp
            340                 345                 350

Ile Ala Ile Ala Ser Val Phe Pro Pro Asp Ala Glu Gln Gln Gln
            355                 360                 365

Gln Gln Pro Pro Pro Ala Ala Phe Ile Lys Leu
    370                 375
```

<210> SEQ ID NO 7
<211> LENGTH: 352
<212> TYPE: PRT
<213> ORGANISM: Homo sapiens -continued

```
<400> SEQUENCE: 7

Met Asp Ile Asp Lys Asp Leu Glu Ala Pro Leu Tyr Leu Thr Pro Glu
1               5                   10                  15

Gly Trp Ser Leu Phe Leu Gln Arg Tyr Tyr Gln Val Val His Glu Gly
            20                  25                  30

Ala Glu Leu Arg His Leu Asp Thr Gln Val Gln Arg Cys Glu Asp Ile
        35                  40                  45

Leu Gln Gln Leu Gln Ala Val Val Pro Gln Ile Asp Met Glu Gly Asp
    50                  55                  60

Arg Asn Ile Trp Ile Val Lys Pro Gly Ala Lys Ser Arg Gly Arg Gly
65                  70                  75                  80

Ile Met Cys Met Asp His Leu Glu Glu Met Leu Lys Leu Val Asn Gly
                85                  90                  95

Asn Pro Val Met Lys Asp Gly Lys Trp Val Val Gln Lys Tyr Ile
            100                 105                 110

Glu Arg Pro Leu Leu Ile Phe Gly Thr Lys Phe Asp Leu Arg Gln Trp
        115                 120                 125

Phe Leu Val Thr Asp Trp Asn Pro Leu Thr Val Trp Phe Tyr Arg Asp
130                 135                 140

Ser Tyr Ile Arg Phe Ser Thr Gln Pro Phe Ser Leu Lys Asn Leu Asp
145                 150                 155                 160

Asn Ser Val His Leu Cys Asn Asn Ser Ile Gln Lys His Leu Glu Asn
                165                 170                 175

Ser Cys His Arg His Pro Leu Leu Pro Pro Asp Asn Met Trp Ser Ser
            180                 185                 190

Gln Arg Phe Gln Ala His Leu Gln Glu Met Gly Ala Pro Asn Ala Trp
        195                 200                 205

Ser Thr Ile Ile Val Pro Gly Met Lys Asp Ala Val Ile His Ala Leu
    210                 215                 220

Gln Thr Ser Gln Asp Thr Val Gln Cys Arg Lys Ala Ser Phe Glu Leu
225                 230                 235                 240

Tyr Gly Ala Asp Phe Val Phe Gly Glu Asp Phe Gln Pro Trp Leu Ile
                245                 250                 255

Glu Ile Asn Ala Ser Pro Thr Met Ala Pro Ser Thr Ala Val Thr Ala
            260                 265                 270

Arg Leu Cys Ala Gly Val Gln Ala Asp Thr Leu Arg Val Val Ile Asp
        275                 280                 285

Arg Met Leu Asp Arg Asn Cys Asp Thr Gly Ala Phe Glu Leu Ile Tyr
    290                 295                 300

Lys Gln Pro Val Thr Thr Ser Pro Ala Ser Thr Pro Arg Pro Ser Cys
305                 310                 315                 320

Leu Leu Pro Met Tyr Ser Asp Thr Arg Ala Arg Ser Ser Asp Asp Ser
                325                 330                 335

Thr Ala Ser Trp Trp Ala Leu Arg Pro Cys Arg Pro Gln Ala Arg Pro
            340                 345                 350

<210> SEQ ID NO 8
<211> LENGTH: 423
<212> TYPE: PRT
<213> ORGANISM: Homo sapiens
```

```
<400> SEQUENCE: 8

Met Ala Gly Lys Val Lys Trp Val Thr Asp Ile Glu Lys Ser Val Leu
1               5                   10                  15

Ile Asn Asn Phe Glu Lys Arg Gly Trp Val Gln Val Thr Glu Asn Glu
                20                  25                  30

Asp Trp Asn Phe Tyr Trp Met Ser Val Gln Thr Ile Arg Asn Val Phe
            35                  40                  45

Ser Val Glu Ala Gly Tyr Arg Leu Ser Asp Asp Gln Ile Val Asn His
        50                  55                  60

Phe Pro Asn His Tyr Glu Leu Thr Arg Lys Asp Leu Met Val Lys Asn
65                  70                  75                  80

Ile Lys Arg Tyr Arg Lys Glu Leu Glu Lys Glu Gly Ser Pro Leu Ala
                85                  90                  95

Glu Lys Asp Glu Asn Gly Lys Tyr Leu Tyr Leu Asp Phe Val Pro Val
            100                 105                 110

Thr Tyr Met Leu Pro Ala Asp Tyr Asn Leu Phe Val Glu Glu Phe Arg
        115                 120                 125

Lys Ser Pro Ser Ser Thr Trp Ile Met Lys Pro Cys Gly Lys Ala Gln
130                 135                 140

Gly Lys Gly Ile Phe Leu Ile Asn Lys Leu Ser Gln Ile Lys Lys Trp
145                 150                 155                 160

Ser Arg Asp Ser Lys Thr Ser Ser Phe Val Ser Gln Ser Asn Lys Glu
                165                 170                 175

Ala Tyr Val Ile Ser Leu Tyr Ile Asn Asn Pro Leu Leu Ile Gly Gly
            180                 185                 190

Arg Lys Phe Asp Leu Arg Leu Tyr Val Leu Val Ser Thr Tyr Arg Pro
        195                 200                 205

Leu Arg Cys Tyr Met Tyr Lys Leu Gly Phe Cys Arg Phe Cys Thr Val
210                 215                 220

Lys Tyr Thr Pro Ser Thr Ser Glu Leu Asp Asn Met Phe Val His Leu
225                 230                 235                 240

Thr Asn Val Ala Ile Gln Lys His Gly Glu Asp Tyr Asn His Ile His
                245                 250                 255

Gly Gly Lys Trp Thr Val Ser Asn Leu Arg Leu Tyr Leu Glu Ser Thr
            260                 265                 270

Arg Gly Lys Glu Val Thr Ser Lys Leu Phe Asp Glu Ile His Trp Ile
        275                 280                 285

Ile Val Gln Ser Leu Lys Ala Val Ala Pro Val Met Asn Asn Asp Lys
290                 295                 300

His Cys Phe Glu Cys Tyr Gly Tyr Asp Ile Ile Asp Asp Lys Leu
305                 310                 315                 320

Lys Pro Trp Leu Ile Glu Val Asn Ala Ser Pro Ser Leu Thr Ser Ser
                325                 330                 335

Thr Ala Asn Asp Arg Ile Leu Lys Tyr Asn Leu Ile Asn Asp Thr Leu
            340                 345                 350

Asn Ile Ala Val Pro Asn Gly Glu Ile Pro Asp Cys Lys Trp Asn Lys
        355                 360                 365

Ser Pro Pro Lys Glu Val Leu Gly Asn Tyr Glu Ile Leu Tyr Asp Glu
370                 375                 380

Glu Leu Ala Gln Gly Asp Gly Ala Asp Arg Glu Leu Arg Ser Arg Gln
385                 390                 395                 400
```

Gly Gln Ser Leu Gly Pro Arg Ala Gly Arg Ser Arg Asp Ser Gly Arg
                405                 410                 415
Ala Val Leu Thr Thr Trp Lys
        420

<210> SEQ ID NO 9
<211> LENGTH: 1939
<212> TYPE: DNA
<213> ORGANISM: Homo sapiens

<400> SEQUENCE: 9

| | | | | | |
|---|---|---|---|---|---|
| tgggagcagg | cctgggcccc | atcggctatg | agggcgggaa | gtggggcggg | ttggggagcc | 60 |
| tccgtggccc | tggccccatc | tccagtcccc | agtcctggct | cggacagata | gggcgaggct | 120 |
| gtgctgtcct | ttcagaagac | ttccggcgca | ccatggcatc | cagcatcctc | aagtgggtgg | 180 |
| tcagccacca | gagctgcagc | aggagcagca | gaagcaagcc | cagggaccag | agggaggagg | 240 |
| ccggagcag | cgacctgagc | agcaggcaag | atgctgaaaa | tgctgaggca | aagctcaggg | 300 |
| gcctcccggg | gcagcttgtg | gacatcgcgt | gcaaggtgtg | ccaggcctac | ctggggcagc | 360 |
| tggagcatga | ggacatcgac | acgtcagcag | atgccgtgga | ggacctcact | gaggccgagt | 420 |
| gggaggacct | gacccagcag | tactactccc | tcgttcatgg | cgatgctttc | atctccaatt | 480 |
| caagaaatta | cttttcgcag | tgccaggctc | tgctgaatag | aatcacgtct | gtgaaccctc | 540 |
| agacggacat | tgacgggctc | cggaacatct | ggattataaa | gcccgcggcc | aagtcccggg | 600 |
| gccgagggac | aacaagtggg | tggtccagaa | gtacatcgag | acgccgctgc | tcatctgtga | 660 |
| caccaagttc | gacatcagac | agtggttcct | cgtcacggac | tggaaccccc | tgaccatctg | 720 |
| gttctacaag | gagagttact | tgcggttctc | aactcagcgc | ttctccctgg | acaagctgga | 780 |
| cagcgccatc | cacctgtgca | caacaccgt | ccagaagtac | ctgaagaatg | atgtgggccg | 840 |
| cagcccctg | ctgcccgcac | acaacatgtg | gaccagcacc | aggttccagg | agtacctgca | 900 |
| gcgccagggc | cgtggcgccg | tgtggggcag | cgtcatctac | ccgtccatga | agaaggccat | 960 |
| cgcccacgcc | atgaaggtgg | cccaggacca | cgtggagcct | cgcaagaaca | gctttgagct | 1020 |
| ctacggggct | gacttcgtcc | ttgggaggga | cttcaggccc | tggctgatcg | agatcaattc | 1080 |
| cagccccacc | atgcacccgt | ccacgccggt | cacggcccag | ctgtgtgcac | aggtgcagga | 1140 |
| ggacaccatc | aaggtggccg | tggaccgcag | ctgtgacatc | ggcaacttcg | agctcctgtg | 1200 |
| gaggcagccg | gtggttgagc | cgcccccatt | cagcgggtcc | gacctctgcg | tggcgggcgt | 1260 |
| cagtgtgagg | agagccagga | ggcaggtgct | gcccgtctgc | aacctcaagg | cctcggcctc | 1320 |
| gctgttggac | gcgcagccgc | tgaaggcacg | gggcccctcg | gccatgccag | accctgccca | 1380 |
| gggaccccca | tcaccagctc | tccagcggga | cttgggactg | aaggaagaga | aggggctccc | 1440 |
| cctggccttg | ctggcaccct | taagggggc | agccgagagc | ggtggagccg | cacagcccac | 1500 |
| ccgcaccaaa | gctgctggga | aggtggagct | cccggcctgc | ccctgtcgcc | acgtggacag | 1560 |
| tcaggcccca | aacaccggtg | tccccgtagc | ccagcccgcc | aaaagctggg | atccaaacca | 1620 |
| gctaaatgag | caccccgctgg | agcctgtgct | gcggagcctg | aagacagcag | agggcgcgct | 1680 |
| gcgtccgccg | cccggaggaa | aaggttcatg | acagcgtcag | attctctgca | gcaggagtac | 1740 |
| aggttgcagc | cactctcccg | ccgaacattg | aatacgtctt | tccaccatct | tgtctttgct | 1800 |
| gtggctctgg | gaaaatcagc | agagtcagcc | atcactctcc | aagggagct | gtcagttcta | 1860 |
| tctgccagct | tttgagtgtt | caatttgatt | tttacttatt | caacctggaa | tttgaatgtc | 1920 |
| aaaaaaaaaa | aaaaaaaaa | | | | | 1939 |

<210> SEQ ID NO 10
<211> LENGTH: 1859
<212> TYPE: DNA
<213> ORGANISM: Homo sapiens

<400> SEQUENCE: 10

```
gtagcagcgt gggaagaagg agttcctgga agacttccgg cgcaccatgg catccagcat    60
cctcaagtgg gtggtcagcc accagagctg cagcaggagc agcagaagca agcccaggga   120
ccagagggag gaggccggga gcagcgacct gagcagcagg caagatgctg aaaatgctga   180
ggcaaagctc aggggcctcc cggggcagct tgtggacatc gcgtgcaagg tgtgccaggc   240
ctacctgggg cagctggagc atgaggacat cgacacgtca gcagatgccg tggaggacct   300
cactgaggcc gagtgggagg acctgaccca gcagtactac tccctcgttc atgccaggct   360
ctgctgaata gaatcacgtc tgtgaaccct cagacggaca ttgacgggct ccggaacatc   420
tggattataa agcccgcggc caagtcccgg ggccgagaca tagtgtgcat ggaccgtgtg   480
gaggagatcc tggagctggc agctgcagac caccctcttt ccaggacaa caagtggggtg   540
gtccagaagt acatcgagac gccgctgctc atctgtgaca ccaagttcga catcagacag   600
tggttcctcg tcacggactg gaaccccctg accatctggt tctacaagga gagttacttg   660
cggttctcaa ctcagcgctt ctccctggac aagctggaca gcgccatcca cctgtgcaac   720
aacgccgtcc agaagtacct gaagaatgat gtgggccgca gccccctgct gcccgcacac   780
aacatgtgga ccagcaccag gttccaggag tacctgcagc gccagggccg tggcgccgtg   840
tggggcagcg tcatctaccc gtccatgaag aaggccatcg cccacgccat gaaggtggcc   900
caggaccacg tggagcctcg caagaacagc tttgagctct acggggctga cttcgtcctt   960
gggagggact caggccctg gctgatcgag atcaattcca gccccaccat gcacccgtcc  1020
acgccggtca cggcccagct gtgtgcacag gtgcaggagg acaccatcaa ggtggccgtg  1080
gaccgcagct gtgacatcgg caacttcgag ctcctgtgga gccggtggtt gagccgcccc  1140
cattcagcgg gtccgacctc tgcgtggcgg gcgtcagtgt gaggagagcc aggaggcagg  1200
tgctgcccgt ctgcaacctc aaggcctcgg cctcgctgtt ggacgcgcag ccgctgaagg  1260
cacggggccc ctcggccatg ccagaccctg cccaggacc cccatcacca gctctccagc  1320
gggacttggg actgaaggaa gagaaggggc tcccccctggc cttgctggca cccttaaggg  1380
gggcagccga gagcggtgga gccgcacagc ccacccgcac caaagctgct gggaaggtgg  1440
agctcccggc ctgcccctgt cgccacgtgg acagtcaggc cccaaacacc ggtgtccccg  1500
tagcccagcc cgccaaaagc tgggatccaa accagctaaa tgagcacccg ctggagcctg  1560
tgctgcggag cctgaagaca gcagagggcg cgctgcgtcc gccgcccgga ggaaaaggtt  1620
catgacagcg tcagattctc tgcagcagga gtacaggttg cagccactct cccgccgaac  1680
attgaatacg tctttccacc atcttgtctt tgctgtggct ctgggaaaat cagcagagtc  1740
agccatcact ctccaagggg agctgtcagt tctatctgcc agcttttgag tgttcaattt  1800
gatttttact tattcaacct ggaatttgaa tgtcaaaaaa aaaaaaaaaa aaaaaaaa    1859
```

<210> SEQ ID NO 11
<211> LENGTH: 3465
<212> TYPE: DNA
<213> ORGANISM: Homo sapiens

```
<400> SEQUENCE: 11
cccaggactc ctggtctaag gccgtggcca gaatcactcg gtgcccaccc caccccagc      60
accctgtgc cctttgctct gtgtctctgg gtgaatccgg ggccccagaa gctccctcct    120
cagggcacag aggccaaaga tggggctgac tgggggctgc caccgggctt tgggtgctga    180
gggggctgtg ggaccccagg ggaagaggtg ccgctccccc cagcaccggg cactcccccg    240
cctcccccgg cctccagccc tgcacaaagc agcttgccac acccttccca ccaaggccca    300
gggctgaggc ctgcccagga cgcagggtgt ggggaccctg ctgagggagg gtcccggaa    360
gagggcttc cctggcacag aggtccctct cagcaggcca ggtgcggctg cctcagcaca    420
gtgtggggcg gaggtgcagg acaaggttcc cttccgcacc taataccca gggtcaggcc    480
agcgccagcg ctgctagtgg caacatggcc ccttcaaaga ccccgtgtgc agagccagtc    540
agcgtgcgct gtgttttctg ggggccagcc actttttcc ttaacggggt gacaaaccag    600
acatcggggt gcgggactt cacgatatgc ctctctaatg gcgcgtgcta cctcgcgtgt    660
ggtgggcagt gctgggcatg tggctgcgtt ccgggccctg cagccgctcc tccctctcct    720
ggggtctgag gtgtgggaca ccctgtggcc cgtttggggg cctggaggga gccccagtgc    780
ccaccgccct cggtgccctc agctgcagcc tccccattcc ctggggcctg ccacgccctc    840
cactgcctca aggatgcgtc tgagcctggc ctgcacatcc atgctcccac cggctggagg    900
gggtgttctg gggccctggg ggaccgtata tctggggagg gggagggatc cgccctaggg    960
gtgctgtgtg gtgccccata gccaggcaag tctgaggtgg acggcccgtc ctcgccttgt   1020
gagcgaggca gagctgagct gagctgcccc tcctgcctaa cacgccactg tctctggaga   1080
tcgggctgtg cgtgaacatg cggagcctgc cctggtacgt cccggccaac cccgactcct   1140
tcttcccacg ctgctacagc ctctgcaccg agagtgagca gcaggagttc ctgggtaagt   1200
gaggagacgg cagagggccc cagtgctgtc agcagagagg cttctagaaa gatccccctg   1260
gtgctgagac agactgatgg ggcagggtct gaggatagag gaccggggag aggcctccca   1320
tggtcatggt catggcagta cagaggccag gggccccggg agggagggcg ggcagtcaag   1380
gagtgtgtgg ttctgtgcta ggcttgtgga cagcgcggcg agcagctggg gcaaggccgg   1440
ctccgtggtc ggaggccgag gggtgcagct ggacggccgc agtcacagag acactgcagg   1500
gagaagggca ggcagactgg gggtgtggga gcaggcctgg gccccatcgg ctatgagggc   1560
gggaagtggg gcgggttggg gagcctccgt ggccctggcc ccatctccag tccccagtcc   1620
tggctcggac agatagggcg aggctgtgct gtcctttcag aagacttccg gcgcaccatg   1680
gcatccagca tcctcaagtg ggtggtcagc caccagagct gcagcaggag cagcagaagc   1740
aagcccaggg accagaggga ggaggccggg agcagcgacc tgagcagcag gcaagatgct   1800
gaaaatgctg aggcaaagct caggggcctc ccggggcagc ttgtggacat cgcgtgcaag   1860
gtgtgccagg cctacctggg gcagctggag catgaggaca tcgacacgtc agcagatgcc   1920
gtggaggacc tcactgaggc cgagtgggag gacctgaccc agcagtacta ctccctcgtt   1980
catggcgatg ctttcatctc caattcaaga aattactttt cgcagtgcca ggctctgctg   2040
aatagaatca cgtctgtgaa ccctcagacg gacattgacg ggctccggaa catctggatt   2100
ataaagcccg cggccaagtc ccggggccga gggacaacaa gtgggtggtc cagaagtaca   2160
tcgagacgcc gctgctcatc tgtgacacca gttcgacat cagacagtgg ttcctcgtca   2220
cggactggaa ccccctgacc atctggttct acaaggagga ttacttgcgg ttctcaactc   2280
agcgcttctc cctggacaag ctggacagcg ccatccacct gtgcaacaac gccgtccaga   2340
```

| | |
|---|---|
| agtacctgaa gaatgatgtg ggccgcagcc ccctgctgcc cgcacacaac atgtggacca | 2400 |
| gcaccaggtt ccaggagtac ctgcagcgcc agggccgtgg cgccgtgtgg ggcagcgtca | 2460 |
| tctacccgtc catgaagaag gccatcgccc acgccatgaa ggtggcccag gaccacgtgg | 2520 |
| agcctcgcaa gaacagcttt gagctctacg ggctgactt cgtccttggg agggacttca | 2580 |
| ggccctggct gatcgagatc aattccagcc ccaccatgca cccgtccacg ccggtcacgg | 2640 |
| cccagctgtg tgcacaggtg caggaggaca ccatcaaggt ggccgtggac cgcagctgtg | 2700 |
| acatcggcaa cttcgagctc ctgtggaggc agccggtggt tgagccgccc ccattcagcg | 2760 |
| ggtccgacct ctgcgtggcg ggcgtcagtg tgaggagagc caggaggcag gtgctgcccg | 2820 |
| tctgcaacct caaggcctcg gcctcgctgt tggacgcgca gccgctgaag cacggggcc | 2880 |
| cctcggccat gccagaccct gcccagggac ccccatcacc agctctccag cgggacttgg | 2940 |
| gactgaagga agagaagggg ctccccctgg ccttgctggc acccttaagg ggggcagccg | 3000 |
| agagcggtgg agccgcacag cccacccgca ccaaagctgc tgggaaggtg gagctcccgg | 3060 |
| cctgcccctg tcgccacgtg gacagtcagg ccccaaacac cggtgtcccc gtagcccagc | 3120 |
| ccgccaaaag ctgggatcca aaccagctaa atgagcaccc gctggagcct gtgctgcgga | 3180 |
| gcctgaagac agcagagggc gcgctgcgtc cgccgcccgg aggaaaaggt tcatgacagc | 3240 |
| gtcagattct ctgcagcagg agtacaggtt gcagccactc tcccgccgaa cattgaatac | 3300 |
| gtcttttccac catcttgtct tgctgtggc tctgggaaaa tcagcagagt cagccatcac | 3360 |
| tctccaaggg gagctgtcag ttctatctgc cagcttttga gtgttcaatt tgattttac | 3420 |
| ttattcaacc tggaatttga atgtcaaaaa aaaaaaaaaa aaaaa | 3465 |

<210> SEQ ID NO 12
<211> LENGTH: 3554
<212> TYPE: DNA
<213> ORGANISM: Homo sapiens

<400> SEQUENCE: 12

| | |
|---|---|
| gtctaaggcc gtggccagaa tcactcggtg cccaccccac ccccagcacc cctgtgccct | 60 |
| ttgctctgtg tctctgggtg aatccggggc cccagaagct ccctcctcag ggcacagagg | 120 |
| ccaaagatgg ggctgactgg gggctgccac cgggctttgg gtgctgaggg ggctgtggga | 180 |
| ccccagggga agaggtgccg ctccccccag caccgggcac tcccccgcct ccccccggcct | 240 |
| ccagccctgc acaaagcagc ttgccacacc cttcccacca aggcccaggg ctgaggcctg | 300 |
| cccaggacgc agggtgtggg gaccctgctg agggagggg ccccggaagag gggcttccct | 360 |
| ggcacagagg tccctctcag caggccaggt gcggctgcct cagcacagtg tggggcggag | 420 |
| gtgcaggaca aggttccctt ccgcacctaa taccccaggg tcaggccagc gccagcgctg | 480 |
| ctagtggcaa catggcccct tcaaagaccc cgtgtgcaga gccagtcagc gtgcgctgtg | 540 |
| tttttctgggg gccagccact ttttccctta acggggtgac aaaccagaca tcgggtgcg | 600 |
| gggacttcac gatatgcctc tctaatggcg cgtgctacct cgcgtgtggt gggcagtgct | 660 |
| gggcatgtgc ctgcgttccg ggccctgcag ccgctcctcc ctctcctggg gtctgaggtg | 720 |
| tgggacaccc tgtggcccgt ttggggggcct ggagggagcc ccagtgccca ccgccctcgg | 780 |
| tgccctcagc tgcagcctcc ccattccctg gggcctgcca cgcccctccac tgcctcaagg | 840 |
| atgcgtctga gctggcctg cacatccatg ctcccaccgg ctggaggggg tgttctgggg | 900 |
| ccctggggga ccgtatatct ggggaggggg agggatccgc cctaggggtg ctgtgtggtg | 960 |
| ccccatagcc aggcaagtct gaggtggacg gcccgtcctc gccttgtgag cgaggcagag | 1020 |

```
ctgagctgag ctgccctcc tgcctaacac gccactgtct ctggagatcg ggctgtgcgt    1080
gaacatgcgg agcctgccct ggtacgtccc ggccaacccc gactccttct tcccacgctg    1140
ctacagcctc tgcaccgaga gtgagcagca ggagttcctg ggtaagtgag gagacggcag    1200
agggccccag tgctgtcagc agagaggctt ctagaaagat ccccctggtg ctgagacaga    1260
ctgatggggc agggtctgag gatagaggac cggggagagg cctcccatgg tcatggtcat    1320
ggcagtacag aggccagggg ccccgggagg gagggcgggc agtcaaggag tgtgtggttc    1380
tgtgctaggc ttgtggacag cgcggcgagc agctggggca aggccggctc cgtggtcgga    1440
ggccgagggg tgcagctgga cggccgcagt cacagagaca ctgcagggag aagggcaggc    1500
agactggggg tgtgggagca ggcctgggcc ccatcggcta tgaggcgggg aagtggggcg    1560
ggttggggag cctccgtggc cctggcccca tctccagtcc ccagtcctgg ctcggacaga    1620
tagggcgagg ctgtgctgtc ctttcagagt agcagcgtgg gaagaaggag ttcctggaag    1680
acttccggcg caccatggca tccagcatcc tcaagtgggt ggtcagccac cagagctgca    1740
gcaggagcag cagaagcaag cccagggacc agagggagga ggccgggagc agcgacctga    1800
gcagcaggca agatgctgaa aatgctgagg caaagctcag gggcctcccg gggcagcttg    1860
tggacatcgc gtgcaaggtg tgccaggcct acctgggca gctggagcat gaggacatcg    1920
acacgtcagc agatgccgtg gaggacctca ctgaggccga gtgggaggac ctgacccagc    1980
agtactactc cctcgttcat ggcgatgctt tcatctccaa ttcaagaaat tacttttcgc    2040
agtgccaggc tctgctgaat agaatcacgt ctgtgaaccc tcagacggac attgacgggc    2100
tccggaacat ctggattata aagcccgcgg ccaagtcccg gggccgagac atagtgtgca    2160
tggaccgtgt ggaggagatc ctggagctgg cagctgcaga ccaccctctt tccagggaca    2220
acaagtgggt ggtccagaag tacatcgaga cgccgctgct catctgtgac accaagttcg    2280
acatcagaca gtggttcctc gtcacggact ggaaccccct gaccatctgg ttctacaagg    2340
agagttactt gcggttctca actcagcgct tctccctgga caagctggac agcgccatcc    2400
acctgtgcaa caacgccgtc cagaagtacc tgaagaatga tgtgggccgc agcccctgc    2460 tgcccgcaca caacatgtgg accagcacca ggttccagga gtacctgcag cgccagggcc    2520
gtggcgccgt gtggggcagc gtcatctacc cgtccatgaa gaaggccatc gcccacgcca    2580
tgaaggtggc ccaggaccac gtggagcctc gcaagaacag ctttgagctc tacggggctg    2640
acttcgtcct tggagggac ttcaggcct ggctgatcga gatcaattcc agccccacca    2700
tgcacccgtc cacgccggtc acggcccagc tgtgtgcaca ggtgcaggag acaccatca    2760 aggtggccgt ggaccgcagc tgtgacatcg gcaacttcga gctcctgtgg aggcagccgg    2820
tggttgagcc gcccccattc agcgggtccg acctctgcgt ggcgggcgtc agtgtgagga    2880
gagccaggag gcaggtgctg cccgtctgca acctcaaggc ctcggcctcg ctgttggacg    2940
cgcagccgct gaaggcacgg ggcccctcgg ccatgccaga ccctgcccag ggaccccat    3000 caccagctct ccagcgggac ttgggactga aggaagagaa ggggctcccc ctggccttgc    3060 tggcacccctt aaggggggca gccgagagcg gtggagccgc acagcccacc cgcaccaaag    3120
ctgctgggaa ggtggagctc ccggcctgcc cctgtcgcca cgtggacagt caggccccaa    3180
acaccggtgt ccccgtagcc cagcccgcca aaagctggga tccaaaccag ctaaatgagc    3240
acccgctgga gcctgtgctg cggagcctga agacagcaga gggcgcgctg cgtccgccgc    3300
ccggaggaaa aggttcatga cagcgtcaga ttctctgcag caggagtaca ggttgcagcc    3360
actctcccgc cgaacattga atacgtcttt ccaccatctt gtctttgctg tggctctggg    3420
```

-continued

```
aaaatcagca gagtcagcca tcactctcca agggagctg tcagttctat ctgccagctt    3480
ttgagtgttc aatttgattt ttacttattc aacctggaat ttgaatgtca aaaaaaaaaa    3540
aaaaaaaaaa aaaa                                                      3554
```

<210> SEQ ID NO 13
<211> LENGTH: 541
<212> TYPE: PRT
<213> ORGANISM: Homo sapiens

<400> SEQUENCE: 13

```
Met Ala Ser Ser Ile Leu Lys Trp Val Val Ser His Gln Ser Cys Ser
1               5                   10                  15

Arg Ser Ser Arg Ser Lys Pro Arg Asp Gln Arg Glu Glu Ala Gly Ser
                20                  25                  30

Ser Asp Leu Ser Ser Arg Gln Asp Ala Glu Asn Ala Glu Ala Lys Leu
            35                  40                  45

Arg Gly Leu Pro Gly Gln Leu Val Asp Ile Ala Cys Lys Val Cys Gln
        50                  55                  60

Ala Tyr Leu Gly Gln Leu Glu His Glu Asp Ile Asp Thr Ser Ala Asp
65                  70                  75                  80

Ala Val Glu Asp Leu Thr Glu Ala Glu Trp Glu Asp Leu Thr Gln Gln
                85                  90                  95

Tyr Tyr Ser Leu Val His Gly Asp Ala Phe Ile Ser Asn Ser Arg Asn
                100                 105                 110

Tyr Phe Ser Gln Cys Gln Ala Leu Leu Asn Arg Ile Thr Ser Val Asn
            115                 120                 125

Pro Gln Thr Asp Ile Asp Gly Leu Arg Asn Ile Trp Ile Ile Lys Pro
        130                 135                 140

Ala Ala Lys Ser Arg Gly Arg Asp Ile Val Cys Met Asp Arg Val Glu
145                 150                 155                 160

Glu Ile Leu Glu Leu Ala Ala Ala Asp His Pro Leu Ser Arg Asp Asn
                165                 170                 175

Lys Trp Val Val Gln Lys Tyr Ile Glu Thr Pro Leu Leu Ile Cys Asp
                180                 185                 190

Thr Lys Phe Asp Ile Arg Gln Trp Phe Leu Val Thr Asp Trp Asn Pro
            195                 200                 205

Leu Thr Ile Trp Phe Tyr Lys Glu Ser Tyr Leu Arg Phe Ser Thr Gln
        210                 215                 220

Arg Phe Ser Leu Asp Lys Leu Asp Ser Ala Ile His Leu Cys Asn Asn
225                 230                 235                 240

Ala Val Gln Lys Tyr Leu Lys Asn Asp Val Gly Arg Ser Pro Leu Leu
                245                 250                 255

Pro Ala His Asn Met Trp Thr Ser Thr Arg Phe Gln Glu Tyr Leu Gln
                260                 265                 270

Arg Gln Gly Arg Gly Ala Val Trp Gly Ser Val Ile Tyr Pro Ser Met
            275                 280                 285

Lys Lys Ala Ile Ala His Ala Met Lys Val Ala Gln Asp His Val Glu
        290                 295                 300

Pro Arg Lys Asn Ser Phe Glu Leu Tyr Gly Ala Asp Phe Val Leu Gly
305                 310                 315                 320

Arg Asp Phe Arg Pro Trp Leu Ile Glu Ile Asn Ser Ser Pro Thr Met
                325                 330                 335

His Pro Ser Thr Pro Val Thr Ala Gln Leu Cys Ala Gln Val Gln Glu
                340                 345                 350
```

-continued

```
Asp Thr Ile Lys Val Ala Val Asp Arg Ser Cys Asp Ile Gly Asn Phe
            355                 360                 365

Glu Leu Leu Trp Arg Gln Pro Val Glu Pro Pro Phe Ser Gly
    370                 375                 380

Ser Asp Leu Cys Val Ala Gly Val Ser Val Arg Arg Ala Arg Arg Gln
385                 390                 395                 400

Val Leu Pro Val Cys Asn Leu Lys Ala Ser Ala Ser Leu Leu Asp Ala
                405                 410                 415

Gln Pro Leu Lys Ala Arg Gly Pro Ser Ala Met Pro Asp Pro Ala Gln
            420                 425                 430

Gly Pro Pro Ser Pro Ala Leu Gln Arg Asp Leu Gly Leu Lys Glu Glu
            435                 440                 445

Lys Gly Leu Pro Leu Ala Leu Ala Pro Leu Arg Gly Ala Ala Glu
    450                 455                 460

Ser Gly Gly Ala Ala Gln Pro Thr Arg Thr Lys Ala Ala Gly Lys Val
465                 470                 475                 480

Glu Leu Pro Ala Cys Pro Cys Arg His Val Asp Ser Gln Ala Pro Asn
                485                 490                 495

Thr Gly Val Pro Val Ala Gln Pro Ala Lys Ser Trp Asp Pro Asn Gln
            500                 505                 510

Leu Asn Glu His Pro Leu Glu Pro Val Leu Arg Ser Leu Lys Thr Ala
            515                 520                 525

Glu Gly Ala Leu Arg Pro Pro Pro Gly Gly Lys Gly Ser
    530                 535                 540

<210> SEQ ID NO 14
<211> LENGTH: 293
<212> TYPE: PRT
<213> ORGANISM: Homo sapiens

<400> SEQUENCE: 14

Glu Asp Ile Asp Thr Ser Ala Asp Ala Val Glu Asp Leu Thr Glu Ala
1               5                   10                  15

Glu Trp Glu Asp Leu Thr Gln Gln Tyr Tyr Ser Leu Val His Gly Asp
            20                  25                  30

Ala Phe Ile Ser Asn Ser Arg Asn Tyr Phe Ser Gln Cys Gln Ala Leu
        35                  40                  45

Leu Asn Arg Ile Thr Ser Val Asn Pro Gln Thr Asp Ile Asp Gly Leu
    50                  55                  60

Arg Asn Ile Trp Ile Ile Lys Pro Ala Lys Ser Arg Gly Arg Asp
65                  70                  75                  80

Ile Val Cys Met Asp Arg Val Glu Glu Ile Leu Glu Leu Ala Ala Ala
                85                  90                  95

Asp His Pro Leu Ser Arg Asp Asn Lys Trp Val Val Gln Lys Tyr Ile
            100                 105                 110

Glu Thr Pro Leu Leu Ile Cys Asp Thr Lys Phe Asp Ile Arg Gln Trp
        115                 120                 125

Phe Leu Val Thr Asp Trp Asn Pro Leu Thr Ile Trp Phe Tyr Lys Glu
    130                 135                 140

Ser Tyr Leu Arg Phe Ser Thr Gln Arg Phe Ser Leu Asp Lys Leu Asp
145                 150                 155                 160

Ser Ala Ile His Leu Cys Asn Asn Ala Val Gln Lys Tyr Leu Lys Asn
                165                 170                 175

Asp Val Gly Arg Ser Pro Leu Leu Pro Ala His Asn Met Trp Thr Ser
            180                 185                 190
```

```
Thr Arg Phe Gln Glu Tyr Leu Gln Arg Gln Gly Arg Gly Ala Val Trp
        195                 200                 205
Gly Ser Val Ile Tyr Pro Ser Met Lys Lys Ala Ile Ala His Ala Met
        210                 215                 220
Lys Val Ala Gln Asp His Val Glu Pro Arg Lys Asn Ser Phe Glu Leu
225                 230                 235                 240
Tyr Gly Ala Asp Phe Val Leu Gly Arg Asp Phe Arg Pro Trp Leu Ile
                245                 250                 255
Glu Ile Asn Ser Ser Pro Thr Met His Pro Ser Thr Pro Val Thr Ala
            260                 265                 270
Gln Leu Cys Ala Gln Val Gln Glu Asp Thr Ile Lys Val Ala Val Asp
        275                 280                 285
Arg Ser Cys Asp Ile
        290
```

<210> SEQ ID NO 15
<211> LENGTH: 9
<212> TYPE: PRT
<213> ORGANISM: Homo sapiens

<400> SEQUENCE: 15

```
Lys Trp Val Val Gln Lys Tyr Ile Glu
1               5
```

<210> SEQ ID NO 16
<211> LENGTH: 13
<212> TYPE: PRT
<213> ORGANISM: Homo sapiens

<400> SEQUENCE: 16

```
Arg Gln Trp Phe Leu Val Thr Asp Trp Asn Pro Leu Thr
1               5                   10
```

<210> SEQ ID NO 17
<211> LENGTH: 10
<212> TYPE: PRT
<213> ORGANISM: Homo sapiens

<400> SEQUENCE: 17

```
Ser Phe Glu Leu Tyr Gly Ala Asp Phe Val
1               5                   10
```

<210> SEQ ID NO 18
<211> LENGTH: 12
<212> TYPE: PRT
<213> ORGANISM: Homo sapiens

<400> SEQUENCE: 18

```
Gln Trp Phe Leu Val Thr Asp Trp Asn Pro Leu Thr
1               5                   10
```

<210> SEQ ID NO 19
<211> LENGTH: 23
<212> TYPE: PRT
<213> ORGANISM: Mus musculus

<400> SEQUENCE: 19

```
Asn Ile Trp Ile Ile Lys Pro Ala Ala Lys Ser Arg Gly Arg Asp Ile
1               5                   10                  15
Val Cys Met Asp Arg Val Glu
            20
```

```
<210> SEQ ID NO 20
<211> LENGTH: 13
<212> TYPE: PRT
<213> ORGANISM: Mus musculus

<400> SEQUENCE: 20

Asp Asn Lys Trp Val Val Gln Lys Tyr Ile Glu Thr Pro
1               5                   10

<210> SEQ ID NO 21
<211> LENGTH: 49
<212> TYPE: PRT
<213> ORGANISM: Mus musculus

<400> SEQUENCE: 21

Asp Thr Lys Phe Asp Ile Arg Gln Trp Phe Leu Val Thr Asp Trp Asn
1               5                   10                  15

Pro Leu Thr Ile Trp Phe Tyr Lys Glu Ser Tyr Leu Arg Phe Ser Thr
                20                  25                  30

Gln Arg Phe Ser Leu Asp Lys Leu Asp Ser Ala Ile His Leu Cys Asn
            35                  40                  45

Asn

<210> SEQ ID NO 22
<211> LENGTH: 49
<212> TYPE: PRT
<213> ORGANISM: Rattus norvegicus

<400> SEQUENCE: 22

Asp Thr Lys Phe Asp Ile Arg Gln Trp Phe Leu Val Thr Asp Trp Asn
1               5                   10                  15

Pro Leu Thr Ile Trp Phe Tyr Lys Glu Ser Tyr Leu Arg Phe Ser Thr
                20                  25                  30

Gln Arg Phe Ser Leu Asp Lys Leu Asp Ser Ala Ile His Leu Cys Asn
            35                  40                  45

Asn

<210> SEQ ID NO 23
<211> LENGTH: 26
<212> TYPE: PRT
<213> ORGANISM: Rattus norvegicus

<400> SEQUENCE: 23

Ser Ser Pro Thr Met His Pro Ser Thr Pro Val Thr Ala Gln Leu Cys
1               5                   10                  15

Ala Gln Val Gln Glu Asp Thr Ile Lys Val
            20                  25

<210> SEQ ID NO 24
<211> LENGTH: 42
<212> TYPE: PRT
<213> ORGANISM: Homo sapiens

<400> SEQUENCE: 24

Leu Pro Ala Cys Pro Cys Arg His Val Asp Ser Gln Ala Pro Asn Thr
1               5                   10                  15

Gly Val Pro Val Ala Gln Pro Ala Lys Ser Trp Asp Pro Asn Gln Leu
                20                  25                  30

Asn Ala His Pro Leu Glu Pro Val Leu Arg
            35                  40
```

<210> SEQ ID NO 25
<211> LENGTH: 17
<212> TYPE: PRT
<213> ORGANISM: Homo sapiens

<400> SEQUENCE: 25

```
Leu Lys Thr Ala Glu Gly Ala Leu Arg Pro Pro Gly Gly Lys Gly
1               5                   10                  15

Ser
```

<210> SEQ ID NO 26
<211> LENGTH: 330
<212> TYPE: PRT
<213> ORGANISM: Homo sapiens

<400> SEQUENCE: 26

```
Ile Arg Leu Asp Glu Arg Tyr Arg Leu Leu His Gln Ala Ile Asn His
1               5                   10                  15

Phe Pro Gly Ser Tyr Glu Ile Thr Arg Lys Asp Leu Leu Trp Lys Asn
                20                  25                  30

Ile Lys Arg Gln Gln Lys Asp Phe Gly Arg Lys Gly Asp Glu Phe Asp
            35                  40                  45

Phe Leu Pro Arg Thr Phe Ile Leu Pro Thr Asp Leu Arg Glu Phe Val
        50                  55                  60

Asp Tyr Phe Glu Lys Arg Glu Arg Glu Gly Asp Asn Thr Trp Ile
65                  70                  75                  80

Val Lys Pro Ser Ala Ser Ala Arg Gly Arg Gly Ile Arg Ile Thr Asn
                85                  90                  95

Lys Leu Ser Gln Ile Pro Lys Trp Val Asp Asp Phe Lys Asp Asn Pro
            100                 105                 110

Phe Val Ser Gln Ile Gln Arg Arg Pro Leu Val Val Gln Lys Tyr Ile
        115                 120                 125

Glu Arg Pro Leu Leu Ile Asp Gly Glu Asp Val Gly Lys Arg Lys Phe
130                 135                 140

Asp Leu Arg Leu Tyr Val Leu Val Thr Ser Val Asp Pro Leu Arg Ile
145                 150                 155                 160

Tyr Val Tyr Arg Glu Gly Leu Leu Arg Phe Ala Ser Val Lys Tyr Ser
                165                 170                 175

Pro Leu Ser Asp Leu Asp Asp Val Glu Met His Leu Thr Asn Tyr Ser
            180                 185                 190

Ile Gln Lys Lys Ser Ser Asn Tyr Ser Arg Leu Asn Glu Asp Tyr Asn
        195                 200                 205

Glu Pro Val Gly His Lys Trp Ser Leu Gln Asn Leu Trp Leu Tyr Leu
210                 215                 220

Glu Glu Met Gly Ile Asp Lys Glu Glu Ile Trp Leu Gln Ile Glu Ser
225                 230                 235                 240

Ile Ile Ile Lys Thr Ile Leu Ala Ala Glu Ile Val Glu Ala Ser Arg
                245                 250                 255

Leu Asn Val Ala Pro Leu Tyr Asn Cys Phe Glu Leu Tyr Gly Phe Asp
            260                 265                 270

Ile Met Leu Lys Trp Asp Asp Asp Glu Asn Leu Lys Pro Trp Leu Leu
        275                 280                 285

Glu Val Asn Ala Ser Pro Ser Leu His Ser Thr Thr Lys Leu Asp Ala
290                 295                 300
```

| Glu | Leu | Lys | Ala | Pro | Leu | Ile | Arg | Asp | Val | Leu | Asn | Leu | Ala | Leu | Ser |
|---|---|---|---|---|---|---|---|---|---|---|---|---|---|---|---|
| 305 | | | | 310 | | | | 315 | | | | 320 | | | |

| Val | Val | Pro | Pro | Asp | Lys | Glu | Lys | Asp | Ile |
|---|---|---|---|---|---|---|---|---|---|
| | | | 325 | | | | 330 | | |

<210> SEQ ID NO 27
<211> LENGTH: 2241
<212> TYPE: DNA
<213> ORGANISM: Homo sapiens

<400> SEQUENCE: 27

| | | | | |
|---|---|---|---|---|
| tgcctgcagc agagcccggc tgggatcctc acgctgcacg ccatttgtcc tctgatggtt | | | | 60 |
| gcctcactcc atcccatcct ggctggtgtg aaccttgaat gctgggcatc aataaagact | | | | 120 |
| tttttcttgc cagtctaggt tggtaaaaaa tgagatgccg tacctcctct ggaccatcaa | | | | 180 |
| gagggacatc attgactatc acagcctgac ctacgaccag atgctgaacc actacgcaaa | | | | 240 |
| gacagcctcc ttcaccacca aggtgagccg gccgcgcttg agcgtggcgg agccggcaa | | | | 300 |
| gggtggtggg gaggagcttc tgcagccatt agggaccctc ggtggctggt cagtggccac | | | | 360 |
| cagtcacctc ctgggtgcat cccaggactc ctggtctaag gccgtggcca gaatcactcg | | | | 420 |
| gtgcccaccc caccccagc accctgtgc cctttgctct gtgtctctgg gtgaatccgg | | | | 480 |
| ggccccagaa gctccctcct cagggcacag aggccaaaga tggggctgac tgggggctgc | | | | 540 |
| caccgggctt tgggtgctga gggggctgtg gaccccagg ggaagaggtg ccgctccccc | | | | 600 |
| cagcaccggg cactccccg cctccccgg cctccagccc tgcacaaagc agcttgccac | | | | 660 |
| acccttccca ccaaggccca gggctgaggc ctgcccagga cgcagggtgt ggggaccctg | | | | 720 |
| ctgagggagg ggtcccggaa gaggggcttc cctggcacag aggtccctct cagcaggcca | | | | 780 |
| ggtgcggctg cctcagcaca gtgtggggcg gaggtgcagg acaaggttcc cttccgcacc | | | | 840 |
| taataccca gggtcaggcc agcgccagcg ctgctagtgg caacatggcc ccttcaaaga | | | | 900 |
| ccccgtgtgc agagccagtc agcgtgcgct gtgttttctg ggggccagcc acttttttcc | | | | 960 |
| ttaacagggt gacaaaccag acatcggggt gcggggactt cacgatatgc ctctctaatg | | | | 1020 |
| gcgcgtgcta cctcgcgtgt ggtgggcagt gctgggcatg tggctgcgtt ccgggccctg | | | | 1080 |
| cagccgctcc tccctctcct ggggtctgag gtgtgggaca ccctgtggcc cgtttggggg | | | | 1140 |
| cctggaggga gccccagtgc ccaccgccct cggtgccctc agctgcagcc tccccattcc | | | | 1200 |
| ctggggcctg ccacgccctc cactgcctca aggatgcgtc tgagcctggc ctgcacatcc | | | | 1260 |
| atgctcccac cggctggagg gggtgttctg gggccctggg ggaccgtata tctggggagg | | | | 1320 |
| gggagggatc cgccctaggg gtgctgtgtg gtgccccata gccaggcaag tctgaggtgg | | | | 1380 |
| acggcccgtc ctcgccttgt gagcgaggca gagctgagct gagctgcccc tcctgcctaa | | | | 1440 |
| cacgccactg tctctggaga tcgggctgtg cgtgaacatg cggagcctgc cctggtacgt | | | | 1500 |
| cccgccaac cccgactcct tcttcccacg ctgctacagc ctctgcaccg agagtgagca | | | | 1560 |
| gcaggagttc ctgggtaagt gaggagacgg cagagggccc cagtgctgtc agcagagagg | | | | 1620 |
| cttctagaaa gatcccctg gtgctgagac agactgatgg ggcagggtct gaggatagag | | | | 1680 |
| gaccggggag aggcctccca tggtcatggt catggcagta cagaggccag ggccccggg | | | | 1740 |
| agggaggcg gcagtcaag gagtgtgtgg ttctgtgcta ggcttgtgga cagcgcggcg | | | | 1800 |
| agcagctggg gcaaggccgg ctccgtggtc ggaggccgag gggtgcagct ggacggccgc | | | | 1860 |
| agtcacagag acactgcagg gagaagggca ggcagactgg gggtgtggga gcaggcctgg | | | | 1920 |
| gccccatcgg ctatgagggc gggaagtggg gcgggttggg gagcctccgt ggccctggcc | | | | 1980 |

-continued

```
ccatctccag tccccagtcc tggctcggac agatagggcg aggctgtgct gtcctttcag    2040
aagacttccg gcgcaccatg gcatccagca tcctcaagtg ggtggtcagc caccagagct    2100
gcagcaggag cagcagaagc aagcccaggg accagaggga ggaggccggg agcagcgacc    2160
tgagcagcag gcaaggtgcg ctgggccggg gcagggcagt gccaggccac cagagctcgg    2220
ggcctccaca ggggccctcc c                                              2241
```

<210> SEQ ID NO 28
<211> LENGTH: 24
<212> TYPE: DNA
<213> ORGANISM: Homo sapiens

<400> SEQUENCE: 28

```
gttcatgaca gcgtcagatt ctct                                              24
```

<210> SEQ ID NO 29
<211> LENGTH: 25
<212> TYPE: DNA
<213> ORGANISM: Homo sapiens

<400> SEQUENCE: 29

```
gacaagatgg tggaaagacg tattc                                             25
```

<210> SEQ ID NO 30
<211> LENGTH: 22
<212> TYPE: DNA
<213> ORGANISM: Homo sapiens

<400> SEQUENCE: 30

```
cagccactct cccgccgaac at                                                22
```

<210> SEQ ID NO 31
<211> LENGTH: 13
<212> TYPE: PRT
<213> ORGANISM: Homo sapiens

<400> SEQUENCE: 31

Gln Ser Cys Ser Arg Ser Ser Arg Ser Lys Pro Arg Asp
1               5                   10

<210> SEQ ID NO 32
<211> LENGTH: 13
<212> TYPE: PRT
<213> ORGANISM: Homo sapiens

<400> SEQUENCE: 32

Gly Ser Ser Asp Leu Ser Ser Arg Gln Asp Ala Glu Asn
1               5                   10

<210> SEQ ID NO 33
<211> LENGTH: 13
<212> TYPE: PRT
<213> ORGANISM: Homo sapiens

<400> SEQUENCE: 33

Tyr Leu Arg Phe Ser Thr Gln Arg Phe Ser Leu Asp Lys
1               5                   10

<210> SEQ ID NO 34
<211> LENGTH: 13
<212> TYPE: PRT
<213> ORGANISM: Homo sapiens

```
<400> SEQUENCE: 34

His Asn Met Trp Thr Ser Thr Arg Phe Gln Glu Tyr Leu
1               5                   10

<210> SEQ ID NO 35
<211> LENGTH: 13
<212> TYPE: PRT
<213> ORGANISM: Homo sapiens

<400> SEQUENCE: 35

Ser Val Ile Tyr Pro Ser Met Lys Lys Ala Ile Ala His
1               5                   10

<210> SEQ ID NO 36
<211> LENGTH: 13
<212> TYPE: PRT
<213> ORGANISM: Homo sapiens

<400> SEQUENCE: 36

Gln Val Gln Glu Asp Thr Ile Lys Val Ala Val Asp Arg
1               5                   10

<210> SEQ ID NO 37
<211> LENGTH: 13
<212> TYPE: PRT
<213> ORGANISM: Homo sapiens

<400> SEQUENCE: 37

Cys Val Ala Gly Val Ser Val Arg Arg Ala Arg Arg Gln
1               5                   10

<210> SEQ ID NO 38
<211> LENGTH: 14
<212> TYPE: PRT
<213> ORGANISM: Homo sapiens

<400> SEQUENCE: 38

Ser Ser Asp Leu Ser Ser Arg Gln Asp Ala Glu Asn Ala Glu
1               5                   10

<210> SEQ ID NO 39
<211> LENGTH: 14
<212> TYPE: PRT
<213> ORGANISM: Homo sapiens

<400> SEQUENCE: 39

His Glu Asp Ile Asp Thr Ser Ala Asp Ala Val Glu Asp Leu
1               5                   10

<210> SEQ ID NO 40
<211> LENGTH: 14
<212> TYPE: PRT
<213> ORGANISM: Homo sapiens

<400> SEQUENCE: 40

Ala Val Glu Asp Leu Thr Glu Ala Glu Trp Glu Asp Leu Thr
1               5                   10

<210> SEQ ID NO 41
<211> LENGTH: 14
<212> TYPE: PRT
<213> ORGANISM: Homo sapiens
```

```
<400> SEQUENCE: 41

Ser Val Asn Pro Gln Thr Asp Ile Asp Gly Leu Arg Asn Ile
1               5                   10

<210> SEQ ID NO 42
<211> LENGTH: 14
<212> TYPE: PRT
<213> ORGANISM: Homo sapiens

<400> SEQUENCE: 42

Leu Leu Ile Cys Asp Thr Lys Phe Asp Ile Arg Gln Trp Phe
1               5                   10

<210> SEQ ID NO 43
<211> LENGTH: 14
<212> TYPE: PRT
<213> ORGANISM: Homo sapiens

<400> SEQUENCE: 43

Glu Pro Pro Pro Phe Ser Gly Ser Asp Leu Cys Val Ala Gly
1               5                   10

<210> SEQ ID NO 44
<211> LENGTH: 14
<212> TYPE: PRT
<213> ORGANISM: Homo sapiens

<400> SEQUENCE: 44

Leu Lys Ala Ser Ala Ser Leu Leu Asp Ala Gln Pro Leu Lys
1               5                   10

<210> SEQ ID NO 45
<211> LENGTH: 14
<212> TYPE: PRT
<213> ORGANISM: Homo sapiens

<400> SEQUENCE: 45

Asp His Val Glu Pro Arg Lys Asn Ser Phe Glu Leu Tyr Gly
1               5                   10

<210> SEQ ID NO 46
<211> LENGTH: 16
<212> TYPE: PRT
<213> ORGANISM: Homo sapiens

<400> SEQUENCE: 46

Gln Arg Gln Gly Arg Gly Ala Val Trp Gly Ser Val Ile Tyr Pro Ser
1               5                   10                  15

<210> SEQ ID NO 47
<211> LENGTH: 16
<212> TYPE: PRT
<213> ORGANISM: Homo sapiens

<400> SEQUENCE: 47

Pro Pro Pro Phe Ser Gly Ser Asp Leu Cys Val Ala Gly Val Ser Val
1               5                   10                  15

<210> SEQ ID NO 48
<211> LENGTH: 16
<212> TYPE: PRT
<213> ORGANISM: Homo sapiens
```

```
<400> SEQUENCE: 48

Leu Lys Glu Glu Lys Gly Leu Pro Leu Ala Leu Leu Ala Pro Leu Arg
1               5                   10                  15

<210> SEQ ID NO 49
<211> LENGTH: 16
<212> TYPE: PRT
<213> ORGANISM: Homo sapiens

<400> SEQUENCE: 49

Leu Ala Pro Leu Arg Gly Ala Ala Glu Ser Gly Gly Ala Ala Gln Pro
1               5                   10                  15

<210> SEQ ID NO 50
<211> LENGTH: 16
<212> TYPE: PRT
<213> ORGANISM: Homo sapiens

<400> SEQUENCE: 50

Gln Ala Pro Asn Thr Gly Val Pro Val Ala Gln Pro Ala Lys Ser Trp
1               5                   10                  15

<210> SEQ ID NO 51
<211> LENGTH: 16
<212> TYPE: PRT
<213> ORGANISM: Homo sapiens

<400> SEQUENCE: 51

Glu Pro Val Leu Arg Gly Leu Lys Thr Ala Glu Gly Ala Leu Arg Pro
1               5                   10                  15

<210> SEQ ID NO 52
<211> LENGTH: 80
<212> TYPE: DNA
<213> ORGANISM: Homo sapiens

<400> SEQUENCE: 52
agaaccagat ggtcaggggg ttccagtccg tgacgaggaa ccactgtctg atgtcgaact      60
tggtgtcaca gatgagcagc                                                 80

<210> SEQ ID NO 53
<211> LENGTH: 20
<212> TYPE: DNA
<213> ORGANISM: Bacteriophage T7

<400> SEQUENCE: 53
taatacgact cactataggg                                                 20

<210> SEQ ID NO 54
<211> LENGTH: 18
<212> TYPE: DNA
<213> ORGANISM: Bacteriophage SP6

<400> SEQUENCE: 54
atttaggtga cactatag                                                   18

<210> SEQ ID NO 55
<211> LENGTH: 20
<212> TYPE: DNA
<213> ORGANISM: Homo sapiens

<400> SEQUENCE: 55
gtgggtggtc cagaagtaca                                                 20
```

```
<210> SEQ ID NO 56
<211> LENGTH: 20
<212> TYPE: DNA
<213> ORGANISM: Homo sapiens

<400> SEQUENCE: 56
gagaagcgct gagttgagaa                                                    20

<210> SEQ ID NO 57
<211> LENGTH: 20
<212> TYPE: DNA
<213> ORGANISM: Homo sapiens

<400> SEQUENCE: 57
caccaggttc caggagtacc                                                    20

<210> SEQ ID NO 58
<211> LENGTH: 20
<212> TYPE: DNA
<213> ORGANISM: Homo sapiens

<400> SEQUENCE: 58
gaattgatct cgatcagcca                                                    20

<210> SEQ ID NO 59
<211> LENGTH: 18
<212> TYPE: DNA
<213> ORGANISM: Homo sapiens

<400> SEQUENCE: 59
agacttccgg cgcaccat                                                      18

<210> SEQ ID NO 60
<211> LENGTH: 20
<212> TYPE: DNA
<213> ORGANISM: Homo sapiens

<400> SEQUENCE: 60
gggagagtgg ctgcaacctg                                                    20

<210> SEQ ID NO 61
<211> LENGTH: 8
<212> TYPE: PRT
<213> ORGANISM: bacteriophage T7

<400> SEQUENCE: 61

Asp Tyr Lys Asp Asp Asp Asp Lys
1               5

<210> SEQ ID NO 62
<211> LENGTH: 733
<212> TYPE: DNA
<213> ORGANISM: homo sapiens

<400> SEQUENCE: 62
gggatccgga gcccaaatct tctgacaaaa ctcacacatg cccaccgtgc ccagcacctg        60
aattcgaggg tgcaccgtca gtcttcctct tccccccaaa acccaaggac accctcatga      120
tctcccggac tcctgaggtc acatgcgtgg tggtggacgt aagccacgaa gaccctgagg      180
tcaagttcaa ctggtacgtg gacggcgtgg aggtgcataa tgccaagaca aagccgcggg      240
aggagcagta caacagcacg taccgtgtgg tcagcgtcct caccgtcctg caccaggact      300
ggctgaatgg caaggagtac aagtgcaagg tctccaacaa agccctccca acccccatcg      360
```

```
agaaaaccat ctccaaagcc aaagggcagc cccgagaacc acaggtgtac accctgcccc    420
catcccggga tgagctgacc aagaaccagg tcagcctgac ctgcctggtc aaaggcttct    480
atccaagcga catcgccgtg gagtgggaga gcaatgggca gccggagaac aactacaaga    540
ccacgcctcc cgtgctggac tccgacggct ccttcttcct ctacagcaag ctcaccgtgg    600
acaagagcag gtggcagcag gggaacgtct tctcatgctc cgtgatgcat gaggctctgc    660
acaaccacta cacgcagaag agcctctccc tgtctccggg taaatgagtg cgacggccgc    720
gactctagag gat                                                      733

<210> SEQ ID NO 63
<211> LENGTH: 38
<212> TYPE: DNA
<213> ORGANISM: Homo sapiens

<400> SEQUENCE: 63
gcagcagcgg ccgcgccggg agcagcgacc tgagcagc                            38

<210> SEQ ID NO 64
<211> LENGTH: 36
<212> TYPE: DNA
<213> ORGANISM: Homo sapiens

<400> SEQUENCE: 64
gcagcagtcg actgaacctt ttcctccggg cggcgg                              36

<210> SEQ ID NO 65
<211> LENGTH: 39
<212> TYPE: DNA
<213> ORGANISM: Homo sapiens

<400> SEQUENCE: 65
gcagcagcgg ccgcatggca tccagcatcc tcaagtggg                           39

<210> SEQ ID NO 66
<211> LENGTH: 37
<212> TYPE: DNA
<213> ORGANISM: Homo sapiens

<400> SEQUENCE: 66
gcagcagtcg acgccgatgt cacagctgcg gtccacg                             37

<210> SEQ ID NO 67
<211> LENGTH: 23
<212> TYPE: DNA
<213> ORGANISM: Homo sapiens

<400> SEQUENCE: 67
caggtgcagc tggtgcagtc tgg                                            23

<210> SEQ ID NO 68
<211> LENGTH: 23
<212> TYPE: DNA
<213> ORGANISM: Homo sapiens

<400> SEQUENCE: 68
caggtcaact aagggagtc tgg                                             23

<210> SEQ ID NO 69
<211> LENGTH: 23
<212> TYPE: DNA
<213> ORGANISM: Homo sapiens
```

```
<400> SEQUENCE: 69
gaggtgcagc tggtggagtc tgg                                          23

<210> SEQ ID NO 70
<211> LENGTH: 23
<212> TYPE: DNA
<213> ORGANISM: Homo sapiens

<400> SEQUENCE: 70
caggtgcagc tgcaggagtc ggg                                          23

<210> SEQ ID NO 71
<211> LENGTH: 23
<212> TYPE: DNA
<213> ORGANISM: Homo sapiens

<400> SEQUENCE: 71
gaggtgcagc tgttgcagtc tgc                                          23

<210> SEQ ID NO 72
<211> LENGTH: 23
<212> TYPE: DNA
<213> ORGANISM: Homo sapiens

<400> SEQUENCE: 72
caggtacagc tgcagcagtc agg                                          23

<210> SEQ ID NO 73
<211> LENGTH: 24
<212> TYPE: DNA
<213> ORGANISM: Homo sapiens

<400> SEQUENCE: 73
tgaggagacg gtgaccaggg tgcc                                         24

<210> SEQ ID NO 74
<211> LENGTH: 24
<212> TYPE: DNA
<213> ORGANISM: Homo sapiens

<400> SEQUENCE: 74
tgaagagacg gtgaccattg tccc                                         24

<210> SEQ ID NO 75
<211> LENGTH: 24
<212> TYPE: DNA
<213> ORGANISM: Homo sapiens

<400> SEQUENCE: 75
tgaggagacg gtgaccaggg ttcc                                         24

<210> SEQ ID NO 76
<211> LENGTH: 24
<212> TYPE: DNA
<213> ORGANISM: Homo sapiens

<400> SEQUENCE: 76
tgaggagacg gtgaccgtgg tccc                                         24

<210> SEQ ID NO 77
<211> LENGTH: 23
<212> TYPE: DNA
<213> ORGANISM: Homo sapiens
```

-continued

```
<400> SEQUENCE: 77
gacatccaga tgacccagtc tcc                                               23

<210> SEQ ID NO 78
<211> LENGTH: 23
<212> TYPE: DNA
<213> ORGANISM: Homo sapiens

<400> SEQUENCE: 78
gatgttgtga tgactcagtc tcc                                               23

<210> SEQ ID NO 79
<211> LENGTH: 23
<212> TYPE: DNA
<213> ORGANISM: Homo sapiens

<400> SEQUENCE: 79
gatattgtga tgactcagtc tcc                                               23

<210> SEQ ID NO 80
<211> LENGTH: 23
<212> TYPE: DNA
<213> ORGANISM: Homo sapiens

<400> SEQUENCE: 80
gaaattgtgt tgacgcagtc tcc                                               23

<210> SEQ ID NO 81
<211> LENGTH: 23
<212> TYPE: DNA
<213> ORGANISM: Homo sapiens

<400> SEQUENCE: 81
gacatcgtga tgacccagtc tcc                                               23

<210> SEQ ID NO 82
<211> LENGTH: 23
<212> TYPE: DNA
<213> ORGANISM: Homo sapiens

<400> SEQUENCE: 82
gaaacgacac tcacgcagtc tcc                                               23

<210> SEQ ID NO 83
<211> LENGTH: 23
<212> TYPE: DNA
<213> ORGANISM: Homo sapiens

<400> SEQUENCE: 83
gaaattgtgc tgactcagtc tcc                                               23

<210> SEQ ID NO 84
<211> LENGTH: 23
<212> TYPE: DNA
<213> ORGANISM: Homo sapiens

<400> SEQUENCE: 84
cagtctgtgt tgacgcagcc gcc                                               23

<210> SEQ ID NO 85
<211> LENGTH: 23
<212> TYPE: DNA
<213> ORGANISM: Homo sapiens
```

-continued

```
<400> SEQUENCE: 85
cagtctgccc tgactcagcc tgc                                            23

<210> SEQ ID NO 86
<211> LENGTH: 23
<212> TYPE: DNA
<213> ORGANISM: Homo sapiens

<400> SEQUENCE: 86
tcctatgtgc tgactcagcc acc                                            23

<210> SEQ ID NO 87
<211> LENGTH: 23
<212> TYPE: DNA
<213> ORGANISM: Homo sapiens

<400> SEQUENCE: 87
tcttctgagc tgactcagga ccc                                            23

<210> SEQ ID NO 88
<211> LENGTH: 23
<212> TYPE: DNA
<213> ORGANISM: Homo sapiens

<400> SEQUENCE: 88
cacgttatac tgactcaacc gcc                                            23

<210> SEQ ID NO 89
<211> LENGTH: 23
<212> TYPE: DNA
<213> ORGANISM: Homo sapiens

<400> SEQUENCE: 89
caggctgtgc tcactcagcc gtc                                            23

<210> SEQ ID NO 90
<211> LENGTH: 23
<212> TYPE: DNA
<213> ORGANISM: Homo sapiens

<400> SEQUENCE: 90
aattttatgc tgactcagcc cca                                            23

<210> SEQ ID NO 91
<211> LENGTH: 24
<212> TYPE: DNA
<213> ORGANISM: Homo sapiens

<400> SEQUENCE: 91
acgtttgatt tccaccttgg tccc                                           24

<210> SEQ ID NO 92
<211> LENGTH: 24
<212> TYPE: DNA
<213> ORGANISM: Homo sapiens

<400> SEQUENCE: 92
acgtttgatc tccagcttgg tccc                                           24

<210> SEQ ID NO 93
<211> LENGTH: 24
<212> TYPE: DNA
<213> ORGANISM: Homo sapiens
```

```
<400> SEQUENCE: 93
acgtttgata tccactttgg tccc                                              24

<210> SEQ ID NO 94
<211> LENGTH: 24
<212> TYPE: DNA
<213> ORGANISM: Homo sapiens

<400> SEQUENCE: 94
acgtttgatc tccaccttgg tccc                                              24

<210> SEQ ID NO 95
<211> LENGTH: 24
<212> TYPE: DNA
<213> ORGANISM: Homo sapiens

<400> SEQUENCE: 95
acgtttaatc tccagtcgtg tccc                                              24

<210> SEQ ID NO 96
<211> LENGTH: 23
<212> TYPE: DNA
<213> ORGANISM: Homo sapiens

<400> SEQUENCE: 96
cagtctgtgt tgacgcagcc gcc                                               23

<210> SEQ ID NO 97
<211> LENGTH: 23
<212> TYPE: DNA
<213> ORGANISM: Homo sapiens

<400> SEQUENCE: 97
cagtctgccc tgactcagcc tgc                                               23

<210> SEQ ID NO 98
<211> LENGTH: 23
<212> TYPE: DNA
<213> ORGANISM: Homo sapiens

<400> SEQUENCE: 98
tcctatgtgc tgactcagcc acc                                               23

<210> SEQ ID NO 99
<211> LENGTH: 23
<212> TYPE: DNA
<213> ORGANISM: Homo sapiens

<400> SEQUENCE: 99
tcttctgagc tgactcagga ccc                                               23

<210> SEQ ID NO 100
<211> LENGTH: 23
<212> TYPE: DNA
<213> ORGANISM: Homo sapiens

<400> SEQUENCE: 100
cacgttatac tgactcaacc gcc                                               23

<210> SEQ ID NO 101
<211> LENGTH: 23
<212> TYPE: DNA
<213> ORGANISM: Homo sapiens
```

-continued

```
<400> SEQUENCE: 101
caggctgtgc tcactcagcc gtc                                              23

<210> SEQ ID NO 102
<211> LENGTH: 23
<212> TYPE: DNA
<213> ORGANISM: Homo sapiens

<400> SEQUENCE: 102
aattttatgc tgactcagcc cca                                              23

<210> SEQ ID NO 103
<211> LENGTH: 314
<212> TYPE: PRT
<213> ORGANISM: Escherichia coli

<400> SEQUENCE: 103
```

Met Ile Lys Leu Gly Ile Val Met Asp Pro Ile Ala Asn Ile Asn Ile
1               5                   10                  15

Lys Lys Asp Ser Ser Phe Ala Met Leu Leu Glu Ala Gln Arg Arg Gly
            20                  25                  30

Tyr Glu Leu His Tyr Met Glu Met Gly Asp Leu Tyr Leu Ile Asn Gly
        35                  40                  45

Glu Ala Arg Ala His Thr Arg Thr Leu Asn Val Lys Gln Asn Tyr Glu
    50                  55                  60

Glu Trp Phe Ser Phe Val Gly Glu Gln Asp Leu Pro Leu Ala Asp Leu
65                  70                  75                  80

Asp Val Ile Leu Met Arg Lys Asp Pro Pro Phe Asp Thr Glu Phe Ile
                85                  90                  95

Tyr Ala Thr Tyr Ile Leu Glu Arg Ala Glu Glu Lys Gly Thr Leu Ile
            100                 105                 110

Val Asn Lys Pro Gln Ser Leu Arg Asp Cys Asn Glu Lys Leu Phe Thr
        115                 120                 125

Ala Trp Phe Ser Asp Leu Thr Pro Glu Thr Leu Val Thr Arg Asn Lys
    130                 135                 140

Ala Gln Leu Lys Ala Phe Trp Glu Lys His Ser Asp Ile Ile Leu Lys
145                 150                 155                 160

Pro Leu Asp Gly Met Gly Gly Ala Ser Ile Phe Arg Val Lys Glu Gly
                165                 170                 175

Asp Pro Asn Leu Gly Val Ile Ala Glu Thr Leu Thr Glu His Gly Thr
            180                 185                 190

Arg Tyr Cys Met Ala Gln Asn Tyr Leu Pro Ala Ile Lys Asp Gly Asp
        195                 200                 205

Lys Arg Val Leu Val Val Asp Gly Glu Pro Val Pro Tyr Cys Leu Ala
    210                 215                 220

Arg Ile Pro Gln Gly Gly Glu Thr Arg Gly Asn Leu Ala Ala Gly Gly
225                 230                 235                 240

Arg Gly Glu Pro Arg Pro Leu Thr Glu Ser Asp Trp Lys Ile Ala Arg
                245                 250                 255

Gln Ile Gly Pro Thr Leu Lys Glu Lys Gly Leu Ile Phe Val Gly Leu
            260                 265                 270

Asp Ile Ile Gly Asp Arg Leu Thr Glu Ile Asn Val Thr Ser Pro Thr
        275                 280                 285

```
-continued

Cys Ile Arg Glu Ile Glu Ala Glu Phe Pro Val Ser Ile Thr Gly Met
    290             295                 300

Leu Met Asp Ala Ile Glu Ala Arg Leu Gln
305                 310
```

US 7,122,358 B2

TESTIS-SPECIFIC TUBULIN TYROSINE-LIGASE-LIKE PROTEIN, BGS42

This application is a continuation-in-part application of non-provisional application U.S. Ser. No. 10/615,659, filed Jul. 9, 2003, pending which claims benefit to provisional application U.S. Ser. No. 60/394,725 filed Jul. 9, 2002, under 35 U.S.C. 119(e).

FIELD OF THE INVENTION

The present invention provides novel polynucleotides encoding BGS-42 polypeptides, fragments and homologues thereof. Also provided are vectors, host cells, antibodies, and recombinant and synthetic methods for producing said polypeptides. The invention further relates to diagnostic and therapeutic methods for applying these novel BGS-42 polypeptides to the diagnosis, treatment, and/or prevention of various diseases and/or disorders related to these polypeptides. The invention further relates to screening methods for identifying agonists and antagonists of the polynucleotides and polypeptides of the present invention.

BACKGROUND OF THE INVENTION

Tubulin, a subunit of microtubules, is subjected to specific enzymatic post-translational modifications, including cyclic tyrosine removal and addition at the COOH terminus of the alpha-subunit, during normal cellular metabolism. Tubulin is normally tyrosinated in cycling cells. It has previously been shown that de-tyrosinated tubulin accumulates in cancer cells during tumor progression in nude mice. Tubulin de-tyrosination, results from the suppression of tubulin tyrosine ligase and leads to an unbalanced activity of another enzyme, tubulin-carboxypeptidase. Apparently the loss of tyrosinate tubulin represents a strong selective advantage for cancer cells.

The occurrence and significance of tubulin de-tyrosination in human breast tumors has been investigated. Cancer cells with de-tyrosinated tubulin were observed in 53% of the tumors and were predominant in 19.4% of the tumors tested. Tubulin de-tyrosination has also been shown to correlate to a high degree of significance with markers of tumor aggressiveness (Mialhe et al., 2001).

There appears to be three genes described in the literature whose gene products could potentially possess tubulin tyrosine ligase activity, HOLLT (Genbank Accession No. gi|6683745), TTLH_Human (Tubulin tyrosine ligase-like protein; Genbank Accession No. gi|20455371) and TTLL_human (Tubulin tyrosine ligase-like protein 1; Genbank Accession No. gi|20455347; Gene 257 1: 109–117 (2000); Genome Res. 11 (3), 422–435 (2001); and Nature 402 (6761), 489–495 (1999)). The regulation of these genes in normal cells, in addition to transformed cells remains to be determined as does the mechanism of their loss in enzymatic tyrosine-ligase activity during tumor progression. It has been proposed that a reversible phosphorylation event of TTL mediated by a protein kinase may be the basis of TTL loss of function (Idriss, 2001).

Using the above examples, it is clear the availability of a novel cloned tubulin tyrosine ligase protein provides an opportunity for further advancements in the physiological function of tubulin tyrosine ligase proteins, and may be useful for the identification of tubulin tyrosine ligase agonists, or stimulators (which might stimulate and/or bias tubulin tyrosine ligase action), as well as, in the identification of tubulin tyrosine ligase inhibitors. All of which might be therapeutically useful under different circumstances.

The present invention also relates to recombinant vectors, which include the isolated nucleic acid molecules of the present invention, and to host cells containing the recombinant vectors, as well as to methods of making such vectors and host cells, in addition to their use in the production of BGS-42 polypeptides or peptides using recombinant techniques. Synthetic methods for producing the polypeptides and polynucleotides of the present invention are provided. Also provided are diagnostic methods for detecting diseases, disorders, and/or conditions related to the BGS-42 polypeptides and polynucleotides, and therapeutic methods for treating such diseases, disorders, and/or conditions. The invention further relates to screening methods for identifying binding partners of the polypeptides.

BRIEF SUMMARY OF THE INVENTION

The present invention provides isolated nucleic acid molecules, that comprise, or alternatively consist of, a polynucleotide encoding the BGS-42 protein having the amino acid sequence shown in FIGS. 1A–C (SEQ ID NO:2) or the amino acid sequence encoded by the contiguous sequence formed by the cDNA clones, BGS-42 clone A, B and C, deposited as ATCC Deposit Number PTA-4454 on Jun. 12, 2002.

The present invention also relates to recombinant vectors, which include the isolated nucleic acid molecules of the present invention, and to host cells containing the recombinant vectors, as well as to methods of making such vectors and host cells, in addition to their use in the production of BGS-42 polypeptides or peptides using recombinant techniques. Synthetic methods for producing the polypeptides and polynucleotides of the present invention are provided. Also provided are diagnostic methods for detecting diseases, disorders, and/or conditions related to the BGS-42 polypeptides and polynucleotides, and therapeutic methods for treating such diseases, disorders, and/or conditions. The invention further relates to screening methods for identifying binding partners of the polypeptides.

The invention further provides an isolated BGS-42 polypeptide having an amino acid sequence encoded by a polynucleotide described herein.

The invention further relates to a polynucleotide encoding a polypeptide fragment of SEQ ID NO:2, or a polypeptide fragment encoded by the cDNA sequence included in the deposited clone, which is hybridizable to SEQ ID NO:1.

The invention further relates to a polynucleotide encoding a polypeptide domain of SEQ ID NO:2 or a polypeptide domain encoded by the cDNA sequence included in the deposited clone, which is hybridizable to SEQ ID NO:1.

The invention further relates to a polynucleotide encoding a polypeptide epitope of SEQ ID NO:2 or a polypeptide epitope encoded by the cDNA sequence included in the deposited clone, which is hybridizable to SEQ ID NO:1.

The invention further relates to a polynucleotide encoding a polypeptide of SEQ ID NO:2 or the cDNA sequence included in the deposited clone, which is hybridizable to SEQ ID NO:1, having biological activity.

The invention further relates to a polynucleotide which is a variant of SEQ ID NO:1.

The invention further relates to a polynucleotide which is an allelic variant of SEQ ID NO:1.

The invention further relates to a polynucleotide which encodes a species homologue of the SEQ ID NO:2.

The invention further relates to a polynucleotide which represents the complimentary sequence (antisense) of SEQ ID NO:1.

The invention further relates to a polynucleotide capable of hybridizing under stringent conditions to any one of the polynucleotides specified herein, wherein said polynucleotide does not hybridize under stringent conditions to a nucleic acid molecule having a nucleotide sequence of only A residues or of only T residues.

The invention further relates to an isolated nucleic acid molecule of SEQ ID NO:2, wherein the polynucleotide fragment comprises a nucleotide sequence encoding an BGS-42 protein.

The invention further relates to an isolated nucleic acid molecule of SEQ ID NO:1, wherein the polynucleotide fragment comprises a nucleotide sequence encoding the sequence identified as SEQ ID NO:2 or the polypeptide encoded by the cDNA sequence included in the deposited clone, which is hybridizable to SEQ ID NO:1.

The invention further relates to an isolated nucleic acid molecule of SEQ ID NO:1, wherein the polynucleotide fragment comprises the entire nucleotide sequence of SEQ ID NO:1 or the cDNA sequence included in the deposited clone, which is hybridizable to SEQ ID NO:1.

The invention further relates to an isolated nucleic acid molecule of SEQ ID NO:1, wherein the nucleotide sequence comprises sequential nucleotide deletions from either the C-terminus or the N-terminus.

The invention further relates to an isolated polypeptide comprising an amino acid sequence that comprises a polypeptide fragment of SEQ ID NO:2 or the encoded sequence included in the deposited clone.

The invention further relates to a polypeptide fragment of SEQ ID NO:2 or the encoded sequence included in the deposited clone, having biological activity.

The invention further relates to a polypeptide domain of SEQ ID NO:2 or the encoded sequence included in the deposited clone.

The invention further relates to a polypeptide epitope of SEQ ID NO:2 or the encoded sequence included in the deposited clone.

The invention further relates to a full length protein of SEQ ID NO:2 or the encoded sequence included in the deposited clone.

The invention further relates to a variant of SEQ ID NO:2.

The invention further relates to an allelic variant of SEQ ID NO:2. The invention further relates to a species homologue of SEQ ID NO:2.

The invention further relates to the isolated polypeptide of SEQ ID NO:2, wherein the full length protein comprises sequential amino acid deletions from either the C-terminus or the N-terminus.

The invention further relates to an isolated antibody that binds specifically to the isolated polypeptide of SEQ ID NO:2.

The invention further relates to a method for preventing, treating, or ameliorating a medical condition, comprising administering to a mammalian subject a therapeutically effective amount of the polypeptide of SEQ ID NO:2 or the polynucleotide of SEQ ID NO:1.

The invention further relates to a method of diagnosing a pathological condition or a susceptibility to a pathological condition in a subject comprising the steps of (a) determining the presence or absence of a mutation in the polynucleotide of SEQ ID NO:1; and (b) diagnosing a pathological condition or a susceptibility to a pathological condition based on the presence or absence of said mutation.

The invention further relates to a method of diagnosing a pathological condition or a susceptibility to a pathological condition in a subject comprising the steps of (a) determining the presence or amount of expression of the polypeptide of SEQ ID NO:2 in a biological sample; and (b) diagnosing a pathological condition or a susceptibility to a pathological condition based on the presence or amount of expression of the polypeptide.

The invention further relates to a method for identifying a binding partner to the polypeptide of SEQ ID NO:2 comprising the steps of (a) contacting the polypeptide of SEQ ID NO:2 with a binding partner; and (b) determining whether the binding partner effects an activity of the polypeptide.

The invention further relates to a gene corresponding to the cDNA sequence of SEQ ID NO:1.

The invention further relates to a method of identifying an activity in a biological assay, wherein the method comprises the steps of (a) expressing SEQ ID NO:1 in a cell, (b) isolating the supernatant; (c) detecting an activity in a biological assay; and (d) identifying the protein in the supernatant having the activity.

The invention further relates to a process for making polynucleotide sequences encoding gene products having altered SEQ ID NO:2 activity comprising the steps of (a) shuffling a nucleotide sequence of SEQ ID NO:1, (b) expressing the resulting shuffled nucleotide sequences and, (c) selecting for altered activity as compared to the activity of the gene product of said unmodified nucleotide sequence.

The invention further relates to a shuffled polynucleotide sequence produced by a shuffling process, wherein said shuffled DNA molecule encodes a gene product having enhanced tolerance to an inhibitor of SEQ ID NO:2 activity.

The invention further relates to a method for preventing, treating, or ameliorating a medical condition with the polypeptide provided as SEQ ID NO:2, in addition to, its encoding nucleic acid, wherein the medical condition is a reproductive disorder The invention further relates to a method for preventing, treating, or ameliorating a medical condition with the polypeptide provided as SEQ ID NO:2, in addition to, its encoding nucleic acid, wherein the medical condition is a male reproductive disorder.

The invention further relates to a method for preventing, treating, or ameliorating a medical condition with the polypeptide provided as SEQ ID NO:2, in addition to, its encoding nucleic acid, wherein the medical condition is a disorder related to aberrant tubulin regulation.

The invention further relates to a method for preventing, treating, or ameliorating a medical condition with the polypeptide provided as SEQ ID NO:2, in addition to, its encoding nucleic acid, wherein the medical condition is a disorder related to aberrant tubulin tyrosinization.

The invention further relates to a method for preventing, treating, or ameliorating a medical condition with the polypeptide provided as SEQ ID NO:2, in addition to, its encoding nucleic acid, wherein the medical condition is a proliferative disorder.

The invention further relates to a method for preventing, treating, or ameliorating a medical condition with the polypeptide provided as SEQ ID NO:2, in addition to, its encoding nucleic acid, wherein the medical condition is a proliferative disorder of the testis.

The present invention also relates to an isolated polynucleotide consisting of a portion of the human BGS-42 gene consisting of at least 8 bases, specifically excluding Genbank Accession Nos. BM808637; BM808516; AA144756; BE102364; and/or AI026623.

The present invention also relates to an isolated polynucleotide consisting of a nucleotide sequence encoding a fragment of the human BGS-42 protein, wherein said fragment displays one or more functional activities specifically excluding Genbank Accession Nos. BM808637; BM808516; AA144756; BE102364; and/or AI026623.

The present invention also relates to the polynucleotide of SEQ ID NO:1 consisting of at least 10 to 50 bases, wherein said at least 10 to 50 bases specifically exclude the polynucleotide sequence of Genbank Accession Nos. BM808637; BM808516; AA144756; BE102364; and/or AI026623.

The present invention also relates to the polynucleotide of SEQ ID NO:1 consisting of at least 15 to 100 bases, wherein said at least 15 to 100 bases specifically exclude the polynucleotide sequence of Genbank Accession Nos. BM808637; BM808516; AA144756; BE102364; and/or AI026623.

The present invention also relates to the polynucleotide of SEQ ID NO:1 consisting of at least 100 to 1000 bases, wherein said at least 100 to 1000 bases specifically exclude the polynucleotide sequence of Genbank Accession Nos. BM808637; BM808516; AA144756; BE102364; and/or AI026623.

The present invention also relates to an isolated polypeptide fragment of the human BGS-42 protein, wherein said polypeptide fragment does not consist of the polypeptide encoded by the polynucleotide sequence of Genbank Accession Nos. BM808637; BM808516; AA144756; BE102364; and/or AI026623.

The invention further relates to a method of identifying a compound that modulates the biological activity of BGS-42, comprising the steps of, (a) combining a candidate modulator compound with BGS-42 having the sequence set forth in one or more of SEQ ID NO:2; and (b) measuring an effect of the candidate modulator compound on the activity of BGS-42.

The invention further relates to a method of identifying a compound that modulates the biological activity of a tubulin tyrosine ligase protein, comprising the steps of, (a) combining a candidate modulator compound with a host cell expressing BGS-42 having the sequence as set forth in SEQ ID NO:2; and, (b) measuring an effect of the candidate modulator compound on the activity of the expressed BGS-42.

The invention further relates to a method of identifying a compound that modulates the biological activity of BGS-42, comprising the steps of, (a) combining a candidate modulator compound with a host cell containing a vector described herein, wherein BGS-42 is expressed by the cell; and, (b) measuring an effect of the candidate modulator compound on the activity of the expressed BGS-42.

The invention further relates to a method of screening for a compound that is capable of modulating the biological activity of BGS-42, comprising the steps of: (a) providing a host cell described herein; (b) determining the biological activity of BGS-42 in the absence of a modulator compound; (c) contacting the cell with the modulator compound; and (d) determining the biological activity of BGS-42 in the presence of the modulator compound; wherein a difference between the activity of BGS-42 in the presence of the modulator compound and in the absence of the modulator compound indicates a modulating effect of the compound.

The invention further relates to a compound that modulates the biological activity of human BGS-42 as identified by the methods described herein.

The invention further relates to a polynucleotide encoding a polypeptide from about amino acids 73 to about amino acid 365 of SEQ ID NO:2, wherein said polynucleotide encodes a tubulin tyrosine ligase domain of BGS-42.

The invention further relates to a polypeptide from about amino acids 73 to about amino acid 365 of SEQ ID NO:2, wherein said amino acids correspond to a tubulin tyrosine ligase domain of BGS-42.

The invention further relates to the isolated polypeptide of SEQ ID NO:2, wherein said polypeptide is phosphorylated.

The invention further relates to the isolated polypeptide of SEQ ID NO:2, wherein said polypeptide is phosphorylated at the cAMP-dependent protein kinase phosphorylation located at amino acid 306 to amino acid 309 of SEQ ID NO:2.

The invention further relates to an isolated polynucleotide of SEQ ID NO:27, wherein said polynucleotide represents at least a portion of the endogenous promoter of nucleotides 153 to 1775 of SEQ ID NO:1.

The invention further relates to a vector comprising at least a portion of the isolated polynucleotide of SEQ ID NO:27, wherein said polynucleotide represents at least a portion of the endogenous promoter of nucleotides 153 to 1775 of SEQ ID NO:1.

The invention further relates to a vector comprising at least a portion of the isolated polynucleotide of SEQ ID NO:27 in operable linkage to the encoding sequence of at least a portion of a gene, wherein said polynucleotide represents at least a portion of the endogenous promoter of nucleotides 153 to 1775 of SEQ ID NO:1.

The invention further relates to a method of controlling the expression of a polypeptide comprising the steps of: a) inserting the encoding polynucleotide sequence of said polypeptide into a vector comprising at least a portion of the isolated polynucleotide of SEQ ID NO:27, wherein said encoding polynucleotide sequence is downstream of the isolated polynucleotide of SEQ ID NO:27 such that the expression of said polypeptide is controlled by the isolated polynucleotide of SEQ ID NO:27; and b) inserting said vector into a host cell under conditions in which the polypeptide will be expressed under the control of the isolated polynucleotide of SEQ ID NO:27.

The invention further relates to an isolated polynucleotide of SEQ ID NO:27, wherein said polynucleotide represents at least a portion of the endogenous promoter of nucleotides 153 to 1775 of SEQ ID NO:1, and wherein said polynucleotide is mutated such that at least one or more of the CpG islands contained therein are not capable of being methylated.

The invention further relates to an isolated polynucleotide of SEQ ID NO:27, wherein said polynucleotide represents at least a portion of the endogenous promoter of nucleotides 153 to 1775 of SEQ ID NO:1, and wherein said polynucleotide is mutated such that the CpG islands contained therein have an increased degree of methylation.

The invention further relates to a vector comprising at least a portion of the isolated polynucleotide of SEQ ID NO:27, wherein said polynucleotide represents at least a portion of the endogenous promoter of nucleotides 153 to 1775 of SEQ ID NO:1, and wherein said polynucleotide is mutated such that at least one or more of the CpG islands contained therein are not capable of being methylated.

The invention further relates to a vector comprising at least a portion of the isolated polynucleotide of SEQ ID NO:27, wherein said polynucleotide represents at least a portion of the endogenous promoter of nucleotides 153 to 1775 of SEQ ID NO:1, and wherein said polynucleotide is mutated such that the CpG islands contained therein have an increased degree of methylation.

The invention further relates to a vector comprising at least a portion of the isolated polynucleotide of SEQ ID NO:27 in operable linkage to the encoding sequence of at least a portion of a gene, wherein said polynucleotide represents at least a portion of the endogenous promoter of nucleotides 153 to 1775 of SEQ ID NO:1, and wherein said polynucleotide is mutated such that at least one or more of the CpG islands contained therein are not capable of being methylated.

The invention further relates to a vector comprising at least a portion of the isolated polynucleotide of SEQ ID NO:27 in operable linkage to the encoding sequence of at least a portion of a gene, wherein said polynucleotide represents at least a portion of the endogenous promoter of nucleotides 153 to 1775 of SEQ ID NO:1, and wherein said polynucleotide is mutated such that the CpG islands contained therein have an increased degree of methylation.

The invention further relates to a method of controlling the expression of a polypeptide comprising the steps of: a) inserting the encoding polynucleotide sequence of said polypeptide into a vector comprising at least a portion of the isolated polynucleotide of SEQ ID NO:27 wherein said polynucleotide is mutated such that at least one or more of the CpG islands contained therein are not capable of being methylated, wherein said encoding polynucleotide sequence is downstream of the isolated polynucleotide of SEQ ID NO:27 such that the expression of said polypeptide is controlled by the isolated polynucleotide of SEQ ID NO:27; and b) inserting said vector into a host cell under conditions in which the polypeptide will be expressed under the control of the isolated polynucleotide of SEQ ID NO:27.

The invention further relates to a method of controlling the expression of a polypeptide comprising the steps of: a) inserting the encoding polynucleotide sequence of said polypeptide into a vector comprising at least a portion of the isolated polynucleotide of SEQ ID NO:27 wherein said polynucleotide is mutated such that the CpG islands contained therein have an increased degree of methylation, wherein said encoding polynucleotide sequence is downstream of the isolated polynucleotide of SEQ ID NO:27 such that the expression of said polypeptide is controlled by the isolated polynucleotide of SEQ ID NO:27; and b) inserting said vector into a host cell under conditions in which the polypeptide will be expressed under the control of the isolated polynucleotide of SEQ ID NO:27.

The invention further relates to a method of ameliorating, preventing, and/or decreasing the level of BGS-42 expression inhibition observed in proliferating cells and tissues by altering the methylation capacity of the endogenous BGS-42 promoter sequence wherein said methylation capacity is decreased.

The invention further relates to a method of treating, ameliorating, and/or preventing a proliferative medical condition, such as testicular, lung, and colon cancer, comprising the step of increasing the expression level of the BGS-42 polypeptide within the proliferative tissues.

The invention further relates to a method of transforming a proliferative tissue and/or cell to a more normal phenotype in vitro, comprising the step of increasing the expression level of the BGS-42 polypeptide within the proliferative tissues.

The invention relates to a method of diagnosing a proliferative condition comprising the steps of a) detecting the expression of the BGS-42 polypeptide using primers directed to the encoding polynucleotide; and b) comparing the BGS-42 expression level to the expression of a control gene; wherein a low level of BGS-42 expression corresponds to the detection of a proliferative tissue or cell, and wherein a high level of expression corresponds to the detection of a normal tissue or cell.

The invention further relates to an isolated polynucleotide representing at least a portion of the BGS-42 gene, comprising at least a portion of the polynucleotide provided as SEQ ID NO:27 in operable linkage to nucleotides 153 to 1775 of SEQ ID NO:1.

The present invention also provides structure coordinates of the homology model of the BGS-42 polypeptide (SEQ ID NO:2) provided in FIG. 13. The complete coordinates are listed in Table IV. The model of the present invention further provide a basis for designing stimulators and inhibitors or antagonists of one or more of the biological functions of BGS-42, or of mutants with altered ligand binding specificity.

The invention also provides a machine readable storage medium which comprises the structure coordinates of BGS-42, including all or any parts conserved ligase regions. Such storage medium encoded with these data are capable of displaying on a computer screen or similar viewing device, a three-dimensional graphical representation of a molecule or molecular complex which comprises said regions or similarly shaped homologous regions.

The invention also provides a machine-readable data storage medium, comprising a data storage material encoded with machine readable data, wherein the data is defined by the structure coordinates of the model BGS-42 according to Table IV or a homologue of said model, wherein said homologue comprises any kind of surrogate atoms that have a root mean square deviation from the backbone atoms of the complex of not more than about 4.0, 3.0. 2.0, 1.0, 0.9, 0.8, 0.7, 0.6, 0.5, 0.4, 0.3, 0.2, or 0.1 Angstroms.

The invention also provides a model comprising all or any part of the model defined by structure coordinates of BGS-42 according to Table IV, or a mutant or homologue of said molecule or molecular complex.

The invention also provides a method for identifying a mutant of BGS-42 with altered biological properties, function, or reactivity, the method comprising one or more of the following steps: (a) use of the model or a homologue of said model according to Table IV, for the design of protein mutants with altered biological function or properties which exhibit any combination of therapeutic effects described herein; and/or (b) use of the model or a homologue of said model, for the design of a protein with mutations in the ligand binding/active site region comprised of the amino acids K143, G150, Q181, Y183, D196, D316, E281, and/or N283 of SEQ ID NO:2 according to Table IV with altered biological function or properties which exhibit any combination of therapeutic effects described herein.

The method also relates to a method for identifying modulators of BGS-42 biological properties, function, or reactivity, the method comprising the step of modeling test compounds that fit spatially into the active site region defined by all or any portion of residues K143, G150, Q181, Y183, D196, D316, E281, and N283 of the three-dimensional structural model according to Table IV, or using a homologue or portion thereof, or analogue in which the original C, N, and O atoms have been replaced with other elements The invention also provides methods for designing, evaluating and identifying compounds which bind to all or parts of the aforementioned regions. The methods include three dimensional model building (homology modeling) and methods of computer assisted-drug design which can be used to identify compounds which bind or modulate the forementioned regions of the BGS-42 polypeptide. Such compounds are potential inhibitors of BGS-42 or its homologues.

The invention also relates to a method of using said structure coordinates as set forth in Table IV to identify structural and chemical features of BGS-42; employing identified structural or chemical features to design or select compounds as potential BGS-42 modulators; employing the three-dimensional structural model to design or select compounds as potential BGS-42 modulators; synthesizing the potential BGS-42 modulators; screening the potential BGS-42 modulators in an assay characterized by binding of a protein to the BGS-42. The invention also relates to said method wherein the potential BGS-42 modulator is selected from a database. The invention further relates to said method wherein the potential BGS-42 modulator is designed de novo. The invention further relates to a method wherein the potential BGS-42 modulator is designed from a known modulator of activity.

BRIEF DESCRIPTION OF THE FIGURES/DRAWINGS

FIGS. 1A–C show the polynucleotide sequence (SEQ ID NO:1) and deduced amino acid sequence (SEQ ID NO:2) of the novel human tubulin tyrosine ligase protein, BGS-42, of the present invention. The standard one-letter abbreviation for amino acids is used to illustrate the deduced amino acid sequence. The polynucleotide sequence contains a sequence of 1838 nucleotides (SEQ ID NO:1), encoding a polypeptide of 541 amino acids (SEQ ID NO:2). An analysis of the BGS-42 polypeptide determined that it comprised the following features: a tubulin-tyrosine ligase family domain (TTL) located from about amino acid 73 to about amino acid 365 (TTL1; SEQ ID NO:14) of SEQ ID NO:2 (FIGS. 1A–C) represented by single underlining; conserved cysteine residues located at amino acid 155, 238, 347, 363, and/or 388 of SEQ ID NO:2 represented by shading; and a conserved cAMP-dependent protein kinase phosphorylation site located at amino acid 306 to amino acid 309 of SEQ ID NO:2 (FIGS. 1A–C) represented by double underlining.

FIG. 2 shows the partial polynucleotide sequence (SEQ ID NO:3) and deduced amino acid sequence (SEQ ID NO:4) of the novel human tubulin tyrosine ligase protein, BGS-42, of the present invention. The standard one-letter abbreviation for amino acids is used to illustrate the deduced amino acid sequence. The polynucleotide sequence contains a sequence of 726 nucleotides (SEQ ID NO:3), encoding a polypeptide of 242 amino acids (SEQ ID NO:4).

FIGS. 3A–B show the regions of identity and similarity between the encoded BGS-42 protein (SEQ ID NO:2) to other tubulin tyrosine ligase proteins, specifically, the human HOTTL protein (HOTTL; Genbank Accession No:gil6683745; SEQ ID NO:5); the human tubulin tyrosine ligase-like protein (TTLH_HUMAN; Genbank Accession No:gil20455371; SEQ ID NO:7); the human tubulin tyrosine ligase-like protein 1 (TTLL_HUMAN; Genbank Accession No:gil20455347; SEQ ID NO:8); and the pig tubulin tyrosine ligase protein (TTL_PIG; Genbank Accession No:gil423218; SEQ ID NO:6). The alignment was performed using the CLUSTALW algorithm using default parameters as described herein (Vector NTI suite of programs). The darkly shaded amino acids represent regions of matching identity. The lightly shaded amino acids represent regions of matching similarity. Dots ("•") between residues indicate gapped regions of non-identity for the aligned polypeptides. The conserved cysteines between BGS-42 and the other tubulin tyrosine ligase proteins are noted and described herein.

FIG. 4 shows the regions of local identity and similarity between the encoded BGS-42 protein (SEQ ID NO:2) to the Pfam TTL Tubulin-tyrosine ligase family consensus model sequence (TTL; Pfam Accession No: PF03133; SEQ ID NO:26). The query ("Q") sequence represents the local matching sequence of the BGS-42 protein (SEQ ID NO:2), whereas the target ("T") represents the human TTL Tubulin-tyrosine ligase family consensus model sequence. The alignment was performed using the BLAST2 algorithm according to default parameters (SF Altschul, et al., Nucleic Acids Res 25:3389–3402, 1997). The amino acids between the query and target sequences represent matching identical amino acids between the two sequences. Plus signs ("+") between the query and target sequences represent similar amino acids between the two sequences. Dots ("•") between the query and target sequences indicate regions of non-identity for the aligned polypeptides. Capital letters of the target sequence in the alignment represent the most conserved residues of the TTL domain. The conserved cysteine between BGS-42 and the consensus TTL Tubulin-tyrosine ligase family polypeptide sequence is noted.

FIG. 5A shows the polynucleotide sequence (SEQ ID NO:9) of clone A of BGS-42 that was isolated and used to arrive at the final consensus polynucleotide sequence of the full-length BGS-42, of the present invention. The polynucleotide sequence contains a sequence of 1939 nucleotides (SEQ ID NO:9).

FIG. 5B shows the polynucleotide sequence (SEQ ID NO:10) of clone B of BGS-42 that was isolated and used to arrive at the final consensus polynucleotide sequence of the full-length BGS-42, of the present invention. The polynucleotide sequence contains a sequence of 1859 nucleotides (SEQ ID NO:10).

FIG. 5C shows the polynucleotide sequence (SEQ ID NO:11) of clone C of BGS-42 that was isolated and used to arrive at the final consensus polynucleotide sequence of the full-length BGS-42, of the present invention. The polynucleotide sequence contains a sequence of 3465 nucleotides (SEQ ID NO:11).

FIG. 6A-D show the consensus polynucleotide sequence (SEQ ID NO:12) and deduced amino acid sequence (SEQ ID NO:13) of the novel human tubulin tyrosine ligase protein, BGS-42, of the present invention based upon the contig formed by clones A, B, and C (SEQ ID NO:9, 10, and 11, respectively). The standard one-letter abbreviation for amino acids is used to illustrate the deduced amino acid sequence. The polynucleotide sequence contains a sequence of 3554 nucleotides (SEQ ID NO:12), encoding a polypeptide of 541 amino acids (SEQ ID NO:13).

FIGS. 7A–B shows the polynucleotide sequence (SEQ ID NO:27) of the upstream promoter sequence of the BGS-42 gene. The polynucleotide sequence contains a sequence of 2241 nucleotides with nucleotides −2057 to −1 representing the upstream promoter sequence. The location of the initating start codon (nucleotide position +1 of SEQ ID NO:27)) and translation of a portion of the BGS-42 polynucleotide are shown. Analysis of the BGS-42 promoter region led to the identification of three CpG islands located from about nucleotide −1968 to about −1746; from about nucleotide −1232 to about −936; and/or from about nucleotide −727 to about −470 of SEQ ID NO:27 represented by double underlining. The location of the CpG islands was determined using the algorithm described by D.T and P.A.J., PNAS 99(6):3740–5 (2002).

Figure 8:
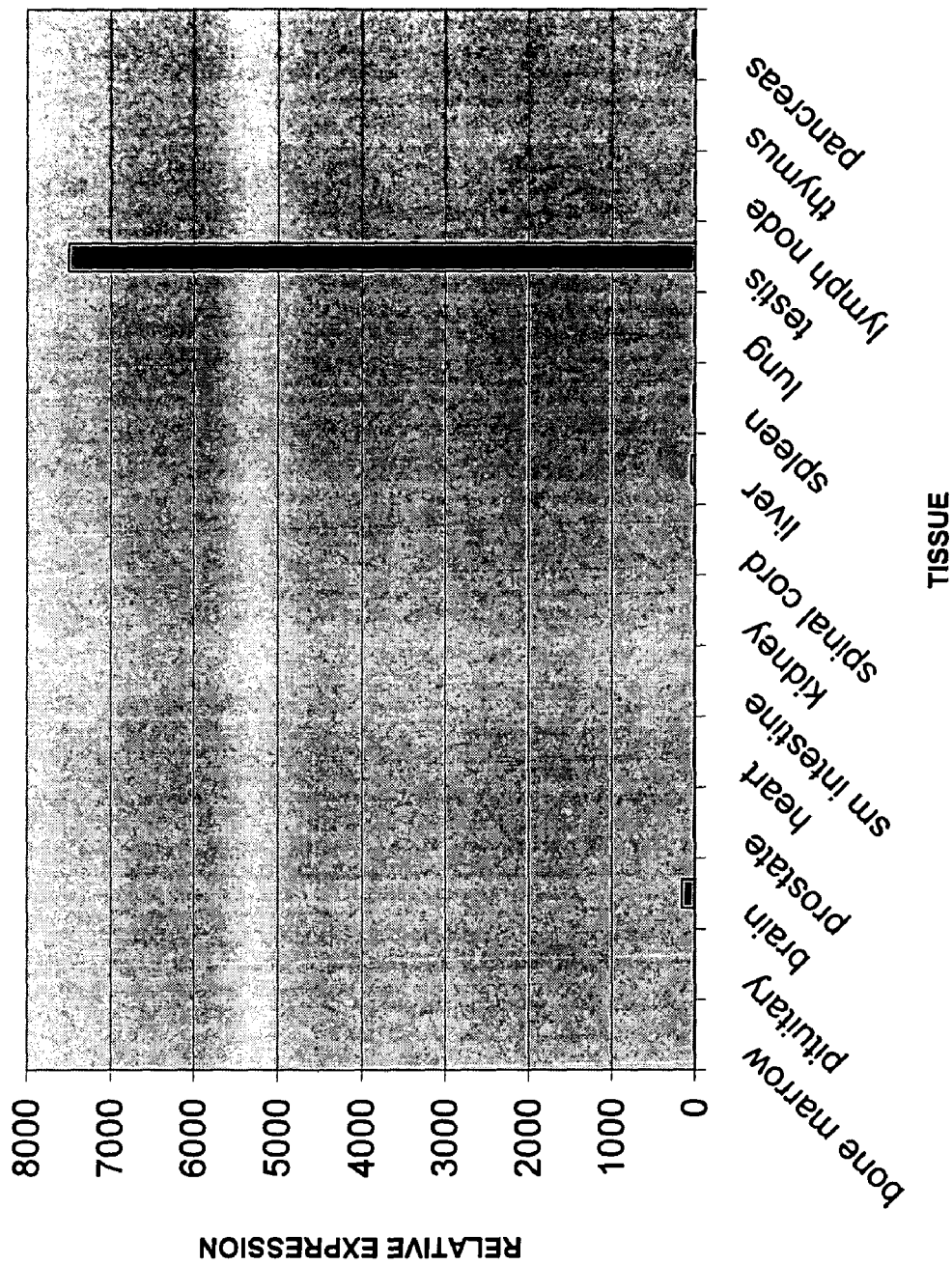

FIG. 8 shows an expression profile of the novel human tubulin tyrosine ligase protein, BGS-42, of the present invention. The figure illustrates the relative expression level of BGS-42 amongst various mRNA tissue sources. As shown, transcripts corresponding to BGS-42 expressed predominately in testis. The BGS-42 polypeptide was also expressed significantly in small intestine, stomach, spinal cord, and to a lesser extent, in brain, and liver. Expression data was obtained by measuring the steady state BGS-42 mRNA levels by quantitative PCR using the PCR primer pair provided as SEQ ID NO:28 and 29 as described in Example 5 herein.

Figure 9:
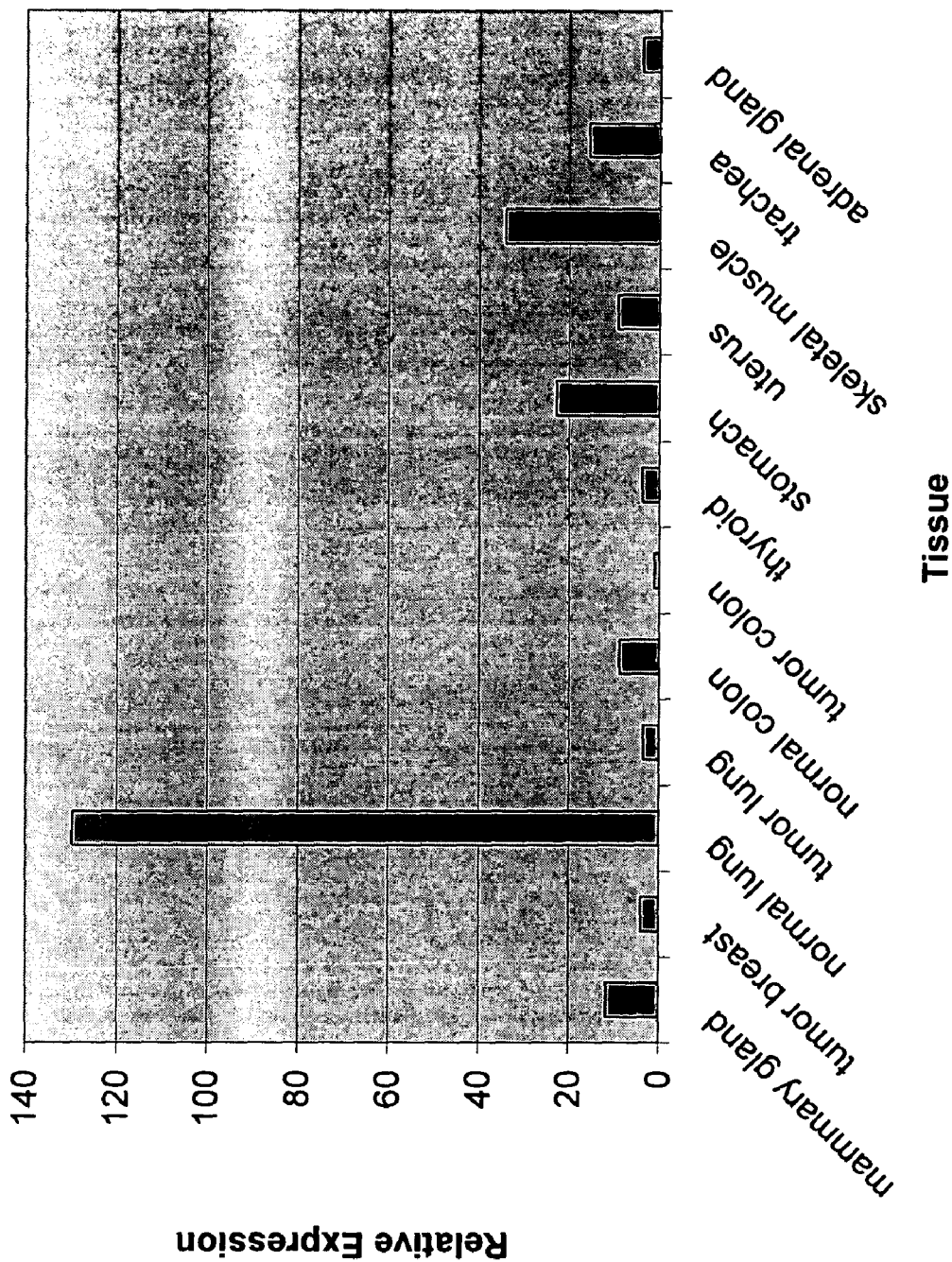

FIG. 9 shows an expression profile of the novel human tubulin tyrosine ligase protein, BGS-42, of the present invention. The figure illustrates the relative expression level of BGS-42 amongst various normal and tumor mRNA tissue sources. As shown, transcripts corresponding to BGS-42 showed differential expression predominately in lung compared to tumor lung tissue, with a 25 fold decrease in expression observed in lung tumors relative to normal lung tissue. This apparent loss of BGS-42 expression in tumor tissues relative to normal tissues suggests BGS-42 may play a role in tumor suppression, either directly or indirectly. Expression data was obtained by measuring the steady state BGS-42 mRNA levels by quantitative PCR using the PCR primer pair provided as SEQ ID NO:28 and 29 as described in Example 5 herein.

Figure 10:
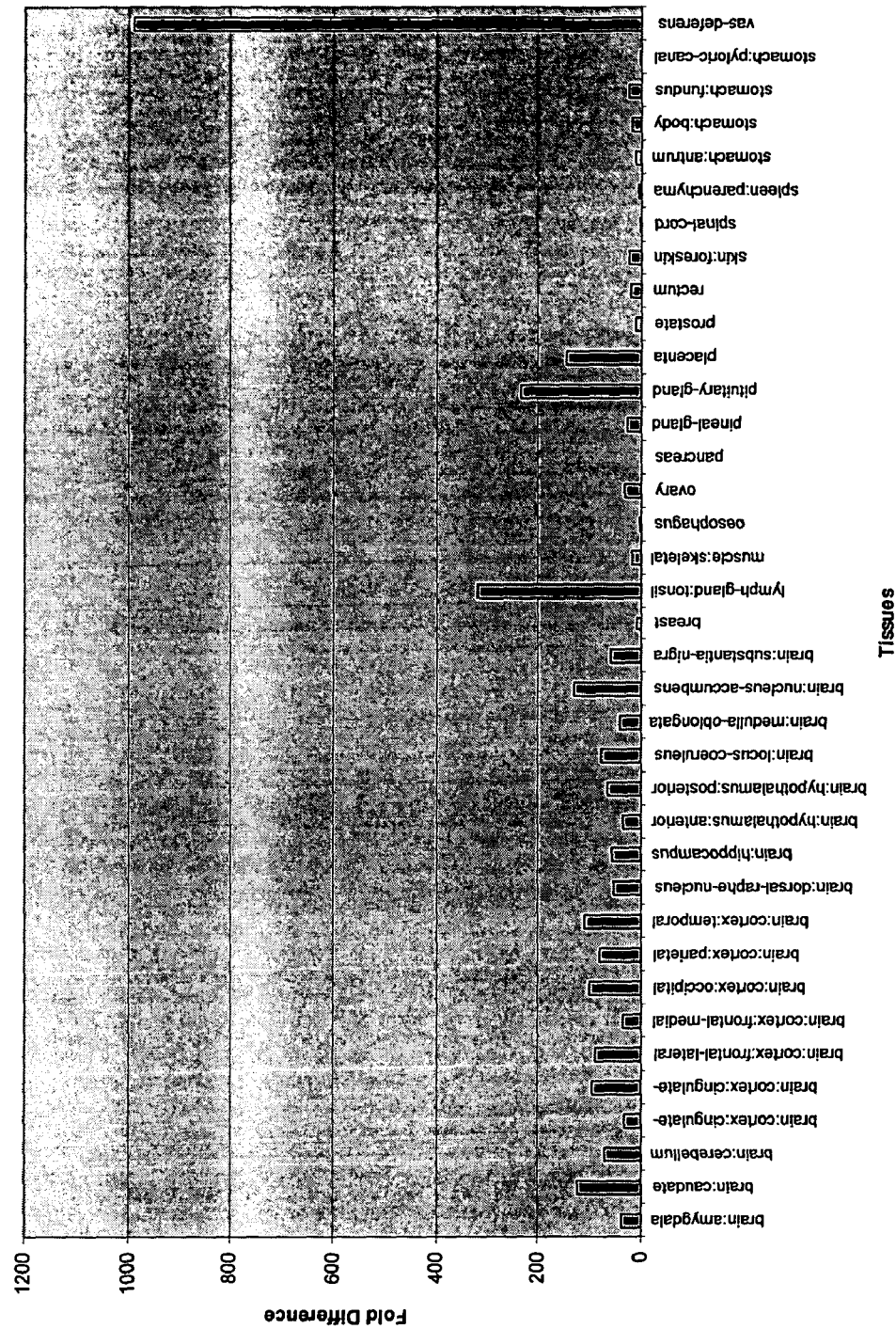

FIG. 10 shows an expanded expression profile of the human tubulin tyrosine ligase protein, BGS-42, of the present invention. The figure illustrates the relative expression level of BGS-42 amongst various mRNA tissue sources. As shown, the BGS-42 polypeptide was expressed predominately in the vas deferens. Expression of BGS-42 was also significantly expressed in lymph gland, pituitary, placenta, and to a lesser extent, in other tissues as shown. Expression data was obtained by measuring the steady state BGS-42 mRNA levels by quantitative PCR using the PCR primer pair provided as SEQ ID NO:28 and 29, and Taqman probe (SEQ ID NO:30) as described in Example 6 herein.

Figure 11:
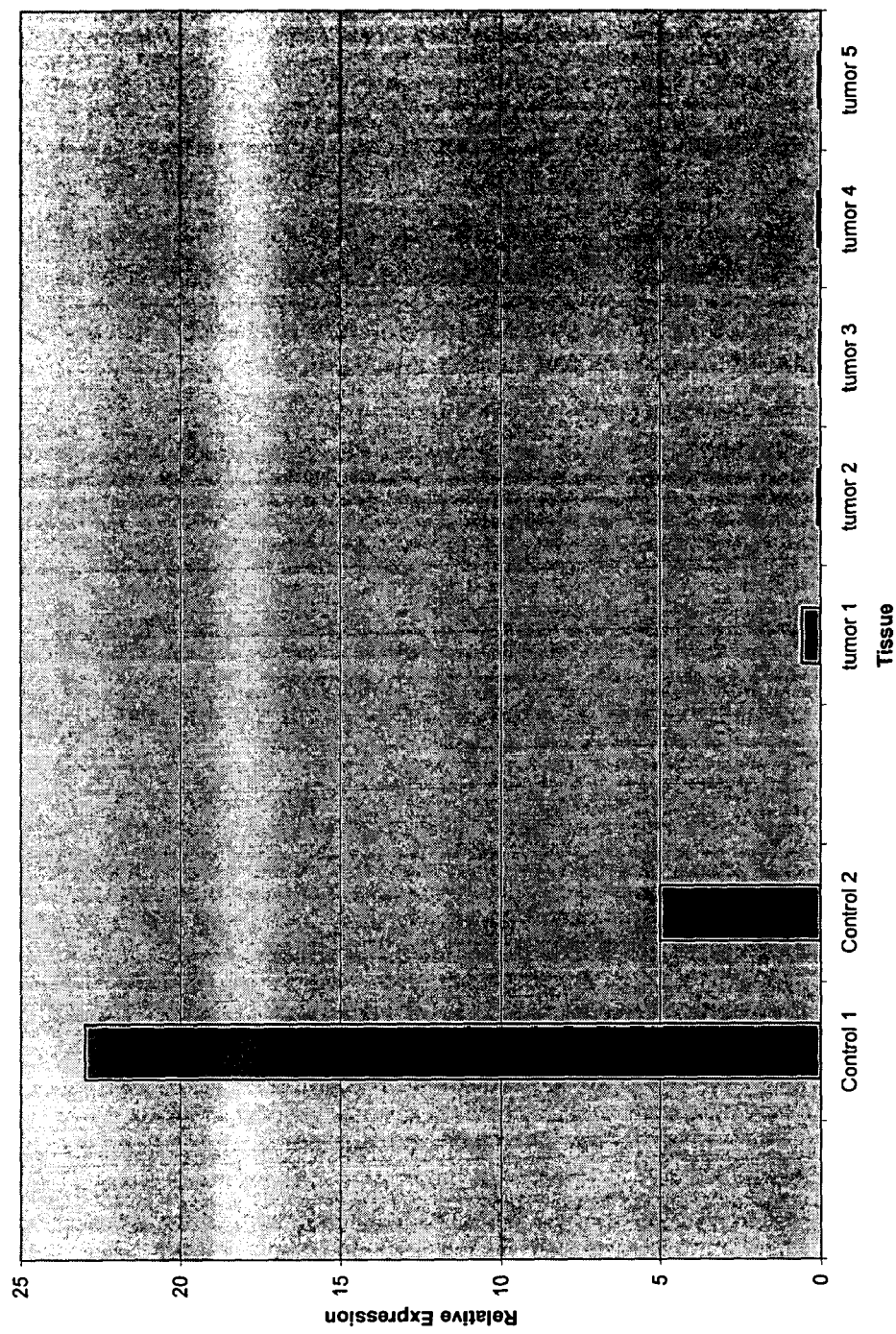

FIG. 11 shows an expanded expression profile of the human tubulin tyrosine ligase protein, BGS-42, of the present invention. The figure illustrates the relative expression level of BGS-42 amongst various both control and five tumor mRNA tissue sources. As shown, expression of the BGS-42 polypeptide was not observed in any of the five testis tumor samples. This apparent loss of BGS-42 expression in tumor tissues relative to normal tissues suggests BGS-42 may play a role in tumor suppression, either directly or indirectly. Expression data was obtained by measuring the steady state BGS-42 mRNA levels by quantitative PCR using the PCR primer pair provided as SEQ ID NO:28 and 29, and Taqman probe (SEQ ID NO:30) as described in Example 6 herein.

FIG. 12 shows a table illustrating the percent identity and percent similarity between the BGS-42 polypeptide of the present invention with other tubulin tyrosine ligase proteins, specifically, the human HOTTL protein (HOTTL; Genbank Accession No:gi|6683745; SEQ ID NO:5); the human tubulin tyrosine ligase-like protein (TTLH_HUMAN; Genbank Accession No:gi|20455371; SEQ ID NO:7); the human tubulin tyrosine ligase-like protein 1 (TTLL_HUMAN; Genbank Accession No:gi|20455347; SEQ ID NO:8); and the pig tubulin tyrosine ligase protein (TTL_PIG; Genbank Accession No:gi|423218; SEQ ID NO:6). The percent identity and percent similarity values were determined using the Gap algorithm using default parameters (Genetics Computer Group suite of programs; Needleman and Wunsch. J. Mol. Biol. 48; 443–453, 1970); GAP parameters: gap creation penalty: 8 and gap extension penalty: 2).

FIG. 13: Sequence alignment of the conceptual translated sequence of BGS-42 of the present invention (SEQ ID NO:2) with *Escherichia coli* glutathione synthetase, a member of the peptide synthases ADP-forming enzymes (acid-D-amino acid ligases) (Protein Data Bank entry 1GSA; Genbank Accession No. gi| 15803486; SEQ ID NO:103). The alignment was used as the basis for building the BGS-42 homology model described herein. The coordinates of the BGS-42 model are provided in Table IV. Amino acids defining the binding and active site regions in both the model and the 1GSA structure are highlighted with an asterisk ("*"). Amino acids defining key hydrophobic residues of the amino acid ligase structural motif as defined by Dideberg and Bertrand (Trends Biochem. Sci. 23:57–58, 1998) are highlighted with a caret ("^").

Figure 14:

FIG. 14 shows the three-dimensional homology model of amino acids M1 to R361 of the BGS-42 polypeptide of the present invention (SEQ ID NO:2). The model is based upon an alignment to a structural homologue *Escherichia coli* glutathione synthetase (Protein Data Bank entry 1GSA; Genbank Accession No. gi| 15803486; SEQ ID NO:103) that was used as the basis for building the BGS-42 homology model. The coordinates of the BGS-42 model are provided in Table IV. The model does not include the structure of the loop region E216 to W262 of SEQ ID NO:2, nor the C-terminal region S362 to V501 of SEQ ID NO:2. Both regions were not able to be modeled using IGSA as the template.

Table I provides a summary of the novel polypeptides and their encoding polynucleotides of the present invention.

Table II illustrates the preferred hybridization conditions for the polynucleotides of the present invention. Other hybridization conditions may be known in the art or are described elsewhere herein.

Table III provides a summary of various conservative substitutions encompassed by the present invention.

Table IV provides the structural coordinates of the three dimensional structure of the BGS-42 polypeptide of the present invention (SEQ ID NO:2).

DETAILED DESCRIPTION OF THE INVENTION

The present invention may be understood more readily by reference to the following detailed description of the preferred embodiments of the invention and the Examples included herein.

The invention provides a novel human sequence that encodes a tubulin tyrosine ligase protein with substantial homology to other tubulin tyrosine ligase proteins. Members of the tubulin tyrosine ligase protein family serve as proliferation inhibitors whereby loss of tubulin tyrosine ligase activity results in cellular proliferation. Tubulin tyrosine ligases have been implicated in a number of diseases and/or disorders, which include, but are not limited to, cancer, aberrant cellular proliferation, and aberrant cellular differentiation. Moreover, members of the tubulin tyrosine ligase protein family have also been implicated in having antiproliferative roles as described herein.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

In as least one embodiment, the polynucleotides comprise the 5' upstream non-coding promoter of the BGS-42 gene (SEQ ID NO:27).

As used herein, a "polynucleotide" refers to a molecule having a nucleic acid sequence contained in SEQ ID NO:1 or the cDNA contained within the clone deposited with the ATCC. For example, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:1 was often generated by overlapping sequences contained in one or more clones (contig analysis). A representative clone containing all or most of the sequence for SEQ ID NO:1 was deposited with the American Type Culture Collection ("ATCC"). As shown in Table I, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure. The deposited clone is inserted in the pSport1 (Life Technologies) using the NotI and SalI restriction endonuclease sites as described herein.

Unless otherwise indicated, all nucleotide sequences determined by sequencing a DNA molecule herein were determined using an automated DNA sequencer (such as the Model 373, preferably a Model 3700, from Applied Biosystems, Inc.), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A–C (SEQ ID NO:1), a nucleic acid molecule of the present invention encoding the BGS-42 polypeptide may be obtained using standard cloning and screening procedures, such as those for cloning cDNAs using mRNA as starting material. Illustrative of the invention, the nucleic acid molecule described in FIGS. 1A–C (SEQ ID NO:1) was discovered in a mixture of human circular brain and testis first strand cDNA library.

A "polynucleotide" of the present invention also includes those polynucleotides capable of hybridizing, under stringent hybridization conditions, to sequences contained in SEQ ID NO:1, the complement thereof, or the cDNA within the clone deposited with the ATCC. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 μg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20×SSPE=3M NaCl; 0.2M NaH2PO4; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide" since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, Proteins—Structure and Molecular Properties, 2nd Ed., T. E. Creighton, W. H. Freeman and Company, New York (1993); Posttranslational Covalent Modification of Proteins, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:1" refers to a polynucleotide sequence while "SEQ ID NO:2" refers to a polypeptide sequence, both sequences are identified by an integer specified in Table I.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.)

As will be appreciated by the skilled practitioner, should the amino acid fragment comprise an antigenic epitope, for example, biological function per se need not be maintained. The terms BGS-42 polypeptide and BGS-42 protein are used interchangeably herein to refer to the encoded product of the BGS-42 nucleic acid sequence according to the present invention.

As used herein the terms "modulate" or "modulates" refer to an increase or decrease in the amount, quality or effect of a particular activity, DNA, RNA, or protein. The definition of "modulate" or "modulates" as used herein is meant to encompass agonists and/or antagonists of a particular activity, DNA, RNA, or protein.

It is another aspect of the present invention to provide modulators of the BGS-42 protein and BGS-42 peptide targets which can affect the function or activity of BGS-42 in a cell in which BGS-42 function or activity is to be modulated or affected. In addition, modulators of BGS-42 can affect downstream systems and molecules that are regulated by, or which interact with, BGS-42 in the cell. Modulators of BGS-42 include compounds, materials, agents, drugs, and the like, that antagonize, inhibit, reduce, block, suppress, diminish, decrease, or eliminate BGS-42 function and/or activity. Such compounds, materials, agents, drugs and the like can be collectively termed "antagonists". Alternatively, modulators of BGS-42 include compounds, materials, agents, drugs, and the like, that agonize, enhance, increase, augment, or amplify BGS-42 function in a cell. Such compounds, materials, agents, drugs and the like can be collectively termed "agonists".

The term "organism" as referred to herein is meant to encompass any organism referenced herein, though preferably to eukaryotic organisms, more preferably to mammals, and most preferably to humans.

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young (Mol Endocrinol., 9(10):1321–9, (1995); and Ann. N. Y. Acad. Sci., 7;766:279–81, (1995)).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify gene expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further preferred embodiments, methods are provided for evolving the polynucleotides and polypeptides of the present invention using molecular evolution techniques in an effort to create and identify novel variants with desired structural, functional, and/or physical characteristics.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

Polynucleotides and Polypeptides of the Invention

Features of the Polypeptide Encoded by Gene No:1

The polypeptide of this gene provided as SEQ ID NO:2 (FIGS. 1A–C), encoded by the polynucleotide sequence according to SEQ ID NO:1 (FIGS. 1A–C), and/or encoded by the polynucleotide contained within the deposited clone, BGS-42, has significant homology at the nucleotide and amino acid level to a number of tubulin tyrosine ligase proteins, which include, for example, the human HOTTL protein (HOTTL; Genbank Accession No:gil6683745; SEQ ID NO:5); the human tubulin tyrosine ligase-like protein (TTLH_HUMAN; Genbank Accession No:gil20455371; SEQ ID NO:7); the human tubulin tyrosine ligase-like protein 1 (TTLL_HUMAN; Genbank Accession No:gil20455347; SEQ ID NO:8); and the pig tubulin tyrosine ligase protein (TTL_PIG; Genbank Accession No:gil423218; SEQ ID NO:6). An alignment of the BGS-42 polypeptide with these proteins is provided in FIGS. 3A–B.

The determined nucleotide sequence of the BGS-42 cDNA in FIGS. 1A–C (SEQ ID NO:1) contains an open reading frame encoding a protein of about 541 amino acid residues, with a deduced molecular weight of about 59.9 kDa. The amino acid sequence of the predicted BGS-42 polypeptide is shown in FIGS. 1A–C (SEQ ID NO:2). The BGS-42 protein shown in FIGS. 1A–C was determined to share significant identity and similarity to several known tubulin tyrosine ligase proteins. Specifically, the BGS-42 protein shown in FIGS. 1A–C was determined to be about 57.5% identical and 65.5% similar to the human HOTTL protein (HOTTL; Genbank Accession No:gil6683745; SEQ ID NO:5); to be about 53.3% identical and 61.4% similar to the human tubulin tyrosine ligase-like protein (TTLH_HUMAN; Genbank Accession No:gil20455371; SEQ ID NO:7); to be about 27.4% identical and 38.4% similar to the human tubulin tyrosine ligase-like protein 1 (TTLL_HUMAN; Genbank Accession No:gil20455347; SEQ ID NO:8); and to be about 29.4% identical and 40.0% similar to the pig tubulin tyrosine ligase protein (TTL_PIG; Genbank Accession No:gil423218; SEQ ID NO:6); as shown in FIG. 7.

The human tubulin tyrosine ligase-like protein 1 (TTLL_HUMAN; Genbank Accession No:gil20455347; SEQ ID NO:8) is a tubulin tyrosine ligase protein that has been mapped to chromosome region 22q13.1 (Gene 257 (1), 109–117 (2000)).

The pig tubulin tyrosine ligase protein (TTL_PIG; Genbank Accession No:gil423218; SEQ ID NO:6) is a validated tubulin tyrosine ligase protein that catalyzes the ATP-dependent posttranslational addition of a tyrosine to the carboxy-terminal end of detyrosinated alpha-tubulin (J. Cell Biol. 120 (3), 725–732 (1993)).

The BGS-42 polypeptide was predicted to comprise one TTL family domain (TTL1) located from about amino acid 73 to about amino acid 365 (TTL1; SEQ ID NO:14) of SEQ ID NO:2 (FIGS. 1A–C). In this context, the term "about" may be construed to mean 1, 2, 3, 4, 5, 6, 7, 8, 9, or 10 amino acids beyond the N-Terminus and/or C-terminus of the above referenced TTL family domain polypeptide.

In preferred embodiments, the following TTL family domain is encompassed by the present invention: EDIDTSADAVEDLTEAEWEDLTQQYYSLVHGDAFISNSRN-YFSQCQALLNRITSVNPQTDIDGLRNIWIIKPAAKSR-GRDIVCMDRVEEILELAAADHPLSRDNKWVVQKYI-ETPLLICDTKFD1IRQWFLVTDWNPLTIWFYKESYLR-FSTQRFSLDKLDSAIHLCNNAVQKYLKNDVGRSPLL-PAHNMWTSTRFQEYLQRQGRGAVWGSVIYPSMKK-AIAHAMKVAQDHVEPRKNSFELYGADFVLGRDFRP-WLIEINSSPTMHPSTPVTAQLCAQVQEDTIKVAVDRS-CDI (SEQ ID NO:14). Polynucleotides encoding this polypeptide are also provided. The present invention also encompasses the use of this BGS-42 TTL family domain polypeptide as an immunogenic and/or antigenic epitope as described elsewhere herein.

The BGS-42 polypeptide was also determined to comprise several conserved cysteines, at amino acid 155, 238, 347, 363, and/or 388 of SEQ ID No: 2 (FIGS. 1A–C). Conservation of cysteines at key amino acid residues is indicative of conserved structural features, which may correlate with conservation of protein function and/or activity.

The BGS-42 polypeptide was also determined to comprise a conserved cAMP-dependent protein kinase phosphorylation site located at amino acid 306 to amino acid 309 of SEQ ID NO:2 (FIGS. 1A–C). This cAMP-dependent protein kinase phosphorylation is found in other tubulin tyrosine ligase proteins and may be essential for either the activation or inhibition of tubulin tyrosine ligase activity.

In preferred embodiments, the present invention encompasses a polynucleotide lacking the initiating start codon, in addition to, the resulting encoded polypeptide of BGS-42. Specifically, the present invention encompasses the polynucleotide corresponding to nucleotides 156 thru 1775 of SEQ ID NO:1, and the polypeptide corresponding to amino acids 2 thru 541 of SEQ ID NO:2. Also encompassed are recombinant vectors comprising said encoding sequence, and host cells comprising said vector.

The present invention also encompasses a polynucleotide that encodes at least 424 contiguous amino acids of SEQ ID NO:2. Preferably such a polypeptide has tubulin ligase activity. The present invention also encompasses a polynucleotide that encodes about 424 contiguois amino acids of SEQ ID NO:2 wherein the term "about" may be construed to mean 1, 2, 3, 4, 5, 6, 7, 8, 9, or 10 amino acids beyond the N-Terminus and/or C-terminus of the above referenced polypeptide. The present invention also encompasses a polynucleotide comprising at least 1272 contiguous nucleotides of SEQ ID NO:1.

Expression profiling designed to measure the steady state mRNA levels encoding the BGS-42 polypeptide using SYBR green quantitative PCR (see FIG. 8) showed predominately in the testis tissue. Expression of BGS-42 was also significantly expressed in brain, liver, and to a lesser extent, in other tissues.

Additional expression profiling designed to measure the steady state mRNA levels encoding the BGS-42 polypeptide using SYBR green quantitative PCR in normal versus tumor samples (see FIG. 8) showed predominate differential expression in lung tissue relative to lung tumor tissue, with lung tumor tissue showing a 25 fold decrease in BGS-42 expression relative to normal lung tissues.

Expanded expression profiling designed to measure the steady state mRNA levels encoding the BGS-42 polypeptide using TaqMan™ quantitative PCR (see FIG. 10) showed BGS-42 was expressed predominately in the vas deferens. Expression of BGS-42 was also significantly expressed in lymph gland, pituitary, placenta, and to a lesser extent, in other tissues.

Additional expanded expression profiling data was also performed on mRNA isoalted from several testis tumors using TaqMan™ quantitative PCR (see FIG. 11) showed that the testis specific expression of BGS-42 was lost in testis tumor tissue. The observation that BGS-42 is specifically downregulated in tumor samples suggests BGS-42 may play a role in tumor suppression, either directly or indirectly. Thus agonists directed against the BGS-42 polynucleotide or polypeptide would be useful for the treatment of tumors, particularly lung and testis tumors. In addition, BGS-42 polynucleotides may be useful as a diagnostic in identifying potential proliferative and/or tumor tissues relative to normal tissues, particularly in the detection of lung and testis tumors or proliferative conditions. Such a diagnostic would utilize the observed loss of BGS-42 expression in lung and/or testis tumor tissue as an indicia of proliferative state relative to the detectable expression in normal lung and/or testis tissues. Moreover, such a diagnostic may be useful for the detection of other tumor types by comparing BGS-42 expression in normal versus test tissue with loss of BGS-42 in the test tissue being diagnostic of a proliferative condition.

Based upon the strong homology to members of the tubulin tyrosine ligase protein family, the BGS-42 polypeptide is expected to share at least some biological activity with tubulin tyrosine ligase proteins (including, but limited to HOTTL, TTL_PIG, TTLH_Hu, and TTLL_Hu), and more preferably tubulin tyrosine ligase proteins found within testis, lymph node, pituitary, placenta, and/or vas deferens cells and tissues, in addition to the tubulin tyrosine ligase proteins referenced elsewhere herein or otherwise known in the art.

The present invention is also directed to the upstream, non-coding, promoter sequence of the BGS-42 gene (FIG. 7A-B; SEQ ID NO:27). The polynucleotide sequence contains a sequence of 2241 nucleotides with nucleotides −2057 to −1 of SEQ ID NO:27 representing the upstream promoter sequence. Analysis of the BGS-42 promoter region led to the identification of three CpG islands located from about nucleotide −1968 to about −1746; from about nucleotide −1232 to about −936; and/or from about nucleotide −727 to about −470 of SEQ ID NO:27 as determined using the algorithm described by D.T and P.A.J., PNAS 99(6):3740–5 (2002).

Recent evidence suggests the pattern of DNA methylation at CpG islands around promoter regions are often altered in cancer cells and that a correlation can be established between hyper-methylation within a promoter and lack of gene expression (Baylin et al., 2001). The silencing of gene expression is due to the recruitment of histone deacetylase to the methylated DNA. This can have the same effect as other types of tumor suppressor gene inactivation such as loss of homozygosity. The BGS-42 promotor region does indeed possess potential CpG beginning at positions −727, −1232 and −1968 relative to the ATG at +1. The altered methylation patterns within these regions might be operating to decrease the transcriptional activity at the BGS42 locus and hence decrease the steady-state RNA levels in proliferative tissues. The latter mechanism could explain the observed descrease in BGS-42 expression in lung and testis tumor tissues.

Therefore, the upstream, non-coding, promoter sequence of the BGS-42 gene from −2057 to −1 (FIG. 7A-B; SEQ ID NO:27) is useful for decreasing the expression of a gene sequence in cells, particularly proliferative cells, when located upstream of a gene in a vector sequence. Alternatively, the location of one or more of th CpG islands identified in the BGS-42 promoter sequence are useful for decreasing the expression of a gene sequence in cells, particularly proliferative cells, when located upstream of a gene in a vector sequence.

The identification of three CpG islands within the BGS-42 promoter sequence, in combination with the observed decrease in BGS-42 expression in proliferative tissues suggests a role for BGS-42 in the etiology of human cancers and that biological and pharmaceutical approaches to replacing BGS-42 function, which include, for example, the alteration of DNA methylation patterns within the BGS-42 promoter (e.g., deletion or alteration of CpG islands in the BGS-42 promoter to decrease the level of methylation), and/or the inhibition of histone deacetylase recruitment may represent a powerful new strategy for slowing tumor progression. Genomic scale approaches to finding other genes that upon inhibition, restore BGS-42 expression and small molecule inhibitors to those gene products may have utility in the treatment of testicular and/or lung cancers. In addition, monitoring the attenuation of BGS42 gene expression may also provide a marker for tumor aggressiveness and have predictive value in determining therapeutic approaches.

The BGS-42 polynucleotides and polypeptides of the present invention, including agonists and/or fragments thereof, have uses that include modulating cellular proliferation and/or differntiation activity, in various cells, tissues, and organisms, and particularly in mammalian testis, lymph node, pituitary, placenta, and/or vas deferens cells and tissues, preferably human tissue.

The strong homology to human tubulin tyrosine ligase proteins, combined with the predominate localized expression in vas deferens/testis tissue suggests the potential utility for BGS-42 polynucleotides and polypeptides in treating, diagnosing, prognosing, and/or preventing testicular, in addition to reproductive disorders.

In preferred embodiments, BGS-42 polynucleotides and polypeptides including agonists and fragments thereof, have uses which include treating, diagnosing, prognosing, and/or preventing the following, non-limiting, diseases or disorders of the testis: spermatogenesis, infertility, Klinefelter's syndrome, XX male, epididymitis, genital warts, germinal cell aplasia, cryptorchidism, varicocele, immotile cilia syndrome, and viral orchitis. The BGS-42 polynucleotides and polypeptides including agonists and fragments thereof, may also have uses related to modulating testicular development, embryogenesis, reproduction, and in ameliorating, treating, and/or preventing testicular proliferative disorders (e.g., cancers, which include, for example, choriocarcinoma, Nonseminoma, seminona, and testicular germ cell tumors).

Likewise, the predominate localized expression in testis tissue also emphasizes the potential utility for BGS-42 polynucleotides and polypeptides in treating, diagnosing, prognosing, and/or preventing metabolic diseases and disorders which include the following, not limiting examples: premature puberty, incomplete puberty, Kallman syndrome, Cushing's syndrome, hyperprolactinemia, hemochromatosis, congenital adrenal hyperplasia, FSH deficiency, and granulomatous disease, for example.

This gene product may also be useful in assays designed to identify binding agents, as such agents (antagonists) are useful as male contraceptive agents. The testes are also a site of active gene expression of transcripts that is expressed, particularly at low levels, in other tissues of the body. Therefore, this gene product may be expressed in other specific tissues or organs where it may play related functional roles in other processes, such as hematopoiesis, inflammation, bone formation, and kidney function, to name a few possible target indications.

The observed loss of BGS-42 expression in testis tumors relative to normal testis tissue suggests loss of the BGS-42 polypeptide may play a critical role in the development of a transformed phenotype leading to the development of cancers and/or a proliferative condition, either directly or indirectly. Alternatively, the loss of BGS-42 polypeptide expression may play a protective role and could be down regulated in response to a cancerous or proliferative phenotype (e.g., as a component of cell cycle regulation to inhibit further cellular damage that may be caused by proliferation). Whether loss of BGS-42 plays a role in directing transformation, or plays the role of protecting cells in response to a transformed phenotype, its role in testis tumors is likely to be enhanced. Therefore, agonists of the BGS-42 polypeptide may be useful in the treatment, amelioration, and/or prevention of a variety of proliferative conditions, including, but not limited to testis, in addition to other cancers or proliferative conditions.

The strong homology to human tubulin tyrosine ligase proteins, combined with the localized expression in lung tissue suggests the BGS-42 polynucleotides and polypeptides may be useful in treating, diagnosing, prognosing, and/or preventing pulmonary diseases and disorders which include the following, not limiting examples: ARDS, emphysema, cystic fibrosis, interstitial lung disease, chronic obstructive pulmonary disease, bronchitis, lymphangioleiomyomatosis, pneumonitis, eosinophilic pneumonias, granulomatosis, pulmonary infarction, pulmonary fibrosis, pneumoconiosis, alveolar hemorrhage, neoplasms, lung abscesses, empyema, and increased susceptibility to lung infections (e.g., immunocompromised, HIV, etc.), for example.

Moreover, polynucleotides and polypeptides, including fragments and/or antagonists thereof, have uses which include, directly or indirectly, treating, preventing, diagnosing, and/or prognosing the following, non-limiting, pulmonary infections: pneumonia, bacterial pneumonia, viral pneumonia (for example, as caused by Influenza virus, Respiratory syncytial virus, Parainfluenza virus, Adenovirus, Coxsackievirus, Cytomegalovirus, Herpes simplex virus, Hantavirus, etc.), mycobacteria pneumonia (for example, as caused by *Mycobacterium tuberculosis*, etc.) mycoplasma pneumonia, fungal pneumonia (for example, as caused by *Pneumocystis carinii, Histoplasma capsulatum, Coccidioides immitis, Blastomyces dermatitidis*, Candida sp., *Cryptococcus neoformans*, Aspergillus sp., Zygomycetes, etc.), Legionnaires' Disease, Chlamydia pneumonia, aspiration pneumonia, *Nocordia* sp. Infections, parasitic pneumonia (for example, as caused by *Strongyloides, Toxoplasma gondii*, etc.) necrotizing pneumonia, in addition to any other pulmonary disease and/or disorder (e.g., non-pneumonia) implicated by the causative agents listed above or elsewhere herein.

The observed loss of BGS-42 expression in lung tumors relative to normal lung tissue suggests loss of the BGS-42 polypeptide may play a critical role in the development of a transformed phenotype leading to the development of cancers and/or a proliferative condition, either directly or indirectly. Alternatively, the loss of BGS-42 polypeptide expression may play a protective role and could be down regulated in response to a cancerous or proliferative phenotype (e.g., as a component of cell cycle regulation to inhibit further cellular damage that may be caused by proliferation). Whether loss of BGS-42 plays a role in directing transformation, or plays the role of protecting cells in response to a transformed phenotype, its role in lung tumors is likely to be enhanced. Therefore, agonists of the BGS-42 polypeptide may be useful in the treatment, amelioration, and/or prevention of a variety of proliferative conditions, including, but not limited to lung, in addition to other cancers or proliferative conditions.

The strong homology to human tubulin tyrosine ligase proteins, combined with the predominate localized expression in lymph node tissue suggests the BGS-42 polynucleotides and polypeptides may be useful in treating, diagnosing, prognosing, and/or preventing immune diseases and/or disorders. Representative uses are described in the "Immune Activity", and "Infectious Disease" sections below, and elsewhere herein. Briefly, the strong expression in immune tissue indicates a role in regulating the proliferation; survival; differentiation; and/or activation of hematopoietic cell lineages, including blood stem cells.

The BGS-42 polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. The BGS-42 polypeptide may be useful for modulating cytokine production, antigen presentation, or other processes, such as for boosting immune responses, etc.

Moreover, the protein may represent a secreted factor that influences the differentiation or behavior of other blood cells, or that recruits hematopoietic cells to sites of injury.

Thus, this gene product is thought to be useful in the expansion of stem cells and committed progenitors of various blood lineages, and in the differentiation and/or proliferation of various cell types. Furthermore, the protein may also be used to determine biological activity, raise antibodies, as tissuemarkers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

The strong homology to human tubulin tyrosine ligase proteins, combined with the localized expression in pituitary gland tissue suggests the BGS-42 polynucleotides and polypeptides may be useful in treating, diagnosing, prognosing, and/or preventing endocrine diseases and/or disorders, which include, but are not limited to, the following: aberrant growth hormone synthesis and/or secretion, aberrant prolactin synthesis and/or secretion, aberrant luteinizing hormone synthesis and/or secretion, aberrant follicle-stimulating hormone synthesis and/or secretion, aberrant thyroid-stimulating hormone synthesis and/or secretion, aberrant adrenocorticotropin synthesis and/or secretion, aberrant vasopressin secretion, aberrant oxytocin secretion, aberrant growth, aberrant lactation, aberrant sexual characteristic development, aberrant testosterone synthesis and/or secretion, aberrant estrogen synthesis and/or secretion, aberrant water homeostasis, hypogonadism, Addison's disease, hypothyroidism, Cushing's disease, agromegaly, gigantism, lethargy, osteoporosis, aberrant calcium homeostasis, aberrant potassium homeostasis, reproductive disorders, and developmental disoders.

The strong homology to human tubulin tyrosine ligase proteins, combined with the localized expression in placenta tissue suggests the BGS-42 polynucleotides and polypeptides may be useful in treating, diagnosing, prognosing, and/or preventing female reproductive diseases and/or disorders, particularly pre-term labor.

The BGS-42 polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. The BGS-42 polypeptide may be useful for modulating cytokine production, antigen presentation, or other processes, such as for boosting immune responses, etc.

Moreover, BGS-42 polynucleotides and polypeptides, including fragments and agonists thereof, may have uses which include treating, diagnosing, prognosing, and/or preventing hyperproliferative disorders, particularly of the reproductive, immune, endocrine, and metabolic system. Such disorders may include, for example, cancers, and metastasis.

The BGS-42 polynucleotides and polypeptides, including fragments and/or antagonsists thereof, may have uses which include identification of modulators of BGS-42 function including antibodies (for detection or neutralization), naturally-occurring modulators and small molecule modulators. Antibodies to domains of the BGS-42 protein could be used as diagnostic agents of reproductive and inflammatory conditions in patients, are useful in monitoring the activation of signal transduction pathways, and can be used as a biomarker for the involvement of tubulin tyrosine ligase proteins in disease states, and in the evaluation of agonists of tubulin tyrosine ligase proteins in vivo.

BGS-42 polypeptides and polynucleotides have additional uses which include diagnosing diseases related to the over and/or under expression of BGS-42 by identifying mutations in the BGS-42 gene by using BGS-42 sequences as probes or by determining BGS-42 protein or mRNA expression levels. BGS-42 polypeptides may be useful for screening compounds that affect the activity of the protein. BGS-42 peptides can also be used for the generation of specific antibodies and as bait in yeast two hybrid screens to find proteins the specifically interact with BGS-42 (described elsewhere herein).

Although it is believed the encoded polypeptide may share at least some biological activities with tubulin tyrosine ligase proteins, a number of methods of determining the exact biological function of this clone are either known in the art or are described elsewhere herein. Briefly, the function of this clone may be determined by applying microarray methodology. Nucleic acids corresponding to the BGS-42 polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from diseased testis cells or tissue, as compared to, normal tissue might indicate a function in modulating reproductive function, for example. In the case of BGS-42, testis, lymph node, pituitary gland, and/or placenta tissue should be used, for example, to extract RNA to prepare the probe.

In addition, the function of the protein may be assessed by applying quantitative PCR methodology, for example. Real time quantitative PCR would provide the capability of following the expression of the BGS-42 gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of BGS-42, a disease correlation related to BGS-42 may be made by comparing the mRNA expression level of BGS-42 in normal tissue, as compared to diseased tissue (particularly diseased tissue isolated from the following: testis, lymph node, pituitary gland, and/or placenta tissue). Significantly higher or lower levels of BGS-42 expression in the diseased tissue may suggest BGS-42 plays a role in disease progression, and antagonists against BGS-42 polypeptides would be useful therapeutically in treating, preventing, and/or ameliorating the disease. Alternatively, significantly higher or lower levels of BGS-42 expression in the diseased tissue may suggest BGS-42 plays a defensive role against disease progression, and agonists of BGS-42 polypeptides may be useful therapeutically in treating, preventing, and/or ameliorating the disease. Also encompassed by the present invention are quantitative PCR probes corresponding to the polynucleotide sequence provided as SEQ ID NO:1 (FIGS. 1A–C).

The function of the protein may also be assessed through complementation assays in yeast. For example, in the case of the BGS-42, transforming yeast deficient in tubulin tyrosine ligase activity, for example, and assessing their ability to grow would provide convincing evidence the BGS-42 polypeptide has tubulin tyrosine ligase activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype. Such knock-out experiments are known in the art, some of which are disclosed elsewhere herein.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., tubulin tyrosine ligase-tissue specific promoter), or it can be expressed at a specified time of development using an inducible and/or a developmentally regulated promoter.

In the case of BGS-42 transgenic mice or rats, if no phenotype is apparent in normal growth conditions, observing the organism under diseased conditions (reproductive, immune, endocrine, and metabolic disorders, in addition to cancers, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal BGS-42 deletion polypeptides are encompassed by the present invention: M1-S541, A2-S541, S3-S541, S4-S541, I5-S541, L6-S541, K7-S541, W8-S541, V9-S541, V10-S541, S11-S541, H12-S541, Q13-S541, S14-S541, C15-S541, S16-S541, R17-S541, S18-S541, S19-S541, R20-S541, S21-S541, K22-S541, P23-S541, R24-S541, D25-S541, Q26-S541, R27-S541, E28-S541, E29-S541, A30-S541, G31-S541, S32-S541, S33-S541, D34-S541, L35-S541, S36-S541, S37-S541, R38-S541, Q39-S541, D40-S541, A41-S541, E42-S541, N43-S541, A44-S541, E45-S541, A46-S541, K47-S541, L48-S541, R49-S541, G50-S541, L51-S541, P52-S541, G53-S541, Q54-S541, L55-S541, V56-S541, D57-S541, I58-S541, A59-S541, C60-S541, K61-S541, V62-S541, C63-S541, Q64-S541, A65-S541, Y66-S541, L67-S541, G68-S541, Q69-S541, L70-S541, E71-S541, H72-S541, E73-S541, D74-S541, I75-S541, D76-S541, T77-S541, S78-S541, A79-S541, D80-S541, A81-S541, V82-S541, E83-S541, D84-S541, L85-S541, T86-S541, E87-S541, A88-S541, E89-S541, W90-S541, E91-S541, D92-S541, L93-S541, T94-S541, Q95-S541, Q96-S541, Y97-S541, Y98-S541, S99-S541, L100-S541, V101-S541, H102-S541, G103-S541, D104-S541, A105-S541, F106-S541, I107-S541, S108-S541, N109-S541, S110-S541, R111-S541, N112-S541, Y113-S541, F114-S541, S115-S541, Q116-S541, C117-S541, Q118-S541, A119-S541, L120-S541, L121-S541, N122-S541, R123-S541, I124-S541, T125-S541, S126-S541, V127-S541, N128-S541, P129-S541, Q130-S541, T131-S541, D132-S541, I133-S541, D134-S541, G135-S541, L136-S541, R137-S541, N138-S541, I139-S541, W140-S541, I141-S541, I142-S541, K143-S541, P144-S541, A145-S541, S541, A146-S541, K147-S541, S148-S541, R149-S541, G150-S541, R151-S541, D152-S541, I153-S541, V154-S541, C155-S541, M156-S541, D157-S541, R158-S541, V159-S541, E160-S541, E161-S541, I162-S541, L163-S541, E164-S541, L165-S541, A166-S541, A167-S541, A168-S541, D169-S541, H170-S541, P171-S541, L172-S541, S173-S541, R174-S541, D175-S541, N176-S541, K177-S541, W178-S541, V179-S541, V180-S541, Q181-S541, K182-S541, Y183-S541, I184-S541, E185-S541, T186-S541, P187-S541, L188-S541, L189-S541, I190-S541, C191-S541, D192-S541, T193-S541, K194-S541, F195-S541, D196-S541, I197-S541, R198-S541, Q199-S541, W200-S541, F201-S541, L202-S541, V203-S541, T204-S541, D205-S541, W206-S541, N207-S541, P208-S541, L209-S541, T210-S541, I211-S541, W212-S541, F213-S541, Y214-S541, K215-S541, E216-S541, S217-S541, Y218-S541, L219-S541, R220-S541, F221-S541, S222-S541, T223-S541, Q224-S541, R225-S541, F226-S541, S227-S541, L228-S541, D229-S541, K230-S541, L231-S541, D232-S541, S233-S541, A234-S541, I235-S541, S541, H236-S541, L237-S541, C238-S541, N239-S541, N240-S541, A241-S541, V242-S541, Q243-S541, K244-S541, Y245-S541, L246-S541, K247-S541, N248-S541, D249-S541, V250-S541, G251-S541, R252-S541, S253-S541, P254-S541, L255-S541, L256-S541, P257-S541, A258-S541, H259-S541, N260-S541, M261-S541, W262-S541, T263-S541, S264-S541, T265-S541, R266-S541, F267-S541, Q268-S541, E269-S541, Y270-S541, L271-S541, Q272-S541, R273-S541, Q274-S541, G275-S541, R276-S541, G277-S541, A278-S541, V279-S541, W280-S541, G281-S541, S282-S541, V283-S541, I284-S541, Y285-S541, P286-S541, S287-S541, M288-S541, K289-S541, S541, K290-S541, A291-S541, I292-S541, A293-S541, H294-S541, A295-S541, M296-S541, K297-S541, V298-S541, A299-S541, Q300-S541, D301-S541, H302-S541, V303-S541, E304-S541, P305-S541, R306-S541, K307-S541, N308-S541, S309-S541, F310-S541, E311-S541, L312-S541, Y313-S541, G314-S541, A315-S541, D316-S541, F317-S541, V318-S541, L319-S541, G320-S541, R321-S541, D322-S541, F323-S541, R324-S541, P325-S541, W326-S541, L327-S541, I328-S541, E329-S541, I330-S541, N331-S541, S332-S541, S333-S541, P334-S541, T335-S541, M336-S541, H337-S541, P338-S541, S339-S541, T340-S541, P341-S541, V342-S541, T343-S541, A344-S541, Q345-S541, L346-S541, C347-S541, A348-S541, Q349-S541, V350-S541, Q351-S541, E352-S541, D353-S541, T354-S541, I355-S541, K356-S541, V357-S541, A358-S541, V359-S541, D360-S541, R361-S541, S362-S541, C363-S541, D364-S541, I365-S541, G366-S541, N367-S541, F368-S541, E369-S541, L370-S541, L371-S541, W372-S541, R373-S541, Q374-S541, P375-S541, V376-S541, V377-S541, E378-S541, P379-S541, S541, P380-S541, P381-S541, F382-S541, S383-S541, G384-S541, S385-S541, D386-S541, L387-S541, C388-S541, V389-S541, A390-S541, G391-S541, V392-S541, S393-S541, V394-S541, R395-S541, R396-S541, A397-S541, R398-S541, R399-S541, Q400-S541, V401-S541, L402-S541, P403-S541, V404-S541, C405-S541, N406-S541, L407-S541, K408-S541, A409-S541, S410-S541, A411-S541, S412-S541, L413-S541, L414-S541, D415-S541, S541, A416-S541, Q417-S541, P418-S541, L419-S541, K420-S541, A421-S541, R422-S541, G423-S541, P424-S541, S425-S541, A426-S541, M427-S541, P428-S541, D429-S541, P430-S541, A431-S541, Q432-S541, G433-

S541, P434-S541, P435-S541, S436-S541, P437-S541, A438-S541, L439-S541, Q440-S541, R441-S541, D442-S541, L443-S541, G444-S541, L445-S541, K446-S541, E447-S541, E448-S541, K449-S541, G450-S541, L451-S541, P452-S541, L453-S541, A454-S541, L455-S541, L456-S541, A457-S541, P458-S541, L459-S541, R460-S541, G461-S541, A462-S541, A463-S541, E464-S541, S465-S541, G466-S541, G467-S541, A468-S541, A469-S541, Q470-S541, P471-S541, T472-S541, R473-S541, T474-S541, K475-S541, A476-S541, A477-S541, G478-S541, K479-S541, V480-S541, E481-S541, L482-S541, P483-S541, A484-S541, C485-S541, P486-S541, C487-S541, R488-S541, H489-S541, V490-S541, D491-S541, S492-S541, Q493-S541, A494-S541, P495-S541, N496-S541, T497-S541, G498-S541, V499-S541, P500-S541, V501-S541, A502-S541, Q503-S541, P504-S541, A505-S541, K506-S541, S507-S541, W508-S541, D509-S541, P510-S541, N511-S541, Q512-S541, L513-S541, N514-S541, A515-S541, H516-S541, P517-S541, L518-S541, E519-S541, P520-S541, V521-S541, L522-S541, R523-S541, G524-S541, L525-S541, K526-S541, T527-S541, A528-S541, E529-S541, G530-S541, A531-S541, L532-S541, R533-S541, P534-S541, and/or P535-S541 of SEQ ID NO:2. Polynucleotide sequences encoding these polypeptides are also provided. The present invention also encompasses the use of these N-terminal BGS-42 deletion polypeptides as immunogenic and/or antigenic epitopes as described elsewhere herein.

In preferred embodiments, the following C-terminal BGS-42 deletion polypeptides are encompassed by the present invention: M1-S541, M1-G540, M1-K539, M1-G538, M1-G537, M1-P536, M1-P535, M1-P534, M1-R533, M1-L532, M1-A531, M1-G530, M1-E529, M1-A528, M1-T527, M1-K526, M1-L525, M1-G524, M1-R523, M1-L522, M1-V521, M1-P520, M1-E519, M1-L518, M1-P517, M1-H516, M1-A515, M1-N514, M1-L513, M1-Q512, M1-N511, M1-P510, M1-D509, M1-W508, M1-S507, M1-K506, M1-A505, M1-P504, M1-Q503, M1-A502, M1-V501, M1-P500, M1-V499, M1-G498, M1-T497, M1-N496, M1-P495, M1-A494, M1-Q493, M1-S492, M1-D491, M1-V490, M1-H489, M1-R488, M1-C487, M1-P486, M1-C485, M1-A484, M1-P483, M1-L482, M1-E481, M1-V480, M1-K479, M1-G478, M1-A477, M1-A476, M1-K475, M1-T474, M1-R473, M1-T472, M1-P471, M1-Q470, M1-A469, M1-A468, M1-G467, M1-G466, M1-S465, M1-E464, M1-A463, M1-A462, M1-G461, M1-R460, M1-L459, M1-P458, M1-A457, M1-L456, M1-L455, M1-A454, M1-L453, M1-P452, M1-L451, M1-G450, M1-K449, M1-E448, M1-E447, M1-K446, M1-L445, M1-G444, M1-L443, M1-D442, M1-R441, M1-Q440, M1-L439, M1-A438, M1-P437, M1-S436, M1-P435, M1-P434, M1-G433, M1-Q432, M1-A431, M1-P430, M1-D429, M1-P428, M1-M427, M1-A426, M1-S425, M1-P424, M1-G423, M1-R422, M1-A421, M1-K420, M1-L419, M1-P418, M1-Q417, M1-A416, M1-D415, M1-L414, M1-L413, M1-S412, M1-A411, M1-S410, M1-A409, M1-K408, M1-L407, M1-N406, M1-C405, M1-V404, M1-P403, M1-L402, M1-V401, M1-Q400, M1-R399, M1-R398, M1-A397, M1-R396, M1-R395, M1-V394, M1-S393, M1-V392, M1-G391, M1-A390, M1-V389, M1-C388, M1-L387, M1-D386, M1-S385, M1-G384, M1-S383, M1-F382, M1-P381, M1-P380, M1-P379, M1-E378, M1-V377, M1-V376, M1-P375, M1-Q374, M1-R373, M1-W372, M1-L371, M1-L370, M1-E369, M1-F368, M1-N367, M1-G366, M1-I365, M1-D364, M1-C363, M1-S362, M1-R361, M1-D360, M1-V359, M1-A358, M1-V357, M1-K356, M1-I355, M1-T354, M1-D353, M1-E352, M1-Q351, M1-V350, M1-Q349, M1-A348, M1-C347, M1-L346, M1-Q345, M1-A344, M1-T343, M1-V342, M1-P341, M1-T340, M1-S339, M1-P338, M1-H337, M1-M336, M1-T335, M1-P334, M1-S333, M1-S332, M1-N331, M1-I330, M1-E329, M1-I328, M1-L327, M1-W326, M1-P325, M1-R324, M1-F323, M1-D322, M1-R321, M1-G320, M1-L319, M1-V318, M1-F317, M1-D316, M1-A315, M1-G314, M1-Y313, M1-L312, M1-E311, M1-F310, M1-S309, M1-N308, M1-K307, M1-R306, M1-P305, M1-E304, M1-V303, M1-H302, M1-D301, M1-Q300, M1-A299, M1-V298, M1-K297, M1-M296, M1-A295, M1-H294, M1-A293, M1-I292, M1-A291, M1-K290, M1-K289, M1-M288, M1-S287, M1-P286, M1-Y285, M1-I284, M1-V283, M1-S282, M1-G281, M1-W280, M1-V279, M1-A278, M1-G277, M1-R276, M1-G275, M1-Q274, M1-R273, M1-Q272, M1-L271, M1-Y270, M1-E269, M1-Q268, M1-F267, M1-R266, M1-T265, M1-S264, M1-T263, M1-W262, M1-M261, M1-N260, M1-H259, M1-A258, M1-P257, M1-L256, M1-L255, M1-P254, M1-S253, M1-R252, M1-G251, M1-V250, M1-D249, M1-N248, M1-K247, M1-L246, M1-Y245, M1-K244, M1-Q243, M1-V242, M1-A241, M1-N240, M1-N239, M1-C238, M1-L237, M1-H236, M1-I235, M1-A234, M1-S233, M1-D232, M1-L231, M1-K230, M1-D229, M1-L228, M1-S227, M1-F226, M1-R225, M1-Q224, M1-T223, M1-S222, M1-F221, M1-R220, M1-L219, M1-Y218, M1-S217, M1-E216, M1-K215, M1-Y214, M1-F213, M1-W212, M1-I211, M1-T210, M1-L209, M1-P208, M1-N207, M1-W206, M1-D205, M1-T204, M1-V203, M1-L202, M1-F201, M1-W200, M1-Q199, M1-R198, M1-I197, M1-D196, M1-F195, M1-K194, M1-T193, M1-D192, M1-C191, M1-I190, M1-L189, M1-L188, M1-P187, M1-T186, M1-E185, M1-I184, M1-Y183, M1-K182, M1-Q181, M1-V180, M1-V179, M1-W178, M1-K177, M1-N176, M1-D175, M1-R174, M1-S173, M1-L172, M1-P171, M1-H170, M1-D169, M1-A168, M1-A167, M1-A166, M1-L165, M1-E164, M1-L163, M1-I162, M1-E161, M1-E160, M1-V159, M1-R158, M1-D157, M1-M156, M1-C155, M1-V154, M1-I153, M1-D152, M1-R151, M1-G150, M1-R149, M1-S148, M1-K147, M1-A146, M1-A145, M1-P144, M1-K143, M1-I142, M1-I141, M1-W140, M1-I139, M1-N138, M1-R137, M1-L136, M1-G135, M1-D134, M1-I133, M1-D132, M1-T131, M1-Q130, M1-P129, M1-N128, M1-V127, M1-S126, M1-T125, M1-I124, M1-R123, M1-N122, M1-L121, M1-L120, M1-A119, M1-Q118, M1-C117, M1-Q116, M1-S115, M1-F114, M1-Y113, M1-N112, M1-R111, M1-S110, M1-N109, M1-S108, M1-I107, M1-F106, M1-A105, M1-D104, M1-G103, M1-H102, M1-V101, M1-L100, M1-S99, M1-Y98, M1-Y97, M1-Q96, M1-Q95, M1-T94, M1-L93, M1-D92, M1-E91, M1-W90, M1-E89, M1-A88, M1-E87, M1-T86, M1-L85, M1-D84, M1-E83, M1-V82, M1-A81, M1-D80, M1-A79, M1-S78, M1-T77, M1-D76, M1-I75, M1-D74, M1-E73, M1-H72, M1-E71, M1-L70, M1-Q69, M1-G68, M1-L67, M1-Y66, M1-A65, M1-Q64, M1-C63, M1-V62, M1-K61, M1-C60, M1-A59, M1-I58, M1-D57, M1-V56, M1-L55, M1-Q54, M1-G53, M1-P52, M1-L51, M1-G50, R49, M1-L48, M1-K47, M1-A46, M1-E45, M1-A44, M1-N43, M1-E42, M1-A41, M1-D40, M1-Q39, M1-R38, M1-S37, M1-S36, M1-L35, M1-D34, M1-S33, M1-S32, M1-G31, M1-A30, M1-E29, M1-E28, M1-R27, M1-Q26, M1-D25, M1-R24, M1-P23, M1-K22, M1-S21, M1-R20, M1-S19, M1-S18, M1-R17, M1-S16, M1-C15, M1-S14, M1-Q13, M1-H12, M1-S11, M1-V0, M1-V9, M1-W8, and/or M1-K7 of SEQ ID NO:2. Polynucleotide sequences encoding these polypeptides are also provided. The present invention also encompasses the use of these C-terminal BGS-42 deletion polypeptides as immunogenic and/or antigenic epitopes as described elsewhere herein.

Alternatively, preferred polypeptides of the present invention may comprise polypeptide sequences corresponding to, for example, internal regions of the BGS-42 polypeptide (e.g., any combination of both N- and C-terminal BGS-42 polypeptide deletions) of SEQ ID NO:2. For example, internal regions could be defined by the equation: amino acid NX to amino acid CX, wherein NX refers to any N-terminal deletion polypeptide amino acid of BGS-42 (SEQ ID NO:2), and where CX refers to any C-terminal deletion polypeptide amino acid of BGS-42 (SEQ ID NO:2). Polynucleotides encoding these polypeptides are also provided. The present invention also encompasses the use of these polypeptides as an immunogenic and/or antigenic epitope as described elsewhere herein.

The present invention also encompasses immunogenic and/or antigenic epitopes of the BGS-42 polypeptide.

The BGS-42 polypeptides of the present invention were determined to comprise several phosphorylation sites based upon the Motif algorithm (Genetics Computer Group, Inc.). The phosphorylation of such sites may regulate some biological activity of the BGS-42 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the BGS-42 polypeptide to associate with other polypeptides, particularly cognate ligand for BGS-42, or its ability to modulate certain cellular signal pathways.

The BGS-42 polypeptide was predicted to comprise seven PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem. 260:12492–12499(1985); which are hereby incorporated by reference herein.

In preferred embodiments, the following PKC phosphorylation site polypeptides are encompassed by the present invention: QSCSRSSRSKPRD (SEQ ID NO:31), GSSDLSSRQDAEN (SEQ ID NO:32), YLRFSTQRFSLDK (SEQ ID NO:33), HNMWTSTRFQEYL (SEQ ID NO:34), SVIYPSMKKAIAH (SEQ ID NO:35), QVQEDTIKVAVDR (SEQ ID NO:36), and/or CVAGVSVRRARRQ (SEQ ID NO:37). Polynucleotides encoding these polypeptides are also provided. The present invention also encompasses the use of the BGS-42 PKC phosphorylation site polypeptides as immunogenic and/or antigenic epitopes as described elsewhere herein.

The BGS-42 polypeptide was predicted to comprise seven casein kinase II phosphorylation sites using the Motif algorithm (Genetics Computer Group, Inc.). Casein kinase II (CK-2) is a protein serine/threonine kinase whose activity is independent of cyclic nucleotides and calcium. CK-2 phosphorylates many different proteins. The substrate specificity [1] of this enzyme can be summarized as follows: (1) Under comparable conditions Ser is favored over Thr.; (2) An acidic residue (either Asp or Glu) must be present three residues from the C-terminal of the phosphate acceptor site; (3) Additional acidic residues in positions +1, +2, +4, and +5 increase the phosphorylation rate. Most physiological substrates have at least one acidic residue in these positions; (4) Asp is preferred to Glu as the provider of acidic determinants; and (5) A basic residue at the N-terminal of the acceptor site decreases the phosphorylation rate, while an acidic one will increase it.

A consensus pattern for casein kinase II phosphorylations site is as follows: [ST]-x(2)-[DE], wherein 'x' represents any amino acid, and S or T is the phosphorylation site.

Additional information specific to casein kinase II phosphorylation sites may be found in reference to the following publication: Pinna L. A., Biochim. Biophys. Acta 1054:267–284(1990); which is hereby incorporated herein in its entirety.

In preferred embodiments, the following casein kinase II phosphorylation site polypeptide is encompassed by the present invention: SSDLSSRQDAENAE (SEQ ID NO:38), HEDIDTSADAVEDL (SEQ ID NO:39), AVEDLTEAEWEDLT (SEQ ID NO:40), SVNPQTDIDGLRNI (SEQ ID NO:41), LLICDTKFDIRQWF (SEQ ID NO:42), EPPPFSGSDLCVAG (SEQ ID NO:43), and/or LKASASLLDAQPLK (SEQ ID NO:44). Polynucleotides encoding these polypeptides are also provided. The present invention also encompasses the use of this casein kinase II phosphorylation site polypeptide as an immunogenic and/or antigenic epitope as described elsewhere herein.

The BGS-42 polypeptide was predicted to comprise one cAMP- and cGMP-dependent protein kinase phosphorylation site using the Motif algorithm (Genetics Computer Group, Inc.). There has been a number of studies relative to the specificity of cAMP- and cGMP-dependent protein kinases. Both types of kinases appear to share a preference for the phosphorylation of serine or threonine residues found close to at least two consecutive N-terminal basic residues.

A consensus pattern for cAMP- and cGMP-dependent protein kinase phosphorylation sites is as follows: [RK](2)-x-[ST], wherein "x" represents any amino acid, and S or T is the phosphorylation site.

Additional information specific to cAMP- and cGMP-dependent protein kinase phosphorylation sites may be found in reference to the following publication: Fremisco J. R., Glass D. B., Krebs E. G, J. Biol. Chem. 255:4240–4245 (1980); Glass D. B., Smith S. B., J. Biol. Chem. 258:14797–14803(1983); and Glass D. B., El-Maghrabi M. R., Pilkis S. J., J. Biol. Chem. 261:2987–2993(1986); which is hereby incorporated herein in its entirety.

In preferred embodiments, the following cAMP- and cGMP-dependent protein kinase phosphorylation site polypeptide is encompassed by the present invention: DHVEPRKNSFELYG (SEQ ID NO:45). Polynucleotides encoding this polypeptide are also provided. The present invention also encompasses the use of this cAMP- and cGMP-dependent protein kinase phosphorylation site polypeptide as an immunogenic and/or antigenic epitope as described elsewhere herein.

The PMN29 polypeptide was predicted to comprise six N-myristoylation sites using the Motif algorithm (Genetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA: protein N-myristoyl transferase (NMT), has been derived from the sequence of known N-myristoylated proteins and from studies using synthetic peptides. The specificity seems to be the following: i.) The N-terminal residue must be glycine; ii.) In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-{EDRKHPFYW}-x(2)-[STAGCN]-{P}, wherein 'x' represents any amino acid, and G is the N-myristoylation site.

Additional information specific to N-myristoylation sites may be found in reference to the following publication: Towler D. A., Gordon J. I., Adams S. P., Glaser L., Annu. Rev. Biochem. 57:69–99(1988); and Grand R. J. A., Biochem. J. 258:625–638(1989); which is hereby incorporated herein in its entirety.

In preferred embodiments, the following N-myristoylation site polypeptides are encompassed by the present invention: QRQGRGAVWGSVIYPS (SEQ ID NO:46), PPPFSGSDLCVAGVSV (SEQ ID NO:47), LKEEKGLPLALLAPLR (SEQ ID NO:48), LAPLR-GAAESGGAAQP (SEQ ID NO:49), QAPNTGVPVAQ-PAKSW (SEQ ID NO:50), and/or EPVLRGLKTAEGALRP (SEQ ID NO:51). Polynucleotides encoding these polypeptides are also provided. The present invention also encompasses the use of these N-myristoylation site polypeptides as immunogenic and/or antigenic epitopes as described elsewhere herein.

The present invention encompasses the identification of compounds and drugs which stimulate BGS-42 on the one hand (i.e., agonists) and which inhibit the function of BGS-42 on the other hand (i.e., antagonists). In general, such screening procedures involve providing appropriate cells which express the polypeptide of the present invention on the surface thereof. Such cells may include, for example, cells from mammals, yeast, Drosophila or *E. coli*. In a preferred embodiment, a polynucleotide encoding the polypeptide of the present invention may be employed to transfect cells to thereby express the BGS-42 polypeptide. The expressed polypeptide may then be contacted with a test compound to observe binding, stimulation or inhibition of a functional response.

In confirmation that the BGS-42 polypeptide is a tyrosine ligase, molecular modeling of BGS-42 determined that it contained a distinct structural domain exemplified by the catalytic domain of glutathione synthetase, a member of the peptide synthases ADP-forming enzymes (acid-D-amino acid ligases), E.C.6.3.2.-. Based upon the sequence, structure, motifs, known binding signature sequences, and homology to known tyrosine ligase proteins, the inventors have determined that BGS-42 contains a novel tubulin-tyrosine ligase domain and have ascribed the BGS-42 polypeptide as having tubulin-tyrosine ligase (E.C.6.3.2.25) activity(s) and cellular and systemic regulatory function(s).

The three dimensional crystallographic structures for several ADP forming enzymes from E.C.6.3.2.-, acid-D-amino acid ligases have been reported and are deposited into the Protein Data Bank (Bernstein et. al., 1977 & Berman et. al., 2000). X-ray structures have been determined for E.C.6.3.2.1, Pantoate-beta-alanine ligase; E.C.6.3.2.3, Glutathione synthase; E.C.6.3.2.4, D-alanine-D-alanine ligase; E.C.6.3.2.8, UDP-N-acetylmuramate-alanine ligase, E.C.6.3.2.9, UDP-N-acetylmuramoylalanine-D-glutamate ligase; E.C.6.3.2.15, UDP-N-acetylmuramoylalanyl-D-glutamyl-2,6-diaminopimelate-D-alanyl; E.C.6.3.2.17, folylpolyglutamate synthase; E.C.6.3.2.19, Ubiquitin-protien ligase. Comparison of the three-dimensional structures (Dideberg & Bertrand, 1998) for several of these family members identified a structural motif which forms the ATP binding site. Dideberg and Bertrand (Trends Biochem. Sci. 23:57–58, 1998) describe structural differences for the ADP-forming peptide synthetases and highlighted distinct structural families including the glutathione synthetases. In their analyses they concluded that tyrosine ligase, E.C.6.3.2.25, an enzyme involved in tubulin modification, most likely belongs to the glutathione synthetase ADP-forming synthetase family, E.C.6.3.2.3.

The glutathione synthetase structure is a structural prototype for the ADP-forming synthetase family (E.C.6.3.2.3). Glutathione synthetase is ubiquitous among organisms and catalyzes the ligation of gamma-L-glutamyl-L-cysteine and glycine with the aid of ATP in the presence of magnesium ion(Mg2+). The structure of glutathione synthetase (Hara et al., Biochemistry. 35:11967–11974. 1996.) was obtained from the Protein Data Bank (PDB) and has the PDB code 1GSA. The ATP binding fold of glutathione synthetase contains two motifs. The first motif consists of a four-stranded beta-sheet with two coupled helices and a small flexible loop. The second motif consists of a five-stranded beta sheet and a large flexible loop that is positioned at the edge of the sheet and the first sheet motif. The flexible loops extend over substrates bound in the active site and moves from the "open" position to the "closed" position when substrates are bound to the active site. Several amino acids are conserved in these ADP-forming enzymes and include amino acids found in direct contact with the nucleotide ADP. For glutathione synthetase K160, G167, Q198, Y200, D208, D273, E281, N283 represent several residues that interact with ADP in the active site via interactions with the nucleotide base, sugar, alpha-phosphate and beta-phosphate.

Homology models are useful when there is no experimental information available on the protein of interest. A three dimensional model can be constructed on the basis of the known structure of a homologous protein (Greer et. al., 1991, Lesk, et. al., 1992, Levitt, 1992, Cardozo, et. al., 1995, Sali, et. al., 1995).

Those of skill in the art will understand that a homology model is constructed on the basis of first identifying a template, or, protein of known structure which is similar to the protein without known structure. This can be accomplished by through pairwise alignment of sequences using such programs as FASTA (Pearson, et. al. 1990) and BLAST (Altschul, et. al., 1990). In cases where sequence similarity is high (greater than 30%) these pairwise comparison methods may be adequate. Likewise, multiple sequence alignments or profile-based methods can be used to align a query sequence to an alignment of multiple (structurally and biochemically) related proteins. When the sequence similarity is low, more advanced techniques are used such as fold recognition (protein threading; Hendlich, et. al., 1990, Koppensteiner et. Al. 2000, Sippl & Weitckus 1992, Sippl 1993), where the compatibility of a particular sequence with the three dimensional fold of a potential template protein is gauged on the basis of a knowledge-based potential. Following the initial sequence alignment, the query template can be optimally aligned by manual manipulation or by incorporation of other features (motifs, secondary structure predictions, and allowed sequence conservation). Next, structurally conserved regions can be identified and are used to construct the core secondary structure (Levitt, 1992, Sali, et. al., 1995) elements in the three dimensional model. Variable regions, called "unconserved regions" and loops can be added using knowledge-based techniques. The complete model with variable regions and loops can be refined performing forcefield calculations (Sali, et. al., 1995, Cardozo, et. al., 1995).

For BGS-42 a hand generated sequence alignment based upon the three structural motifs identified by Dideberg and Bertrand (1998) produced 13% overall identity (for amino acids M1 to R361) of BGS-42 aligned with the sequence human glutathione synthetase, E.C. number 6.3.2.3 (Hara et al., 1998), (Protein Data Bank code 1GSA). The alignment of BGS-42 with PDB entry 1GSA is set forth in FIG. 13. In this invention, the homology model of BGS-42 was derived from the sequence alignment set forth in FIG. 13. An overall atomic model including plausible sidechain orientations was generated using the program LOOK (Levitt, 1992). The three dimensional model for BGS-42 is defined by the set of structure coordinates as set forth in Table IV and is shown in FIG. 14 rendered by backbone secondary structures.

The term "structure coordinates" refers to Cartesian coordinates generated from the building of a homology model.

Those of skill in the art will understand that a set of structure coordinates for a protein is a relative set of points that define a shape in three dimensions. Thus, it is possible that an entirely different set of coordinates could define a similar or identical shape. Moreover, slight variations in the individual coordinates, as emanate from generation of similar homology models using different alignment templates (i.e., other than the structure coordinates of 1GSA), and/or using different methods in generating the homology model, will have minor effects on the overall shape. Variations in coordinates may also be generated because of mathematical manipulations of the structure coordinates. For example, the structure coordinates set forth in Table IV could be manipulated by fractionalization of the structure coordinates; integer additions or subtractions to sets of the structure coordinates, inversion of the structure coordinates or any combination of the above.

Various computational analyses are therefore necessary to determine whether a molecule or a portion thereof is sufficiently similar to all or parts of BGS-42 described above as to be considered the same. Such analyses may be carried out in current software applications, such as INSIGHTII (Accelrys Inc., San Diego, Calif.) version 2000 as described in the User's Guide, online (www.accelrys.com) or software applications available in the SYBYL software suite (Tripos Inc., St. Louis, Mo.).

Using the superimposition tool in the program INSIGHTII comparisons can be made between different structures and different conformations of the same structure. The procedure used in INSIGHTII to compare structures is divided into four steps: 1) load the structures to be compared; 2) define the atom equivalencies in these structures; 3) perform a fitting operation; and 4) analyze the results. Each structure is identified by a name. One structure is identified as the target (i.e., the fixed structure); the second structure (i.e., moving structure) is identified as the source structure. Since atom equivalency within INSIGHTII is defined by user input, for the purpose of this invention, equivalent atoms are defined as protein backbone atoms (N, Cα, C and O) for all conserved residues between the two structures being compared. Also, only rigid fitting operations were considered. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atoms are an absolute minimum. This number, given in angstroms, is reported by INSIGHTII. For the purpose of this invention, any homology model of a BGS-42 that has a root mean square deviation of conserved residue backbone atoms (N, Cα, C, O) of less than about 4.0, 3.0. 2.0, 1.0, 0.9, 0.8, 0.7, 0.6, 0.5, 0.4, 0.3, 0.2, or 0.1 angstroms when superimposed on the relevant backbone atoms described by structure coordinates listed in Table IV are considered identical.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the relevant portion of the backbone of BGS-42 as defined by the structure coordinates described herein.

This invention as embodied by the three-dimensional model enables the structure-based design of modulators of the biological function of BGS-42, as well as mutants with altered biological function and/or specificity.

The sequence alignment (FIG. 13) used to provide a template for creation of the three-dimensional model of BGS-42 tyrosine ligase domain has 13% sequence identity between catalytic domain of BGS-42 and *Escherichia coli* glutathione synthetase, PDB code 1GSA. For the peptide synthases ADP-forming enzymes (acid-D-amino acid ligases), E.C.6.3.2.-, the functionally important residues are located in the active site and bind substrate and nucleotide, ATP. Residues of glutathione synthetase that interact with ADP in the active site via interactions with the nucleotide base, sugar, and phosphate groups include K160, G167, Q198, Y200, D208, D273, E281, N283. These residues are highlighted in the sequence alignment provided in FIG. 13. The other active site residues are also highlighted in FIG. 13 and are described by (Dideberg & Bertrand, 1998) as conserved hydrophobic residues in the structural motifs associated with the ATP active site. The following is a list of residues within the BGS-42 polypeptide sequence that correspond to the above mentioned active site residues of glutathione synthetase: K143 of SEQ ID NO:2 corresponds to K160, G150 of SEQ ID NO:2 corresponds to G167, Q181 of SEQ ID NO:2 corresponds to Q198, Y183 of SEQ ID NO:2 corresponds to Y200, D196 of SEQ ID NO:2 corresponds to D208, D316 of SEQ ID NO:2 corresponds to D273, E281 of SEQ ID NO:2 corresponds to E329, and N283 of SEQ ID NO:2 corresponds to N331. Clearly, as evidenced by the latter in addition to the 3D model of BGS-42, the active site residues required for tyrosine ligase activity are completely conserved between BGS42 and glutathione synthetase. This conservation suggests that a structural model of the active site can be accurately created even though the overall identity for the domain is 13%.

FIG. 14 shows the structure of the BGS-42 and has highlighted the active site side chains that are conserved and are homologous to those in the template glutathione synthetase, 1GSA. The structure of glutathione synthetase has two motifs with flexible loops that extend over the bound substrate. For BGS there is a large insertion, residues E216-W262 that cannot be aligned with any region of the template 1GSA. This loop region is not provided in the homology model as this region may form a large flexible loop that may interact with tubulin when it binds with the enzyme (BGS42). This potential flexible loop is consistent with and analagous to the two structural motifs found in glutathione synthetase.

This is a strong indication that the functional activity for this domain of BGS-42 is a tyrosine ligase (E.C.6.3.2.-) and most probably a tubulin-tyrosine ligase (E.C.6.3.2.25). In addition the three-dimensional model of BGS-42 (FIG. 14) shows that the active site residues are located in exactly the same three-dimensional position as the 1GSA structure which allows for these residues to interact with ATP in using the same binding mode.

The structure coordinates of a BGS-42 homology model portion thereof are stored in a machine-readable storage medium. Such data may be used for a variety of purposes, such as drug discovery and target prioritization and validation.

Accordingly, in one embodiment of this invention is provided a machine-readable data storage medium comprising a data storage material encoded with the structure coordinates set forth in Table IV.

For the first time, the present invention permits the use, through homology modeling based upon the sequence of BGS-42 (FIGS. 13 and 14) of structure-based or rational drug design techniques to design, select, and synthesizes chemical entities that are capable of modulating the biological function of BGS-42. Comparison of the BGS-42 homology model with the structures of other amino acid ligases enable the use of rational or structure based drug design methods to design, select or synthesize specific chemical modulators of BGS-42.

Accordingly, the present invention is also directed to the entire sequence in FIGS. 1A–C, or any portion thereof for the purpose of generating a homology model for the purpose of three dimensional structure-based drug designs.

For purposes of this invention, we include mutants or homologues of the sequence in FIGS. 1A–C, or any portion thereof. In a preferred embodiment, the mutants or homologues have at least 25% identity, more preferably 50% identity, more preferably 75% identity, and most preferably 90% identity to the amino acid residues in FIGS. 1A–C.

The three-dimensional model structure of the BGS-42 will also provide methods for identifying modulators of biological function. Various methods or combination thereof can be used to identify these compounds.

Structure coordinates of the active site region defined above can also be used to identify structural and chemical features. Identified structural or chemical features can then be employed to design or select compounds as potential BGS-42 modulators. By structural and chemical features it is meant to include, but is not limited to, van der Waals interactions, hydrogen bonding interactions, charge interaction, hydrophobic interactions, and dipole interaction. Alternatively, or in conjunction, the three-dimensional structural model can be employed to design or select compounds as potential BGS-42 modulators. Compounds identified as potential BGS-42 modulators can then be synthesized and screened in an assay characterized by binding of a test compound to the BGS-42, or in characterizing BGS-42 deactivation in the presence of a small molecule. Examples of assays useful in screening of potential BGS-42 modulators include, but are not limited to, screening in silico, in vitro assays and high throughput assays. Finally, these methods may also involve modifying or replacing one or more amino acids from BGS-42 according to Table IV.

However, as will be understood by those of skill in the art upon this disclosure, other structure based design methods can be used. Various computational structure based design methods have been disclosed in the art.

For example, a number of computer modeling systems are available in which the sequence of the BGS-42 and the BGS-42 structure (i.e., atomic coordinates of BGS-42 and/or the atomic coordinates of the active site region as provided in Table IV) can be input. The computer system then generates the structural details of one or more these regions in which a potential BGS-42 modulator binds so that complementary structural details of the potential modulators can be determined. Design in these modeling systems is generally based upon the compound being capable of physically and structurally associating with BGS-42. In addition, the compound must be able to assume a conformation that allows it to associate with BGS-42. Some modeling systems estimate the potential inhibitory or binding effect of a potential BGS-42 modulator prior to actual synthesis and testing.

Methods for screening chemical entities or fragments for their ability to associate with a given protein target are well known. Often these methods begin by visual inspection of the binding site on the computer screen. Selected fragments or chemical entities are then positioned in one or more positions and orientations within the active site region in BGS-42. Molecular docking is accomplished using software such as INSIGHTII, ICM (Molsoft LLC, La Jolla, Calif.), and SYBYL, following by energy minimization and molecular dynamics with standard molecular mechanic forcefields such as CHARMM and MMFF. Examples of computer programs which assist in the selection of chemical fragment or chemical entities useful in the present invention include, but are not limited to, GRID (Goodford, 1985), AUTODOCK (Goodsell, 1990), and DOCK (Kuntz et. al. 1982).

Alternatively, compounds may be designed de novo using either an empty active site or optionally including some portion of a known inhibitor. Methods of this type of design include, but are not limited to LUDI (Bohm 1992), Leap-Frog (Tripos Associates, St. Louis Mo.) and DOCK (Kuntz et. al., 1982). Programs such as DOCK (Kuntz et. al. 1982) can be used with the atomic coordinates from the homology model to identify potential ligands from databases or virtual databases which potentially bind the in the active site region, and which may therefore be suitable candidates for synthesis and testing. The computer programs may utilize a combination of the following steps: a.) Selection of fragments or chemical entities from a database and then positioning the chemical entity in one or more orientations within the BGS-42 active site defined by residues K143, G150, Q181, Y183, D196, D316, E281, and N283 or portion thereof; b.) Characterization of the structural and chemical features of the chemical entity and active site including van der Waals interactions, hydrogen bonding interactions, charge interaction, hydrophobic bonding interaction, and dipole interactions; c.) Search databases for molecular fragments which can be joined to or replace the docked chemical entity and spatially fit into regions defined by the said BGS-2 active site site defined by residues K143, G150, Q181, Y183, D196, D316, E281, and N283 or portion thereof; and/or d.) Evaluate the docked chemical entity and fragments using a combination of scoring schemes which account for van der Waals interactions, hydrogen bonding interactions, charge interaction, hydrophobic interactions Databases that may be used include ACD (Molecular Designs Limited), Aldrich (Aldrich Chemical Company), NCI (National Cancer Institute), Maybridge(Maybridge Chemical Company Ltd), CCDC (Cambridge Crystallographic Data Center), CAST (Chemical Abstract Service), Derwent (Derwent Information Limited).

Upon selection of preferred chemical entities or fragments, their relationship to each other and BGS-42 can be visualized and then assembled into a single potential modulator. Programs useful in assembling the individual chemical entities include, but are not limited to SYBYL and LeapFrog (Tripos Associates, St. Louis Mo.), LUDI (Bohm 1992) as well as 3D Database systems (Martin 1992).

Additionally, the three-dimensional homology model of BGS-42 will aid in the design of mutants with altered biological activity. Site directed mutagenesis can be used to generate proteins with similar or varying degrees of biological activity compared to native BGS-42. This invention also relates to the generation of mutants or homologs of BGS-42. It is clear that molecular modeling using the three dimensional structure coordinates set forth in Table IV and visualization of the BGS-42 models, FIG. 14 can be utilized to design homologs or mutant polypeptides of BGS-42 that have similar or altered biological activities, function or reactivities.

In preferred embodiments, the following BGS-42 active site domain amino acid substitutions are encompassed by the present invention: wherein K143 is substituted with either an A, C, D, E, F, G, H, I, L, M, N, P, Q, R, S, T, V, W, or Y; wherein P144 is substituted with either an A, C, D, E, F, G, H, I, K, L, M, N, Q, R, S, T, V, W, or Y; wherein A145 is substituted with either a C, D, E, F, G, H, I, K, L, M, N, P, Q, R, S, T, V, W, or Y; wherein A146 is substituted with either a C, D, E, F, G, H, I, K, L, M, N, P, Q, R, S, T, V, W, or Y; wherein K147 is substituted with either an A, C, D, E, F, G, H, I, L, M, N, P, Q, R, S, T, V, W, or Y; wherein S148 is substituted with either an A, C, D, E, F, G, H, I, K, L, M, N, P, Q, R, T, V, W, or Y; wherein R149 is substituted with either an A, C, D, E, F, G, H, I, K, L, M, N, P, Q, S, T, V, W, or Y; wherein G150 is substituted with either an A, C, D, E, F, H, I, K, L, M, N, P, Q, R, S, T, V, W, or Y; wherein R151 is substituted with either an A, C, D, E, F, G, H, I, K, L, M, N, P, Q, S, T, V, W, or Y; wherein D152 is substituted with either an A, C, E, F, G, H, I, K, L, M, N, P, Q, R, S, T, V, W, or Y; wherein I153 is substituted with either an A, C, D, E, F, G, H, K, L, M, N, P, Q, R, S, T, V, W, or Y; wherein V154 is substituted with either an A, C, D, E, F, G, H, I, K, L, M, N, P, Q, R, S, T, W, or Y; wherein C155 is substituted with either an A, D, E, F, G, H, I, K, L, M, N, P, Q, R, S, T, V, W, or Y; wherein M156 is substituted with either an A, C, D, E, F, G, H, I, K, L, N, P, Q, R, S, T, V, W, or Y; wherein D157 is substituted with either an A, C, E, F, G, H, I, K, L, M, N, P, Q, R, S, T, V, W, or Y; wherein R158 is substituted with either an A, C, D, E, F, G, H, I, K, L, M, N, P, Q, S, T, V, W, or Y; wherein V159 is substituted with either an A, C, D, E, F, G, H, I, K, L, M, N, P, Q, R, S, T, W, or Y; wherein E160 is substituted with either an A, C, D, F, G, H, I, K, L, M, N, P, Q, R, S, T, V, W, or Y; wherein E161 is substituted with either an A, C, D, F, G, H, I, K, L, M, N, P, Q, R, S, T, V, W, or Y; wherein I162 is substituted with either an A, C, D, E, F, G, H, K, L, M, N, P, Q, R, S, T, V, W, or Y; wherein L163 is substituted with either an A, C, D, E, F, G, H, I, K, M, N, P, Q, R, S, T, V, W, or Y; wherein E164 is substituted with either an A, C, D, F, G, H, I, K, L, M, N, P, Q, R, S, T, V, W, or Y; wherein L165 is substituted with either an A, C, D, E, F, G, H, I, K, M, N, P, Q, R, S, T, V, W, or Y; wherein A166 is substituted with either a C, D, E, F, G, H, I, K, L, M, N, P, Q, R, S, T, V, W, or Y; wherein A167 is substituted with either a C, D, E, F, G, H, I, K, L, M, N, P, Q, R, S, T, V, W, or Y; wherein A168 is substituted with either a C, D, E, F, G, H, I, K, L, M, N, P, Q, R, S, T, V, W, or Y; wherein D169 is substituted with either an A, C, E, F, G, H, I, K, L, M, N, P, Q, R, S, T, V, W, or Y; wherein H170 is substituted with either an A, C, D, E, F, G, I, K, L, M, N, P, Q, R, S, T, V, W, or Y; wherein P171 is substituted with either an A, C, D, E, F, G, H, I, K, L, M, N, Q, R, S, T, V, W, or Y; wherein L172 is substituted with either an A, C, D, E, F, G, H, I, K, M, N, P, Q, R, S, T, V, W, or Y; wherein S173 is substituted with either an A, C, D, E, F, G, H, I, K, L, M, N, P, Q, R, T, V, W, or Y; wherein R174 is substituted with either an A, C, D, E, F, G, H, I, K, L, M, N, P, Q, S, T, V, W, or Y; wherein D175 is substituted with either an A, C, E, F, G, H, I, K, L, M, N, P, Q, R, S, T, V, W, or Y; wherein N176 is substituted with either an A, C, D, E, F, G, H, I, K, L, M, P, Q, R, S, T, V, W, or Y; wherein K177 is substituted with either an A, C, D, E, F, G, H, I, L, M, N, P, Q, R, S, T, V, W, or Y; wherein W178 is substituted with either an A, C, D, E, F, G, H, I, K, L, M, N, P, Q, R, S, T, V, or Y; wherein V179 is substituted with either an A, C, D, E, F, G, H, I, K, L, M, N, P, Q, R, S, T, W, or Y; wherein V180 is substituted with either an A, C, D, E, F, G, H, I, K, L, M, N, P, Q, R, S, T, W, or Y; wherein Q181 is substituted with either an A, C, D, E, F, G, H, I, K, L, M, N, P, R, S, T, V, W, or Y; wherein K182 is substituted with either an A, C, D, E, F, G, H, I, L, M, N, P, Q, R, S, T, V, W, or Y; wherein Y183 is substituted with either an A, C, D, E, F, G, H, I, K, L, M, N, P, Q, R, S, T, V, or W; wherein I184 is substituted with either an A, C, D, E, F, G, H, K, L, M, N, P, Q, R, S, T, V, W, or Y; wherein E185 is substituted with either an A, C, D, F, G, H, I, K, L, M, N, P, Q, R, S, T, V, W, or Y; wherein T186 is substituted with either an A, C, D, E, F, G, H, I, K, L, M, N, P, Q, R, S, V, W, or Y; wherein P187 is substituted with either an A, C, D, E, F, G, H, I, K, L, M, N, Q, R, S, T, V, W, or Y; wherein L188 is substituted with either an A, C, D, E, F, G, H, I, K, M, N, P, Q, R, S, T, V, W, or Y; wherein L189 is substituted with either an A, C, D, E, F, G, H, I, K, M, N, P, Q, R, S, T, V, W, or Y; wherein I190 is substituted with either an A, C, D, E, F, G, H, K, L, M, N, P, Q, R, S, T, V, W, or Y; wherein C191 is substituted with either an A, D, E, F, G, H, I, K, L, M, N, P, Q, R, S, T, V, W, or Y; wherein D192 is substituted with either an A, C, E, F, G, H, I, K, L, M, N, P, Q, R, S, T, V, W, or Y; wherein T193 is substituted with either an A, C, D, E, F, G, H, I, K, L, M, N, P, Q, R, S, V, W, or Y; wherein K194 is substituted with either an A, C, D, E, F, G, H, I, L, M, N, P, Q, R, S, T, V, W, or Y; wherein F195 is substituted with either an A, C, D, E, G, H, I, K, L, M, N, P, Q, R, S, T, V, W, or Y; wherein D196 is substituted with either an A, C, E, F, G, H, I, K, L, M, N, P, Q, R, S, T, V, W, or Y; wherein I197 is substituted with either an A, C, D, E, F, G, H, K, L, M, N, P, Q, R, S, T, V, W, or Y; wherein R198 is substituted with either an A, C, D, E, F, G, H, I, K, L, M, N, P, Q, S, T, V, W, or Y; wherein Q199 is substituted with either an A, C, D, E, F, G, H, I, K, L, M, N, P, R, S, T, V, W, or Y; wherein W200 is substituted with either an A, C, D, E, F, G, H, I, K, L, M, N, P, Q, R, S, T, V, or Y; wherein F201 is substituted with either an A, C, D, E, G, H, I, K, L, M, N, P, Q, R, S, T, V, W, or Y; wherein L202 is substituted with either an A, C, D, E, F, G, H, I, K, M, N, P, Q, R, S, T, V, W, or Y; wherein V203 is substituted with either an A, C, D, E, F, G, H, I, K, L, M, N, P, Q, R, S, T, W, or Y; wherein T204 is substituted with either an A, C, D, E, F, G, H, I, K, L, M, N, P, Q, R, S, V, W, or Y; wherein D205 is substituted with either an A, C, E, F, G, H, I, K, L, M, N, P, Q, R, S, T, V, W, or Y; wherein W206 is substituted with either an A, C, D, E, F, G, H, I, K, L, M, N, P, Q, R, S, T, V, or Y; wherein N207 is substituted with either an A, C, D, E, F, G, H, I, K, L, M, P, Q, R, S, T, V, W, or Y; wherein P208 is substituted with either an A, C, D, E, F, G, H, I, K, L, M, N, Q, R, S, T, V, W, or Y; wherein L209 is substituted with either an A, C, D, E, F, G, H, I, K, M, N, P, Q, R, S, T, V, W, or Y; wherein T210 is substituted with either an A, C, D, E, F, G, H, I, K, L, M, N, P, Q, R, S, V, W, or Y; wherein I211 is substituted with either an A, C, D, E, F, G, H, K, L, M, N, P, Q, R, S, T, V, W, or Y; wherein W212 is substituted with either an A, C, D, E, F, G, H, I, K, L, M, N, P, Q, R, S, T, V, or Y; wherein F213 is substituted with either an A, C, D, E, G, H, I, K, L, M, N, P, Q, R, S, T, V, W, or Y; wherein Y214 is substituted with either an A, C, D, E, F, G, H, I, K, L, M, N, P, Q, R, S, T, V, or W; wherein K215 is substituted with either an A, C, D, E, F, G, H, I, L, M, N, P, Q, R, S, T, V, W, or Y; wherein E216 is substituted with either an A, C, D, F, G, H, I, K, L, M, N, P, Q, R, S, T, V, W, or Y; wherein S217 is substituted with either an A, C, D, E, F, G, H, I, K, L, M, N, P, Q, R, T, V, W, or Y; wherein Y218 is substituted with either an A, C, D, E, F, G, H, I, K, L, M, N, P, Q, R, S, T, V, or W; wherein L219 is substituted with either an A, C, D, E, F, G, H, I, K, M, N, P, Q, R, S, T, V, W, or Y; wherein R220 is substituted with either an A, C, D, E, F, G, H, I, K, L, M, N, P, Q, S, T, V, W, or Y; wherein F221 is substituted with either an A, C, D, E, G, H, I, K, L, M, N, P, Q, R, S, T, V, W, or Y; wherein S222 is substituted with either an A, C, D, E, F, G, H, I, K, L, M, N, P, Q, R, T, V, W, or Y; wherein T223 is substituted with either an A, C, D, E, F, G, H, I, K, L, M, N, P, Q, R, S, V, W, or Y; wherein Q224 is substituted with either an A, C, D, E, F, G, H, I, K, L, M, N, P, R, S, T, V, W, or Y; wherein R225 is substituted with either an A, C, D, E, F, G, H, I, K, L, M, N, P, Q, S, T, V, W, or Y; wherein F226 is substituted with either an A, C, D, E, G, H, I, K, L, M, N, P, Q, R, S, T, V, W, or Y; wherein S227 is substituted with either an A, C, D, E, F, G, H, I, K, L, M, N, P, Q, R, T, V, W, or Y; wherein L228 is substituted with either an A, C, D, E, F, G, H, I, K, M, N, P, Q, R, S, T, V, W, or Y; wherein D229 is substituted with either an A, C, E, F, G, H, I, K, L, M, N, P, Q, R, S, T, V, W, or Y; wherein K230 is substituted with either an A, C, D, E, F, G, H, I, L, M, N, P, Q, R, S, T, V, W, or Y; wherein L231 is substituted with either an A, C, D, E, F, G, H, I, K, M, N, P, Q, R, S, T, V, W, or Y; wherein D232 is substituted with either an A, C, E, F, G, H, I, K, L, M, N, P, Q, R, S, T, V, W, or Y; wherein S233 is substituted with either an A, C, D, E, F, G, H, I, K, L, M, N, P, Q, R, T, V, W, or Y; wherein A234 is substituted with either a C, D, E, F, G, H, I, K, L, M, N, P, Q, R, S, T, V, W, or Y; wherein I235 is substituted with either an A, C, D, E, F, G, H, K, L, M, N, P, Q, R, S, T, V, W, or Y; wherein H236 is substituted with either an A, C, D, E, F, G, I, K, L, M, N, P, Q, R, S, T, V, W, or Y; wherein L237 is substituted with either an A, C, D, E, F, G, H, I, K, M, N, P, Q, R, S, T, V, W, or Y; wherein C238 is substituted with either an A, D, E, F, G, H, I, K, L, M, N, P, Q, R, S, T, V, W, or Y; wherein N239 is substituted with either an A, C, D, E, F, G, H, I, K, L, M, P, Q, R, S, T, V, W, or Y; wherein N240 is substituted with either an A, C, D, E, F, G, H, I, K, L, M, P, Q, R, S, T, V, W, or Y; wherein A241 is substituted with either a C, D, E, F, G, H, I, K, L, M, N, P, Q, R, S, T, V, W, or Y; wherein V242 is substituted with either an A, C, D, E, F, G, H, I, K, L, M, N, P, Q, R, S, T, W, or Y; wherein Q243 is substituted with either an A, C, D, E, F, G, H, I, K, L, M, N, P, R, S, T, V, W, or Y; wherein K244 is substituted with either an A, C, D, E, F, G, H, I, L, M, N, P, Q, R, S, T, V, W, or Y; wherein Y245 is substituted with either an A, C, D, E, F, G, H, I, K, L, M, N, P, Q, R, S, T, V, or W; wherein L246 is substituted with either an A, C, D, E, F, G, H, I, K, M, N, P, Q, R, S, T, V, W, or Y; wherein K247 is substituted with either an A, C, D, E, F, G, H, I, L, M, N, P, Q, R, S, T, V, W, or Y; wherein N248 is substituted with either an A, C, D, E, F, G, H, I, K, L, M, P, Q, R, S, T, V, W, or Y; wherein D249 is substituted with either an A, C, E, F, G, H, I, K, L, M, N, P, Q, R, S, T, V, W, or Y; wherein V250 is substituted with either an A, C, D, E, F, G, H, I, K, L, M, N, P, Q, R, S, T, W, or Y; wherein G251 is substituted with either an A, C, D, E, F, H, I, K, L, M, N, P, Q, R, S, T, V, W, or Y; wherein R252 is substituted with either an A, C, D, E, F, G, H, I, K, L, M, N, P, Q, S, T, V, W, or Y; wherein S253 is substituted with either an A, C, D, E, F, G, H, I, K, L, M, N, P, Q, R, T, V, W, or Y; wherein P254 is substituted with either an A, C, D, E, F, G, H, I, K, L, M, N, Q, R, S, T, V, W, or Y; wherein L255 is substituted with either an A, C, D, E, F, G, H, I, K, M, N, P, Q, R, S, T, V, W, or Y; wherein L256 is substituted with either an A, C, D, E, F, G, H, I, K, M, N, P, Q, R, S, T, V, W, or Y; wherein P257 is substituted with either an A, C, D, E, F, G, H, I, K, L, M, N, Q, R, S, T, V, W, or Y; wherein A258 is substituted with either a C, D, E, F, G, H, I, K, L, M, N, P, Q, R, S, T, V, W, or Y; wherein H259 is substituted with either an A, C, D, E, F, G, I, K, L, M, N, P, Q, R, S, T, V, W, or Y; wherein N260 is substituted with either an A, C, D, E, F, G, H, I, K, L, M, P, Q, R, S, T, V, W, or Y; wherein M261 is substituted with either an A, C, D, E, F, G, H, I, K, L, N, P, Q, R, S, T, V, W, or Y; wherein W262 is substituted with either an A, C, D, E, F, G, H, I, K, L, M, N, P, Q, R, S, T, V, or Y; wherein T263 is substituted with either an A, C, D, E, F, G, H, I, K, L, M, N, P, Q, R, S, V, W, or Y; wherein S264 is substituted with either an A, C, D, E, F, G, H, I, K, L, M, N, P, Q, R, T, V, W, or Y; wherein T265 is substituted with either an A, C, D, E, F, G, H, I, K, L, M, N, P, Q, R, S, V, W, or Y; wherein R266 is substituted with either an A, C, D, E, F, G, H, I, K, L, M, N, P, Q, S, T, V, W, or Y; wherein F267 is substituted with either an A, C, D, E, G, H, I, K, L, M, N, P, Q, R, S, T, V, W, or Y; wherein Q268 is substituted with either an A, C, D, E, F, G, H, I, K, L, M, N, P, R, S, T, V, W, or Y; wherein E269 is substituted with either an A, C, D, F, G, H, I, K, L, M, N, P, Q, R, S, T, V, W, or Y; wherein Y270 is substituted with either an A, C, D, E, F, G, H, I, K, L, M, N, P, Q, R, S, T, V, or W; wherein L271 is substituted with either an A, C, D, E, F, G, H, I, K, M, N, P, Q, R, S, T, V, W, or Y; wherein Q272 is substituted with either an A, C, D, E, F, G, H, I, K, L, M, N, P, R, S, T, V, W, or Y; wherein R273 is substituted with either an A, C, D, E, F, G, H, I, K, L, M, N, P, Q, S, T, V, W, or Y; wherein Q274 is substituted with either an A, C, D, E, F, G, H, I, K, L, M, N, P, R, S, T, V, W, or Y; wherein G275 is substituted with either an A, C, D, E, F, H, I, K, L, M, N, P, Q, R, S, T, V, W, or Y; wherein R276 is substituted with either an A, C, D, E, F, G, H, I, K, L, M, N, P, Q, S, T, V, W, or Y; wherein G277 is substituted with either an A, C, D, E, F, H, I, K, L, M, N, P, Q, R, S, T, V, W, or Y; wherein A278 is substituted with either a C, D, E, F, G, H, I, K, L, M, N, P, Q, R, S, T, V, W, or Y; wherein V279 is substituted with either an A, C, D, E, F, G, H, I, K, L, M, N, P, Q, R, S, T, W, or Y; wherein W280 is substituted with either an A, C, D, E, F, G, H, I, K, L, M, N, P, Q, R, S, T, V, or Y; wherein G281 is substituted with either an A, C, D, E, F, H, I, K, L, M, N, P, Q, R, S, T, V, W, or Y; wherein S282 is substituted with either an A, C, D, E, F, G, H, I, K, L, M, N, P, Q, R, T, V, W, or Y; and/or wherein V283 is substituted with either an A, C, D, E, F, G, H, I, K, L, M, N, P, Q, R, S, T, W, or Y of SEQ ID NO:2, in addition to any combination thereof. The present invention also encompasses the use of these BGS-42 active site domain amino acid substituted polypeptides as immunogenic and/or antigenic epitopes as described elsewhere herein.

In preferred embodiments, the following BGS-42 active site domain conservative amino acid substitutions are encompassed by the present invention: wherein K143 is substituted with either a R, or H; wherein P144 is a P; wherein A145 is substituted with either a G, I, L, M, S, T, or V; wherein A146 is substituted with either a G, I, L, M, S, T, or V; wherein K147 is substituted with either a R, or H;

wherein S148 is substituted with either an A, G, M, or T; wherein R149 is substituted with either a K, or H; wherein G150 is substituted with either an A, M, S, or T; wherein R151 is substituted with either a K, or H; wherein D152 is substituted with an E; wherein I153 is substituted with either an A, V, or L; wherein V154 is substituted with either an A, I, or L; wherein C155 is a C; wherein M156 is substituted with either an A, G, S, or T; wherein D157 is substituted with an E; wherein R158 is substituted with either a K, or H; wherein V159 is substituted with either an A, I, or L; wherein E160 is substituted with a D; wherein E161 is substituted with a D; wherein I162 is substituted with either an A, V, or L; wherein L163 is substituted with either an A, I, or V; wherein E164 is substituted with a D; wherein L165 is substituted with either an A, I, or V; wherein A166 is substituted with either a G, I, L, M, S, T, or V; wherein A167 is substituted with either a G, I, L, M, S, T, or V; wherein A168 is substituted with either a G, I, L, M, S, T, or V; wherein D169 is substituted with an E; wherein H170 is substituted with either a K, or R; wherein P171 is a P; wherein L172 is substituted with either an A, I, or V; wherein S173 is substituted with either an A, G, M, or T; wherein R174 is substituted with either a K, or H; wherein D175 is substituted with an E; wherein N176 is substituted with a Q; wherein K177 is substituted with either a R, or H; wherein W178 is either an F, or Y; wherein V179 is substituted with either an A, I, or L; wherein V180 is substituted with either an A, I, or L; wherein Q181 is substituted with a N; wherein K182 is substituted with either a R, or H; wherein Y183 is either an F, or W; wherein I184 is substituted with either an A, V, or L; wherein E185 is substituted with a D; wherein T186 is substituted with either an A, G, M, or S; wherein P187 is a P; wherein L188 is substituted with either an A, I, or V; wherein L189 is substituted with either an A, I, or V; wherein I190 is substituted with either an A, V, or L; wherein C191 is a C; wherein D192 is substituted with an E; wherein T193 is substituted with either an A, G, M, or S; wherein K194 is substituted with either a R, or H; wherein F195 is substituted with either a W, or Y; wherein D196 is substituted with an E; wherein I197 is substituted with either an A, V, or L; wherein R198 is substituted with either a K, or H; wherein Q199 is substituted with a N; wherein W200 is either an F, or Y; wherein F201 is substituted with either a W, or Y; wherein L202 is substituted with either an A, I, or V; wherein V203 is substituted with either an A, I, or L; wherein T204 is substituted with either an A, G, M, or S; wherein D205 is substituted with an E; wherein W206 is either an F, or Y; wherein N207 is substituted with a Q; wherein P208 is a P; wherein L209 is substituted with either an A, I, or V; wherein T210 is substituted with either an A, G, M, or S; wherein I211 is substituted with either an A, V, or L; wherein W212 is either an F, or Y; wherein F213 is substituted with either a W, or Y; wherein Y214 is either an F, or W; wherein K215 is substituted with either a R, or H; wherein E216 is substituted with a D; wherein S217 is substituted with either an A, G, M, or T; wherein Y218 is either an F, or W; wherein L219 is substituted with either an A, I, or V; wherein R220 is substituted with either a K, or H; wherein F221 is substituted with either a W, or Y; wherein S222 is substituted with either an A, G, M, or T; wherein T223 is substituted with either an A, G, M, or S; wherein Q224 is substituted with a N; wherein R225 is substituted with either a K, or H; wherein F226 is substituted with either a W, or Y; wherein S227 is substituted with either an A, G, M, or T; wherein L228 is substituted with either an A, I, or V; wherein D229 is substituted with an E; wherein K230 is substituted with either a R, or H; wherein L231 is substituted with either an A, I, or V; wherein D232 is substituted with an E; wherein S233 is substituted with either an A, G, M, or T; wherein A234 is substituted with either a G, I, L, M, S, T, or V; wherein I235 is substituted with either an A, V, or L; wherein H236 is substituted with either a K, or R; wherein L237 is substituted with either an A, I, or V; wherein C238 is a C; wherein N239 is substituted with a Q; wherein N240 is substituted with a Q; wherein A241 is substituted with either a G, I, L, M, S, T, or V; wherein V242 is substituted with either an A, I, or L; wherein Q243 is substituted with a N; wherein K244 is substituted with either a R, or H; wherein Y245 is either an F, or W; wherein L246 is substituted with either an A, I, or V; wherein K247 is substituted with either a R, or H; wherein N248 is substituted with a Q; wherein D249 is substituted with an E; wherein V250 is substituted with either an A, I, or L; wherein G251 is substituted with either an A, M, S, or T; wherein R252 is substituted with either a K, or H; wherein S253 is substituted with either an A, G, M, or T; wherein P254 is a P; wherein L255 is substituted with either an A, I, or V; wherein L256 is substituted with either an A, I, or V; wherein P257 is a P; wherein A258 is substituted with either a G, I, L, M, S, T, or V; wherein H259 is substituted with either a K, or R; wherein N260 is substituted with a Q; wherein M261 is substituted with either an A, G, S, or T; wherein W262 is either an F, or Y; wherein T263 is substituted with either an A, G, M, or S; wherein S264 is substituted with either an A, G, M, or T; wherein T265 is substituted with either an A, G, M, or S; wherein R266 is substituted with either a K, or H; wherein F267 is substituted with either a W, or Y; wherein Q268 is substituted with a N; wherein E269 is substituted with a D; wherein Y270 is either an F, or W; wherein L271 is substituted with either an A, I, or V; wherein Q272 is substituted with a N; wherein R273 is substituted with either a K, or H; wherein Q274 is substituted with a N; wherein G275 is substituted with either an A, M, S, or T; wherein R276 is substituted with either a K, or H; wherein G277 is substituted with either an A, M, S, or T; wherein A278 is substituted with either a G, I, L, M, S, T, or V; wherein V279 is substituted with either an A, I, or L; wherein W280 is either an F, or Y; wherein G281 is substituted with either an A, M, S, or T; wherein S282 is substituted with either an A, G, M, or T; and/or wherein V283 is substituted with either an A, I, or L of SEQ ID NO:2 in addition to any combination thereof. Other suitable substitutions within the BGS-42 active site domain are encompassed by the present invention and are referenced elsewhere herein. The present invention also encompasses the use of these BGS-42 active site domain conservative amino acid substituted polypeptides as immunogenic and/or antigenic epitopes as described elsewhere herein.

Many polynucleotide sequences, such as EST sequences, are publicly available and accessible through sequence databases. Some of these sequences are related to SEQ ID NO: 1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a-b, where a is any integer between 1 to 1824 of SEQ ID NO:1, b is an integer between 15 to 1838, where both a and b correspond to the positions of nucleotide residues shown in SEQ ID NO:1, and where b is greater than or equal to a+14.

In one embodiment, a BGS-42 polypeptide comprises a portion of the amino sequence depicted in FIGS. 1A–C. In another embodiment, a BGS-42 polypeptide comprises at least 4, 5, 6, 7, 8, 9, 10, 11, 12, 13, 14, 15, 16, 17, 18, 19 or 20 amino acids of the amino sequence depicted in Figures FIGS. 1A–C. In further embodiments, the following BGS-42 polypeptide fragments are specifically excluded from the present invention: KWVVQKYIE (SEQ ID NO:15); RQW-FLVTDWNPLT (SEQ ID NO:16); SFELYGADFV (SEQ ID NO:17); QWFLVTDWNPLT (SEQ ID NO:18); NIWIIK-PAAKSRGRDIVCMDRVE (SEQ ID NO:19); DNKWV-VQKYIETP (SEQ ID NO:20); DTKFDIRQWFLVTDWN-PLTIWFYKESYLRFSTQRFSLDKLDSAIHLCNN (SEQ ID NO:21); SSPTMHPSTPVTAQLCAQVQEDTIKV (SEQ ID NO:22); CDIGNFELLWRQP (SEQ ID NO:23); LPACPCRHVDSQAPNTGVPVAQPAKSWD-PNQLNAHPLEPVLR (SEQ ID NO:24); and/or LKTAE-GALRPPPGGKGS (SEQ ID NO:25).

acid molecules in biological samples, thereby enabling a variety of forensic and diagnostic methods of the invention. Similarly, polypeptides identified from SEQ ID NO:Y may be used, for example, to generate antibodies which bind specifically to proteins containing the polypeptides and the proteins encoded by the cDNA clones identified in Table I.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acid sequence, even though the generated DNA sequence may be greater than 99.9% iden-

TABLE I

| Gene No. | cDNA Clone ID | ATCC Deposit No. Z and Date | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| 1. | BGS-42 | PTA-4454 Jun. 12, 2002 | pSport1 | 1 | 1838 | 153 | 1775 | 2 | 541 |

Table I summarizes the information corresponding to each "Gene No." described above. The nucleotide sequence identified as "NT SEQ ID NO:X" was assembled from partially homologous ("overlapping") sequences obtained from the "cDNA clone ID" identified in Table I and, in some cases, from additional related DNA clones. The overlapping sequences were assembled into a single contiguous sequence of high redundancy (usually several overlapping sequences at each nucleotide position), resulting in a final sequence identified as SEQ ID NO:X.

The cDNA Clone ID was deposited on the date and given the corresponding deposit number listed in "ATCC Deposit No:Z and Date." "Vector" refers to the type of vector contained in the cDNA Clone ID.

"Total NT Seq. Of Clone" refers to the total number of nucleotides in the clone contig identified by "Gene No." The deposited clone may contain all or most of the sequence of SEQ ID NO:X. The nucleotide position of SEQ ID NO:X of the putative start codon (methionine) is identified as "5' NT of Start Codon of ORF."

The translated amino acid sequence, beginning with the methionine, is identified as "AA SEQ ID NO:Y" although other reading frames can also be easily translated using known molecular biology techniques. The polypeptides produced by these alternative open reading frames are specifically contemplated by the present invention.

The total number of amino acids within the open reading frame of SEQ ID NO:Y is identified as "Total AA of ORF".

SEQ ID NO:X (where X may be any of the polynucleotide sequences disclosed in the sequence listing) and the translated SEQ ID NO:Y (where Y may be any of the polypeptide sequences disclosed in the sequence listing) are sufficiently accurate and otherwise suitable for a variety of uses well known in the art and described further herein. For instance, SEQ ID NO:X is useful for designing nucleic acid hybridization probes that will detect nucleic acid sequences contained in SEQ ID NO:X or the cDNA contained in the deposited clone. These probes will also hybridize to nucleic tical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:1 and the predicted translated amino acid sequence identified as SEQ ID NO:2, but also a sample of plasmid DNA containing a cDNA of the invention deposited with the ATCC, as set forth in Table I. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited cDNA, collecting the protein, and determining its sequence.

The present invention also relates to the genes corresponding to SEQ ID NO:1, SEQ ID NO:2, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologues of genes corresponding to SEQ ID NO:1, SEQ ID NO:2, or a deposited clone, relying on the sequence from the sequences disclosed herein or the clones deposited with the ATCC. For example, allelic variants and/or species homologues may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, can be substantially purified using techniques described herein or otherwise known in the art, such as, for example, by the one-step method described in Smith and Johnson, Gene 67:31–40 (1988). Polypeptides of the invention also can be purified from natural, synthetic or recombinant sources using protocols described herein or otherwise known in the art, such as, for example, antibodies of the invention raised against the full-length form of the protein.

The present invention provides a polynucleotide comprising, or alternatively consisting of, the sequence identified as SEQ ID NO:1, and/or a cDNA provided in ATCC Deposit No. Z:. The present invention also provides a polypeptide comprising, or alternatively consisting of, the sequence identified as SEQ ID NO:2, and/or a polypeptide encoded by the cDNA provided in ATCC Deposit NO:Z. The present invention also provides polynucleotides encoding a polypeptide comprising, or alternatively consisting of the polypeptide sequence of SEQ ID NO:2, and/or a polypeptide sequence encoded by the cDNA contained in ATCC Deposit No:Z.

Preferably, the present invention is directed to a polynucleotide comprising, or alternatively consisting of, the sequence identified as SEQ ID NO:1, and/or a cDNA provided in ATCC Deposit No.: that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:1, the sequence contained in a deposit, and/or the nucleic acid sequence encoding the sequence disclosed as SEQ ID NO:2.

The present invention also encompasses polynucleotides capable of hybridizing, preferably under reduced stringency conditions, more preferably under stringent conditions, and most preferably under highly stringent conditions, to polynucleotides described herein. Examples of stringency conditions are shown in Table II below: highly stringent conditions are those that are at least as stringent as, for example, conditions A–F; stringent conditions are at least as stringent as, for example, conditions G–L; and reduced stringency conditions are at least as stringent as, for example, conditions M–R.

TABLE II

| Stringency Condition | Polynucleotide Hybrid± | Hybrid Length (bp)‡ | Hybridization Temperature and Buffer† | Wash Temperature and Buffer† |
|---|---|---|---|---|
| A | DNA:DNA | >or equal to 50 | 65° C.; 1xSSC - or- 42° C.; 1xSSC, 50% formamide | 65° C.; 0.3xSSC |
| B | DNA:DNA | <50 | Tb*; 1xSSC | Tb*; 1xSSC |
| C | DNA:RNA | >or equal to 50 | 67° C.; 1xSSC - or- 45° C.; 1xSSC, 50% formamide | 67° C.; 0.3xSSC |
| D | DNA:RNA | <50 | Td*; 1xSSC | Td*; 1xSSC |
| E | RNA:RNA | >or equal to 50 | 70° C.; 1xSSC - or- 50° C.; 1xSSC, 50% formamide | 70° C.; 0.3xSSC |
| F | RNA:RNA | <50 | Tf*; 1xSSC | Tf*; 1xSSC |
| G | DNA:DNA | >or equal to 50 | 65° C.; 4xSSC - or- 45° C.; 4xSSC, 50% formamide | 65° C.; 1xSSC |
| H | DNA:DNA | <50 | Th*; 4xSSC | Th*; 4xSSC |
| I | DNA:RNA | >or equal to 50 | 67° C.; 4xSSC - or- 45° C.; 4xSSC, 50% formamide | 67° C.; 1xSSC |
| J | DNA:RNA | <50 | Tj*; 4xSSC | Tj*; 4xSSC |
| K | RNA:RNA | >or equal to 50 | 70° C.; 4xSSC - or- 40° C.; 6xSSC, 50% formamide | 67° C.; 1xSSC |

TABLE II-continued

| Stringency Condition | Polynucleotide Hybrid± | Hybrid Length (bp)‡ | Hybridization Temperature and Buffer† | Wash Temperature and Buffer† |
|---|---|---|---|---|
| L | RNA:RNA | <50 | Tl*; 2xSSC | Tl*; 2xSSC |
| M | DNA:DNA | >or equal to 50 | 50° C.; 4xSSC - or- 40° C. 6xSSC, 50% formamide | 50° C.; 2xSSC |
| N | DNA:DNA | <50 | Tn*; 6xSSC | Tn*; 6xSSC |
| O | DNA:RNA | >or equal to 50 | 55° C.; 4xSSC - or- 42° C.; 6xSSC, 50% formamide | 55° C.; 2xSSC |
| P | DNA:RNA | <50 | Tp*; 6xSSC | Tp*; 6xSSC |
| Q | RNA:RNA | >or equal to 50 | 60° C.; 4xSSC - or- 45° C.; 6xSSC, 50% formamide | 60° C.; 2xSSC |
| R | RNA:RNA | <50 | Tr*; 4xSSC | Tr*; 4xSSC |

‡The "hybrid length" is the anticipated length for the hybridized region(s) of the hybridizing polynucleotides. When hybridizing a polynucleotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., MegAlign program of the DNA*Star suite of programs, etc).
†SSPE (1xSSPE is 0.15 M NaCl, 10 mM NaH2PO4, and 1.25 mM EDTA, pH 7.4) can be substituted for SSC (1xSSC is 0.15 M NaCl and 15 mM sodium citrate) in the hybridization and wash buffers; washes are performed for 15 minutes after hybridization is complete. The hydridizations and washes may additionally include 5X Denhardt's reagent, .5–1.0% SDS, 100 ug/ml denatured, fragmented salmon sperm DNA, 0.5% sodium pyrophosphate, and up to 50% formamide.
*Tb – Tr: The hybridization temperature for hybrids anticipated to be less than 50 base pairs in length should be 5–10° C. less than the melting temperature Tm of the hybrids there Tm is determined according to the following equations. For hybrids less than 18 base pairs in length, Tm(° C.) = 2(# of A + T bases) + 4(# of G + C bases). For hybrids between 18 and 49 base pairs in length, Tm(° C.) = 81.5 + 16.6(log$_{10}$[Na+]) + 0.41 (% G + C) – (600/N), where N is the number of bases in the hybrid, and [Na+] is the concentration of sodium ions in the hybridization buffer ([Na+] for 1xSSC = .165 M).
±The present invention encompasses the substitution of any one, or more DNA or RNA hybrid partners with either a PNA, or a modified polynucleotide. Such modified polynucleotides are known in the art and are more particularly described elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3–6.4, which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

The invention encompasses the application of PCR methodology to the polynucleotide sequences of the present invention, the clone deposited with the ATCC, and/or the cDNA encoding the polypeptides of the present invention. PCR techniques for the amplification of nucleic acids are described in U.S. Pat. No. 4,683,195 and Saiki et al., Science, 239:487–491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, N.Y., 1989; Ehrlich et al., Science, 252:1643–1650, (1991); and "PCR Protocols, A Guide to Methods and Applications", Eds., Innis et al., Academic Press, New York, (1990).

Polynucleotide and Polypeptide Variants

The present invention also encompasses variants (e.g., allelic variants, orthologs, etc.) of the polynucleotide sequence disclosed herein in SEQ ID NO:1, the complementary strand thereto, and/or the cDNA sequence contained in the deposited clone.

The present invention also encompasses variants of the polypeptide sequence, and/or fragments therein, disclosed in SEQ ID NO:2, a polypeptide encoded by the polynucleotide sequence in SEQ ID NO:1, and/or a polypeptide encoded by a cDNA in the deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence encoding a BGS-42 related polypeptide having an amino acid sequence as shown in the sequence listing and described in SEQ ID NO:1 or the cDNA contained in ATCC deposit No:Z; (b) a nucleotide sequence encoding a mature BGS-42 related polypeptide having the amino acid sequence as shown in the sequence listing and described in SEQ ID NO:1 or the cDNA contained in ATCC deposit No:Z; (c) a nucleotide sequence encoding a biologically active fragment of a BGS-42 related polypeptide having an amino acid sequence shown in the sequence listing and described in SEQ ID NO:1 or the cDNA contained in ATCC deposit No:Z; (d) a nucleotide sequence encoding an antigenic fragment of a BGS-42 related polypeptide having an amino acid sequence sown in the sequence listing and described in SEQ ID NO:1 or the cDNA contained in ATCC deposit No:Z; (e) a nucleotide sequence encoding a BGS-42 related polypeptide comprising the complete amino acid sequence encoded by a human cDNA plasmid contained in SEQ ID NO:1 or the cDNA contained in ATCC deposit No:Z; (f) a nucleotide sequence encoding a mature BGS-42 related polypeptide having an amino acid sequence encoded by a human cDNA plasmid contained in SEQ ID NO:1 or the cDNA contained in ATCC deposit No:Z; (g) a nucleotide sequence encoding a biologically active fragment of a BGS-42 related polypeptide having an amino acid sequence encoded by a human cDNA plasmid contained in SEQ ID NO:1 or the cDNA contained in ATCC deposit No:Z; (h) a nucleotide sequence encoding an antigenic fragment of a BGS-42 related polypeptide having an amino acid sequence encoded by a human cDNA plasmid contained in SEQ ID NO:1 or the cDNA contained in ATCC deposit No:Z; (I) a nucleotide sequence complimentary to any of the nucleotide sequences in (a), (b), (c), (d), (e), (f), (g), or (h), above.

The present invention is also directed to polynucleotide sequences which comprise, or alternatively consist of, a polynucleotide sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above. Polynucleotides encoded by these nucleic acid molecules are also encompassed by the invention. In another embodiment, the invention encompasses nucleic acid molecules which comprise, or alternatively consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

Another aspect of the invention provides an isolated nucleic acid molecule comprising, or alternatively, consisting of, a polynucleotide having a nucleotide sequence selected from the group consisting of: (a) a nucleotide sequence encoding a BGS-42 related polypeptide having an amino acid sequence as shown in the sequence listing and descried in Table I; (b) a nucleotide sequence encoding a mature BGS-42 related polypeptide having the amino acid sequence as shown in the sequence listing and descried in Table I; (c) a nucleotide sequence encoding a biologically active fragment of a BGS-42 related polypeptide having an amino acid sequence as shown in the sequence listing and descried in Table I; (d) a nucleotide sequence encoding an antigenic fragment of a BGS-42 related polypeptide having an amino acid sequence as shown in the sequence listing and descried in Table I; (e) a nucleotide sequence encoding a BGS-42 related polypeptide comprising the complete amino acid sequence encoded by a human cDNA in a cDNA plasmid contained in the ATCC Deposit and described in Table I; (f) a nucleotide sequence encoding a mature BGS-42 related polypeptide having an amino acid sequence encoded by a human cDNA in a cDNA plasmid contained in the ATCC Deposit and described in Table I: (g) a nucleotide sequence encoding a biologically active fragment of a BGS-42 related polypeptide having an amino acid sequence encoded by a human cDNA in a cDNA plasmid contained in the ATCC Deposit and described in Table I; (h) a nucleotide sequence encoding an antigenic fragment of a BGS-42 related polypeptide having an amino acid sequence encoded by a human cDNA in a cDNA plasmid contained in the ATCC deposit and described in Table I; (i) a nucleotide sequence complimentary to any of the nucleotide sequences in (a), (b), (c), (d), (e), (f), (g), or (h) above.

The present invention is also directed to nucleic acid molecules which comprise, or alternatively, consist of, a nucleotide sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, any of the nucleotide sequences in (a), (b), (c), (d), (e), (f), (g), or (h), above.

The present invention encompasses polypeptide sequences which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, the following non-limited examples, the polypeptide sequence identified as SEQ ID NO:2, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for example, the polypeptide sequence shown in SEQ ID NO:2, a polypeptide sequence encoded by the nucleotide sequence in SEQ ID NO:1, a polypeptide sequence encoded by the cDNA in cDNA plasmid:Z, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in Table I, the ORF (open reading frame), or any fragment specified as described herein.

As a practical matter, whether any particular nucleic acid molecule or polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673–4680, (1994)), which is based on the algorithm of Higgins, D. G., et al., Computer Applications in the Biosciences (CABIOS), 8(2):189–191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps: Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino- or carboxy-terminal positions of the reference amino acid sequence or anywhere between those terminal positions, interspersed either individually among residues in the reference sequence or in one or more contiguous groups within the reference sequence.

As a practical matter, whether any particular polypeptide is at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to, for instance, an amino acid sequence referenced in Table 1 (SEQ ID NO:2) or to the amino acid sequence encoded by cDNA contained in a deposited clone, can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673–4680, (1994)), which is based on the algorithm of Higgins, D. G., et al., Computer Applications in the Biosciences (CABIOS), 8(2):189–191, (1992). In a sequence alignment the query and subject sequences are both amino acid sequences. The result of said global sequence alignment is in percent identity. Preferred parameters used in a CLUSTALW alignment of DNA sequences to calculate percent identity via pairwise alignments are: Matrix=BLOSUM, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps:Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of N- or C-terminal deletions, not because of internal deletions. If only the local pairwise percent identity is required, no manual correction is needed. However, a manual correction may be applied to determine the global percent identity from a global polypeptide alignment. Percent identity calculations based upon global polypeptide alignments are often preferred since they reflect the percent identity between the polypeptide molecules as a whole (i.e., including any polypeptide overhangs, not just overlapping regions), as opposed to, only local matching polypeptides. Manual corrections for global percent identity determinations are required since the CLUSTALW program does not account for N- and C-terminal truncations of the subject sequence when calculating percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the CLUSTALW sequence alignment. This percentage is then subtracted from the percent identity, calculated by the above CLUSTALW program using the specified parameters, to arrive at a final percent identity score. This final percent identity score is what may be used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the CLUSTALW alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the CLUSTALW program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence, which are not matched/aligned with the query. In this case the percent identity calculated by CLUSTALW is not manually corrected. Once again, only residue positions outside the N- and C-terminal ends of the subject sequence, as displayed in the CLUSTALW alignment, which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modifed CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as E. coli).

Naturally occurring variants are called "allelic variants" and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem. 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein (Dobeli et al., J. Biotechnology 7:199–216 (1988)).

Moreover, ample evidence demonstrates that variants often retain a biological activity similar to that of the naturally occurring protein. For example, Gayle and coworkers (J. Biol. Chem. 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

Thus, the invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247: 1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306–1310 (1990).

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306–1310 (1990).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table III below.

TABLE III

| For Amino Acid | Code | Replace with any of: |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |

TABLE III-continued

| For Amino Acid | Code | Replace with any of: |
|---|---|---|
| Proline | P | D-Pro, L-1-thioazolidine-4-carboxylic acid, D- or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple genes with related function and assessing the relative penalty of each substitution to proper gene function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

Besides conservative amino acid substitution, variants of the present invention include, but are not limited to, the following: (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

Moreover, the invention further includes polypeptide variants created through the application of molecular evolution ("DNA Shuffling") methodology to the polynucleotide disclosed as SEQ ID NO:1, the sequence of the clone submitted in a deposit, and/or the cDNA encoding the polypeptide disclosed as SEQ ID NO:2. Such DNA Shuffling technology is known in the art and more particularly described elsewhere herein (e.g., WPC, Stemmer, PNAS, 91:10747, (1994)), and in the Examples provided herein).

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:1 or the complementary strand thereto, or is a portion of a polynucleotide sequence encoding the polypeptide of SEQ ID NO:2. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length" for example, is intended to include 20 or more contiguous bases from the cDNA sequence contained in a deposited clone or the nucleotide sequence shown in SEQ ID NO:1. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 175, 200, 225, 250, 275, 300, 325, 350, 375, 400, 425, 450, 475, 500, 525, 550, 575, 600, 650, 700, 750, 850, 900, 950, 1000, 1100, 1200, 1300, 1400, 1500, 1600, 1700, 1800, 1900, 2000 nucleotides) are preferred.

Moreover, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:1, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NO:2 or encoded by the cDNA contained in a deposited clone. Protein (polypeptide) fragments may be "free-standing" or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the full-length protein. Further preferred polypeptide fragments include the full-length protein having a continuous series of deleted residues from the amino or the carboxy terminus, or both. For example, any number of amino acids, ranging from 1–60, can be deleted from the amino terminus of the full-length polypeptide. Similarly, any number of amino acids, ranging from 1–30, can be deleted from the carboxy terminus of the full-length protein. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2 falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at lease one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in ATCC deposit No. Z or encoded by a polynucleotide that hybridizes to the complement of the sequence of SEQ ID NO:1 or contained in ATCC deposit No. Z under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes" as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope" as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope" as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length, or longer. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimido-benzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues.

The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605, 793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. 24:316–325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S. Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5\times10^{-2}$ M, $10^{-2}$ M, $5\times10^{-3}$ M, $10^{-3}$ M, $5\times10^{-4}$ M, $10^{-4}$ M, $5\times10^{-6}$ M, $10^{-6}$ M, $5\times10^{-7}$ M, $10^{7}$ M, $5\times10^{-8}$ M, $10^{-8}$ M, $5\times10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15): 3209–3214 (1998); Yoon et al., J. Immunol. 160(7):3170–3179 (1998); Prat et al., J. Cell. Sci. 111(Pt2): 237–247 (1998); Pitard et al., J. Immunol. Methods 205(2): 177–190 (1997); Liautard et al., Cytokine 9(4):233–241 (1997); Carlson et al., J. Biol. Chem. 272(17):11295–11301 (1997); Taryman et al., Neuron 14(4):755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988); and Current Protocols, Chapter 2; which are hereby incorporated herein by reference in its entirety). In a preferred method, a preparation of the BGS-42 protein is prepared and purified to render it substantially free of natural contaminants. Such a preparation is then introduced into an animal in order to produce polyclonal antisera of greater specific activity. For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, $2^{nd}$ ed. (1988), by Hammerling, et al., Monoclonal Antibodies and T-Cell Hybridomas (Elsevier, N.Y., pp. 563–681 (1981); Köhler et al., Eur. J. Immunol. 6:511 (1976); Kohler et al., Eur. J. Immunol. 6:292 (1976), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Preferably, the immunizing agent consists of an BGS-42 polypeptide or, more preferably, with a BGS-42 polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59–103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. More preferred are the parent myeloma cell line (SP2O) as provided by the ATCC. As inferred throughout the specification, human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51–63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoabsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra, and/or according to Wands et al. (Gastroenterology 80:225–232 (1981)). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4, 816, 567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hydridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4, 816, 567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples described herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182: 41–50 (1995); Ames et al., J. Immunol. Methods 184: 177–186 (1995); Kettleborough et al., Eur. J. Immunol.

24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; Cabilly et al., Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985); U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489–498 (1991); Studnicka et al., Protein Engineering 7(6):805–814 (1994); Roguska. et al., PNAS 91:969–973 (1994)), and chain shuffling (U.S. Pat. No. 5,565,332). Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522–525 (1986); Reichmann et al., Nature, 332:323–327 (1988); Verhoeyen et al., Science, 239:1534–1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522–525 (1986); Riechmann et al., Nature 332:323–329 (1988)1 and Presta, Curr. Op. Struct. Biol., 2:593–596 (1992).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of cole et al., and Boerder et al., are also available for the preparation of human monoclonal antibodies (cole et al., Monoclonal Antibodies and Cancer Therapy, Alan R. Riss, (1985); and Boerner et al., J. Immunol., 147(1):86–95, (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., Biotechnol., 10:779–783 (1992); Lonberg et al., Nature 368:856–859 (1994); Fishwild et al., Nature Biotechnol., 14:845–51 (1996); Neuberger, Nature Biotechnol., 14:826 (1996); Lonberg and Huszer, Intern. Rev. Immunol., 13:65–93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Such anti-idiotypic antibodies capable of binding to the BGS-42 polypeptide can be produced in a two-step procedure. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise anti-idiotypic antibodies to the protein-specific antibody and can be used to immunize an animal to induce formation of further protein-specific antibodies.

The antibodies of the present invention may be bispecific antibodies. Bispecific antibodies are monoclonal, Preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242: 1038–1041 (1988)).

More preferably, a clone encoding an antibody of the present invention may be obtained according to the method described in the Example section herein.

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g.; *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem. . . 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, N.Y. (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem. 270:9459–9471 (1995).

Moreover, the antibodies or fragments thereof the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111 In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, coichicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve tubulin tyrosine ligase protein, platelet derived tubulin tyrosine ligase protein, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567–1574 (1994)), VEGI (See, International Publication No. WO 99/23105), a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other tubulin tyrosine ligase proteins.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

The present invention also encompasses the creation of synthetic antibodies directed against the polypeptides of the present invention. One example of synthetic antibodies is described in Radrizzani, M., et al., Medicina, (Aires), 59(6): 753–8, (1999)). Recently, a new class of synthetic antibodies has been described and are referred to as molecularly imprinted polymers (MIPs) (Semorex, Inc.). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins' with equal or greater potency than that of natural antibodies. These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent 'super' MIPs can be coated onto beads or wells for use in highly sensitive separations or assays, or for use in high throughput screening of proteins.

Moreover, MIPs based upon the structure of the polypeptide(s) of the present invention may be useful in screening for compounds that bind to the polypeptide(s) of the invention. Such a MIP would serve the role of a synthetic "receptor" by minimicking the native architecture of the polypeptide. In fact, the ability of a MIP to serve the role of a synthetic receptor has already been demonstrated for the estrogen receptor (Ye, L., Yu, Y., Mosbach, K, Analyst., 126(6):760–5, (2001); Dickert, F, L., Hayden, O., Halikias, K, P, Analyst., 126(6):766–71, (2001)). A synthetic receptor may either be mimicked in its entirety (e.g., as the entire protein), or mimicked as a series of short peptides corresponding to the protein (Rachkov, A., Minoura, N, Biochim, Biophys, Acta., 1544(1–2):255–66, (2001)). Such a synthetic receptor MIPs may be employed in any one or more of the screening methods described elsewhere herein.

MIPs have also been shown to be useful in "sensing" the presence of its mimicked molecule (Cheng, Z., Wang, E., Yang, X, Biosens, Bioelectron., 16(3):179–85, (2001); Jenkins, A, L., Yin, R., Jensen, J. L, Analyst., 126(6):798–802, (2001); Jenkins, A, L., Yin, R., Jensen, J. L, Analyst., 126(6):798–802, (2001)). For example, a MIP designed using a polypeptide of the present invention may be used in assays designed to identify, and potentially quantitate, the level of said polypeptide in a sample. Such a MIP may be used as a substitute for any component described in the assays, or kits, provided herein (e.g., ELISA, etc.).

A number of methods may be employed to create MIPs to a specific receptor, ligand, polypeptide, peptide, organic molecule. Several preferred methods are described by Esteban et al in J. Anal, Chem., 370(7):795–802, (2001), which is hereby incorporated herein by reference in its entirety in addition to any references cited therein. Additional methods are known in the art and are encompassed by the present invention, such as for example, Hart, B, R., Shea, K, J. J. Am. Chem, Soc., 123(9):2072–3, (2001); and Quaglia, M., Chenon, K., Hall, A, J., De, Lorenzi, E., Sellergren, B, J. Am. Chem, Soc., 123(10):2146–54, (2001); which are hereby incorporated by reference in their entirety herein.

Uses for Antibodies Directed Against Polypeptides of the Invention

The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278(2):123–131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp147–158). The antibodies used in the diagnostic assays can be labeled with a detectable moiety. The detectable moiety should be capable of producing, either directly or indirectly, a detectable signal. For example, the detectable moiety may be a radioisotope, such as 2H, 14C, 32P, or 125I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219(1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a Sephadex resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses of Antibodies

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic tubulin tyrosine ligase proteins (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than 5×10−2 M, 10−2 M, 5×10−3 M, 10−3 M, 5×10−4 M, 10−4 M, 5×10−5 M, 10−5 M, 5×10−6 M, 10−6 M, 5×10−7 M, 10−7 M, 5×10−8 M, 10−8 M, 5×10−9 M, 10−9 M, 5×10−10 M, 10−10 M, 5×10−11 M, 10−11 M, 5×10−12 M, 10−12 M, 5×10−13 M, 10−13 M, 5×10−14 M, 10−14 M, 5×10−15 M, and 10−15 M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one could envision cloning the gene encoding an antibody directed against a polypeptide of the present invention, said polypeptide having the potential to elicit an allergic and/or immune response in an organism, and transforming the organism with said antibody gene such that it is expressed (e.g., constitutively, inducibly, etc.) in the organism. Thus, the organism would effectively become resistant to an allergic response resulting from the ingestion or presence of such an immune/allergic reactive polypeptide. Moreover, such a use of the antibodies of the present invention may have particular utility in preventing and/or ameliorating autoimmune diseases and/or disorders, as such conditions are typically a result of antibodies being directed against endogenous proteins. For example, in the instance where the polypeptide of the present invention is responsible for modulating the immune response to auto-antigens, transforming the organism and/or individual with a construct comprising any of the promoters disclosed herein or otherwise known in the art, in addition, to a polynucleotide encoding the antibody directed against the polypeptide of the present invention could effective inhibit the organisms immune system from eliciting an immune response to the auto-antigen(s). Detailed descriptions of therapeutic and/or gene therapy applications of the present invention are provided elsewhere herein.

Alternatively, antibodies of the present invention could be produced in a plant (e.g., cloning the gene of the antibody directed against a polypeptide of the present invention, and transforming a plant with a suitable vector comprising said gene for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting gene expression of a particular gene, or genes, in a human, mammal, and/or other organism. See, for example, International Publication Number WO 00/05391, published Feb. 3, 2000, to Dow Agrosciences LLC. The application of such methods for the antibodies of the present invention are known in the art, and are more particularly described elsewhere herein.

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

Antibody-Based Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, N.Y. (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342: 435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342:435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Compositions

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, N.Y., pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, J., Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging with Antibodies

Labeled antibodies, and derivatives and analogs thereof, which specifically bind to a polypeptide of interest can be used for diagnostic purposes to detect, diagnose, or monitor diseases, disorders, and/or conditions associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell. Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced in-between such peptide moieties, which could additionally be subjected to protease activity to remove said peptide(s) from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331: 84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of the constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem. 270: 9459–9471 (1995).) Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984)).

The skilled artisan would acknowledge the existence of other "tags" which could be readily substituted for the tags referred to supra for purification and/or identification of polypeptides of the present invention (Jones C., et al., J Chromatogr A. 707(1):3–22 (1995)). For example, the c-myc tag and the 8F9, 3C7, 6E10, G4m B7 and 9E10 antibodies thereto (Evan et al., Molecular and Cellular Biology 5:3610–3616 (1985)); the Herpes Simplex virus glycoprotein D (gD) tag and its antibody (Paborsky et al., Protein Engineering, 3(6):547–553 (1990), the Flag-peptide—i.e., the octapeptide sequence DYKDDDDK (SEQ ID NO:61), (Hopp et al., Biotech. 6:1204–1210 (1988); the KT3 epitope peptide (Martin et al., Science, 255:192–194 (1992)); a-tubulin epitope peptide (Skinner et al., J. Biol. Chem., 266:15136–15166, (1991)); the T7 gene 10 protein peptide tag (Lutz-Freyermuth et al., Proc. Natl. Sci. USA, 87:6363–6397 (1990)), the FITC epitope (Zymed, Inc.), the GFP epitope (Zymed, Inc.), and the Rhodamine epitope (Zymed, Inc.).

The present invention also encompasses the attachment of up to nine codons encoding a repeating series of up to nine arginine amino acids to the coding region of a polynucleotide of the present invention. The invention also encompasses chemically derivitizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender, P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivatized to attach hapten molecules (e.g., DNP, (Zymed, Inc.)). Due to the availability of monoclonal antibodies specific to such haptens, the protein could be readily purified using immunoprecipation, for example.

Polypeptides of the present invention, including fragments and/or variants thereof, in addition to, antibodies directed against such polypeptides, fragments, and/or variants, may be fused to any of a number of known, and yet to be determined, toxins such as ricin, saporin (Mashiba H, et al., Ann. N. Y. Acad. Sci. 1999;886:233–5), or HC toxin (Tonukari N.J., et al., Plant Cell. 2000 Feb; 12(2):237–248), for example. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell, to specific tissues, and/or to specific species. Such bifunctional antibodies are known in the art, though a review describing additional advantageous fusions, including citations for methods of production, can be found in P. J. Hudson, Curr. Opp. In. Imm. 11:548–557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. In view of the present disclosure, one skilled in the art could determine whether any particular "toxin" could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and Salmonella typhimurium cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast Pichia pastoris is used to express the polypeptide of the present invention in a eukaryotic system. Pichia pastoris is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, Pichia pastoris must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in Pichia pastoris. See, Ellis, S. B., et al., Mol. Cell. Biol. 5:1111–21 (1985); Koutz, P. J, et al., Yeast 5:167–77 (1989); Tschopp, J. F., et al., Nucl. Acids Res. 15:3859–76 (1987). Thus, a heterologous coding sequence, such as, for example, a polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a polypeptide of the invention, as set forth herein, in a Pichea yeast system essentially as described in "Pichia Protocols: Methods in Molecular Biology" D. R. Higgins and J. Cregg, eds. The Humana Press, Totowa, N.J., 1998. This expression vector allows expression and secretion of a protein of the invention by virtue of the strong AOX1 promoter linked to the Pichia pastoris alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO0815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W. H. Freeman & Co., N.Y., and Hunkapiller et al., Nature, 310:105–111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Nonclassical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The invention further encompasses chemical derivitization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above, etc.). stabilizing agents.

The invention encompasses derivitization of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics.RTM., commercially available from BASF, Parsippany, N.J.), polyoxyethylene, and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2 or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in mammals. Further, the trans-acting transcription factors of such "artificial" promoters could also be "artificial" or chimeric in design themselves and could act as activators or repressors to said "artificial" promoter.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:1. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:1 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques" Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Furthermore, increased or decreased expression of the gene in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may Preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The U.S. Patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point ($T_m$) by 8°–20° C., vs. 4°–16° C. for the DNA/DNA 15-mer duplex. Also, the absence of charge groups in PNA means that hybridization can be done at low ionic strengths and reduce possible interference by salt during the analysis.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression", CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991)) or to the mRNA itself (antisense—Okano, J. Neurochem. 56:560 (1991); Oligodeoxynucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention. See, for example, G. Cutrona, et al., Nat. Biotech., 18:300–303, (2000); which is hereby incorporated herein by reference.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., Nat. Biotech, 18:615–622 (2000), which is hereby incorporated by reference herein in its entirety). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see EP1007712, which is hereby incorporated by reference herein in its entirety).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organisms genome. These sequences can be used to prepare PCR primers for amplifying and isolating such selected DNA, which can then be sequenced. Using this technique, organisms can be identified because each organism will have a unique set of DNA sequences. Once an unique ID database is established for an organism, positive identification of that organism, living or dead, can be made from extremely small tissue samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell. Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207–216 (1993); Ferrantini et al., Cancer Research, 53:107–1112 (1993); Ferrantini et al., J. Immunology 153: 4604–4615 (1994); Kaido, T., et al., Int. J. Cancer 60: 221–229 (1995); Ogura et al., Cancer Research 50: 5102–5106 (1990); Santodonato, et al., Human Gene Therapy 7:1–10 (1996); Santodonato, et al., Gene Therapy 4:1246–1255 (1997); and Zhang, et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA, 84:7413–7416 (1987), which is herein incorporated by reference); mRNA (Malone et al., Proc. Natl. Acad. Sci. USA, 86:6077–6081 (1989), which is herein incorporated by reference); and purified transcription factors (Debs et al., J. Biol. Chem., 265:10189–10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl. Acad. Sci. USA, 84:7413–7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Felgner et al., Proc. Natl. Acad. Sci. USA, 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512–527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta, 394:483 (1975); Wilson et al., Cell, 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA, 76:145 (1979)); and reverse-phase evaporation (REV) (Fraley et al., J. Biol. Chem., 255:10431 (1980); Szoka et al., Proc. Natl. Acad.

Sci. USA, 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+en-vAm12, and DAN cell lines as described in Miller, Human Gene Therapy, 1:5–14 (1990), which is incorporated herein by reference in its entirety. The vector may transduce the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartzet al., Am. Rev. Respir. Dis., 109:233–238 (1974)). Finally, adenovirus mediated gene transfer has been demonstrated in a number of instances including transfer of alpha-1-antitrypsin and CFTR to the lungs of cotton rats (Rosenfeld et al., Science, 252:431–434 (1991); Rosenfeld et al., Cell, 68:143–155 (1992)). Furthermore, extensive studies to attempt to establish adenovirus as a causative agent in human cancer were uniformly negative (Green et al. Proc. Natl. Acad. Sci. USA, 76:6606 (1979)).

Suitable adenoviral vectors useful in the present invention are described, for example, in Kozarsky and Wilson, Curr. Opin. Genet. Devel., 3:499–503 (1993); Rosenfeld et al., Cell, 68:143–155 (1992); Engelhardt et al., Human Genet. Ther., 4:759–769 (1993); Yang et al., Nature Genet., 7:362–369 (1994); Wilson et al., Nature, 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci.

USA, 86:8932–8935 (1989); and Zijlstra et al., Nature, 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding angiogenic proteins. Angiogenic proteins include, but are not limited to, acidic and basic fibroblast tubulin tyrosine ligase proteins, VEGF-1, VEGF-2 (VEGF-C), VEGF-3 (VEGF-B), epidermal tubulin tyrosine ligase protein alpha and beta, platelet-derived endothelial cell tubulin tyrosine ligase protein, platelet-derived tubulin tyrosine ligase protein, tumor necrosis factor alpha, hepatocyte tubulin tyrosine ligase protein, insulin like tubulin tyrosine ligase protein, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189:11277–11281 (1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention may be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions of hematopoietic cells. A polynucleotides or polypeptides, or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat or prevent blood coagulation diseases, disorders, and/or conditions (e.g., afibrinogenemia, factor deficiencies, arterial thrombosis, venous thrombosis, etc.), blood platelet diseases, disorders, and/or conditions (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting. Polynucleotides or polypeptides, or agonists or antagonists of the present invention are may also be useful for the detection, prognosis, treatment, and/or prevention of heart attacks (infarction), strokes, scarring, fibrinolysis, uncontrolled bleeding, uncontrolled coagulation, uncontrolled complement fixation, and/or inflammation.

A polynucleotides or polypeptides, or agonists or antagonists of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitis, and autoimmune inflammatory eye disease.

Similarly, allergic reactions and conditions, such as asthma (particularly allergic asthma) or other respiratory problems, may also be treated, prevented, and/or diagnosed by polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide or agonists or antagonist may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinemias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more Preferably an adenoviral vector (See G J. Nabel, et. al., PNAS 1999 96: 324–326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic tubulin tyrosine ligase proteins, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than 5×10−6M, 10−6M, 5×10−7M, 10−7M, 5×10−8M, 10−8M, 5×10−9M, 10−9M, 5×10−10M, 10−10M, 5×10−11M, 10−11M, 5×10−12M, 10−12M, 5×10−13M, 10−13M, 5×10−14M, 10−14M, 5×10−15M, and 10−15M.

Moreover, polypeptides of the present invention may be useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph IB, et al. J Natl Cancer Inst, 90(21):1648–53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155–61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et al., Eur J Biochem 254(3):439–59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuvants, such as apoptonin, galectins, thioredoxins, anti-inflammatory proteins (See for example, Mutat. Res. 400 (1–2):447–55 (1998), Med Hypotheses.50(5):423–33 (1998), Chem. Biol. Interact. April 24;111–112:23–34 (1998), J Mol Med.76(6):402–12 (1998), Int. J. Tissue React. 20(1):3–15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998;231: 125–41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the invention may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a Therapeutic, described in more detail below. Methods of delivering polynucleotides of the invention are described in more detail herein.

Anti-Angiogenesis Activity

The naturally occurring balance between endogenous stimulators and inhibitors of angiogenesis is one in which inhibitory influences predominate. Rastinejad et al., Cell 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye diseases, disorders, and/or conditions, and psoriasis. See, e.g., reviews by Moses et al., Biotech. 9:630–634 (1991); Folkman et al., N. Engl. J. Med., 333:1757–1763 (1995); Auerbach et al., J. Microvasc. Res. 29:401–411 (1985); Folkman, Advances in Cancer Research, eds. Klein and Weinhouse, Academic Press, New York, pp. 175–203 (1985); Patz, Am. J. Opthalmol. 94:715–743 (1982); and Folkman et al., Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, Science 235:442–447 (1987).

The present invention provides for treatment of diseases, disorders, and/or conditions associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)).Thus, the present invention provides a method of treating, preventing, and/or diagnosing an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat or prevent a cancer or tumor. Cancers which may be treated, prevented, and/or diagnosed with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non-small cell lung cancer; colorectal cancer; advanced malignancies; and blood born tumors such as leukemias. For example, polynucleotides, polypeptides, antagonists and/or agonists may be delivered topically, in order to treat or prevent cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating, preventing, and/or diagnosing other diseases, disorders, and/or conditions, besides cancers, which involve angiogenesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating, preventing, and/or diagnosing hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating, preventing, and/or diagnosing neovascular diseases of the eye, including for example, corneal neovascularization, neovascular glaucoma, proliferative diabetic retinopathy, retrolental fibroplasia and macular degeneration.

Moreover, Ocular diseases, disorders, and/or conditions associated with neovascularization which can be treated, prevented, and/or diagnosed with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., Am. J. Ophthal. 85:704–710 (1978) and Gartner et al., Surv. Ophthal. 22:291–312 (1978).

Thus, within one aspect of the present invention methods are provided for treating or preventing neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of diseases, disorders, and/or conditions can result in corneal neovascularization, including for example, corneal infections (e.g., trachoma, herpes simplex keratitis, leishmaniasis and onchocerciasis), immunological processes (e.g., graft rejection and Stevens- Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

Within another aspect of the present invention, methods are provided for treating or preventing neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat or prevent early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating or preventing proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating or preventing retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, diseases, disorders, and/or conditions which can be treated, prevented, and/or diagnosed with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, diseases, disorders, and/or conditions and/or states, which can be treated, prevented, and/or diagnosed with the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (Helicobacter pylori), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem. 262(4): 1659–1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312–316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated, prevented, and/or diagnosed by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metastasis of cancers, in particular those listed above.

Additional diseases or conditions associated with increased cell survival that could be treated, prevented or diagnosed by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by the polynucleotides or polypeptides, and/or agonists or antagonists of the invention, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss.

The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepidermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intestine, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A tubulin tyrosine ligase protein such as the polynucleotides or polypeptides, and/or agonists or antagonists of the invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and burns, that cause necrosis of the bronchiolar epithelium and alveoli could be effectively treated, prevented, and/or diagnosed using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Parvoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia. polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., *Corynebacterium, Mycobacterium, Norcardia*), *Cryptococcus neoformans*, Aspergillosis, Bacillaceae (e.g., Anthrax, Clostridium), Bacteroidaceae, *Blastomycosis, Bordetella, Borrelia*(e.g., *Borrelia burgdorferi*), *Brucellosis, Candidiasis, Campylobacter, Coccidioidomycosis, Cryptococcosis*, Dermatocycoses, *E. coli* (e.g., Enterotoxigenic *E. coli* and Enterohemorrhagic *E. coli*), Enterobacteriaceae (*Klebsiella, Salmonella*(e.g., *Salmonella typhi*, and *Salmonella paratyphi*), *Serratia, Yersinia*), Erysipelothrix, *Helicobacter*, Legionellosis, Leptospirosis, Listeria, Mycoplasmatales, *Mycobacterium* leprae, Vibrio cholerae, Neisseriaceae (e.g., Acinetobacter, Gonorrhea, Menigococcal), *Meisseria meningitidis*, Pasteurellacea Infections (e.g., Actinobacillus, Heamophilus (e.g., Heamophilus influenza type B), Pasteurella), *Pseudomonas*, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., *Plasmodium virax, Plasmodium falciparium, Plasmodium malariae* and *Plasmodium ovale*). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used totreat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors),or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2): Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or *E. coli*. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605,793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a tubulin tyrosine ligase protein such as, for example, platelet-derived tubulin tyrosine ligase protein (PDGF), insulin-like tubulin tyrosine ligase protein (IGF-I), transforming tubulin tyrosine ligase protein (TGF)-alpha, epidermal tubulin tyrosine ligase protein (EGF), fibroblast tubulin tyrosine ligase protein (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3[H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/ molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (c) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, nonneutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

The human BGS-42 polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a BGS-42 polypeptide, or a bindable peptide fragment, of this invention, comprising providing a plurality of compounds, combining the BGS-42 polypeptide, or a bindable peptide fragment, with each of a plurality of compounds for a time sufficient to allow binding under suitable conditions and detecting binding of the BGS-42 polypeptide or peptide to each of the plurality of test compounds, thereby identifying the compounds that specifically bind to the BGS-42 polypeptide or peptide.

Methods of identifying compounds that modulate the activity of the novel human BGS-42 polypeptides and/or peptides are provided by the present invention and comprise combining a potential or candidate compound or drug modulator of tubulin tyrosine ligase protein biological activity with an BGS-42 polypeptide or peptide, for example, the BGS-42 amino acid sequence as set forth in SEQ ID NOS:2, and measuring an effect of the candidate compound or drug modulator on the biological activity of the BGS-42 polypeptide or peptide. Such measurable effects include, for example, physical binding interaction; the ability to cleave a suitable tubulin tyrosine ligase protein substrate; effects on native and cloned BGS-42-expressing cell line; and effects of modulators or other tubulin tyrosine ligase protein-mediated physiological measures.

Another method of identifying compounds that modulate the biological activity of the novel BGS-42 polypeptides of the present invention comprises combining a potential or candidate compound or drug modulator of a tubulin tyrosine ligase protein biological activity with a host cell that expresses the BGS-42 polypeptide and measuring an effect of the candidate compound or drug modulator on the biological activity of the BGS-42 polypeptide. The host cell can also be capable of being induced to express the BGS-42 polypeptide, e.g., via inducible expression. Physiological effects of a given modulator candidate on the BGS-42 polypeptide can also be measured. Thus, cellular assays for particular tubulin tyrosine ligase protein modulators may be either direct measurement or quantification of the physical biological activity of the BGS-42 polypeptide, or they may be measurement or quantification of a physiological effect. Such methods preferably employ a BGS-42 polypeptide as described herein, or an overexpressed recombinant BGS-42 polypeptide in suitable host cells containing an expression vector as described herein, wherein the BGS-42 polypeptide is expressed, overexpressed, or undergoes upregulated expression.

Another aspect of the present invention embraces a method of screening for a compound that is capable of modulating the biological activity of a BGS-42 polypeptide, comprising providing a host cell containing an expression vector harboring a nucleic acid sequence encoding a BGS-42 polypeptide, or a functional peptide or portion thereof (e.g., SEQ ID NOS:2); determining the biological activity of the expressed BGS-42 polypeptide in the absence of a modulator compound; contacting the cell with the modulator compound and determining the biological activity of the expressed BGS-42 polypeptide in the presence of the modulator compound. In such a method, a difference between the activity of the BGS-42 polypeptide in the presence of the modulator compound and in the absence of the modulator compound indicates a modulating effect of the compound.

Essentially any chemical compound can be employed as a potential modulator or ligand in the assays according to the present invention. Compounds tested as tubulin tyrosine ligase protein modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel BGS-42 polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.*, 37:487–493; and Houghton et al., 1991, *Nature*, 354:84–88). Other chemistries for generating chemical diversity libraries can also be used. Nonlimiting examples of chemical diversity library chemistries include, peptides (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA*, 90:6909–6913), vinylogous polypeptides (Hagihara et al., 1992, *J. Amer. Chem. Soc.*, 114:6568), nonpeptidal peptidomimetics with glucose scaffolding (Hirschmann et al., 1992, *J. Amer. Chem. Soc.*, 114:9217–9218), analogous organic synthesis of small compound libraries (Chen et al., 1994, *J. Amer. Chem. Soc.*, 116:2661), oligocarbamates (Cho et al., 1993, *Science*, 261: 1303), and/or peptidyl phosphonates (Campbell et al., 1994, *J. Org. Chem.*, 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology*, 14(3):309–314) and PCT/US96/10287), carbohydrate libraries (e.g., Liang et al., 1996, *Science*, 274–1520–1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000–20,000 different compounds are possible using the described integrated systems.

In another of its aspects, the present invention encompasses screening and small molecule (e.g., drug) detection assays which involve the detection or identification of small molecules that can bind to a given protein, i.e., a BGS-42 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, *Gen. Eng. News*, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a BGS-42 polypeptide or peptide to measure a biological binding or ligand binding activity, the source may be a whole cell lysate that can be prepared by successive freeze-thaw cycles (e.g., one to three) in the presence of standard protease inhibitors. The BGS-42 polypeptide may be partially or completely purified by standard protein purification methods, e.g., affinity chromatography using specific antibody described infra, or by ligands specific for an epitope tag engineered into the recombinant BGS-42 polypeptide molecule, also as described herein. Binding activity can then be measured as described.

Compounds which are identified according to the methods provided herein, and which modulate or regulate the biological activity or physiology of the BGS-42 polypeptides according to the present invention are a preferred embodiment of this invention. It is contemplated that such modulatory compounds may be employed in treatment and therapeutic methods for treating a condition that is mediated by the novel BGS-42 polypeptides by administering to an individual in need of such treatment a therapeutically effective amount of the compound identified by the methods described herein.

In addition, the present invention provides methods for treating an individual in need of such treatment for a disease, disorder, or condition that is mediated by the BGS-42 polypeptides of the invention, comprising administering to the individual a therapeutically effective amount of the BGS-42-modulating compound identified by a method provided herein.

Antisense and Ribozyme (Antagonists)

In specific embodiments, antagonists according to the present invention are nucleic acids corresponding to the sequences contained in SEQ ID NO:1, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)).

These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10 MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide. Antisense oligonucleotides may be single or double stranded. Double stranded RNA's may be designed based upon the teachings of Paddison et al., Proc. Nat. Acad. Sci., 99:1443–1448 (2002); and International Publication Nos. WO 01/29058, and WO 99/32619; which are hereby incorporated herein by reference.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature, 29:304–310 (1981), the promoter contained in the 3' long terminal repeat of Rous sarcoma virus (Yamamoto et al., Cell, 22:787–797 (1980), the herpes thymidine promoter (Wagner et al., Proc. Natl. Acad. Sci. U.S.A., 78:1441–1445 (1981), the regulatory sequences of the metallothionein gene (Brinster et al., Nature, 296:39–42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA" referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372: 333–335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553–6556 (1989); Lemaitre et al., Proc. Natl. Acad. Sci., 84:648–652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958–976 (1988)) or intercalating agents. (See, e.g., Zon, Pharm. Res., 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625–6641 (1987)). The oligonucleotide is a 2-0-methylribonucleotide (Inoue et al., Nucl. Acids Res., 15:6131–6148 (1987)), or a chimeric RNA-DNA analogue (Inoue et al., FEBS Lett. 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448–7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222–1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585–591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention.

Biotic Associations

A polynucleotide or polypeptide and/or agonist or antagonist of the present invention may increase the organisms ability, either directly or indirectly, to initiate and/or maintain biotic associations with other organisms. Such associations may be symbiotic, nonsymbiotic, endosymbiotic, macrosymbiotic, and/or microsymbiotic in nature. In general, a polynucleotide or polypeptide and/or agonist or antagonist of the present invention may increase the organisms ability to form biotic associations with any member of the fungal, bacterial, lichen, mycorrhizal, cyanobacterial, dinoflaggellate, and/or algal, kingdom, phylums, families, classes, genuses, and/or species.

The mechanism by which a polynucleotide or polypeptide and/or agonist or antagonist of the present invention may increase the host organisms ability, either directly or indirectly, to initiate and/or maintain biotic associations is variable, though may include, modulating osmolarity to desirable levels for the symbiont, modulating pH to desirable levels for the symbiont, modulating secretions of organic acids, modulating the secretion of specific proteins, phenolic compounds, nutrients, or the increased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

In an alternative embodiment, a polynucleotide or polypeptide and/or agonist or antagonist of the present invention may decrease the host organisms ability to form biotic associations with another organism, either directly or indirectly. The mechanism by which a polynucleotide or polypeptide and/or agonist or antagonist of the present invention may decrease the host organisms ability, either directly or indirectly, to initiate and/or maintain biotic associations with another organism is variable, though may include, modulating osmolarity to undesirable levels, modulating pH to undesirable levels, modulating secretions of organic acids, modulating the secretion of specific proteins, phenolic compounds, nutrients, or the decreased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

The hosts ability to maintain biotic associations with a particular pathogen has significant implications for the overall health and fitness of the host. For example, human hosts have symbiosis with enteric bacteria in their gastrointestinal tracts, particularly in the small and large intestine. In fact, bacteria counts in feces of the distal colon often approach $10^{12}$ per milliliter of feces. Examples of bowel flora in the gastrointestinal tract are members of the Enterobacteriaceae, Bacteriodes, in addition to a-hemolytic *streptococci, E. coli, Bifobacteria, Anaerobic cocci*, Eubacteria, Costridia, *lactobacilli*, and yeasts. Such bacteria, among other things, assist the host in the assimilation of nutrients by breaking down food stuffs not typically broken down by the hosts digestive system, particularly in the hosts bowel. Therefore, increasing the hosts ability to maintain such a biotic association would help assure proper nutrition for the host.

Aberrations in the enteric bacterial population of mammals, particularly humans, has been associated with the following disorders: diarrhea, ileus, chronic inflammatory disease, bowel obstruction, duodenal diverticula, biliary calculus disease, and malnutrition. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant enteric flora population.

The composition of the intestinal flora, for example, is based upon a variety of factors, which include, but are not limited to, the age, race, diet, malnutrition, gastric acidity, bile salt excretion, gut motility, and immune mechanisms. As a result, the polynucleotides and polypeptides, including agonists, antagonists, and fragments thereof, may modulate the ability of a host to form biotic associations by affecting, directly or indirectly, at least one or more of these factors.

Although the predominate intestinal flora comprises anaerobic organisms, an underlying percentage represents aerobes (e.g., *E. coli*). This is significant as such aerobes rapidly become the predominate organisms in intraabdominal infections—effectively becoming opportunistic early in infection pathogenesis. As a result, there is an intrinsic need to control aerobe populations, particularly for immune compromised individuals.

In a preferred embodiment, a polynucleotides and polypeptides, including agonists, antagonists, and fragments thereof, are useful for inhibiting biotic associations with specific enteric symbiont organisms in an effort to control the population of such organisms.

Biotic associations occur not only in the gastrointestinal tract, but also on an in the integument. As opposed to the gastrointestinal flora, the cutaneous flora is comprised almost equally with aerobic and anaerobic organisms. Examples of cutaneous flora are members of the gram-positive cocci (e.g., *S. aureus, coagulase-negative staphylococci, micrococcus, M. sedentarius*), gram-positive bacilli (e.g., *Corynebacterium* species, *C. minutissimum, Brevibacterium* species, *Propoionibacterium* species, *P. acnes*), gram-negative *bacilli* (e.g., *Acinebacter* species), and fungi (*Pityrosporum orbiculare*). The relatively low number of flora associated with the integument is based upon the inability of many organisms to adhere to the skin. The organisms referenced above have acquired this unique ability. Therefore, the polynucleotides and polypeptides of the present invention may have uses which include modulating the population of the cutaneous flora, either directly or indirectly.

Aberrations in the cutaneous flora are associated with a number of significant diseases and/or disorders, which include, but are not limited to the following: impetigo, ecthyma, blistering distal dactulitis, pustules, folliculitis, cutaneous abscesses, pitted keratolysis, trichomycosis axcillaris, dermatophytosis complex, axillary odor, erthyrasma, cheesy foot odor, acne, tinea versicolor, seborrheic dermititis, and *Pityrosporum folliculitis*, to name a few. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant cutaneous flora population.

Additional biotic associations, including diseases and disorders associated with the aberrant growth of such associations, are known in the art and are encompassed by the invention. See, for example, "Infectious Disease", Second Edition, Eds., S. L., Gorbach, J. G., Bartlett, and N. R., Blacklow, W. B. Saunders Company, Philadelphia, (1998); which is hereby incorporated herein by reference).

Pheromones

In another embodiment, a polynucleotide or polypeptide and/or agonist or antagonist of the present invention may increase the organisms ability to synthesize and/or release a pheromone. Such a pheromone may, for example, alter the organisms behavior and/or metabolism.

A polynucleotide or polypeptide and/or agonist or antagonist of the present invention may modulate the biosynthesis and/or release of pheromones, the organisms ability to respond to pheromones (e.g., behaviorally, and/or metabolically), and/or the organisms ability to detect pheromones. Preferably, any of the pheromones, and/or volatiles released from the organism, or induced, by a polynucleotide or polypeptide and/or agonist or antagonist of the invention have behavioral effects the organism.

Other Activities

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, prevent, and/or diagnose neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptides of the present invention may be employed to stimulate growth and differentiation of hematopoietic cells and bone marrow cells when used in combination with other cytokines.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

Polypeptide or polynucleotides and/or agonist or antagonists of the present invention may also be used to prepare individuals for extraterrestrial travel, low gravity environments, prolonged exposure to extraterrestrial radiation levels, low oxygen levels, reduction of metabolic activity, exposure to extraterrestrial pathogens, etc. Such a use may be administered either prior to an extraterrestrial event, during an extraterrestrial event, or both. Moreover, such a use may result in a number of beneficial changes in the recipient, such as, for example, any one of the following, non-limiting, effects: an increased level of hematopoietic cells, particularly red blood cells which would aid the recipient in coping with low oxygen levels; an increased level of B-cells, T-cells, antigen presenting cells, and/or macrophages, which would aid the recipient in coping with exposure to extraterrestrial pathogens, for example; a temporary (i.e., reversible) inhibition of hematopoietic cell production which would aid the recipient in coping with exposure to extraterrestrial radiation levels; increase and/or stability of bone mass which would aid the recipient in coping with low gravity environments; and/or decreased metabolism which would effectively facilitate the recipients ability to prolong their extraterrestrial travel by any one of the following, non-limiting means: (i) aid the recipient by decreasing their basal daily energy requirements; (ii) effectively lower the level of oxidative and/or metabolic stress in recipient (i.e., to enable recipient to cope with increased extraterrestrial radiation levels by decreasing the level of internal oxidative/metabolic damage acquired during normal basal energy requirements; and/or (iii) enabling recipient to subsist at a lower metabolic temperature (i.e., cryogenic, and/or sub-cryogenic environment).

Also preferred is a method of treatment of an individual in need of an increased level of a protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

REFERENCES

Altschul, S F, et al. Nucleic Acids Res 25:3389–3402, 1997.

Altschul, S. F., Gish, W., Miller, W., Myers, E W., Lipman, D. J. Basic local alignment search tool. J. Mol. Biol. 215:403–410, 1990.

Bateman, A E, Birney, R. Durbin, S. R. Eddy, K. L. Howe, and E. L. L. Sonnhammer (2000) The Pfam protein families database. Nucleic Acids Research, 28:263–266.

Baylin, S. B., Esteller, M., Myohenen, S., Bachman, K. E., Schuebel, K., and Herman, J. G. (2001). Aberrant patterns of DNA methylation, chromatin formation and gene expression in cancer. Hum. Mol. Genet. 10, 687–692.

Berman, H. M., Westbrook, J., Feng, Z., Gilliland, G., Bhat, T. N., Weissig, H., Shindyalov, I. N., Bourne, P. E. The Protein Data Bank Nucleic Acids Research, 28:235–242, 2000

Bernstein, F C, Koetzle, T F, Williams, G J B, Meyer, E F Jr., Brice, M D, Rodgers, J R, Kennard, O, Simanouchi, T, Tasumi, M. 1977. The Protein Data Bank: A computer-based archival file for macromolecular structures. J. Mol. Biol. 112:535–542.

Birney E, Durbin R (2000). Using GeneWise in the Drosophila annotation experiment. Genome Res. 10:547–8.

Bohm, H-J., LUDI: rule-based automatic design of new substituents for enzyme inhibitor leads. J. Comp. Aid. Molec. Design 6:61–78, 1992.

Cardozo, T., Totrov, M., Abagyan, R. Homology modeling by the ICM method. Proteins 23:403–14, 1995.

Dideberg, O., Bertrand, J. Tubulin tyrosine ligase: a shared fold with the glutathione synthetase ADP-forming family. Trends Biochem. Sci. 23:57–58, 1998

Goodford, P. J. A computational procedure for determining energetically favorable binding sites on biologically important macromolecules. J. Med. Chem. 28:849–857, 1985.

Goodsell, D. S. and Olsen, A. J. Automated docking of substrates to proteins by simulated annealing. Proteins 8:195–202, 1990.

Greer, J. Comparative modeling of homologous proteins. Meth. Enzymol. 202:239–52, 1991.

Hara, T., Kato, H., Katsube, Y., and Oda, J. A pseudo-michaelis quaternary complex in the reverse reaction of a ligase: structure of *escherichia coli* B glutathione synthetase complexed with ADP, glutathione, and sulfate at 2.0 A resolution. Biochemistry. 35:11967–11974. 1996.

Hendlich, M., Lackner, P., Weitckus, S., Floeckner, H., Froschauer, R., Gottsbacher, K., Casari, G., Sippl, M. J. Identification of native protein folds amongst a large number of incorrect models. The calculation of low energy conformations from potentials of mean force. J. Mol. Biol. 216: 167–80, 1990.

Herman, J. G., Graff, J. R., Myohanen, S., Nelkin, B. D., and Baylin, S. B. (1996). Methylation-specific PCR: A novel assay for methylation status of CpG Islands. Proc. Natl. Acad. Sci. USA 93, 9821–9826.

Idriss, H. T. (2001). Suppression of tubulin tyrosine ligase activity through reversible phosphorylation: a mechanism for inhibition of alpha-tubulin tyrosinylation. Med Hypotheses 56, 129–133.

Koppensteiner, W. A., lackner, P., Wiederstein, M., and Sippl, M. Characterization of novel proteins based upon know protein structures. J. Mol. Biol. 296:1139–1152, 2000.

Kuntz, I. D., Blaney, J. M., Oatley, S. J., Langridge, R., and Ferrin, T. E. A geometric approach to macromolecule-ligand interactions. J. Mol. Biol. 161:269–288, 1982.

Lesk, A. M., Boswell, D. R. Homology Modeling: Inferences from Tables of Aligned Sequences. Curr. Op. Struc. Biol. 2: 242–247, 1992.

Levitt, M. Accurate modeling of protein conformation by automatic segment matching J. Mol. Biol. 226: 507–533, 1992.

Martin, Y. C. 3D database searching in drug design. J. Med. Chem. 35:2145–2154, 1992.

Mialhe, A., Lafanechere, L., Treilleux, I., Peloux, N., Dumontet, C., Bremond, A., Panh, M. H., R., P., J., W., L., M. R., and Job, D. (2001). Tubulin detyrosination is a frequent occurrence in breast cancers of poor prognosis. Cancer Res 61 61, 5024–5027.

Novotny, J., Rashin, A. A., and Bruccoleri, R. E. Criteria that discriminate between native proteins and incorrectly folded models. Proteins 4:19–30, 1988.

Pearson, W. R. Rapid and sensitive sequence comparison with FASTP and FASTA. Meth. Enzymol. 183:63–98, 1990.

Raybin, D., and Flavin, M. (1977). Biochemistry 16, 2189–2194.

Sali, A., Potterton, L., Yuan, F., van Vlijmen H. and Karplus, M. Evaluation of comparative protein modeling by MODELLER. Proteins 23:318–326, 1995.

Sippl. M and Weitckus S. Detection of native-like models for amino acid sequences of unknown three-diemnsional structure in a data base of protein conformations. Proteins 13: 258–271, 1992.

Sippl, M. Boltzmann's principle, knowledge-based mean fields and protein folding. An approach to computational determination of protein structures. J. Computer-Aided Molecular Design 7:473–501, 1993.

EXAMPLES

Description of the Preferred Embodiments

Example 1

Bioinformatics Analysis

Tubulin tyrosine ligase domain sequences from several different species were used as probes to search the human genomic sequence database. The search program used was gapped BLAST (Altschul, S F, et al. Nucleic Acids Res 25:3389–3402, 1997.). The top genomic exon hits from the BLAST results were searched back against the non-redundant protein and patent sequence databases. From this analysis, exons encoding potential novel tubulin tyrosine ligases were identified based on sequence homology and their most similar protein sequence were then used as a template to predict more exons using the GENEWISEDB program (Birney and Durbin, 2000). The final predicted exons were assembled and full-length clones of genes were obtained using the predicted exon sequences. With these analyses, a predicted full-length sequence of a novel human secreted protein, named BGS-42 was identified directly from a piece of human genomic sequence (Genbank accession number: AL022327). The complete polynucleotide (SEQ ID NO:1) and polypeptide (SEQ ID NO:2) sequences of BGS-42 are shown FIGS. 1A–C. Mapping BGS-42 cDNA to human genome found that BGS-42 is located at chromosome 22q13.33 and there are three predicted CpG islands 2.0 kb upsteam of its first methionine (FIG. 7A-B), indicating BGS-42 has a typical transcription signature.

BGS-42 was then analyzed for protein domains in Pfam database (Bateman et. al., 2000). The Pfam is a database of multiple alignments of protein domains or conserved protein regions. The alignments provide insight into protein families evolutionary conserved structure, which often has implications for the protein's function. Such Pfams can be very useful for automatically recognizing that a new protein belongs to an existing protein family, even if the homology is weak (A. Bateman, E. Birney, R. Durbin, S. R. Eddy, K. L. Howe, and E. L. L. Sonnhammer. *The Pfam Protein Families Database. Nucleic Acids Research*, 28:263–266, 2000).

Based upon the Pfam analysis, the BGS-42 polypeptide was found to have significant sequence homology with TTL domains (amino acids 73 to 365 of SEQ ID NO:2) as shown in FIG. 4. Based on sequence, structure and known TTL signature sequences, this novel protein, BGS-42, is a novel human tubulin tyrosine ligase protein.

Example 2

Method of Constructing a Size Fractionated Brain and Testis cDNA Library

Poly A⁺ RNA from Clontech is treated with DNase I to remove genomic DNA contamination. The RNA is converted into double stranded cDNA using the SuperScrip™ Plasmid System for cDNA Synthesis and Plasmid Cloning (Life Technologies). The cDNA is size fractionated on a TransGenomics HPLC size exclusion column (TosoHass) with dimensions of 7.8 mm×30 cm and a particle size of 10 µm. Tris buffered saline is used as the mobile phase, and the column is run at a flow rate of 0.5 ml/min. The system is calibrated using a 1 kb ladder to determine which fractions are to be pooled to obtain the largest cDNA library. Generally, fractions that eluted in the range of 12 to 15 minutes are used. The cDNA is precipitated, concentrated and then ligated into the Sal I/Not I sites in pSPORT. Following electroporation of the cDNA into DH12S, DNA from the resulting colonies is prepared and subjected to Sal I/Not I restriction enzyme digestion. Generally, the average insert size of libraries made by this procedure is greater than 3.5 Kb and the overall complexity of the library is greater than $10^7$ independent clones. The library is amplified in semisolid agar for 2 days at 30 C. An aliquot (200 microliters) of the amplified library is inoculated into a 200 ml culture for single-stranded DNA isolation by super-infection with a fi helper phage. The single-stranded circular DNA is concentrated by ethanol precipitation, resuspended at a concentration of one microgram per microliter and used for the cDNA capture experiments.

Example 3

Method of Converting Double Stranded cDNA Libraries into Single Strand Circular Forms I. Preparation of Culture.

LB medium (200 mL+400 ul carb) is inoculated with 0.2 to 1 ml of thawed cDNA library. The culture is incubated, shaking at 250 rpm at 37° C. for 45 min. The optical density of the culture is measured. The OD600 is preferably between 0.025 and 0.040. One mL M13K07 helper phage is added to the culture and grown for 2 hours. At that time, 500 uL Kanamycin (30 mg/mL) is added and incubation continued for 15–18 hours.

II. Preparation of Cells for Precipitation.

Cultures are poured into six 50 mL tubes. Cells are centrifuged at 10000 rpm in an HB-6 rotor for 15 minutes at 4° C. The supernatant is retrieved and cells discarded. The supernatant is filtered through a 0.2 um filter. DNase I (12000 units from Gibco) is added and incubated at room temperature for 90 minutes.

III. PEG precipitation of DNA.

Fifty mL of ice-cold 40% PEG 8000, 2.5 M NaCl, 10 mM $MgSO_4$ is added to the cell pellets. The solution is mixed and distributed into 6 centrifuge tubes and covered with parafilm. The tubes are incubated on wet ice for 1 hour (or at 4° C. overnight).

Phage are pelleted at 10000 rpm in an HB-6 rotor for 20 minutes at 4° C. The supernatant is discarded and the sides of the tubes wiped dry. The pellets are resuspended in 1 mL TE, pH 8.

The resuspended pellets are placed in a 14 mL Sarstedt tube (6 mL total). SDS is added to 0.1% (60 uL of stock 10% SDS). Proteinase K (60 uL of 20 mg/mL) is then added and incubated at 42C for 1 hour.

DNA is extracted with phenol/chloroform by first adding 1 mL of SM NaCl followed by an equal volume of phenol/chloroform (6 mL). The mixture is vortexed and centrifuged at 5K in an HB-6 rotor for 5 minutes at 4° C. The aqueous (top) phase is transferred to a new Sarstedt tube. Extractions are repeated until no interface is visible.

The DNA is precipitated in ethanol by adding 2 volumes of 100% ethanol and precipitating overnight at −20° C. The DNA is centrifuged at 10000 rpm in HB-6 rotor for 20 minutes at 4° C. The ethanol is discarded and the pellets resuspended in 700 uL 70% ethanol. The resuspended pellets are centrifuged at 14000 rpm for 10 minutes at 4° C. The ethanol is discarded and the pellets dried by vacuum.

Oligosaccharides are then removed by resuspending the pellet in 50 uL TE, pH 8. The solutions are frozen on dry ice for 10 minutes and centrifuged at 14000 rpm for 15 minutes at 4° C. The supernatant is transferred to a new tube and the volume recorded.

The concentration of DNA is determined by measuring absorbance at 260/280. DNA is diluted 1:100 in a quartz cuvette (3 uL DNA+297 uL TE). The following equation is used to calculate DNA concentration:

(32 ug/mL*$OD$)(mL/100 uL)(100)($OD$260)=DNA concentration

The preferred purity ratio is 1.7–2.0.

The DNA is diluted to 1 ug/uL with TB, pH 8 and stored at 4° C.

To test the quality of single-stranded DNA (ssDNA) the following reaction mixtures are prepared:
1. DNA mix per reaction
   a. 1 uL of 5 ng/uL ssDNA (1:200 dilution of VI.D.2 above)
   b. 11 uL dH2O
   c. 1.5 uL 10 uM T7 SPORT primer (fresh dilution of stock)
   d. 1.5 uL 10×Precision-Taq buffer
2. Repair mix per reaction
   a. 4 uL 5 mM dNTPs (1.25 mM each)
   b. 1.5 uL 10×Precision-Taq buffer
   c. 9.25 uL dH2O
   d. 0.25 uL Precision-Taq polymerase
   e. Preheat cocktail at 70° C. until middle of thermal cycle The DNA mixes are aliquoted into PCR tubes and thermal cycle carried out as follows:
1. 95° C., 20 sec
2. 59° C., 1 min; add 15 uL repair mix
3. 73° C., 23 min Ethanol precipitation of the ssDNA is performed by adding 15 ug glycogen, 16 uL 7.5 M $NH_4OAc$, 125 uL 100% ethanol. The sample is centrifuged at 14000 rpm for 30 minutes at 4° C. and the pellet washed with 125 uL 70% ethanol. The ethanol is discarded and pellet dried by vacuum. The pellet is resuspended in 10 uL TB, pH 8.

The DNA is electroporated into DH10B or DH12S cells. A DNA mixture consisting of:
1. 2 uL repaired library (=1.0×10−3 ug)
2. 1 uL 1 ng/uL unrepaired library (=1.0×10−3 ug)
3. 1 uL 0.01 ug/uL pUC19 positive control DNA (=×10−5 ug) is aliquoted to Eppendorf tubes. Cells are thawed on ice-water. Forty uL of cells are added to each DNA aliquot by pipetting into a chilled cuvette placed between metal plates. Electroporation is carried out at 1.8 kV. Immediately following electroporation, 1 mL SOC (SOB+glucose+$Mg^{++}$) media is added to the cuvette, then transferred to a 15 mL tube. Cells are allowed to recover for 1 hr at 37° C. with shaking (225 rpm). Cells are then plated according to the following dilution scheme:

A. Dilutions of Culture
1. Serial dilutions of culture in 1:10 increments (20 uL into 180 uL LB broth)
2. Repaired dilutions
   a. 1:100
   b. 1:1K
   c. 1:10K
3. Unrepaired dilutions
   a. 1:10
   b. 1:100
4. Positive control dilutions
   a. 1:10
   b. 1:100

100 uL of each dilution is plated on small LB+carb plates and incubated at 37° C. overnight. Colonies are counted to calculate titer as follows:
1. use smallest countable dilution
2. (# of colonies)(dilution factor)(200 uL/100 uL)(1000 uL/20 uL)=CFUs
3. CFUs/ug DNA used=CFU/ug % Background=(unrepaired CFU/ug/repaired CFU/ug)×100%

Example 4

Method of Cloning the Novel Human BGS-42 Polypeptide of the Present Invention

One microliter of anti-sense biotinylated oligos (or sense oligos when annealing to single stranded DNA from pSPORT2 vector), containing one hundred and fifty nanograms of 1 to 50 different 80 mer oligo probes, is added to six microliters (six micrograms) of a mixture of up to 15 single-stranded covalently closed circular cDNA libraries and seven microliters of 100% formamide in a 0.5 ml PCR tube. The sequence of the 80mer oligos used is as follows:

5'-AGAACCAGATGGTCAGGGGGTTCCAGTCCGTGA (SEQ ID NO:52)

CGAGGAACCACTGTCTGATGTCGAACTTGGTGTCAC

AGATGAGCAGC-3'.

The mixture is heated in a thermal cycler to 95° C. for 2 min. Fourteen microliters of 2×hybridization buffer (50% formamide, 1.5 M NaCl, 0.04 M NaPO₄, pH 7.2, 5 min EDTA, 0.2% SDS) is added to the heated probe/cDNA library mixture and incubated at 42° C. for 26 hours. Hybrids between the biotinylated oligo and the circular cDNA are isolated by diluting the hybridization mixture to 220 microliters solution containing 1 M NaCl, 10 mm Tris-HCl pH 7.5, 1 mM EDTA, pH 8.0 and adding 125 microliters of streptavidin magnetic beads. This solution is incubated at 42° C. for 60 min, and mixed every 5 min to re-suspend the beads. The beads are separated from the solution with a magnet and washed three times in 200 microliters of 0.1× SSPE, 0.1% SDS at 45° C.

The single stranded cDNA is released from the biotinylated oligo/streptavidin magnetic bead complex by adding 50 microliters of 0.1 N NaOH and incubating at room temperature for 10 min. Six microliters of 3 M sodium acetate is added along with 15 micrograms of glycogen and the solution ethanol precipitated with 120 microliters of 100% ethanol. The precipitated DNA is resuspended in 12 microliters of TB (10 min Tris-HCl, pH 8.0), 1 mM EDTA, pH 8.0). The single-stranded cDNA is converted into double-stranded DNA in a thermal cycler by mixing 5 microliters of the captured DNA with 1.5 microliters of 10 micromolar standard SP6 primer for libraries in pSPORT 1 and 2 and 17 primer for libraries in pCMVSPORT and 1.5 microliters of 10×PCR buffer.

Sequences of primers used to repair single-stranded circular DNA isolated from the primary selection are as follows:

```
T7Sport5'-TAATACGACTCACTATAGGG-3'    (SEQ ID NO:53)

SP6Sport5'-ATTTAGGTGACACTATAG-3'     (SEQ ID NO:54)
```

The mixture is heated to 95° C. for 20 seconds and the temperature gradually brought down to 59° C. Fifteen microliters of a repair mix, that was preheated to 70° C. is added to the DNA (repair mix contains 4 microliters of 5 mM dNTPs (1.25 mM each), 1.5 microliters of 10×PCR buffer, 9.25 microliters of water, and 0.25 microliters of Taq polymerase). The solution incubation temperature is raised back to 73° C. and incubated for 23 mm. The repaired DNA is ethanol precipitated and resuspended in 10 microliters of TB. Electroporation is carried out using two microliters DNA per 40 microliters of E. coli DH12S cells. Three hundred and thirty three microliters are plated onto one 150-mm plate of LB agar plus 100 micrograms/milliliter of ampicillin. After overnight incubation at 37° C., the colonies from all plates are harvested by scraping into 10 ml of LB medium +50 micrograms/milliliter of ampicillin and 2 ml of sterile glycerol.

The second round of selection is initiated by making single-stranded circular DNA from the primary selected library using the method listed above. The purified single-stranded circular DNA is then assayed with gene-specific primers for each of the targeted sequences using standard PCR conditions.

The sequences of the Gene-Specific-Primer ("GSP") pairs used to identify the various targeted cDNAs in the primary selected single stranded cDNA libraries are as follows:

```
Left Primer 1:
GTGGGTGGTCCAGAAGTACA        (SEQ ID NO:55)

Right Primer 1:
GAGAAGCGCTGAGTTGAGAA        (SEQ ID NO:56)

Left Primer 2:
CACCAGGTTCCAGGAGTACC        (SEQ ID NO:57)

Right Primer 2:
GAATTGATCTCGATCAGCCA        (SEQ ID NO:58)
```

The secondary hybridization is carried out using only those 80mer biotinylated probes whose targeted sequences were positive with the GSPs. The resulting single-stranded circular DNA is converted to double strands using the antisense oligo for each target sequence as the repair primer (the sense primer is used for material captured from pSPORT2 libraries. The resulting double stranded DNA is electroporated into DH1OB and the resulting colonies inoculated into 96 deep well blocks. Following overnight growth, DNA is prepared and sequentially screened for each of the targeted sequences using the GSPs. The DNA is also cut with Sal I and Not I and the inserts sized by agarose gel electrophoresis.

Those cDNA clones that were positive by PCR had the inserts sized and three clones (Clone A, B, and C; SEQ ID NO:9, 10, and 11, respectively) were chosen for DNA sequencing. Clones A, B, and C were used to form a contig and thus derive the full-length consensus sequence provided in FIG. 6A-D (SEQ ID NO:12).

The consensus sequence (SEQ ID NO:12) was then used to design RT-PCR primers to verify the chimeric assembly. The sequences of the primers are:

```
BGS42-cloning-L
AGACTTCCGGCGCACCAT          (SEQ ID NO:59)

BGS42-cloning-R
GGGAGAGTGGCTGCAACCTG        (SEQ ID NO:60)
```

The full-length nucleotide sequence and the encoded polypeptide for BGS-42 is shown in FIGS. 1A–C (SEQ ID NO:1).

Example 5

Expression Profiling of the Novel Human BGS-42 Polypeptide

The following PCR primer pair was used to measure the steady state levels of BGS-42 mRNA by quantitative PCR:

```
Sense:
5'-GTTCATGACAGCGTCAGATTCTCT-3'      (SEQ ID NO:28)

Antisense:
5'-GACAAGATGGTGGAAAGACGTATTC-3'     (SEQ ID NO:29)
```

Briefly, first strand cDNA was made from commercially available mRNA. The relative amount of cDNA used in each assay was determined by performing a parallel experiment using a primer pair for a gene expressed in equal amounts in all tissues, cyclophilin. The cyclophilin primer pair detected small variations in the amount of cDNA in each sample and these data were used for normalization of the data obtained with the primer pair for this gene. The PCR data was converted into a relative assessment of the difference in transcript abundance amongst the tissues tested and the data is presented in FIG. 8. Transcripts corresponding to the novel tubulin tyrosine ligase protein, BGS-42, were expressed predominately in testis. The BGS-42 polypeptide was also expressed significantly in small intestine, stomach, spinal cord, and to a lesser extent, in brain, and liver.

Additional expression profiling was performed to compare the expression pattern of BGS-42 amongst various normal and tumor mRNA tissue sources as shown in FIG. 9. As shown, transcripts corresponding to BGS-42 showed differential expression predominately in lung compared to tumor lung tissue, with a 25 fold decrease in expression observed in lung tumors relative to normal lung tissue. The levels of the control transcript, cyclophilin, used in normalization were approximately equal in all samples indicating that the RNA was of good quality. This apparent loss of BGS-42 expression in tumor tissues relative to normal tissues suggests BGS-42 may play a role in tumor suppression, either directly or indirectly. These data also show skeletal muscle as a tissue with relative high abundance.

Example 6

Method of Assessing the Expression Profile of the Novel BGS-42 Polypeptides of the Present Invention Using Expanded mRNA Tissue and Cell Sources Total RNA from tissues was isolated using the TriZol protocol (Invitrogen) and quantified by determining its absorbance at 260 nM. An assessment of the 18s and 28s ribosomal RNA bands was made by denaturing gel electrophoresis to determine RNA integrity.

The specific sequence to be measured was aligned with related genes found in GenBank to identity regions of significant sequence divergence to maximize primer and probe specificity. Gene-specific primers and probes were designed using the ABI primer express software to amplify small amplicons (150 base pairs or less) to maximize the likelihood that the primers function at 100% efficiency. All primer/probe sequences were searched against Public Genbank databases to ensure target specificity. Primers and probes were obtained from ABI.

For BGS-42, the primer probe sequences were as follows:

```
Forward Primer
5'-TCAGAGAATGGGCCAACAAGA-3'         (SEQ ID NO:28)

Reverse Primer
5'-CGAAAACGCTCGAGGAATGA-3'          (SEQ ID NO:29)

TaqMan Probe
5'-CAGGCCTAGGTTCCTCCTCTCGGAAA-3'    (SEQ ID NO:30)
```

DNA Contamination

To access the level of contaminating genomic DNA in the RNA, the RNA was divided into 2 aliquots and one half was treated with Rnase-free Dnase (Invitrogen). Samples from both the Dnase-treated and non-treated were then subjected to reverse transcription reactions with (RT+) and without (RT−) the presence of reverse transcriptase. TaqMan assays were carried out with gene-specific primers (see above) and the contribution of genomic DNA to the signal detected was evaluated by comparing the threshold cycles obtained with the RT+/RT− non-Dnase treated RNA to that on the RT+/RT− Dnase treated RNA. The amount of signal contributed by genomic DNA in the Dnased RT−RNA must be less that 10% of that obtained with Dnased RT+RNA. If not the RNA was not used in actual experiments.

Reverse Transcription reaction and Sequence Detection 100 ng of Dnase-treated total RNA was annealed to 2.5 μM of the respective gene-specific reverse primer in the presence of 5.5 mM Magnesium Chloride by heating the sample to 72° C. for 2 min and then cooling to 55° C. for 30 min. 1.25 U/μl of MuLv reverse transcriptase and 500 μM of each dNTP was added to the reaction and the tube was incubated at 37° C. for 30 min. The sample was then heated to 90° C. for 5 min to denature enzyme.

Quantitative sequence detection was carried out on an ABI PRISM 7700 by adding to the reverse transcribed reaction 2.5 μM forward and reverse primers, 500 μM of each dNTP, buffer and 5U AmpliTaq Gold™. The PCR reaction was then held at 94° C. for 12 min, followed by 40 cycles of 94° C. for 15 sec and 60° C. for 30 sec.

Data Handling

The threshold cycle (Ct) of the lowest expressing tissue (the highest Ct value) was used as the baseline of expression and all other tissues were expressed as the relative abundance to that tissue by calculating the difference in Ct value between the baseline and the other tissues and using it as the exponent in $2^{(\Delta Ct)}$ The expanded expression profile of the BGS-42 polypeptide is provided in FIG. 10. The BGS-42 polypeptide was expressed predominately in the vas deferens. Expression of BGS-42 was also significantly expressed in lymph gland, pituitary, placenta, and to a lesser extent, in other tissues as shown.

Additional expression profiling was performed to compare the BGS-42 expression in normal versus tumor tissues. The expression of the BGS-42 polypeptide was not observed in any of the five testis tumor samples. This apparent loss of BGS-42 expression in tumor tissues relative to normal tissues suggests BGS-42 may play a role in tumor suppression, either directly or indirectly.

Example 7

Method of Assessing the Ability of BGS-42 to Ligate Tyrosine to Tubulin

The method of Raybin and Flavin may be followed essentially as dscribed in Biochemistry 16, 2189–2194. Briefly, purified BGS42 protein may be tested for tubulin tyrosine ligase activity by incubating with appropriate levels of tubulin and tyrosine and $^{14}$C-tyrosine in the presence of ATP. The reaction may be stopped after an appropriate period of time, and the reaction products precipitated with trichloroacetic acetic acid and filtering onto Whatman 3 MM. The specificity of the reaction may be checked by SDS-polyacrylamide electrophoresis and autoradiography. Incorporation of $^{14}$C-tyrosine onto tubulin would be diagnostic of active tubulin tyrosine ligase activity. The skilled artisan would appreciate that appropriate levels of tubulin, tyrosine, and $^{14}$C-tyrosine would need to be emperically determined based upon the Kcat and Km, and other catalytic rate constants, of the purified BGS-42 polypeptide. The same rate constants would also influence selection of an appropriate incution period.

One skilled in the art could easily modify the exemplified studies to test the activity of polynucleotides of the invention, agonists, and/or antagonists of polynucleotides or polypeptides of the invention.

Example 8

Method of Demonstrating Altered Methylation Patterns in the BGS-42 Promotor

The method of Herman et al., may be followed essentially as described by Herman et al., Proc. Natl. Acad. Sci. USA 93, 9821–9826. Briefly, breast, colon and lung tumor cell lines may be assayed for BGS-42 expression by real time quantitative PCR. Expression levels may be ranked as being either high or low expression. Genomic DNA may be isolated by standard techniques, denatured with sodium hydroxide and treated with sodium bisulfite. Two sets of PCR primers may then be designed across several regions upstream of the start of BGS-42 translation that include CpG islands. To amplify the genomic DNA from high expression cell lines (non-methylated DNA), a T may be used in the position 5' to the G where normally a C would reside. To amplify the genomic DNA isolated from the low expressing cell lines (methylated DNA); the normal C will be used in the position 5' to the G. These primer sets will take advantage of the fact the methylation protects cytosine from conversion to uracil by bisulfite treatment. Using primers with both C and T will distinguish methylated DNA from non-methylated. Thus, the changes in expression levels between the "C" and "T" containing primers will provide evidence that DNA methylation does have an effect on BGS-42 expression, in tumor samples relative to normal samples.

One skilled in the art could easily modify the exemplified studies to test the activity of polynucleotides of the invention, agonists, and/or antagonists of polynucleotides or polypeptides of the invention.

Example 9

Method of Assessing the Physiological Function of the BGS-42 Polypeptide at the Cellular Level The physiological function of the BGS-42 polypeptide may be assessed by expressing the sequences encoding BGS-42 at physiologically elevated levels in mammalian cell culture systems. cDNA is subcloned into a mammalian expression vector containing a strong promoter that drives high levels of cDNA expression (examples are provided elsewhere herein). Vectors of choice include pCMV SPORT (Life Technologies) and pCR3.1 (Invitrogen, Carlsbad Calif.), both of which contain the cytomegalovirus promoter. 5–10, ug of recombinant vector are transiently transfected into a human cell line, preferably of endothelial or hematopoietic origin, using either liposome formulations or electroporation. 1–2 ug of an additional plasmid containing sequences encoding a marker protein are cotransfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) Flow Cvtometrv, Oxford, New York N.Y.

The influence of BGS-42 polypeptides on gene expression can be assessed using highly purified populations of cells transfected with sequences encoding BGS-42 and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding BGS-42 polypeptides and other genes of interest can be analyzed by northern analysis or microarray techniques.

Example 10

Method of Screening for Compounds that Interact with the BGS-42 Polypeptide

The following assays are designed to identify compounds that bind to the BGS-42 polypeptide, bind to other cellular proteins that interact with the BGS-42 polypeptide, and to compounds that interfere with the interaction of the BGS-42 polypeptide with other cellular proteins.

Such compounds can include, but are not limited to, other cellular proteins. Specifically, such compounds can include, but are not limited to, peptides, such as, for example, soluble peptides, including, but not limited to Ig-tailed fusion peptides, comprising extracellular portions of BGS-42 polypeptide transmembrane receptors, and members of random peptide libraries (see, e.g., Lam, K. S. et al., 1991, Nature 354:82–84; Houghton, R. et al., 1991, Nature 354:84–86), made of D-and/or L-configuration amino acids, phosphopeptides (including, but not limited to, members of random or partially degenerate phosphopeptide libraries; see, e.g., Songyang, Z., et al., 1993, Cell 72:767–778), antibodies (including, but not limited to, polyclonal, monoclonal, humanized, anti-idiotypic, chimeric or single chain antibodies, and FAb, F(ab').sub.2 and FAb expression libary fragments, and epitope-binding fragments thereof), and small organic or inorganic molecules.

Compounds identified via assays such as those described herein can be useful, for example, in elaborating the biological function of the BGS-42 polypeptide, and for ameliorating symptoms of tumor progression, for example. In instances, for example, whereby a tumor progression state or disorder results from a lower overall level of BGS-42 expression, BGS-42 polypeptide, and/or BGS-42 polypeptide activity in a cell involved in the tumor progression state or disorder, compounds that interact with the BGS-42 polypeptide can include ones which accentuate or amplify the activity of the bound BGS-42 polypeptide. Such compounds would bring about an effective increase in the level of BGS-42 polypeptide activity, thus ameliorating symptoms of the tumor progression disorder or state. In instances whereby mutations within the BGS-42 polypeptide cause aberrant BGS-42 polypeptides to be made which have a deleterious effect that leads to tumor progression, compounds that bind BGS-42 polypeptide can be identified that inhibit the activity of the bound BGS-42 polypeptide. Assays for testing the effectiveness of such compounds are known in the art and discussed, elsewhere herein.

Example 11

Method of Screening, in Vitro, Compounds that Bind to the BGS-42 Polypeptide

In vitro systems can be designed to identify compounds capable of binding the BGS-42 polypeptide of the invention. Compounds identified can be useful, for example, in modulating the activity of wild type and/or mutant BGS-42 polypeptide, preferably mutant BGS-42 polypeptide, can be useful in elaborating the biological function of the BGS-42 polypeptide, can be utilized in screens for identifying compounds that disrupt normal BGS-42 polypeptide interactions, or can in themselves disrupt such interactions.

The principle of the assays used to identify compounds that bind to the BGS-42 polypeptide involves preparing a reaction mixture of the BGS-42 polypeptide and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring BGS-42 polypeptide or the test substance onto a solid phase and detecting BGS-42 polypeptide /test compound complexes anchored on the solid phase at the end of the reaction. In one embodiment of such a method, the BGS-42 polypeptide can be anchored onto a solid surface, and the test compound, which is not anchored, can be labeled, either directly or indirectly.

In practice, microtitre plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for BGS-42 polypeptide or the test compound to anchor any complexes formed in solution, and a labeled antibody specific for the other component of the possible complex to detect anchored complexes.

Example 12

Method of Identifying Compounds that Interfere with BGS-42 Polypeptide/Cellular Product Interaction The BGS-42 polypeptide of the invention can, in vivo, interact with one or more cellular or extracellular macromolecules, such as proteins. Such macromolecules include, but are not limited to, polypeptides, particularly GPCR ligands, and those products identified via screening methods described, elsewhere herein. For the purposes of this discussion, such cellular and extracellular macromolecules are referred to herein as "binding partner(s)". For the purpose of the present invention, "binding partner" may also encompass polypeptides, small molecule compounds, polysaccarides, lipids, and any other molecule or molecule type referenced herein. Compounds that disrupt such interactions can be useful in regulating the activity of the BGS-42 polypeptide, especially mutant BGS-42 polypeptide. Such compounds can include, but are not limited to molecules such as antibodies, peptides, and the like described in elsewhere herein.

The basic principle of the assay systems used to identify compounds that interfere with the interaction between the BGS-42 polypeptide and its cellular or extracellular binding partner or partners involves preparing a reaction mixture containing the BGS-42 polypeptide, and the binding partner under conditions and for a time sufficient to allow the two products to interact and bind, thus forming a complex. In order to test a compound for inhibitory activity, the reaction mixture is prepared in the presence and absence of the test compound. The test compound can be initially included in the reaction mixture, or can be added at a time subsequent to the addition of BGS-42 polypeptide and its cellular or extracellular binding partner. Control reaction mixtures are incubated without the test compound or with a placebo. The formation of any complexes between the BGS-42 polypeptide and the cellular or extracellular binding partner is then detected. The formation of a complex in the control reaction, but not in the reaction mixture containing the test compound, indicates that the compound interferes with the interaction of the BGS-42 polypeptide and the interactive binding partner. Additionally, complex formation within reaction mixtures containing the test compound and normal BGS-42 polypeptide can also be compared to complex formation within reaction mixtures containing the test compound and mutant BGS-42 polypeptide. This comparison can be important in those cases wherein it is desirable to identify compounds that disrupt interactions of mutant but not normal BGS-42 polypeptide.

The assay for compounds that interfere with the interaction of the BGS-42 polypeptide and binding partners can be conducted in a heterogeneous or homogeneous format. Heterogeneous assays involve anchoring either the BGS-42 polypeptide or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the BGS-42 polypeptide and the binding partners, e.g., by competition, can be identified by conducting the reaction in the presence of the test substance; i.e., by adding the test substance to the reaction mixture prior to or simultaneously with the BGS-42 polypeptide and interactive cellular or extracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the BGS-42 polypeptide or the interactive cellular or extracellular binding partner, is anchored onto a solid surface, while the non-anchored species is labeled, either directly or indirectly. In practice, microtitre plates are conveniently utilized. The anchored species can be immobilized by non-covalent or covalent attachments. Non-covalent attachment can be accomplished simply by coating the solid surface with a solution of the BGS-42 polypeptide or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the BGS-42 polypeptide and the interactive cellular or extracellular binding partner product is prepared in which either the BGS-42 polypeptide or their binding partners are labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt BGS-42 polypeptide-cellular or extracellular binding partner interaction can be identified.

In a particular embodiment, the BGS-42 polypeptide can be prepared for immobilization using recombinant DNA techniques known in the art. For example, the BGS-42 polypeptide coding region can be fused to a glutathione-S-transferase (GST) gene using a fusion vector such as pGEX-5X-1, in such a manner that its binding activity is maintained in the resulting fusion product. The interactive cellular or extracellular product can be purified and used to raise a monoclonal antibody, using methods routinely practiced in the art and described above. This antibody can be labeled with the radioactive isotope $^{125}$I, for example, by methods routinely practiced in the art. In a heterogeneous assay, e.g., the GST-BGS-42 polypeptide fusion product can be anchored to glutathione-agarose beads. The interactive cellular or extracellular binding partner product can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the BGS-42 polypeptide and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-BGS-42 polypeptide fusion product and the interactive cellular or extracellular binding partner product can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

In another embodiment of the invention, these same techniques can be employed using peptide fragments that correspond to the binding domains of the BGS-42 polypeptide product and the interactive cellular or extracellular binding partner (in case where the binding partner is a product), in place of one or both of the full length products.

Any number of methods routinely practiced in the art can be used to identify and isolate the protein's binding site. These methods include, but are not limited to, mutagenesis of one of the genes encoding one of the products and screening for disruption of binding in a co-immunoprecipitation assay. Compensating mutations in the gene encoding the second species in the complex can be selected. Sequence analysis of the genes encoding the respective products will reveal the mutations that correspond to the region of the product involved in interactive binding. Alternatively, one product can be anchored to a solid surface using methods described in this Section above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the cellular or extracellular binding partner product is obtained, short gene segments can be engineered to express peptide fragments of the product, which can then be tested for binding activity and purified or synthesized.

Example 13

Isolation of a Specific Clone from the Deposited Sample

The deposited material in the sample assigned the ATCC Deposit Number cited in Table I for any given cDNA clone also may contain one or more additional plasmids, each comprising a cDNA clone different from that given clone. Thus, deposits sharing the same ATCC Deposit Number contain at least a plasmid for each cDNA clone identified in Table I. Typically, each ATCC deposit sample cited in Table I comprises a mixture of approximately equal amounts (by weight) of about 1–10 plasmid DNAs, each containing a different cDNA clone and/or partial cDNA clone; but such a deposit sample may include plasmids for more or less than 2 cDNA clones.

Two approaches can be used to isolate a particular clone from the deposited sample of plasmid DNA(s) cited for that clone in Table I. First, a plasmid is directly isolated by screening the clones using a polynucleotide probe corresponding to SEQ ID NO:1.

Particularly, a specific polynucleotide with 30–40 nucleotides is synthesized using an Applied Biosystems DNA synthesizer according to the sequence reported. The oligonucleotide is labeled, for instance, with 32P-(-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ ID NO:1 (i.e., within the region of SEQ ID NO:1 bounded by the 5' NT and the 3' NT of the clone defined in Table I) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5–5 mM MgCl2, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

The polynucleotide(s) of the present invention, the polynucleotide encoding the polypeptide of the present invention, or the polypeptide encoded by the deposited clone may represent partial, or incomplete versions of the complete coding region (i.e., full-length gene). Several methods are known in the art for the identification of the 5' or 3' non-coding and/or coding portions of a gene which may not be present in the deposited clone. The methods that follow are exemplary and should not be construed as limiting the scope of the invention. These methods include but are not limited to, filter probing, clone enrichment using specific probes, and protocols similar or identical to 5' and 3' "RACE" protocols that are well known in the art. For instance, a method similar to 5' RACE is available for generating the missing 5' end of a desired full-length transcript. (Fromont-Racine et al., Nucleic Acids Res. 21(7): 1683–1684 (1993)).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full-length gene.

This above method starts with total RNA isolated from the desired source, although poly-A+RNA can be used. The RNA preparation can then be treated with phosphatase if necessary to eliminate 5' phosphate groups on degraded or damaged RNA that may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene. Moreover, it may be advantageous to optimize the RACE protocol to increase the probability of isolating additional 5' or 3' coding or non-coding sequences. Various methods of optimizing a RACE protocol are known in the art, though a detailed description summarizing these methods can be found in B. C. Schaefer, Anal. Biochem., 227:255–273, (1995).

An alternative method for carrying out 5' or 3' RACE for the identification of coding or non-coding sequences is provided by Frohman, M. A., et al., Proc. Nat'l. Acad. Sci. USA, 85:8998–9002 (1988). Briefly, a cDNA clone missing either the 5' or 3' end can be reconstructed to include the absent base pairs extending to the translational start or stop codon, respectively. In some cases, cDNAs are missing the start of translation, therefor. The following briefly describes a modification of this original 5' RACE procedure. Poly A+ or total RNAs reverse transcribed with Superscript II (Gibco/BRL) and an antisense or I complementary primer specific to the cDNA sequence. The primer is removed from the reaction with a Microcon Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoIJ SaiI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (Promega), restriction digested with XhoI or SalI, and ligated to a plasmid such as pBluescript SKII (Stratagene) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are commercially available for purchase. Similar reagents and methods to those above are supplied in kit form from Gibco/BRL for both 5' and 3' RACE for recovery of full length genes. A second kit is available from Clontech which is a modification of a related technique, SLIC (single-stranded ligation to single-stranded cDNA), developed by Dumas et al., Nucleic Acids Res., 19:5227–32(1991). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

RNA Ligase Protocol for Generating the 5' or 3' End Sequences to Obtain Full Length Genes Once a gene of interest is identified, several methods are available for the identification of the 5' or 3' portions of the gene which may not be present in the original cDNA plasmid. These methods include, but are not limited to, filter probing, clone enrichment using specific probes and protocols similar and identical to 5' and 3'RACE. While the full-length gene may be present in the library and can be identified by probing, a useful method for generating the 5' or 3' end is to use the existing sequence information from the original cDNA to generate the missing information. A method similar to 5'RACE is available for generating the missing 5' end of a desired full-length gene. (This method was published by Fromont-Racine et al., Nucleic Acids Res., 21(7): 1683–1694 (1993)). Briefly, a specific RNA oligonucleotide is ligated to the 5' ends of a population of RNA presumably 30 containing full-length gene RNA transcript and a primer set containing a primer specific to the ligated RNA oligonucleotide and a primer specific to a known sequence of the gene of interest, is used to PCR amplify the 5' portion of the desired full length gene which may then be sequenced and used to generate the full length gene. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a gene specific oligonucleotide. The first strand synthesis reaction can then be used as a template for PCR amplification of the desired 5' end using a primer specific to the ligated RNA oligonucleotide and a primer specific to the known sequence of the apoptosis related of interest. The resultant product is then sequenced and analyzed to confirm that the 5' end sequence belongs to the relevant apoptosis related.

Example 14

Bacterial Expression of a Polypeptide

A polynucleotide encoding a polypeptide of the present invention is amplified using PCR oligonucleotide primers corresponding to the 5' and 3' ends of the DNA sequence, as outlined in Example 13, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.600) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4 degree C. The cell debris is removed by centrifugation, and the supernatant containing the polypeptide is loaded onto a nickel-nitrilo-tri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Example 15

Purification of a Polypeptide from an Inclusion Body

The following alternative method can be used to purify a polypeptide expressed in E coli when it is present in the form of inclusion bodies. Unless otherwise specified, all of the following steps are conducted at 4–10 degree C.

Upon completion of the production phase of the *E. coli* fermentation, the cell culture is cooled to 4–10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perceptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perceptive Biosystems) and weak anion (Poros CM-20, Perceptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 16

Cloning and Expression of a Polypeptide in a Baculovirus Expression System

In this example, the plasmid shuttle vector pAc373 is used to insert a polynucleotide into a baculovirus to express a polypeptide. A typical baculovirus expression vector contains the strong polyhedrin promoter of the *Autographa californica* nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

A polynucleotide encoding a polypeptide of the present invention is amplified using PCR oligonucleotide primers corresponding to the 5' and 3' ends of the DNA sequence, as outlined in Example 13, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described in Example 13. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures" Texas Agricultural Experimental Station Bulletin No. 1555 (1987).

The amplified fragment is isolated from a 1% agarose gel using a commercially available kit ("Geneclean" BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. E. coli HB101 or other suitable E. coli hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized baculovirus DNA ("BaculoGoldtm baculovirus DNA", Pharmingen, San Diego, Calif.), using the lipofection method described by Felgner et al., Proc. Natl. Acad. Sci. USA 84:7413–7417 (1987). One ug of BaculoGoldtm virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 17

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1–3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem . . . 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10:169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("Geneclean" BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five pg of an expression plasmid is cotransformed with 0.5 ug of the plasmid pSVneo using lipofectin (Feigner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM. Expression of the desired gene product is analyzed, for instance, by SDS-PAGE and Western blot or by reversed phase HPLC analysis.

Example 18

Method of Creating N- and C-Terminal Deletion Mutants Corresponding to the BGS-42 Polypeptide of the Present Invention As described elsewhere herein, the present invention encompasses the creation of N- and C-terminal deletion mutants, in addition to any combination of N- and C-terminal deletions thereof, corresponding to the BGS-42 polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length BGS-42 polypeptide sequence (as described in Example 13, for example), appropriate primers of about 15–25 nucleotides derived from the desired 5' and 3' positions of SEQ ID NO:1 may be designed to PCR amplify, and subsequently clone, the intended N- and/or C-terminal deletion mutant. Such primers could comprise, for example, an inititation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the E89 to G306 N-terminal deletion mutant, the following primers could be used to amplify a cDNA fragment corresponding to this deletion mutant:

```
5' Primer        5'-GCAGCA GCGGCCGC GCGGGGAGCAGCGACCTGAGCAGC-3'         (SEQ ID NO:63)
                         NotI 3' Primer        5'-GCAGCA GTCGAC TGAACCTTTTCCTCCGGGCGGCGG-3'           (SEQ ID NO:64)
                         SalI
```

For example, in the case of the M1 to D171 C-terminal deletion mutant, the following primers could be used to amplify a cDNA fragment corresponding to this deletion mutant:

```
5' Primer 5'-GCAGCA GCGGCCGC ATGGCATCCAGCATCCTCAAGTGGG-3'   (SEQ ID NO:65)
                   NotI 3' Primer 5'-GCAGCA GTCGAC GCCGATGTCACAGCTGCGGTCCACG-3'    (SEQ ID NO:66)
                   SalI
```

Representative PCR amplification conditions are provided below, although the skilled artisan would appreciate that other conditions may be required for efficient amplification. A 100 ul PCR reaction mixture may be prepared using long of the template DNA (cDNA clone of BGS-42), 200 uM 4dNTPs, 1 uM primers, 0.25U Taq DNA polymerase (PE), and standard Taq DNA polymerase buffer. Typical PCR cycling condition are as follows:

| 20–25 cycles: | 45 sec, 93 degrees |
|---|---|
|  | 2 min, 50 degrees |
|  | 2 min, 72 degrees |
| 1 cycle: | 10 min, 72 degrees |

After the final extension step of PCR, 5U Kienow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent E. coli cells using methods provided herein and/or otherwise known in the art.

The 5' primer sequence for amplifying any additional N-terminal deletion mutants may be determined by reference to the following formula: (S+(X*3)) to ((S+(X*3))+25), wherein 'S' is equal to the nucleotide position of the initiating start codon of the BGS-42 gene (SEQ ID NO:1), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula: (S+(X*3)) to ((S+(X*3))-25), wherein 'S' is equal to the nucleotide position of the initiating start codon of the BGS-42 gene (SEQ ID NO:1), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

Example 19

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EP A 394,827; Traunecker, et al., Nature 331:84–86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

```
Human IgG Fc region:

GGGATCCGGAGCCCAAATCTTCTGACAAAACTCACACATGCCCACCGTGC    (SEQ ID NO:62)

CCAGCACCTGAATTCGAGGGTGCACCGTCAGTCTTCCTCTTCCCCCCAAAA

CCCAAGGACACCCTCATGATCTCCCGGACTCCTGAGGTCACATGCGTGGT

GGTGGACGTAAGCCACGAAGACCCTGAGGTCAAGTTCAACTGGTACGTGG

ACGGCGTGGAGGTGCATAATGCCAAGACAAAGCCGCGGGAGGAGCAGTA

CAACAGCACGTACCGTGTGGTCAGCGTCCTCACCGTCCTGCACCAGGACT

GGCTGAATGGCAAGGAGTACAAGTGCAAGGTCTCCAACAAAGCCCTCCCA

ACCCCCATCGAGAAAACCATCTCCAAAGCCAAAGGGCAGCCCCGAGAAC

CACAGGTGTACACCCTGCCCCCATCCCGGGATGAGCTGACCAAGAACCAG

GTCAGCCTGACCTGCCTGGTCAAAGGCTTCTATCCAAGCGACATCGCCGT

GGAGTGGGAGAGCAATGGGCAGCCGGAGAACAACTACAAGACCACGCCT

CCCGTGCTGGACTCCGACGGCTCCTTCTTCCTCTACAGCAAGCTCACCGTG

GACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGG

GTAAATGAGTGCGACGGCCGCGACTCTAGAGGAT
```

Example 20

Regulation of Protein Expression Via Controller Aggregation in the Endoplasmic Reticulum As described more particularly herein, proteins regulate diverse cellular processes in higher organisms, ranging from rapid metabolic changes to growth and differentiation. Increased production of specific proteins could be used to prevent certain diseases and/or disease states. Thus, the ability to modulate the expression of specific proteins in an organism would provide significant benefits.

Numerous methods have been developed to date for introducing foreign genes, either under the control of an inducible, constitutively active, or endogenous promoter, into organisms. Of particular interest are the inducible promoters (see, M. Gossen, et al., Proc. Natl. Acad. Sci. USA., 89:5547 (1992); Y. Wang, et al., Proc. Natl. Acad. Sci. USA, 91:8180 (1994), D. No., et al., Proc. Natl. Acad. Sci. USA, 93:3346 (1996); and V. M. Rivera, et al., Nature Med, 2:1028 (1996); in addition to additional examples disclosed elsewhere herein). In one example, the gene for erthropoietin (Epo) was transferred into mice and primates under the control of a small molecule inducer for expression (e.g., tetracycline or rapamycin) (see, D. Bohl, et al., Blood, 92:1512, (1998); K. G. Rendahl, et al., Nat. Biotech, 16:757, (1998); V. M. Rivera, et al., Proc. Natl. Acad. Sci. USA, 96:8657 (1999); and X.Ye et al., Science, 283:88 (1999). Although such systems enable efficient induction of the gene of interest in the organism upon addition of the inducing agent (i.e., tetracycline, rapamycin, etc,.), the levels of expression tend to peak at 24 hours and trail off to background levels after 4 to 14 days. Thus, controlled transient expression is virtually impossible using these systems, though such control would be desirable.

A new alternative method of controlling gene expression levels of a protein from a transgene (i.e., includes stable and transient transformants) has recently been elucidated (V. M. Rivera., et al., Science, 287:826–830, (2000)). This method does not control gene expression at the level of the mRNA like the aforementioned systems. Rather, the system controls the level of protein in an active secreted form. In the absence of the inducing agent, the protein aggregates in the ER and is not secreted. However, addition of the inducing agent results in dis-aggregation of the protein and the subsequent secretion from the ER. Such a system affords low basal secretion, rapid, high level secretion in the presence of the inducing agent, and rapid cessation of secretion upon removal of the inducing agent. In fact, protein secretion reached a maximum level within 30 minutes of induction, and a rapid cessation of secretion within 1 hour of removing the inducing agent. The method is also applicable for controlling the level of production for membrane proteins.

Detailed methods are presented in V. M. Rivera., et al., Science, 287:826–830, (2000)), briefly:

Fusion protein constructs are created using polynucleotide sequences of the present invention with one or more copies (preferably at least 2, 3, 4, or more) of a conditional aggregation domain (CAD) a domain that interacts with itself in a ligand-reversible manner (i.e., in the presence of an inducing agent) using molecular biology methods known in the art and discussed elsewhere herein. The CAD domain may be the mutant domain isolated from the human FKBP12 (Phe$^{36}$ to Met) protein (as disclosed in V. M. Rivera., et al., Science, 287:826–830, (2000), or alternatively other proteins having domains with similar ligand-reversible, self-aggregation properties. As a principle of design the fusion protein vector would contain a furin cleavage sequence operably linked between the polynucleotides of the present invention and the CAD domains. Such a cleavage site would enable the proteolytic cleavage of the CAD domains from the polypeptide of the present invention subsequent to secretion from the ER and upon entry into the trans-Golgi (J. B. Denault, et al., FEBS Lett., 379:113, (1996)). Alternatively, the skilled artisan would recognize that any proteolytic cleavage sequence could be substituted for the furin sequence provided the substituted sequence is cleavable either endogenously (e.g., the furin sequence) or exogenously (e.g., post secretion, post purification, post production, etc.). The preferred sequence of each feature of the fusion protein construct, from the 5' to 3' direction with each feature being operably linked to the other, would be a promoter, signal sequence, "X" number of (CAD)x domains, the furin sequence (or other proteolytic sequence), and the coding sequence of the polypeptide of the present invention. The artisan would appreciate that the promotor and signal sequence, independent from the other, could be either the endogenous promotor or signal sequence of a polypeptide of the present invention, or alternatively, could be a heterologous signal sequence and promotor.

The specific methods described herein for controlling protein secretion levels through controlled ER aggregation are not meant to be limiting are would be generally applicable to any of the polynucleotides and polypeptides of the present invention, including variants, homologues, orthologs, and fragments therein.

Example 21

Alteration of Protein Glycosylation Sites to Enhance Characteristics of Polypeptides of the Invention Many eukaryotic cell surface and proteins are post-translationally processed to incorporate N-linked and O-linked carbohydrates (Kornfeld and Kornfeld (1985) Annu. Rev. Biochem. 54:631–64; Rademacher et al., (1988) Annu. Rev. Biochem. 57:785–838). Protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion (Fieldier and Simons (1995) Cell, 81:309–312; Helenius (1994) Mol. Biol. Of the Cell 5:253–265; Olden et al., (1978) Cell, 13:461–473; Caton et al., (1982) Cell, 37:417–427; Alexamnder and Elder (1984), Science, 226:1328–1330; and Flack et al., (1994), J. Biol. Chem., 269:14015–14020). In higher organisms, the nature and extent of glycosylation can markedly affect the circulating half-life and bio-availability of proteins by mechanisms involving receptor mediated uptake and clearance (Ashwell and Morrell, (1974), Adv. Enzymol., 41:99–128; Ashwell and Harford (1982), Ann. Rev. Biochem., 51:531–54). Receptor systems have been identified that are thought to play a major role in the clearance of serum proteins through recognition of various carbohydrate structures on the glycoproteins (Stockert (1995), Physiol. Rev., 75:591–609; Kery et al., (1992), Arch. Biochem. Biophys., 298:49–55). Thus, production strategies resulting in incomplete attachment of terminal sialic acid residues might provide a means of shortening the bioavailability and half-life of glycoproteins. Conversely, expression strategies resulting in saturation of terminal sialic acid attachment sites might lengthen protein bioavailability and half-life.

In the development of recombinant glycoproteins for use as pharmaceutical products, for example, it has been speculated that the pharmacodynamics of recombinant proteins can be modulated by the addition or deletion of glycosylation sites from a glycoproteins primary structure (Berman and Lasky (1985a) Trends in Biotechnol., 3:51–53). However, studies have reported that the deletion of N-linked glycosylation sites often impairs intracellular transport and results in the intracellular accumulation of glycosylation site variants (Machamer and Rose (1988), J. Biol Chem., 263: 5955–5960; Gallagher et al., (1992), J. Virology., 66:7136–7145; Collier et al., (1993), Biochem., 32:7818–7823; Claffey et al., (1995) Biochemica et Biophysica Acta, 1246:1–9; Dube et al., (1988), J. Biol. Chem. 263:17516–17521). While glycosylation site variants of proteins can be expressed intracellularly, it has proved difficult to recover useful quantities from growth conditioned cell culture medium.

Moreover, it is unclear to what extent a glycosylation site in one species will be recognized by another species glycosylation machinery. Due to the importance of glycosylation in protein metabolism, particularly the secretion and/or expression of the protein, whether a glycosylation signal is recognized may profoundly determine a proteins ability to be expressed, either endogenously or recombinately, in another organism (i.e., expressing a human protein in E. coli, yeast, or viral organisms; or an E. coli, yeast, or viral protein in human, etc.). Thus, it may be desirable to add, delete, or modify a glycosylation site, and possibly add a glycosylation site of one species to a protein of another species to improve the proteins functional, bioprocess purification, and/or structural characteristics (e.g., a polypeptide of the present invention).

A number of methods may be employed to identify the location of glycosylation sites within a protein. One preferred method is to run the translated protein sequence through the PROSITE computer program (Swiss Institute of Bioinformatics). Once identified, the sites could be systematically deleted, or impaired, at the level of the DNA using mutagenesis methodology known in the art and available to the skilled artisan, Preferably using PCR-directed mutagenesis (See Maniatis, Molecular Cloning: A Laboratory Manual, Cold Spring Harbor Press, Cold Spring, N.Y. (1982)). Similarly, glycosylation sites could be added, or modified at the level of the DNA using similar methods, preferably PCR methods (See, Maniatis, supra). The results of modifying the glycosylation sites for a particular protein (e.g., solubility, secretion potential, activity, aggregation, proteolytic resistance, etc.) could then be analyzed using methods know in the art.

The skilled artisan would acknowledge the existence of other computer algorithms capable of predicting the location of glycosylation sites within a protein. For example, the Motif computer program (Genetics Computer Group suite of programs) provides this function, as well.

Example 22

Method of Enhancing the Biological Activity/Functional Characteristics of Invention Through Molecular Evolution Although many of the most biologically active proteins known are highly effective for their specified function in an organism, they often possess characteristics that make them undesirable for transgenic, therapeutic, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

For example, an engineered tubulin tyrosine ligase protein may have altered specificity for its cognate receptor. In yet another example, an engineered tubulin tyrosine ligase protein may be capable of being activated with less than all of the regulatory factors and/or conditions typically required for tubulin tyrosine ligase protein activation (e.g., phosphorylation, conformational changes, etc.). Such a tubulin tyrosine ligase protein would be useful in screens to identify tubulin tyrosine ligase protein modulators, among other uses described herein.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145–152, (1986), and Hill, D E, et al, Methods Enzymol., 55:559–568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments -further diversifying the potential hybridization sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2–4 ug of the DNA substrate(s) would be digested with 0.0015 units of Dnase I (Sigma) per ul in 100 ul of 50 mM Tris-HCL, pH 7.4/1 mM MgCl2 for 10–20 min. at room temperature. The resulting fragments of 10–50 bp could then be purified by running them through a 2% low-melting point agarose gel by electrophoresis onto DE81 ion-exchange paper (Whatmann) or could be purified using Microcon concentrators (Amicon) of the appropriate molecular weight cutoff, or could use oligonucleotide purification columns (Qiagen), in addition to other methods known in the art. If using DE81 ion-exchange paper, the 10–50 bp fragments could be eluted from said paper using 1M NaCl, followed by ethanol precipitation.

The resulting purified fragments would then be subjected to a PCR assembly reaction by re-suspension in a PCR mixture containing: 2 mM of each dNTP, 2.2 mM MgCl2, 50 mM KCl, 10 mM Tris.HCL, pH 9.0, and 0.1% Triton X-100, at a final fragment concentration of 10–30 ng/ul. No primers are added at this point. Taq DNA polymerase (Promega) would be used at 2.5 units per 100 ul of reaction mixture. A PCR program of 94 C for 60 s; 94 C for 30 s, 50–55 C for 30 s, and 72 C for 30 s using 30–45 cycles, followed by 72 C for 5 min using an MJ Research (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8um of each primer and subjecting this mixture to 15 cycles of PCR (using 94 C for 30 s, 50 C for 30 s, and 72 C for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutagenesis using the methods described by Zhao, et al. (Nucl Acid Res., 25(6): 1307–1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336–347, (1997), F. R., Cross, et al., Mol. Cell. Biol., 18:2923–2931, (1998), and A. Crameri., et al., Nat. Biotech., 15:436–438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436–438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

Example 23

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 degrees C. for 30 seconds; 60–120 seconds at 52–58 degrees C.; and 60–120 seconds at 70 degrees C., using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products are cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to the methods described herein are nick-translated with digoxigenindeoxy-uridine 5'-triphosphate (Boehringer Manheim), and FISH performed as described in Johnson et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 24

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described elsewhere herein. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 25

Formulation

The invention also provides methods of treatment and/or prevention diseases, disorders, and/or conditions (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrasternal, subcutaneous and intraarticular injection and infusion.

In yet an additional embodiment, the Therapeutics of the invention are delivered orally using the drug delivery technology described in U.S. Pat. No. 6,258,789, which is hereby incorporated by reference herein.

Therapeutics of the invention are also suitably administered by sustained-release systems. Suitable examples of sustained-release Therapeutics are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention may also be suitably administered by sustained-release systems. Suitable examples of sustained-release Therapeutics include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., J. Biomed. Mater. Res. 15:167–277 (1981), and Langer, Chem. Tech. 12:98–105 (1982)), ethylene vinyl acetate (Langer et al., Id.) or poly-D-(−)-3-hydroxybutyric acid (EP 133,988).

Sustained-release Therapeutics also include liposomally entrapped Therapeutics of the invention (see, generally, Langer, Science 249:1527–1533 (1990); Treat et al., in Liposomes in the Therapy of Infectious Disease and Cancer, Lopez-Berestein and Fidler (eds.), Liss, N.Y., pp. 317–327 and 353–365 (1989)). Liposomes containing the Therapeutic are prepared by methods known per se: DE 3,218,121; Epstein et al., Proc. Natl. Acad. Sci. (USA) 82:3688–3692 (1985); Hwang et al., Proc. Natl. Acad. Sci.(USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527–1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The Therapeutic will typically be formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (ImmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or tubulin tyrosine ligase proteins. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve tubulin tyrosine ligase protein (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892),TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR (zidovudine/AZT), VIDEX (didanosine/ddI), HIVID (zalcitabine/ddC), ZERIT (stavudine/d4T), EPIVIR (lamivudine/3TC), and COMBIVIR (zidovudine/lamivudine). Non-nucleoside reverse transcriptase inhibitors that may be administered in combination with the Therapeutics of the invention, include, but are not limited to, VIRAMUNE (nevirapine), RESCRIPTOR (delavirdine), and SUSTIVA (efavirenz). Protease inhibitors that may be administered in combination with the Therapeutics of the invention, include, but are not limited to, CRIXIVAN (indinavir), NORVIR (ritonavir), INVIRASE (saquinavir), and VIRACEPT (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE, DAPSONE, PENTAMIDINE, ATOVAQUONE, ISONIAZID, RIFAMPIN, PYRAZINAMIDE, ETHAMBUTOL, RIFABUTIN, CLARITHROMYCIN, AZITHROMYCIN, GANCICLOVIR, FOSCARNET, CIDOFOVIR, FLUCONAZOLE, ITRACONAZOLE, KETOCONAZOLE, ACYCLOVIR, FAMCICOLVIR, PYRIMETHAMINE, LEUCOVORIN, NEUPOGEN (filgrastim/G-CSF), and LEUKINE (sargramostim/GM-CSF). In a specific embodiment, Therapeutics of the invention are used in any combination with TRIMETHOPRIM-SULFAMETHOXAZOLE, DAPSONE, PENTAMIDINE, and/or ATOVAQUONE to prophylactically treat or prevent an opportunistic Pneumocystis carinii pneumonia infection. In another specific embodiment, Therapeutics of the invention are used in any combination with ISONIAZID, RIFAMPIN, PYRAZINAMIDE, and/or ETHAMBUTOL to prophylactically treat or prevent an opportunistic Mycobacterium avium complex infection. In another specific embodiment, Therapeutics of the invention are used in any combination with RIFABUTIN, CLARITHROMYCIN, and/or AZITHROMYCIN to prophylactically treat or prevent an opportunistic Mycobacterium tuberculosis infection. In another specific embodiment, Therapeutics of the invention are used in any combination with GANCICLOVIR, FOSCARNET, and/or CIDOFOVIR to prophylactically treat or prevent an opportunistic cytomegalovirus infection. In another specific embodiment, Therapeutics of the invention are used in any combination with FLUCONAZOLE, ITRACONAZOLE, and/or KETOCONAZOLE to prophylactically treat or prevent an opportunistic fungal infection. In another specific embodiment, Therapeutics of the invention are used in any combination with ACYCLOVIR and/or FAMCICOLVIR to prophylactically treat or prevent an opportunistic herpes simplex virus type I and/or type II infection. In another specific embodiment, Therapeutics of the invention are used in any combination with PYRIMETHAMINE and/or LEUCOVORIN to prophylactically treat or prevent an opportunistic Toxoplasma gondii infection. In another specific embodiment, Therapeutics of the invention are used in any combination with LEUCOVORIN and/or NEUPOGEN to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE (OKT3), SANDIMMUNE/NEORAL/SANGDYA (cyclosporin), PROGRAF (tacrolimus), CELLCEPT (mycophenolate), Azathioprine, glucorticosteroids, and RAPAMUNE (sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR, IVEEGAM, SANDOGLOBULIN, GAMMAGARD S/D, and GAMIMUNE. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, IL4, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-6821 10; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PIGF-2), as disclosed in Hauser et al., Gorwth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic tubulin tyrosine ligase proteins. Hematopoietic tubulin tyrosine ligase proteins that may be administered with the Therapeutics of the invention include, but are not limited to, LEUKINE (SARGRAMOSTIM) and NEUPOGEN (FILGRASTIM).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In a specific embodiment, formulations of the present invention may further comprise antagonists of P-glycoprotein (also referred to as the multiresistance protein, or PGP), including antagonists of its encoding polynucleotides (e.g., antisense oligonucleotides, ribozymes, zinc-finger proteins, etc.). P-glycoprotein is well known for decreasing the efficacy of various drug administrations due to its ability to export intracellular levels of absorbed drug to the cell exterior. While this activity has been particularly pronounced in cancer cells in response to the administration of chemotherapy regimens, a variety of other cell types and the administration of other drug classes have been noted (e.g., T-cells and anti-HIV drugs). In fact, certain mutations in the PGP gene significantly reduces PGP function, making it less able to force drugs out of cells. People who have two versions of the mutated gene—one inherited from each parent—have more than four times less PGP than those with two normal versions of the gene. People may also have one normal gene and one mutated one. Certain ethnic populations have increased incidence of such PGP mutations. Among individuals from Ghana, Kenya, the Sudan, as well as African Americans, frequency of the normal gene ranged from 73% to 84%. In contrast, the frequency was 34% to 59% among British whites, Portuguese, Southwest Asian, Chinese, Filipino and Saudi populations. As a result, certain ethnic populations may require increased administration of PGP antagonist in the formulation of the present invention to arrive at the an efficacious dose of the therapeutic (e.g., those from African descent). Conversely, certain ethnic populations, particularly those having increased frequency of the mutated PGP (e.g., of Caucasian descent, or non-African descent) may require less pharmaceutical compositions in the formulation due to an effective increase in efficacy of such compositions as a result of the increased effective absorption (e.g., less PGP activity) of said composition.

Moreover, in another specific embodiment, formulations of the present invention may further comprise antagonists of OATP2 (also referred to as the multiresistance protein, or MRP2), including antagonists of its encoding polynucleotides (e.g., antisense oligonucleotides, ribozymes, zinc-finger proteins, etc.). The invention also further comprises any additional antagonists known to inhibit proteins thought to be attributable to a multidrug resistant phenotype in proliferating cells.

Preferred antagonists that formulations of the present may comprise include the potent P-glycoprotein inhibitor elacridar, and/or LY-335979. Other P-glycoprotein inhibitors known in the art are also encompassed by the present invention.

In additional embodiments, the Therapeutics of the invention are administered in combination with other therapeutic or prophylactic regimens, such as, for example, radiation therapy.

Example 26

Method of Treating Decreased levels of the Polypeptide

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided herein.

Example 27

Method of Treating Increased Levels of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided herein.

Example 28

Method of Treatment Using Gene Therapy-Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks. pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 13 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 29

Gene Therapy Using Endogenous Genes Corresponding to Polynucleotides of the Invention Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932-8935 (1989); and Zijlstra et al., Nature, 342:435-438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately 3×106 cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MBI Fermentas, Amherst, N.Y.) is digested with HindIII. The CMV promoter is amplified by PCR with an XbaI site on the 5' end and a BamHIII site on the 3' end. Two non-coding sequences are amplified via PCR:

one non-coding sequence (fragment 1) is amplified with a HindIII site at the 5' end and an Xba site at the 3'end; the other non-coding sequence (fragment 2) is amplified with a BamHI site at the 5'end and a HindIII site at the 3'end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC 18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately 1.5.×106 cells) is then added to the cuvette, and the cell suspension and DNA solutions are gently mixed. Electroporation is performed with a Gene-Pulser apparatus (Bio-Rad). Capacitance and voltage are set at 960 µF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 30

Method of Treating Using Gene Therapy—in Vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Pat. Nos. 5693622, 5705151, 5580859; Tabata et al., Cardiovasc. Res. 35(3):470–479 (1997); Chao et al., Pharmacol. Res. 35(6): 517–522 (1997); Wolff, Neuromuscul. Disord. 7(5):314–318 (1997); Schwartz et al., Gene Ther. 3(5):405–411 (1996); Tsurumi et al., Circulation 94(12):3281–3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 31

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals" Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR(RT-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 32

Knock-Out Animals

Endogenous gene expression can also be reduced by inactivating or "knocking out" the gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 33

Method of Isolating Antibody Fragments Directed Against BGS-42 from a Library of scFvs Naturally occurring V-genes isolated from human PBLs are constructed into a library of antibody fragments which contain reactivities against BGS-42 to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 E. coli harboring the phagemid are used to inoculate 50 ml of 2xTY containing 1% glucose and 100 µg/ml of ampicillin (2xTY-AMP-GLU) and grown to an O.D. of 0.8 with shaking. Five ml of this culture is used to inoculate 50 ml of 2xTY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2xTY containing 100 µg/ml ampicillin and 50 ug/ml kanamycin and grown overnight. Phage are prepared as described in PCT publication WO 92/01047.

M13 delta gene III is prepared as follows: M13 delta gene mi helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2xTY broth containing 100 µg ampicillin/ml and 25 µg kanamycin/ml (2xTY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

Example 34

Identification and Cloning of VH and VL Domains of Antibodies Directed Against the BGS-42 Polypeptide VH and VL domains may be identified and cloned from cell lines expressing an antibody directed against a BGS-42 epitope by performing PCR with VH and VL specific primers on cDNA made from the antibody expressing cell lines. Briefly, RNA is isolated from the cell lines and used as a template for RT-PCR designed to amplify the VH and VL domains of the antibodies expressed by the EBV cell lines. Cells may be lysed using the TRIzol reagent (Life Technologies, Rockville, Md.) and extracted with one fifth volume of chloroform. After addition of chloroform, the solution is allowed to incubate at room temperature for 10 minutes, and then centrifuged at 14, 000 rpm for 15 minutes at 4 C in a tabletop centrifuge. The supernatant is collected and RNA is precipitated using an equal volume of isopropanol. Precipitated RNA is pelleted by centrifuging at 14, 000 rpm for 15 minutes at 4 C in a tabletop centrifuge.

Following centrifugation, the supernatant is discarded and washed with 75% ethanol. Follwing the wash step, the RNA is centrifuged again at 800 rpm for 5 minutes at 4 C. The supernatant is discarded and the pellet allowed to air dry. RNA is the dissolved in DEPC water and heated to 60 C for 10 minutes. Quantities of RNA can be determined using optical density measurements. cDNA may be synthesized, according to methods well-known in the art and/or described herein, from 1.5–2.5 micrograms of RNA using reverse transciptase and random hexamer primers. cDNA is then used as a template for PCR amplification of VH and VL domains.

Primers used to amplify VH and VL genes are shown below. Typically a PCR reaction makes use of a single 5'primer and a single 3'primer. Sometimes, when the amount of available RNA template is limiting, or for greater efficiency, groups of 5' and/or 3'primers may be used. For example, sometimes all five VH-5'primers and all JH3'primers are used in a single PCR reaction. The PCR reaction is carried out in a 50 microliter volume containing 1×PCR buffer, 2 mM of each dNTP, 0.7 units of High Fidelity Taq polymerse, 5'primer mix, 3'primer mix and 7.5 microliters of cDNA. The 5' and 3'primer mix of both VH and VL can be made by pooling together 22 pmole and 28 pmole, respectively, of each of the individual primers. PCR conditions are: 96 C for 5 minutes; followed by 25 cycles of 94 C for 1 minute, 50 C for 1 minute, and 72 C for 1 minute; followed by an extension cycle of 72 C for 10 minutes. After the reaction has been completed, sample tubes may be stored at 4 C.

Primer Sequences Used to Amplify VH domains

| Primer name | Primer Sequence | SEQ ID NO: |
|---|---|---|
| Hu VH1 -5' | CAGGTGCAGCTGGTGCAGTCTGG | 67 |
| Hu VH2 -5' | CAGGTCAACTTAAGGGAGTCTGG | 68 |
| Hu VH3 -5' | GAGGTGCAGCTGGTGGAGTCTGG | 69 |
| Hu VH4 -5' | CAGGTGCAGCTGCAGGAGTCGGG | 70 |
| Hu VH5 -5' | GAGGTGCAGCTGTTGCAGTCTGC | 71 |
| Hu VH6 -5' | CAGGTACAGCTGCAGCAGTCAGG | 72 |
| Hu JH1 -5' | TGAGGAGACGGTGACCAGGGTGCC | 73 |
| Hu JH3 -5' | TGAAGAGACGGTGACCATTGTCCC | 74 |
| Hu JH4 -5' | TGAGGAGACGGTGACCAGGGTTCC | 75 |
| Hu JH6 -5' | TGAGGAGACGGTGACCGTGGTCCC | 76 |

Primer Sequences Used to Amplify VL domains

| Primer name | Primer Sequence | SEQ ID NO: |
|---|---|---|
| Hu Vkappa1-5' | GACATCCAGATGACCCAGTCTCC | 77 |
| Hu Vkappa2a-5' | GATGTTGTGATGACTCAGTCTCC | 78 |
| Hu Vkappa2b-5' | GATATTGTGATGACTCAGTCTCC | 79 |
| Hu Vkappa3-5' | GAAATTGTGTTGACGCAGTCTCC | 80 |
| Hu Vkappa4-5' | GACATCGTGATGACCCAGTCTCC | 81 |
| Hu Vkappa5-5' | GAAACGACACTCACGCAGTCTCC | 82 |

-continued

Primer Sequences Used to Amplify VL domains

| Primer name | Primer Sequence | SEQ ID NO: |
|---|---|---|
| Hu Vkappa6-5' | GAAATTGTGCTGACTCAGTCTCC | 83 |
| Hu Vlambda1-5' | CAGTCTGTGTTGACGCAGCCGCC | 84 |
| Hu Vlambda2-5' | CAGTCTGCCCTGACTCAGCCTGC | 85 |
| Hu Vlambda3-5' | TCCTATGTGCTGACTCAGCCACC | 86 |
| Hu Vlambda3b-5' | TCTTCTGAGCTGACTCAGGACCC | 87 |
| Hu Vlambda4-5' | CACGTTATACTGACTCAACCGCC | 88 |
| Hu Vlambda5-5' | CAGGCTGTGCTCACTCAGCCGTC | 89 |
| Hu Vlambda6-5' | AATTTTATGCTGACTCAGCCCCA | 90 |
| Hu Jkappa1-3' | ACGTTTGATTTCCACCTTGGTCCC | 91 |
| Hu Jkappa2-3' | ACGTTTGATCTCCAGCTTGGTCCC | 92 |
| Hu Jkappa3-3' | ACGTTTGATATCCACTTTGGTCCC | 93 |
| Hu Jkappa4-3' | ACGTTTGATCTCCACCTTGGTCCC | 94 |
| Hu Jkappa5-3' | ACGTTTAATCTCCAGTCGTGTCCC | 95 |
| Hu Vlambda1-3' | CAGTCTGTGTTGACGCAGCCGCC | 96 |
| Hu Vlambda2-3' | CAGTCTGCCCTGACTCAGCCTGC | 97 |
| Hu Vlambda3-3' | TCCTATGTGCTGACTCAGCCACC | 98 |
| Hu Vlambda3b-3' | TCTTCTGAGCTGACTCAGGACCC | 99 |
| Hu Vlambda4-3' | CACGTTATACTGACTCAACCGCC | 100 |
| Hu Vlambda5-3' | CAGGCTGTGCTCACTCAGCCGTC | 101 |
| Hu Vlambda6-3' | AATTTTATGCTGACTCAGCCCCA | 102 |

PCR samples are then electrophoresed on a 1.3% agarose gel. DNA bands of the expected sizes (~506 base pairs for VH domains, and 344 base pairs for VL domains) can be cut out of the gel and purified using methods well known in the art and/or described herein.

Purified PCR products can be ligated into a PCR cloning vector (TA vector from Invitrogen Inc., Carlsbad, Calif.). Individual cloned PCR products can be isolated after transfection of E. coli and blue/white color selection. Cloned PCR products may then be sequenced using methods commonly known in the art and/or described herein.

The PCR bands containing the VH domain and the VL domains can also be used to create full-length Ig expression vectors. VH and VL domains can be cloned into vectors containing the nucleotide sequences of a heavy (e. g., human IgG1 or human IgG4) or light chain (human kappa or human ambda) constant regions such that a complete heavy or light chain molecule could be expressed from these vectors when transfected into an appropriate host cell. Further, when cloned heavy and light chains are both expressed in one cell line (from either one or two vectors), they can assemble into a complete functional antibody molecule that is secreted into the cell culture medium. Methods using polynucleotides encoding VH and VL antibody domain to generate expression vectors that encode complete antibody molecules are well known within the art.

Example 35

Assays Detecting Stimulation or Inhibition of B Cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay-Purified polypeptides of the invention, or truncated forms thereof, is assessed for its ability to induce activation, proliferation, differentiation or inhibition and/or death in B-cell populations and their precursors. The activity of the polypeptides of the invention on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed Staphylococcus aureus Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added 105 B-cells suspended in culture medium (RPMI 1640 containing 10% FBS, 5×10-5M 2ME, 100 U/ml penicillin, 10 ug/ml streptomycin, and 10-5 dilution of SAC) in a total volume of 150 ul. Proliferation or inhibition is quantitated by a 20 h pulse (1 uCi/well) with 3H-thymidine (6.7 Ci/mM) beginning 72 h post factor addition. The positive and negative controls are IL2 and medium respectively.

In Vivo Assay-BALB/c mice are injected (i.p.) twice per day with buffer only, or 2 mg/Kg of a polypeptide of the invention, or truncated forms thereof. Mice receive this treatment for 4 consecutive days, at which time they are sacrificed and various tissues and serum collected for analyses. Comparison of H&E sections from normal spleens and spleens treated with polypeptides of the invention identify the results of the activity of the polypeptides on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from mice treated with polypeptide is used to indicate whether the polypeptide specifically increases the proportion of ThB+, CD45R (B220)dull B cells over that which is observed in control mice.

Likewise, a predicted consequence of increased mature B-cell representation in vivo is a relative increase in serum Ig titers. Accordingly, serum IgM and IgA levels are compared between buffer and polypeptide-treated mice.

One skilled in the art could easily modify the exemplified studies to test the activity of polynucleotides of the invention (e.g., gene therapy), agonists, and/or antagonists of polynucleotides or polypeptides of the invention.

Example 36

T Cell Proliferation Assay

A CD3-induced proliferation assay is performed on PBMCs and is measured by the uptake of 3H-thymidine. The assay is performed as follows. Ninety-six well plates are coated with 100 (1/well of mAb to CD3 (HIT3a, Pharmingen) or isotype-matched control mAb (B33.1) overnight at 4 degrees C. (1 (g/ml in .05M bicarbonate buffer, pH 9.5), then washed three times with PBS. PBMC are isolated by F/H gradient centrifugation from human peripheral blood and added to quadruplicate wells (5×104/well) of mAb coated plates in RPMI containing 10% FCS and P/S in the presence of varying concentrations of polypeptides of the invention (total volume 200 ul). Relevant protein buffer and medium alone are controls. After 48 hr. culture at 37 degrees C., plates are spun for 2 min. at 1000 rpm and 100 (1 of supernatant is removed and stored −20 degrees C. for measurement of IL-2 (or other cytokines) if effect on proliferation is observed. Wells are supplemented with 100 ul of medium containing 0.5 uCi of 3H-thymidine and cultured at 37 degrees C. for 18–24 hr. Wells are harvested and incorporation of 3H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of polypeptides of the invention.

One skilled in the art could easily modify the exemplified studies to test the activity of polynucleotides of the invention (e.g., gene therapy), agonists, and/or antagonists of polynucleotides or polypeptides of the invention.

Example 37

Effect of Polypeptides of the Invention on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL4 (20 ng/ml). These dendritic cells have the characteristic phenotype of immature cells (expression of CD1, CD80, CD86, CD40 and MHC class II antigens). Treatment with activating factors, such as TNF-, causes a rapid change in surface phenotype (increased expression of MHC class I and II, costimulatory and adhesion molecules, downregulation of FC(RII, upregulation of CD83). These changes correlate with increased antigen-presenting capacity and with functional maturation of the dendritic cells.

FACS analysis of surface antigens is performed as follows. Cells are treated 1–3 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Effect on the production of cytokines. Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells (106/ml) are treated with increasing concentrations of polypeptides of the invention for 24 hours. LPS (100 ng/ml) is added to the cell culture as positive control. Supernatants from the cell cultures are then collected and analyzed for IL-12 content using commercial ELISA kit(e.g., R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. Polypeptides, agonists, or antagonists of the invention can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of 2×106/ml in PBS containing PI at a final concentration of 5 (g/ml, and then incubated at room temperature for 5 minutes before FACScan analysis. PI uptake has been demonstrated to correlate with DNA fragmentation in this experimental paradigm.

Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of 5×105 cells/ml with increasing concentrations of the a polypeptide of the invention and under the same conditions, but in the absence of the polypeptide. For IL-12 production, the cells are primed overnight with WFN (100 U/ml) in presence of a polypeptide of the invention. LPS (10 ng/ml) is then added. Conditioned media are collected after 24 h and kept frozen until use. Measurement of TNF-alpha, IL-10, MCP-1 and IL-8 is then performed using a commercially available ELISA kit (e.g., R & D Systems (Minneapolis, Minn.)) and applying the standard protocols provided with the kit.

Oxidative burst. Purified monocytes are plated in 96-w plate at 2-1×105 cell/well. Increasing concentrations of polypeptides of the invention are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37(C for 2 hours and the reaction is stopped by adding 20 µl 1N NaOH per well. The absorbance is read at 610 nm. To calculate the amount of H2O2 produced by the macrophages, a standard curve of a H2O2 solution of known molarity is performed for each experiment.

One skilled in the art could easily modify the exemplified studies to test the activity of polynucleotides of the invention (e.g., gene therapy), agonists, and/or antagonists of polynucleotides or polypeptides of the invention.

Example 38 the Effect of the BGS-42 Polypeptides of the Invention on the Growth of Vascular Endothelial Cells On day 1, human umbilical vein endothelial cells (HU-VEC) are seeded at 2-5×104 cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. A polypeptide having the amino acid sequence of SEQ ID NO:2, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that the polypeptide of the invention may proliferate vascular endothelial cells.

One skilled in the art could easily modify the exemplified studies to test the activity of polynucleotides of the invention (e.g., gene therapy), agonists, and/or antagonists of polynucleotides or polypeptides of the invention.

Example 39

Stimulatory Effect of Polypeptides of the Invention on the Proliferation of Vascular Endothelial Cells For evaluation of mitogenic activity of tubulin tyrosine ligase proteins, the colorimetric MTS (3-(4,5-dimethylthiazol-2-yl)-5-(3-carboxymethoxyphenyl)-2-(4-sulfophenyl) 2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, VEGF165 or a polypeptide of the invention in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. In Vitro Cell. Dev. Biol. 30A:512–518 (1994).

One skilled in the art could easily modify the exemplified studies to test the activity of polynucleotides of the invention (e.g., gene therapy), agonists, and/or antagonists of polynucleotides or polypeptides of the invention.

Example 40

Inhibition of PDGF-Induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4 degrees C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., J. Biol. Chem . . . 6:271 (36):21985–21992 (1996).

One skilled in the art could easily modify the exemplified studies to test the activity of polynucleotides of the invention (e.g., gene therapy), agonists, and/or antagonists of polynucleotides or polypeptides of the invention.

Example 41

Stimulation of Endothelial Migration

This example will be used to explore the possibility that a polypeptide of the invention may stimulate lymphatic endothelial cell migration.

Endothelial cell migration assays are performed using a 48 well microchemotaxis chamber (Neuroprobe Inc., Cabin John, M D; Falk, W., et al., J. Immunological Methods 1980;33:239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, 2.5×105 cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

One skilled in the art could easily modify the exemplified studies to test the activity of polynucleotides of the invention (e.g., gene therapy), agonists, and/or antagonists of polynucleotides or polypeptides of the invention.

Example 42

Rat Corneal Would Healing Model

This animal model shows the effect of a polypeptide of the invention on neovascularization. The experimental protocol includes:

a) Making a 1–1.5 mm long incision from the center of cornea into the stromal layer.

b) Inserting a spatula below the lip of the incision facing the outer corner of the eye.

c) Making a pocket (its base is 1–1.5 mm form the edge of the eye).

d) Positioning a pellet, containing 50 ng–5 ug of a polypeptide of the invention, within the pocket.

e) Treatment with a polypeptide of the invention can also be applied topically to the corneal wounds in a dosage range of 20 mg–500 mg (daily treatment for five days).

One skilled in the art could easily modify the exemplified studies to test the activity of polynucleotides of the invention (e.g., gene therapy), agonists, and/or antagonists of polynucleotides or polypeptides of the invention.

Example 43

Diabetic Mouse and Glucocorticoid-Impaired Would Healing Models

A. Diabetic db+/db+ Mouse Model.

To demonstrate that a polypeptide of the invention accelerates the healing process, the genetically diabetic mouse model of wound healing is used. The full thickness wound healing model in the db+/db+mouse is a well characterized, clinically relevant and reproducible model of impaired wound healing. Healing of the diabetic wound is dependent on formation of granulation tissue and re-epithelialization rather than contraction (Gartner, M. H. et al., J. Surg. Res. 52:389 (1992); Greenhalgh, D. G. et al., Am. J. Pathol. 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. Proc. Natl. Acad. Sci. USA 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., J. Immunol. 120:1375 (1978); Debray-Sachs, M. et al., Clin. Exp. Immunol. 51(1):1–7 (1983); Leiter et al., Am. J. of Pathol. 114:46–55 (1985)). Peripheral neuropathy, myocardial complications, and microvascular lesions, basement membrane thickening and glomerular filtration abnormalities have been described in these animals (Norido, F. et al., Exp. Neurol. 83(2):221–232 (1984); Robertson et al., Diabetes 29(1):60–67 (1980); Giacomelli et al., Lab Invest. 40(4):460–473 (1979); Coleman, D. L., Diabetes 31 (Suppl):1–6 (1982)). These homozygous diabetic mice develop hyperglycemia that is resistant to insulin analogous to human type II diabetes (Mandel et al., J. Immunol. 120:1375–1377 (1978)).

The characteristics observed in these animals suggests that healing in this model may be similar to the healing observed in human diabetes (Greenhalgh, et al., Am. J. of Pathol. 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Bristol-Myers Squibb Company's Institutional Animal Care and Use Committee and the Guidelines for the Care and Use of Laboratory Animals.

Wounding protocol is performed according to previously reported methods (Tsuboi, R. and Rifkin, D. B., J. Exp. Med. 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

A polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) untreated group, and 3) treated group.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 mm2, the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with a polypeptide of the invention. This assessment included verification of the presence of cell accumulation, inflammatory cells, capillaries, fibroblasts, re-epithelialization and epidermal maturity (Greenhalgh, D. G. et al., Am. J. Pathol. 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer can serve as a positive tissue control and human brain tissue can be used as a negative tissue control. Each specimen includes a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, Glucocorticoids and Wound healing. In: Anti-Inflammatory Steroid Action: Basic and Clinical Aspects. 280–302 (1989); Wahl et al., J. Immunol. 115: 476–481 (1975); Werb et al., J. Exp. Med. 147:1684–1694 (1978)). Glucocorticoids retard wound healing by inhibiting angiogenesis, decreasing vascular permeability (Ebert et al., An. Intern. Med. 37:701–705 (1952)), fibroblast proliferation, and collagen synthesis (Beck et al., Growth Factors. 5: 295–304 (1991); Haynes et al., J. Clin. Invest. 61: 703–797 (1978)) and producing a transient reduction of circulating monocytes (Haynes et al., J. Clin. Invest. 61: 703–797 (1978); Wahl, "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck et al., Growth Factors. 5: 295–304 (1991); Haynes et al., J. Clin. Invest. 61: 703–797 (1978); Wahl, "Glucocorticoids and wound healing", In: Antiinflammatory Steroid Action: Basic and Clinical Aspects, Academic Press, New York, pp. 280–302 (1989); Pierce et al., Proc. Natl. Acad. Sci. USA 86: 2229–2233 (1989)).

To demonstrate that a polypeptide of the invention can accelerate the healing process, the effects of multiple topical applications of the polypeptide on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study would be conducted according to the rules and guidelines of Bristol-Myers Squibb Corporations Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

The polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) are evaluated: 1) Untreated group 2) Vehicle placebo control 3) treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 mm2, the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with a polypeptide of the invention. A calibrated lens micrometer is used by a blinded observer to determine the distance of the wound gap.

Experimental data are analyzed using an unpaired t test. A p value of <0.05 is considered significant.

One skilled in the art could easily modify the exemplified studies to test the activity of polynucleotides of the invention (e.g., gene therapy), agonists, and/or antagonists of polynucleotides or polypeptides of the invention.

Example 44

Suppression of TNF Alpha-Induced Adhesion Molecule Expression by a Polypeptide of the Invention The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and tubulin tyrosine ligase protein participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of a polypeptide of the invention to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% CO2. HUVECs are seeded in 96-well plates at concentrations of 1×104 cells/well in EGM medium at 37 degree C. for 18–24 hrs or until confluent. The monolayers are subsequently washed 3 times with a serum-free solution of RPMI1640 supplemented with 100 U/ml penicillin and 100 mg/ml streptomycin, and treated with a given cytokine and/or tubulin tyrosine ligase protein(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either 5 h (selectin and integrin expression) or 24 h (integrin expression only). Plates are aspirated to remove medium and 100 µl of 0.1% paraformaldehyde-PBS(with Ca++ and Mg++) is added to each well. Plates are held at 4° C. for 30 min.

Fixative is then removed from the wells and wells are washed 1× with PBS(+Ca,Mg)+0.5% BSA and drained. Do not allow the wells to dry. Add 10 µl of diluted primary antibody to the test and control wells. Anti-ICAM-1-Biotin, Anti-VCAM-1-Biotin and Anti-E-selectin-Biotin are used at a concentration of 10 µg/ml (1:10 dilution of 0.1 mg/ml stock antibody). Cells are incubated at 37° C. for 30 min. in a humidified environment. Wells are washed X3 with PBS (+Ca,Mg)+0.5% BSA.

Then add 20 µl of diluted ExtrAvidin-Alkaline Phosphatase (1:5,000 dilution) to each well and incubated at 37° C. for 30 min. Wells are washed X3 with PBS(+Ca,Mg)+ 0.5% BSA. 1 tablet of p-Nitrophenol Phosphate pNPP is dissolved in 5 ml of glycine buffer (pH 10.4). 100 µl of pNPP substrate in glycine buffer is added to each test well. Standard wells in triplicate are prepared from the working dilution of the ExtrAvidin-Alkaline Phosphatase in glycine buffer: 1:5,000 (100)>10-0.5>10-1>10-1.5. 5 µl of each dilution is added to triplicate wells and the resulting AP content in each well is 5.50 ng, 1.74 ng, 0.55 ng, 0.18 ng. 100 µl of pNNP reagent must then be added to each of the standard wells. The plate must be incubated at 37° C. for 4 h. A volume of 50 µl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

One skilled in the art could easily modify the exemplified studies to test the activity of polynucleotides of the invention (e.g., gene therapy), agonists, and/or antagonists of polynucleotides or polypeptides of the invention.

Example 45

Site Directed/Site-Specific Mutagenesis

In vitro site-directed mutagenesis is an invaluable technique for studying protein structure-function relationships and gene expression, for example, as well as for vector modification. Site-directed mutagenesis can also be used for creating any of one or more of the mutants of the present invention, particularly the conservative and/or non-conservative amino acid substitution mutants of the present invention. Approaches utilizing single stranded DNA (ssDNA) as the template have been reported (e.g., T. A. Kunkel et al., 1985, *Proc. Natl. Acad. Sci. USA*), 82:488–492; M. A. Vandeyar et al., 1988, *Gene*, 65(1):129–133; M. Sugimoto et al., 1989, *Anal. Biochem.*, 179(2):309–311; and J. W. Taylor et al., 1985, *Nuc. Acids. Res.*, 13(24):8765–8785).

The use of PCR in site-directed mutagenesis accomplishes strand separation by using a denaturing step to separate the complementary strands and to allow efficient polymerization of the PCR primers. PCR site-directed mutagenesis methods thus permit site specific mutations to be incorporated in virtually any double stranded plasmid, thus eliminating the need for re-subcloning into M13-based bacteriophage vectors or single-stranded rescue. (M. P. Weiner et al., 1995, *Molecular Biology: Current Innovations and Future Trends*, Eds. A. M. Griffin and H. G. Griffin, Horizon Scientific Press, Norfolk, UK; and C. Papworth et al., 1996, *Strategies*, 9(3):3–4).

A protocol for performing site-directed mutagenesis, particularly employing the QuikChange™ site-directed mutagenesis kit (Stratagene, La Jolla, Calif.; U.S. Pat. Nos. 5,789,166 and 5,923,419) is provided for making point mutations, to switch or substitute amino acids, and to delete or insert single or multiple amino acids in the RATL1d6 amino acid sequence of this invention.

Primer Design

For primer design using this protocol, the mutagenic oligonucleotide primers are designed individually according to the desired mutation. The following considerations should be made for designing mutagenic primers: 1) Both of the mutagenic primers must contain the desired mutation and anneal to the same sequence on opposite strands of the plasmid; 2) Primers should be between 25 and 45 bases in length, and the melting temperature ($T_m$) of the primers should be greater than, or equal to, 78° C. The following formula is commonly used for estimating the $T_m$ of primers: T=81.5+0.41 (% GC)−675/N−% mismatch. For calculating $T_m$, N is the primer length in bases; and values for % GC and % mismatch are whole numbers. For calculating $T_m$ for primers intended to introduce insertions or deletions, a modified version of the above formula is employed: T=81.5+0.41 (% GC)−675/N, where N does not include the bases which are being inserted or deleted; 3) The desired mutation (deletion or insertion) should be in the middle of the primer with approximately 10–15 bases of correct sequence on both sides; 4) The primers optimally should have a minimum GC content of 40%, and should terminate in one or more C or G bases; 5) Primers need not be 5'-phosphorylated, but must be purified either by fast polynucleotide liquid chromatography (FPLC) or by polyacrylamide gel electrophoresis (PAGE). Failure to purify the primers results in a significant decrease in mutation efficiency; and 6) It is important that primer concentration is in excess. It is suggested to vary the amount of template while keeping the concentration of the primers constantly in excess (QuikChange™ Site-Directed Mutagenesis Kit, Stratagene, La Jolla, Calif.).

Protocol for Setting Up the Reactions

Using the above-described primer design, two complimentary oligonucleotides containing the desired mutation, flanked by unmodified nucleic acid sequence, are synthesized. The resulting oligonucleotide primers are purified.

A control reaction is prepared using 5 µl 10×reaction buffer (100 mM KCl; 100 mM $(NH_4)_2SO_4$; 200 mM Tris-HCl, pH 8.8; 20 mM $MgSO_4$; 1% Triton® X-100; 1 mg/ml nuclease-free bovine serum albumin, BSA); 2 µl (10 ng) of pWhitescrip™, 4.5-kb control plasmid (5 ng/µl); 1.25 µl (125 ng) of oligonucleotide control primer #1 (34-mer, 100 ng/µl); 1.25 µl (125 ng) of oligonucleotide control primer #2 (34-mer, 100 ng/µl); 1 µl of dNTP mix; double distilled $H_2O$; to a final volume of 50 µl. Thereafter, 1 µl of DNA polymerase (PfuTurbo® DNA Polymerase, Stratagene), (2.5 U/µl) is added. PfuTurbo® DNA Polymerase is stated to have 6-fold higher fidelity in DNA synthesis than does Taq polymerase. To maximize temperature cycling performance, use of thin-walled test tubes is suggested to ensure optimum contact with the heating blocks of the temperature cycler.

The sample reaction is prepared by combining 5 µl of 10×reaction buffer; x µl (5–50 ng) of dsDNA template; x µl (125 ng) of oligonucleotide primer #1; x µl (5–50 ng) of dsDNA template; x µl (125 ng) of oligonucleotide primer #2; 1 µl of dNTP mix; and dd$H_2O$ to a final volume of 50 µl. Thereafter, 1 µl of DNA polymerase (PfuTurbo DNA Polymerase, Stratagene), (2.5 U/µl) is added.

It is suggested that if the thermal cycler does not have a hot-top assembly, each reaction should be overlaid with approximately 30 µl of mineral oil.

Cycling the Reactions

Each reaction is cycled using the following cycling parameters:

| Segment | Cycles | Temperature | Time |
|---------|--------|-------------|------|
| 1 | 1 | 95° C. | 30 seconds |
| 2 | 12–18 | 95° C. | 30 seconds |
|   |       | 55° C. | 1 minute |
|   |       | 68° C. | 2 minutes/kb of plasmid length |

For the control reaction, a 12-minute extension time is used and the reaction is run for 12 cycles. Segment 2 of the above cycling parameters is adjusted in accordance with the type of mutation desired. For example, for point mutations, 12 cycles are used; for single amino acid changes, 16 cycles are used; and for multiple amino acid deletions or insertions, 18 cycles are used. Following the temperature cycling, the reaction is placed on ice for 2 minutes to cool the reaction to $\leq 37°$ C.

Digesting the Products and Transforming Competent Cells

One µl of the DpnI restriction enzyme (10 U/∥l) is added directly (below mineral oil overlay) to each amplification reaction using a small, pointed pipette tip. The reaction mixture is gently and thoroughly mixed by pipetting the solution up and down several times. The reaction mixture is then centrifuged for 1 minute in a microcentrifuge. Immediately thereafter, each reaction is incubated at 37° C. for 1 hour to digest the parental (i.e., the non-mutated) supercoiled dsDNA.

Competent cells (i.e., XL1-Blue supercompetent cells, Stratagene) are thawed gently on ice. For each control and sample reaction to be transformed, 50 µl of the supercompetent cells are aliquotted to a prechilled test tube (Falcon 2059 polypropylene). Next, 1 µl of the DpnI-digested DNA is transferred from the control and the sample reactions to separate aliquots of the supercompetent cells. The transformation reactions are gently swirled to mix and incubated for 30 minutes on ice. Thereafter, the transformation reactions are heat-pulsed for 45 seconds at 42° C. for 2 minutes.

0.5 ml of NZY+broth, preheated to 42° C. is added to the transformation reactions which are then incubated at 37° C. for 1 hour with shaking at 225–250 rpm. An aliquot of each transformation reaction is plated on agar plates containing the appropriate antibiotic for the vector. For the mutagenesis and transformation controls, cells are spread on LB-ampicillin agar plates containing 80 µg/ml of X-gal and 20 mM IPTG. Transformation plates are incubated for >16 hours at 37° C.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

TABLE IV

| Atom No. | Atom Type | Residue | Residue Position | X Coord. | Y Coord. | Z Coord. |
|---|---|---|---|---|---|---|
| 1 | N | MET | 1 | 39.078 | 12.834 | 68.219 |
| 2 | CA | MET | 1 | 38.470 | 12.062 | 67.126 |
| 3 | C | MET | 1 | 36.989 | 12.378 | 66.980 |
| 4 | O | MET | 1 | 36.371 | 13.008 | 67.846 |
| 5 | CB | MET | 1 | 38.644 | 10.569 | 67.365 |
| 6 | CG | MET | 1 | 40.112 | 10.173 | 67.285 |
| 7 | SD | MET | 1 | 40.891 | 10.457 | 65.678 |
| 8 | CE | MET | 1 | 42.551 | 9.850 | 66.054 |
| 9 | N | ALA | 2 | 36.440 | 11.938 | 65.865 |
| 10 | CA | ALA | 2 | 35.020 | 12.139 | 65.596 |
| 11 | C | ALA | 2 | 34.338 | 10.813 | 65.304 |
| 12 | O | ALA | 2 | 34.979 | 9.858 | 64.846 |
| 13 | CB | ALA | 2 | 34.865 | 13.066 | 64.397 |
| 14 | N | SER | 3 | 33.016 | 10.874 | 65.293 |
| 15 | CA | SER | 3 | 32.191 | 9.686 | 65.035 |
| 16 | C | SER | 3 | 32.242 | 9.282 | 63.575 |
| 17 | O | SER | 3 | 32.311 | 8.087 | 63.276 |
| 18 | CB | SER | 3 | 30.740 | 10.014 | 65.335 |
| 19 | OG | SER | 3 | 30.673 | 10.482 | 66.665 |
| 20 | N | SER | 4 | 32.526 | 10.255 | 62.724 |
| 21 | CA | SER | 4 | 32.633 | 9.995 | 61.288 |
| 22 | C | SER | 4 | 33.908 | 9.219 | 60.978 |
| 23 | O | SER | 4 | 33.868 | 8.247 | 60.214 |
| 24 | CB | SER | 4 | 32.699 | 11.337 | 60.571 |
| 25 | OG | SER | 4 | 31.574 | 12.111 | 60.966 |
| 26 | N | ILE | 5 | 34.914 | 9.433 | 61.811 |
| 27 | CA | ILE | 5 | 36.197 | 8.766 | 61.632 |
| 28 | C | ILE | 5 | 36.136 | 7.354 | 62.194 |
| 29 | O | ILE | 5 | 36.636 | 6.427 | 61.548 |
| 30 | CB | ILE | 5 | 37.252 | 9.576 | 62.373 |
| 31 | CG1 | ILE | 5 | 37.267 | 11.013 | 61.865 |
| 32 | CG2 | ILE | 5 | 38.629 | 8.942 | 62.223 |
| 33 | CD1 | ILE | 5 | 38.319 | 11.845 | 62.589 |
| 34 | N | LEU | 6 | 35.275 | 7.156 | 63.178 |
| 35 | CA | LEU | 6 | 35.082 | 5.818 | 63.738 |
| 36 | C | LEU | 6 | 34.283 | 4.941 | 62.789 |
| 37 | O | LEU | 6 | 34.655 | 3.779 | 62.583 |
| 38 | CB | LEU | 6 | 34.309 | 5.930 | 65.043 |
| 39 | CG | LEU | 6 | 35.101 | 6.650 | 66.121 |

TABLE IV-continued

| Atom No. | Atom Type | Residue | Residue Position | X Coord. | Y Coord. | Z Coord. |
|---|---|---|---|---|---|---|
| 40 | CD1 | LEU | 6 | 34.224 | 6.860 | 67.346 |
| 41 | CD2 | LEU | 6 | 36.360 | 5.869 | 66.483 |
| 42 | N | LYS | 7 | 33.383 | 5.551 | 62.036 |
| 43 | CA | LYS | 7 | 32.587 | 4.785 | 61.079 |
| 44 | C | LYS | 7 | 33.396 | 4.442 | 59.834 |
| 45 | O | LYS | 7 | 33.296 | 3.309 | 59.345 |
| 46 | CB | LYS | 7 | 31.355 | 5.604 | 60.722 |
| 47 | CG | LYS | 7 | 30.587 | 5.949 | 61.992 |
| 48 | CD | LYS | 7 | 29.346 | 6.789 | 61.723 |
| 49 | CE | LYS | 7 | 28.706 | 7.236 | 63.033 |
| 50 | NZ | LYS | 7 | 28.427 | 6.084 | 63.905 |
| 51 | N | TRP | 8 | 34.371 | 5.274 | 59.508 |
| 52 | CA | TRP | 8 | 35.256 | 4.934 | 58.397 |
| 53 | C | TRP | 8 | 36.284 | 3.887 | 58.807 |
| 54 | O | TRP | 8 | 36.399 | 2.876 | 58.108 |
| 55 | CB | TRP | 8 | 35.954 | 6.189 | 57.881 |
| 56 | CG | TRP | 8 | 35.041 | 7.209 | 57.221 |
| 57 | CD1 | TRP | 8 | 35.134 | 8.578 | 57.348 |
| 58 | CD2 | TRP | 8 | 33.921 | 6.958 | 56.339 |
| 59 | NE1 | TRP | 8 | 34.145 | 9.149 | 56.616 |
| 60 | CE2 | TRP | 8 | 33.397 | 8.217 | 55.997 |
| 61 | CE3 | TRP | 8 | 33.340 | 5.803 | 55.833 |
| 62 | CZ2 | TRP | 8 | 32.297 | 8.303 | 55.156 |
| 63 | CZ3 | TRP | 8 | 32.238 | 5.898 | 54.992 |
| 64 | CH2 | TRP | 8 | 31.718 | 7.143 | 54.655 |
| 65 | N | VAL | 9 | 36.774 | 3.953 | 60.034 |
| 66 | CA | VAL | 9 | 37.766 | 2.968 | 60.478 |
| 67 | C | VAL | 9 | 37.152 | 1.586 | 60.692 |
| 68 | O | VAL | 9 | 37.691 | 0.615 | 60.143 |
| 69 | CB | VAL | 9 | 38.423 | 3.458 | 61.764 |
| 70 | CG1 | VAL | 9 | 39.313 | 2.384 | 62.380 |
| 71 | CG2 | VAL | 9 | 39.227 | 4.728 | 61.512 |
| 72 | N | VAL | 10 | 35.917 | 1.536 | 61.165 |
| 73 | CA | VAL | 10 | 35.270 | 0.236 | 61.362 |
| 74 | C | VAL | 10 | 34.711 | −0.332 | 60.060 |
| 75 | O | VAL | 10 | 34.774 | −1.553 | 59.866 |
| 76 | CB | VAL | 10 | 34.185 | 0.380 | 62.423 |
| 77 | CG1 | VAL | 10 | 33.372 | −0.901 | 62.581 |
| 78 | CG2 | VAL | 10 | 34.814 | 0.770 | 63.755 |
| 79 | N | SER | 11 | 34.468 | 0.520 | 59.076 |
| 80 | CA | SER | 11 | 34.084 | −0.009 | 57.766 |
| 81 | C | SER | 11 | 35.318 | −0.470 | 56.990 |
| 82 | O | SER | 11 | 35.228 | −1.482 | 56.287 |
| 83 | CB | SER | 11 | 33.296 | 1.030 | 56.971 |
| 84 | OG | SER | 11 | 34.130 | 2.147 | 56.702 |
| 85 | N | HIS | 12 | 36.488 | 0.042 | 57.345 |
| 86 | CA | HIS | 12 | 37.732 | −0.467 | 56.753 |
| 87 | C | HIS | 12 | 38.077 | −1.826 | 57.355 |
| 88 | O | HIS | 12 | 38.413 | −2.754 | 56.610 |
| 89 | CB | HIS | 12 | 38.897 | 0.478 | 57.049 |
| 90 | CG | HIS | 12 | 38.796 | 1.896 | 56.518 |
| 91 | ND1 | HIS | 12 | 38.139 | 2.321 | 55.421 |
| 92 | CD2 | HIS | 12 | 39.385 | 3.003 | 57.082 |
| 93 | CE1 | HIS | 12 | 38.292 | 3.655 | 55.299 |
| 94 | NE2 | HIS | 12 | 39.063 | 4.076 | 56.326 |
| 95 | N | GLN | 13 | 37.720 | −2.008 | 58.618 |
| 96 | CA | GLN | 13 | 37.949 | −3.285 | 59.309 |
| 97 | C | GLN | 13 | 36.909 | −4.347 | 58.948 |
| 98 | O | GLN | 13 | 37.148 | −5.543 | 59.144 |
| 99 | CB | GLN | 13 | 37.887 | −3.009 | 60.805 |
| 100 | CG | GLN | 13 | 38.962 | −2.008 | 61.207 |
| 101 | CD | GLN | 13 | 38.749 | −1.545 | 62.643 |
| 102 | OE1 | GLN | 13 | 37.666 | −1.073 | 63.012 |
| 103 | NE2 | GLN | 13 | 39.809 | −1.632 | 63.426 |
| 104 | N | SER | 14 | 35.810 | −3.915 | 58.351 |
| 105 | CA | SER | 14 | 34.799 | −4.835 | 57.829 |
| 106 | C | SER | 14 | 34.975 | −5.089 | 56.330 |
| 107 | O | SER | 14 | 34.138 | −5.774 | 55.727 |
| 108 | CB | SER | 14 | 33.426 | −4.223 | 58.077 |
| 109 | OG | SER | 14 | 33.303 | −3.993 | 59.474 |
| 110 | N | CYS | 15 | 36.022 | −4.512 | 55.751 |
| 111 | CA | CYS | 15 | 36.316 | −4.600 | 54.311 |
| 112 | C | CYS | 15 | 35.152 | −4.065 | 53.486 |
| 113 | O | CYS | 15 | 34.659 | −4.715 | 52.556 |
| 114 | CB | CYS | 15 | 36.628 | −6.044 | 53.934 |
| 115 | SG | CYS | 15 | 38.049 | −6.774 | 54.782 |

TABLE IV-continued

| Atom No. | Atom Type | Residue | Residue Position | X Coord. | Y Coord. | Z Coord. |
|---|---|---|---|---|---|---|
| 116 | N | SER | 16 | 34.716 | −2.876 | 53.856 |
| 117 | CA | SER | 16 | 33.572 | −2.246 | 53.207 |
| 118 | C | SER | 16 | 34.021 | −1.179 | 52.223 |
| 119 | O | SER | 16 | 34.968 | −0.421 | 52.475 |
| 120 | CB | SER | 16 | 32.705 | −1.616 | 54.286 |
| 121 | OG | SER | 16 | 32.480 | −2.608 | 55.280 |
| 122 | N | ARG | 17 | 33.299 | −1.119 | 51.117 |
| 123 | CA | ARG | 17 | 33.542 | −0.124 | 50.065 |
| 124 | C | ARG | 17 | 32.975 | 1.234 | 50.481 |
| 125 | O | ARG | 17 | 31.809 | 1.556 | 50.227 |
| 126 | CB | ARG | 17 | 32.855 | −0.634 | 48.802 |
| 127 | CG | ARG | 17 | 33.214 | 0.174 | 47.563 |
| 128 | CD | ARG | 17 | 34.726 | 0.239 | 47.369 |
| 129 | NE | ARG | 17 | 35.075 | 0.700 | 46.015 |
| 130 | CZ | ARG | 17 | 35.197 | 1.977 | 45.647 |
| 131 | NH1 | ARG | 17 | 34.965 | 2.959 | 46.521 |
| 132 | NH2 | ARG | 17 | 35.535 | 2.271 | 44.390 |
| 133 | N | SER | 18 | 33.810 | 1.994 | 51.166 |
| 134 | CA | SER | 18 | 33.403 | 3.281 | 51.725 |
| 135 | C | SER | 18 | 33.545 | 4.400 | 50.697 |
| 136 | O | SER | 18 | 34.314 | 4.289 | 49.734 |
| 137 | CB | SER | 18 | 34.265 | 3.546 | 52.951 |
| 138 | OG | SER | 18 | 34.133 | 2.435 | 53.828 |
| 139 | N | SER | 19 | 32.731 | 5.427 | 50.868 |
| 140 | CA | SER | 19 | 32.714 | 6.545 | 49.920 |
| 141 | C | SER | 19 | 32.575 | 7.899 | 50.612 |
| 142 | O | SER | 19 | 31.554 | 8.202 | 51.241 |
| 143 | CB | SER | 19 | 31.557 | 6.333 | 48.952 |
| 144 | OG | SER | 19 | 31.900 | 5.247 | 48.104 |
| 145 | N | ARG | 20 | 33.584 | 8.729 | 50.420 |
| 146 | CA | ARG | 20 | 33.608 | 10.075 | 50.999 |
| 147 | C | ARG | 20 | 33.009 | 11.095 | 50.027 |
| 148 | O | ARG | 20 | 33.477 | 11.239 | 48.890 |
| 149 | CB | ARG | 20 | 35.065 | 10.429 | 51.278 |
| 150 | CG | ARG | 20 | 35.194 | 11.786 | 51.957 |
| 151 | CD | ARG | 20 | 36.647 | 12.232 | 52.043 |
| 152 | NE | ARG | 20 | 37.439 | 11.318 | 52.875 |
| 153 | CZ | ARG | 20 | 38.676 | 10.934 | 52.556 |
| 154 | NH1 | ARG | 20 | 39.422 | 10.300 | 53.461 |
| 155 | NH2 | ARG | 20 | 39.226 | 11.346 | 51.412 |
| 156 | N | SER | 21 | 31.966 | 11.781 | 50.464 |
| 157 | CA | SER | 21 | 31.340 | 12.804 | 49.616 |
| 158 | C | SER | 21 | 30.904 | 14.041 | 50.391 |
| 159 | O | SER | 21 | 30.315 | 13.952 | 51.474 |
| 160 | CB | SER | 21 | 30.114 | 12.207 | 48.945 |
| 161 | OG | SER | 21 | 30.554 | 11.152 | 48.109 |
| 162 | N | LYS | 22 | 31.179 | 15.190 | 49.802 |
| 163 | CA | LYS | 22 | 30.704 | 16.465 | 50.346 |
| 164 | C | LYS | 22 | 29.283 | 16.724 | 49.850 |
| 165 | O | LYS | 22 | 28.872 | 16.161 | 48.826 |
| 166 | CB | LYS | 22 | 31.649 | 17.569 | 49.875 |
| 167 | CG | LYS | 22 | 33.053 | 17.324 | 50.403 |
| 168 | CD | LYS | 22 | 34.020 | 18.431 | 50.009 |
| 169 | CE | LYS | 22 | 35.443 | 18.079 | 50.425 |
| 170 | NZ | LYS | 22 | 35.505 | 17.761 | 51.860 |
| 171 | N | PRO | 23 | 28.554 | 17.609 | 50.519 |
| 172 | CA | PRO | 23 | 27.174 | 17.917 | 50.103 |
| 173 | C | PRO | 23 | 27.064 | 18.624 | 48.743 |
| 174 | O | PRO | 23 | 26.054 | 18.441 | 48.054 |
| 175 | CB | PRO | 23 | 26.624 | 18.786 | 51.193 |
| 176 | CG | PRO | 23 | 27.722 | 19.094 | 52.200 |
| 177 | CD | PRO | 23 | 28.952 | 18.337 | 51.730 |
| 178 | N | ARG | 24 | 28.176 | 19.152 | 48.246 |
| 179 | CA | ARG | 24 | 28.234 | 19.767 | 46.913 |
| 180 | C | ARG | 24 | 28.338 | 18.724 | 45.793 |
| 181 | O | ARG | 24 | 28.387 | 19.076 | 44.612 |
| 182 | CB | ARG | 24 | 29.481 | 20.635 | 46.862 |
| 183 | CG | ARG | 24 | 29.573 | 21.559 | 48.068 |
| 184 | CD | ARG | 24 | 30.889 | 22.325 | 48.055 |
| 185 | NE | ARG | 24 | 32.025 | 21.390 | 47.987 |
| 186 | CZ | ARG | 24 | 32.997 | 21.492 | 47.078 |
| 187 | NH1 | ARG | 24 | 32.979 | 22.488 | 46.189 |
| 188 | NH2 | ARG | 24 | 33.991 | 20.601 | 47.060 |
| 189 | N | ASP | 25 | 28.422 | 17.457 | 46.165 |
| 190 | CA | ASP | 25 | 28.442 | 16.369 | 45.194 |
| 191 | C | ASP | 25 | 27.046 | 15.789 | 44.953 |
| 192 | O | ASP | 25 | 26.918 | 14.869 | 44.135 |
| 193 | CB | ASP | 25 | 29.359 | 15.274 | 45.728 |
| 194 | CG | ASP | 25 | 30.804 | 15.762 | 45.821 |
| 195 | OD1 | ASP | 25 | 31.394 | 15.968 | 44.770 |
| 196 | OD2 | ASP | 25 | 31.239 | 16.071 | 46.924 |
| 197 | N | GLN | 26 | 26.042 | 16.306 | 45.652 |
| 198 | CA | GLN | 26 | 24.656 | 15.815 | 45.535 |
| 199 | C | GLN | 26 | 23.864 | 16.469 | 44.406 |
| 200 | O | GLN | 26 | 23.219 | 17.506 | 44.602 |
| 201 | CB | GLN | 26 | 23.923 | 16.103 | 46.844 |
| 202 | CG | GLN | 26 | 24.223 | 15.085 | 47.939 |
| 203 | CD | GLN | 26 | 23.460 | 13.786 | 47.682 |
| 204 | OE1 | GLN | 26 | 23.497 | 13.232 | 46.579 |
| 205 | NE2 | GLN | 26 | 22.710 | 13.362 | 48.684 |
| 206 | N | ARG | 27 | 23.817 | 15.794 | 43.272 |
| 207 | CA | ARG | 27 | 23.057 | 16.302 | 42.122 |
| 208 | C | ARG | 27 | 21.842 | 15.428 | 41.814 |
| 209 | O | ARG | 27 | 21.977 | 14.263 | 41.425 |
| 210 | CB | ARG | 27 | 23.982 | 16.358 | 40.910 |
| 211 | CG | ARG | 27 | 25.120 | 17.349 | 41.132 |
| 212 | CD | ARG | 27 | 24.581 | 18.754 | 41.386 |
| 213 | NE | ARG | 27 | 25.669 | 19.715 | 41.625 |
| 214 | CZ | ARG | 27 | 25.812 | 20.397 | 42.764 |
| 215 | NH1 | ARG | 27 | 24.984 | 20.171 | 43.787 |
| 216 | NH2 | ARG | 27 | 26.808 | 21.275 | 42.896 |
| 217 | N | GLU | 28 | 20.676 | 16.053 | 41.788 |
| 218 | CA | GLU | 28 | 19.411 | 15.327 | 41.561 |
| 219 | C | GLU | 28 | 19.011 | 15.280 | 40.073 |
| 220 | O | GLU | 28 | 17.844 | 15.485 | 39.709 |
| 221 | CB | GLU | 28 | 18.337 | 16.009 | 42.408 |
| 222 | CG | GLU | 28 | 17.065 | 15.177 | 42.544 |
| 223 | CD | GLU | 28 | 16.105 | 15.851 | 43.515 |
| 224 | OE1 | GLU | 28 | 14.935 | 15.958 | 43.178 |
| 225 | OE2 | GLU | 28 | 16.595 | 16.399 | 44.495 |
| 226 | N | GLU | 29 | 19.968 | 14.922 | 39.231 |
| 227 | CA | GLU | 29 | 19.759 | 14.891 | 37.777 |
| 228 | C | GLU | 29 | 18.682 | 13.876 | 37.403 |
| 229 | O | GLU | 29 | 18.685 | 12.752 | 37.917 |
| 230 | CB | GLU | 29 | 21.091 | 14.525 | 37.120 |
| 231 | CG | GLU | 29 | 21.030 | 14.506 | 35.592 |
| 232 | CD | GLU | 29 | 20.665 | 15.884 | 35.042 |
| 233 | OE1 | GLU | 29 | 19.475 | 16.139 | 34.907 |
| 234 | OE2 | GLU | 29 | 21.573 | 16.674 | 34.836 |
| 235 | N | ALA | 30 | 17.696 | 14.346 | 36.649 |
| 236 | CA | ALA | 30 | 16.564 | 13.532 | 36.181 |
| 237 | C | ALA | 30 | 15.659 | 13.028 | 37.301 |
| 238 | O | ALA | 30 | 15.054 | 11.957 | 37.167 |
| 239 | CB | ALA | 30 | 17.115 | 12.334 | 35.412 |
| 240 | N | GLY | 31 | 15.614 | 13.758 | 38.407 |
| 241 | CA | GLY | 31 | 14.840 | 13.334 | 39.579 |
| 242 | C | GLY | 31 | 15.489 | 12.151 | 40.302 |
| 243 | O | GLY | 31 | 14.817 | 11.423 | 41.041 |
| 244 | N | SER | 32 | 16.780 | 11.965 | 40.086 |
| 245 | CA | SER | 32 | 17.482 | 10.818 | 40.651 |
| 246 | C | SER | 32 | 18.499 | 11.271 | 41.683 |
| 247 | O | SER | 32 | 18.342 | 12.316 | 42.327 |
| 248 | CB | SER | 32 | 18.190 | 10.093 | 39.514 |
| 249 | OG | SER | 32 | 17.243 | 9.931 | 38.466 |
| 250 | N | SER | 33 | 19.536 | 10.473 | 41.844 |
| 251 | CA | SER | 33 | 20.551 | 10.790 | 42.848 |
| 252 | C | SER | 33 | 21.959 | 10.495 | 42.361 |
| 253 | O | SER | 33 | 22.422 | 9.350 | 42.409 |
| 254 | CB | SER | 33 | 20.260 | 9.955 | 44.078 |
| 255 | OG | SER | 33 | 18.997 | 10.357 | 44.588 |
| 256 | N | ASP | 34 | 22.636 | 11.541 | 41.925 |
| 257 | CA | ASP | 34 | 24.016 | 11.441 | 41.446 |
| 258 | C | ASP | 34 | 25.000 | 12.006 | 42.471 |
| 259 | O | ASP | 34 | 24.887 | 13.164 | 42.886 |
| 260 | CB | ASP | 34 | 24.094 | 12.232 | 40.146 |
| 261 | CG | ASP | 34 | 25.532 | 12.319 | 39.662 |
| 262 | OD1 | ASP | 34 | 26.125 | 13.377 | 39.830 |
| 263 | OD2 | ASP | 34 | 26.017 | 11.321 | 39.154 |
| 264 | N | LEU | 35 | 25.974 | 11.193 | 42.843 |
| 265 | CA | LEU | 35 | 26.960 | 11.586 | 43.852 |
| 266 | C | LEU | 35 | 28.399 | 11.391 | 43.376 |
| 267 | O | LEU | 35 | 28.816 | 10.279 | 43.022 |

TABLE IV-continued

| Atom No. | Atom Type | Residue | Residue Position | X Coord. | Y Coord. | Z Coord. |
|---|---|---|---|---|---|---|
| 268 | CB | LEU | 35 | 26.734 | 10.701 | 45.070 |
| 269 | CG | LEU | 35 | 27.533 | 11.144 | 46.287 |
| 270 | CD1 | LEU | 35 | 27.072 | 12.518 | 46.759 |
| 271 | CD2 | LEU | 35 | 27.390 | 10.128 | 47.414 |
| 272 | N | SER | 36 | 29.138 | 12.486 | 43.347 |
| 273 | CA | SER | 36 | 30.589 | 12.390 | 43.150 |
| 274 | C | SER | 36 | 31.261 | 12.039 | 44.477 |
| 275 | O | SER | 36 | 31.071 | 12.719 | 45.494 |
| 276 | CB | SER | 36 | 31.130 | 13.705 | 42.610 |
| 277 | OG | SER | 36 | 32.542 | 13.576 | 42.511 |
| 278 | N | SER | 37 | 32.021 | 10.960 | 44.455 |
| 279 | CA | SER | 37 | 32.612 | 10.433 | 45.686 |
| 280 | C | SER | 37 | 34.055 | 9.959 | 45.543 |
| 281 | O | SER | 37 | 34.398 | 9.189 | 44.639 |
| 282 | CB | SER | 37 | 31.768 | 9.252 | 46.135 |
| 283 | OG | SER | 37 | 32.368 | 8.750 | 47.318 |
| 284 | N | ARG | 38 | 34.863 | 10.359 | 46.507 |
| 285 | CA | ARG | 38 | 36.249 | 9.898 | 46.613 |
| 286 | C | ARG | 38 | 36.301 | 8.685 | 47.530 |
| 287 | O | ARG | 38 | 35.324 | 8.388 | 48.225 |
| 288 | CB | ARG | 38 | 37.060 | 11.012 | 47.258 |
| 289 | CG | ARG | 38 | 36.938 | 12.298 | 46.461 |
| 290 | CD | ARG | 38 | 37.407 | 13.498 | 47.269 |
| 291 | NE | ARG | 38 | 36.580 | 13.639 | 48.477 |
| 292 | CZ | ARG | 38 | 35.468 | 14.375 | 48.538 |
| 293 | NH1 | ARG | 38 | 35.086 | 15.112 | 47.491 |
| 294 | NH2 | ARG | 38 | 34.768 | 14.423 | 49.670 |
| 295 | N | GLN | 39 | 37.409 | 7.970 | 47.522 |
| 296 | CA | GLN | 39 | 37.578 | 6.920 | 48.533 |
| 297 | C | GLN | 39 | 38.085 | 7.511 | 49.843 |
| 298 | O | GLN | 39 | 37.845 | 8.689 | 50.133 |
| 299 | CB | GLN | 39 | 38.493 | 5.825 | 48.021 |
| 300 | CG | GLN | 39 | 37.817 | 5.104 | 46.865 |
| 301 | CD | GLN | 39 | 38.717 | 4.002 | 46.331 |
| 302 | OE1 | GLN | 39 | 39.355 | 3.272 | 47.098 |
| 303 | NE2 | GLN | 39 | 38.813 | 3.945 | 45.015 |
| 304 | N | ASP | 40 | 38.625 | 6.660 | 50.699 |
| 305 | CA | ASP | 40 | 39.007 | 7.110 | 52.048 |
| 306 | C | ASP | 40 | 40.167 | 6.340 | 52.681 |
| 307 | O | ASP | 40 | 40.484 | 5.207 | 52.297 |
| 308 | CB | ASP | 40 | 37.781 | 7.049 | 52.962 |
| 309 | CG | ASP | 40 | 36.841 | 5.903 | 52.585 |
| 310 | OD1 | ASP | 40 | 37.255 | 4.755 | 52.672 |
| 311 | OD2 | ASP | 40 | 35.759 | 6.212 | 52.109 |
| 312 | N | ALA | 41 | 40.801 | 6.996 | 53.643 |
| 313 | CA | ALA | 41 | 41.893 | 6.393 | 54.421 |
| 314 | C | ALA | 41 | 41.740 | 6.662 | 55.915 |
| 315 | O | ALA | 41 | 40.646 | 6.967 | 56.405 |
| 316 | CB | ALA | 41 | 43.219 | 6.985 | 53.972 |
| 317 | N | GLU | 42 | 42.842 | 6.458 | 56.624 |
| 318 | CA | GLU | 42 | 42.927 | 6.760 | 58.062 |
| 319 | C | GLU | 42 | 44.388 | 6.751 | 58.528 |
| 320 | O | GLU | 42 | 45.095 | 5.741 | 58.412 |
| 321 | CB | GLU | 42 | 42.045 | 5.794 | 58.868 |
| 322 | CG | GLU | 42 | 42.429 | 4.316 | 58.779 |
| 323 | CD | GLU | 42 | 43.360 | 3.937 | 59.931 |
| 324 | OE1 | GLU | 42 | 43.883 | 2.832 | 59.902 |
| 325 | OE2 | GLU | 42 | 43.411 | 4.707 | 60.881 |
| 326 | N | ASN | 43 | 44.821 | 7.891 | 59.040 |
| 327 | CA | ASN | 43 | 46.199 | 8.065 | 59.522 |
| 328 | C | ASN | 43 | 46.312 | 9.423 | 60.212 |
| 329 | O | ASN | 43 | 45.824 | 10.421 | 59.671 |
| 330 | CB | ASN | 43 | 47.145 | 8.003 | 58.321 |
| 331 | CG | ASN | 43 | 48.604 | 7.960 | 58.761 |
| 332 | OD1 | ASN | 43 | 49.218 | 8.998 | 59.037 |
| 333 | ND2 | ASN | 43 | 49.107 | 6.749 | 58.910 |
| 334 | N | ALA | 44 | 47.107 | 9.507 | 61.267 |
| 335 | CA | ALA | 44 | 47.211 | 10.764 | 62.026 |
| 336 | C | ALA | 44 | 47.996 | 11.873 | 61.311 |
| 337 | O | ALA | 44 | 47.811 | 13.053 | 61.626 |
| 338 | CB | ALA | 44 | 47.877 | 10.463 | 63.364 |
| 339 | N | GLU | 45 | 48.782 | 11.521 | 60.305 |
| 340 | CA | GLU | 45 | 49.489 | 12.534 | 59.519 |
| 341 | C | GLU | 45 | 48.848 | 12.699 | 58.141 |
| 342 | O | GLU | 45 | 49.131 | 13.675 | 57.436 |
| 343 | CB | GLU | 45 | 50.939 | 12.099 | 59.328 |
| 344 | CG | GLU | 45 | 51.633 | 11.754 | 60.643 |
| 345 | CD | GLU | 45 | 51.627 | 12.939 | 61.605 |
| 346 | OE1 | GLU | 45 | 51.043 | 12.779 | 62.667 |
| 347 | OE2 | GLU | 45 | 52.388 | 13.866 | 61.364 |
| 348 | N | ALA | 46 | 47.960 | 11.780 | 57.793 |
| 349 | CA | ALA | 46 | 47.347 | 11.775 | 56.459 |
| 350 | C | ALA | 46 | 46.127 | 10.861 | 56.405 |
| 351 | O | ALA | 46 | 46.177 | 9.761 | 55.841 |
| 352 | CB | ALA | 46 | 48.376 | 11.284 | 55.446 |
| 353 | N | LYS | 47 | 45.013 | 11.356 | 56.915 |
| 354 | CA | LYS | 47 | 43.781 | 10.560 | 56.930 |
| 355 | C | LYS | 47 | 42.944 | 10.736 | 55.666 |
| 356 | O | LYS | 47 | 42.140 | 9.856 | 55.333 |
| 357 | CB | LYS | 47 | 42.965 | 10.995 | 58.145 |
| 358 | CG | LYS | 47 | 42.756 | 12.506 | 58.156 |
| 359 | CD | LYS | 47 | 41.926 | 12.968 | 59.347 |
| 360 | CE | LYS | 47 | 41.698 | 14.475 | 59.291 |
| 361 | NZ | LYS | 47 | 41.019 | 14.853 | 58.040 |
| 362 | N | LEU | 48 | 43.325 | 11.703 | 54.851 |
| 363 | CA | LEU | 48 | 42.454 | 12.154 | 53.771 |
| 364 | C | LEU | 48 | 42.959 | 11.742 | 52.389 |
| 365 | O | LEU | 48 | 43.160 | 12.608 | 51.531 |
| 366 | CB | LEU | 48 | 42.400 | 13.676 | 53.861 |
| 367 | CG | LEU | 48 | 41.119 | 14.258 | 53.275 |
| 368 | CD1 | LEU | 48 | 39.928 | 13.917 | 54.164 |
| 369 | CD2 | LEU | 48 | 41.237 | 15.771 | 53.134 |
| 370 | N | ARG | 49 | 43.196 | 10.459 | 52.167 |
| 371 | CA | ARG | 49 | 43.600 | 10.083 | 50.808 |
| 372 | C | ARG | 49 | 42.360 | 9.767 | 49.973 |
| 373 | O | ARG | 49 | 41.514 | 8.931 | 50.317 |
| 374 | CB | ARG | 49 | 44.627 | 8.944 | 50.780 |
| 375 | CG | ARG | 49 | 44.026 | 7.545 | 50.715 |
| 376 | CD | ARG | 49 | 45.096 | 6.482 | 50.503 |
| 377 | NE | ARG | 49 | 46.057 | 6.463 | 51.613 |
| 378 | CZ | ARG | 49 | 46.686 | 5.351 | 52.001 |
| 379 | NH1 | ARG | 49 | 47.524 | 5.387 | 53.040 |
| 380 | NH2 | ARG | 49 | 46.455 | 4.199 | 51.367 |
| 381 | N | GLY | 50 | 42.233 | 10.520 | 48.898 |
| 382 | CA | GLY | 50 | 41.113 | 10.335 | 47.979 |
| 383 | C | GLY | 50 | 41.516 | 9.472 | 46.792 |
| 384 | O | GLY | 50 | 41.877 | 9.988 | 45.728 |
| 385 | N | LEU | 51 | 41.534 | 8.167 | 47.012 |
| 386 | CA | LEU | 51 | 41.749 | 7.233 | 45.902 |
| 387 | C | LEU | 51 | 40.598 | 7.453 | 44.931 |
| 388 | O | LEU | 51 | 39.440 | 7.421 | 45.368 |
| 389 | CB | LEU | 51 | 41.756 | 5.807 | 46.439 |
| 390 | CG | LEU | 51 | 42.889 | 5.584 | 47.432 |
| 391 | CD1 | LEU | 51 | 42.738 | 4.243 | 48.142 |
| 392 | CD2 | LEU | 51 | 44.249 | 5.690 | 46.749 |
| 393 | N | PRO | 52 | 40.889 | 7.465 | 43.639 |
| 394 | CA | PRO | 52 | 40.417 | 8.550 | 42.775 |
| 395 | C | PRO | 52 | 38.978 | 8.996 | 43.052 |
| 396 | O | PRO | 52 | 38.718 | 9.683 | 44.046 |
| 397 | CB | PRO | 52 | 40.645 | 8.022 | 41.397 |
| 398 | CG | PRO | 52 | 41.767 | 6.993 | 41.504 |
| 399 | CD | PRO | 52 | 42.052 | 6.855 | 42.997 |
| 400 | N | GLY | 53 | 38.049 | 8.613 | 42.200 |
| 401 | CA | GLY | 53 | 36.675 | 9.042 | 42.453 |
| 402 | C | GLY | 53 | 35.674 | 8.456 | 41.478 |
| 403 | O | GLY | 53 | 36.017 | 8.112 | 40.340 |
| 404 | N | GLN | 54 | 34.440 | 8.381 | 41.941 |
| 405 | CA | GLN | 54 | 33.316 | 7.910 | 41.129 |
| 406 | C | GLN | 54 | 32.239 | 8.989 | 41.002 |
| 407 | O | GLN | 54 | 32.203 | 9.952 | 41.775 |
| 408 | CB | GLN | 54 | 32.726 | 6.647 | 41.761 |
| 409 | CG | GLN | 54 | 32.194 | 6.877 | 43.176 |
| 410 | CD | GLN | 54 | 33.063 | 6.172 | 44.221 |
| 411 | OE1 | GLN | 54 | 32.914 | 6.393 | 45.427 |
| 412 | NE2 | GLN | 54 | 33.947 | 5.314 | 43.743 |
| 413 | N | LEU | 55 | 31.462 | 8.877 | 39.940 |
| 414 | CA | LEU | 55 | 30.305 | 9.750 | 39.698 |
| 415 | C | LEU | 55 | 29.108 | 8.819 | 39.549 |
| 416 | O | LEU | 55 | 28.641 | 8.513 | 38.446 |
| 417 | CB | LEU | 55 | 30.585 | 10.552 | 38.425 |
| 418 | CG | LEU | 55 | 29.682 | 11.761 | 38.196 |
| 419 | CD1 | LEU | 55 | 28.487 | 11.460 | 37.298 |

TABLE IV-continued

| Atom No. | Atom Type | Residue | Residue Position | X Coord. | Y Coord. | Z Coord. |
|---|---|---|---|---|---|---|
| 420 | CD2 | LEU | 55 | 29.285 | 12.441 | 39.499 |
| 421 | N | VAL | 56 | 28.684 | 8.307 | 40.688 |
| 422 | CA | VAL | 56 | 27.761 | 7.174 | 40.701 |
| 423 | C | VAL | 56 | 26.363 | 7.590 | 41.150 |
| 424 | O | VAL | 56 | 26.200 | 8.588 | 41.858 |
| 425 | CB | VAL | 56 | 28.374 | 6.150 | 41.665 |
| 426 | CG1 | VAL | 56 | 28.336 | 6.644 | 43.108 |
| 427 | CG2 | VAL | 56 | 27.745 | 4.765 | 41.560 |
| 428 | N | ASP | 57 | 25.347 | 6.938 | 40.611 |
| 429 | CA | ASP | 57 | 24.032 | 7.074 | 41.232 |
| 430 | C | ASP | 57 | 24.159 | 6.400 | 42.594 |
| 431 | O | ASP | 57 | 24.645 | 5.264 | 42.684 |
| 432 | CB | ASP | 57 | 22.946 | 6.420 | 40.377 |
| 433 | CG | ASP | 57 | 21.560 | 6.694 | 40.969 |
| 434 | OD1 | ASP | 57 | 20.898 | 7.613 | 40.502 |
| 435 | OD2 | ASP | 57 | 21.200 | 5.991 | 41.906 |
| 436 | N | ILE | 58 | 23.660 | 7.046 | 43.634 |
| 437 | CA | ILE | 58 | 23.952 | 6.592 | 44.998 |
| 438 | C | ILE | 58 | 23.234 | 5.309 | 45.410 |
| 439 | O | ILE | 58 | 23.733 | 4.626 | 46.309 |
| 440 | CB | ILE | 58 | 23.587 | 7.686 | 45.982 |
| 441 | CG1 | ILE | 58 | 23.708 | 9.059 | 45.348 |
| 442 | CG2 | ILE | 58 | 24.518 | 7.600 | 47.181 |
| 443 | CD1 | ILE | 58 | 23.341 | 10.146 | 46.349 |
| 444 | N | ALA | 59 | 22.284 | 4.847 | 44.612 |
| 445 | CA | ALA | 59 | 21.641 | 3.550 | 44.855 |
| 446 | C | ALA | 59 | 22.492 | 2.350 | 44.413 |
| 447 | O | ALA | 59 | 22.049 | 1.204 | 44.539 |
| 448 | CB | ALA | 59 | 20.318 | 3.526 | 44.108 |
| 449 | N | CYS | 60 | 23.670 | 2.606 | 43.861 |
| 450 | CA | CYS | 60 | 24.619 | 1.526 | 43.587 |
| 451 | C | CYS | 60 | 25.473 | 1.270 | 44.829 |
| 452 | O | CYS | 60 | 26.083 | 0.204 | 44.976 |
| 453 | CB | CYS | 60 | 25.502 | 1.930 | 42.414 |
| 454 | SG | CYS | 60 | 24.622 | 2.309 | 40.880 |
| 455 | N | LYS | 61 | 25.492 | 2.249 | 45.718 |
| 456 | CA | LYS | 61 | 26.057 | 2.061 | 47.053 |
| 457 | C | LYS | 61 | 24.922 | 1.578 | 47.948 |
| 458 | O | LYS | 61 | 23.780 | 2.024 | 47.799 |
| 459 | CB | LYS | 61 | 26.606 | 3.390 | 47.565 |
| 460 | CG | LYS | 61 | 27.683 | 3.960 | 46.645 |
| 461 | CD | LYS | 61 | 28.931 | 3.080 | 46.600 |
| 462 | CE | LYS | 61 | 29.988 | 3.666 | 45.669 |
| 463 | NZ | LYS | 61 | 31.195 | 2.824 | 45.630 |
| 464 | N | VAL | 62 | 25.211 | 0.648 | 48.839 |
| 465 | CA | VAL | 62 | 24.127 | 0.081 | 49.649 |
| 466 | C | VAL | 62 | 23.948 | 0.745 | 51.014 |
| 467 | O | VAL | 62 | 22.877 | 0.591 | 51.613 |
| 468 | CB | VAL | 62 | 24.363 | −1.417 | 49.815 |
| 469 | CG1 | VAL | 62 | 24.165 | −2.146 | 48.491 |
| 470 | CG2 | VAL | 62 | 25.742 | −1.717 | 50.395 |
| 471 | N | CYS | 63 | 24.901 | 1.560 | 51.436 |
| 472 | CA | CYS | 63 | 24.817 | 2.190 | 52.761 |
| 473 | C | CYS | 63 | 25.467 | 3.569 | 52.783 |
| 474 | O | CYS | 63 | 26.656 | 3.715 | 52.475 |
| 475 | CB | CYS | 63 | 25.518 | 1.312 | 53.796 |
| 476 | SG | CYS | 63 | 24.752 | −0.279 | 54.184 |
| 477 | N | GLN | 64 | 24.686 | 4.562 | 53.171 |
| 478 | CA | GLN | 64 | 25.230 | 5.914 | 53.361 |
| 479 | C | GLN | 64 | 24.906 | 6.453 | 54.755 |
| 480 | O | GLN | 64 | 23.745 | 6.459 | 55.179 |
| 481 | CB | GLN | 64 | 24.640 | 6.835 | 52.300 |
| 482 | CG | GLN | 64 | 25.112 | 8.278 | 52.449 |
| 483 | CD | GLN | 64 | 24.352 | 9.165 | 51.472 |
| 484 | OE1 | GLN | 64 | 24.129 | 10.356 | 51.728 |
| 485 | NE2 | GLN | 64 | 23.935 | 8.560 | 50.373 |
| 486 | N | ALA | 65 | 25.945 | 6.808 | 55.492 |
| 487 | CA | ALA | 65 | 25.761 | 7.484 | 56.782 |
| 488 | C | ALA | 65 | 25.819 | 8.990 | 56.565 |
| 489 | O | ALA | 65 | 26.784 | 9.483 | 55.969 |
| 490 | CB | ALA | 65 | 26.874 | 7.057 | 57.733 |
| 491 | N | TYR | 66 | 24.808 | 9.718 | 57.007 |
| 492 | CA | TYR | 66 | 24.844 | 11.149 | 56.704 |
| 493 | C | TYR | 66 | 25.304 | 11.994 | 57.882 |
| 494 | O | TYR | 66 | 24.684 | 12.066 | 58.949 |
| 495 | CB | TYR | 66 | 23.526 | 11.637 | 56.130 |
| 496 | CG | TYR | 66 | 23.778 | 12.381 | 54.821 |
| 497 | CD1 | TYR | 66 | 25.076 | 12.433 | 54.327 |
| 498 | CD2 | TYR | 66 | 22.744 | 12.996 | 54.128 |
| 499 | CE1 | TYR | 66 | 25.345 | 13.099 | 53.141 |
| 500 | CE2 | TYR | 66 | 23.012 | 13.662 | 52.938 |
| 501 | CZ | TYR | 66 | 24.311 | 13.711 | 52.447 |
| 502 | OH | TYR | 66 | 24.578 | 14.356 | 51.262 |
| 503 | N | LEU | 67 | 26.378 | 12.709 | 57.594 |
| 504 | CA | LEU | 67 | 27.087 | 13.531 | 58.576 |
| 505 | C | LEU | 67 | 26.753 | 15.028 | 58.492 |
| 506 | O | LEU | 67 | 27.508 | 15.851 | 59.023 |
| 507 | CB | LEU | 67 | 28.576 | 13.293 | 58.359 |
| 508 | CG | LEU | 67 | 28.891 | 11.797 | 58.407 |
| 509 | CD1 | LEU | 67 | 30.283 | 11.499 | 57.862 |
| 510 | CD2 | LEU | 67 | 28.701 | 11.212 | 59.805 |
| 511 | N | GLY | 68 | 25.665 | 15.376 | 57.819 |
| 512 | CA | GLY | 68 | 25.215 | 16.778 | 57.764 |
| 513 | C | GLY | 68 | 24.657 | 17.184 | 59.127 |
| 514 | O | GLY | 68 | 23.633 | 16.658 | 59.576 |
| 515 | N | GLN | 69 | 25.341 | 18.107 | 59.780 |
| 516 | CA | GLN | 69 | 25.053 | 18.370 | 61.189 |
| 517 | C | GLN | 69 | 24.542 | 19.784 | 61.464 |
| 518 | O | GLN | 69 | 23.330 | 20.032 | 61.450 |
| 519 | CB | GLN | 69 | 26.352 | 18.135 | 61.941 |
| 520 | CG | GLN | 69 | 26.106 | 17.830 | 63.408 |
| 521 | CD | GLN | 69 | 27.430 | 17.880 | 64.145 |
| 522 | OE1 | GLN | 69 | 28.178 | 18.860 | 64.035 |
| 523 | NE2 | GLN | 69 | 27.722 | 16.804 | 64.847 |
| 524 | N | LEU | 70 | 25.462 | 20.685 | 61.770 |
| 525 | CA | LEU | 70 | 25.087 | 22.042 | 62.186 |
| 526 | C | LEU | 70 | 24.370 | 22.801 | 61.076 |
| 527 | O | LEU | 70 | 24.544 | 22.524 | 59.883 |
| 528 | CB | LEU | 70 | 26.307 | 22.840 | 62.659 |
| 529 | CG | LEU | 70 | 27.267 | 23.276 | 61.549 |
| 530 | CD1 | LEU | 70 | 27.876 | 24.637 | 61.868 |
| 531 | CD2 | LEU | 70 | 28.362 | 22.249 | 61.263 |
| 532 | N | GLU | 71 | 23.515 | 23.710 | 61.518 |
| 533 | CA | GLU | 71 | 22.706 | 24.564 | 60.638 |
| 534 | C | GLU | 71 | 21.847 | 23.755 | 59.671 |
| 535 | O | GLU | 71 | 22.150 | 23.690 | 58.472 |
| 536 | CB | GLU | 71 | 23.615 | 25.501 | 59.845 |
| 537 | CG | GLU | 71 | 24.398 | 26.440 | 60.754 |
| 538 | CD | GLU | 71 | 25.278 | 27.376 | 59.926 |
| 539 | OE1 | GLU | 71 | 26.407 | 26.988 | 59.657 |
| 540 | OE2 | GLU | 71 | 24.884 | 28.523 | 59.771 |
| 541 | N | HIS | 72 | 20.751 | 23.214 | 60.180 |
| 542 | CA | HIS | 72 | 19.785 | 22.493 | 59.335 |
| 543 | C | HIS | 72 | 18.870 | 23.462 | 58.587 |
| 544 | O | HIS | 72 | 17.757 | 23.775 | 59.021 |
| 545 | CB | HIS | 72 | 18.940 | 21.566 | 60.202 |
| 546 | CG | HIS | 72 | 19.404 | 20.121 | 60.254 |
| 547 | ND1 | HIS | 72 | 20.671 | 19.659 | 60.247 |
| 548 | CD2 | HIS | 72 | 18.581 | 19.021 | 60.322 |
| 549 | CE1 | HIS | 72 | 20.653 | 18.311 | 60.296 |
| 550 | NE2 | HIS | 72 | 19.361 | 17.917 | 60.344 |
| 551 | N | GLU | 73 | 19.388 | 23.967 | 57.481 |
| 552 | CA | GLU | 73 | 18.662 | 24.923 | 56.644 |
| 553 | C | GLU | 73 | 17.986 | 24.224 | 55.472 |
| 554 | O | GLU | 73 | 18.089 | 23.000 | 55.316 |
| 555 | CB | GLU | 73 | 19.673 | 25.940 | 56.134 |
| 556 | CG | GLU | 73 | 20.388 | 26.612 | 57.301 |
| 557 | CD | GLU | 73 | 21.512 | 27.505 | 56.789 |
| 558 | OE1 | GLU | 73 | 21.420 | 27.921 | 55.643 |
| 559 | OE2 | GLU | 73 | 22.465 | 27.696 | 57.530 |
| 560 | N | ASP | 74 | 17.485 | 25.026 | 54.545 |
| 561 | CA | ASP | 74 | 16.783 | 24.486 | 53.371 |
| 562 | C | ASP | 74 | 17.731 | 23.831 | 52.364 |
| 563 | O | ASP | 74 | 17.342 | 22.849 | 51.727 |
| 564 | CB | ASP | 74 | 16.025 | 25.618 | 52.684 |
| 565 | CG | ASP | 74 | 14.966 | 26.197 | 53.619 |
| 566 | OD1 | ASP | 74 | 14.917 | 27.414 | 53.727 |
| 567 | OD2 | ASP | 74 | 14.335 | 25.414 | 54.316 |
| 568 | N | ILE | 75 | 19.012 | 24.159 | 52.447 |
| 569 | CA | ILE | 75 | 20.014 | 23.505 | 51.596 |
| 570 | C | ILE | 75 | 20.349 | 22.103 | 52.117 |
| 571 | O | ILE | 75 | 20.453 | 21.157 | 51.325 |

TABLE IV-continued

| Atom No. | Atom Type | Residue | Residue Position | X Coord. | Y Coord. | Z Coord. |
|---|---|---|---|---|---|---|
| 572 | CB | ILE | 75 | 21.270 | 24.372 | 51.610 |
| 573 | CG1 | ILE | 75 | 20.974 | 25.781 | 51.104 |
| 574 | CG2 | ILE | 75 | 22.378 | 23.735 | 50.778 |
| 575 | CD1 | ILE | 75 | 20.554 | 25.779 | 49.637 |
| 576 | N | ASP | 76 | 20.161 | 21.924 | 53.417 |
| 577 | CA | ASP | 76 | 20.404 | 20.631 | 54.058 |
| 578 | C | ASP | 76 | 19.207 | 19.723 | 53.808 |
| 579 | O | ASP | 76 | 19.383 | 18.581 | 53.361 |
| 580 | CB | ASP | 76 | 20.578 | 20.888 | 55.554 |
| 581 | CG | ASP | 76 | 20.760 | 19.596 | 56.343 |
| 582 | OD1 | ASP | 76 | 21.890 | 19.127 | 56.391 |
| 583 | OD2 | ASP | 76 | 19.816 | 19.213 | 57.015 |
| 584 | N | THR | 77 | 18.057 | 20.368 | 53.692 |
| 585 | CA | THR | 77 | 16.810 | 19.664 | 53.394 |
| 586 | C | THR | 77 | 16.740 | 19.245 | 51.924 |
| 587 | O | THR | 77 | 16.287 | 18.130 | 51.640 |
| 588 | CB | THR | 77 | 15.658 | 20.612 | 53.713 |
| 589 | OG1 | THR | 77 | 15.792 | 21.041 | 55.063 |
| 590 | CG2 | THR | 77 | 14.300 | 19.938 | 53.552 |
| 591 | N | SER | 78 | 17.448 | 19.963 | 51.066 |
| 592 | CA | SER | 78 | 17.501 | 19.606 | 49.644 |
| 593 | C | SER | 78 | 18.419 | 18.410 | 49.401 |
| 594 | O | SER | 78 | 18.024 | 17.483 | 48.682 |
| 595 | CB | SER | 78 | 18.015 | 20.806 | 48.858 |
| 596 | OG | SER | 78 | 17.109 | 21.882 | 49.059 |
| 597 | N | ALA | 79 | 19.461 | 18.289 | 50.210 |
| 598 | CA | ALA | 79 | 20.344 | 17.120 | 50.109 |
| 599 | C | ALA | 79 | 19.726 | 15.893 | 50.781 |
| 600 | O | ALA | 79 | 19.965 | 14.757 | 50.350 |
| 601 | CB | ALA | 79 | 21.676 | 17.452 | 50.770 |
| 602 | N | ASP | 80 | 18.770 | 16.138 | 51.664 |
| 603 | CA | ASP | 80 | 18.015 | 15.054 | 52.293 |
| 604 | C | ASP | 80 | 16.867 | 14.583 | 51.391 |
| 605 | O | ASP | 80 | 16.505 | 13.401 | 51.424 |
| 606 | CB | ASP | 80 | 17.452 | 15.559 | 53.619 |
| 607 | CG | ASP | 80 | 18.540 | 15.989 | 54.599 |
| 608 | OD1 | ASP | 80 | 19.623 | 15.420 | 54.557 |
| 609 | OD2 | ASP | 80 | 18.262 | 16.889 | 55.383 |
| 610 | N | ALA | 81 | 16.480 | 15.417 | 50.437 |
| 611 | CA | ALA | 81 | 15.473 | 15.018 | 49.451 |
| 612 | C | ALA | 81 | 16.101 | 14.172 | 48.346 |
| 613 | O | ALA | 81 | 15.470 | 13.220 | 47.868 |
| 614 | CB | ALA | 81 | 14.841 | 16.270 | 48.854 |
| 615 | N | VAL | 82 | 17.403 | 14.332 | 48.161 |
| 616 | CA | VAL | 82 | 18.137 | 13.442 | 47.254 |
| 617 | C | VAL | 82 | 18.408 | 12.098 | 47.937 |
| 618 | O | VAL | 82 | 18.281 | 11.046 | 47.296 |
| 619 | CB | VAL | 82 | 19.452 | 14.109 | 46.864 |
| 620 | CG1 | VAL | 82 | 20.189 | 13.289 | 45.813 |
| 621 | CG2 | VAL | 82 | 19.214 | 15.520 | 46.341 |
| 622 | N | GLU | 83 | 18.426 | 12.123 | 49.264 |
| 623 | CA | GLU | 83 | 18.535 | 10.892 | 50.057 |
| 624 | C | GLU | 83 | 17.240 | 10.093 | 50.045 |
| 625 | O | GLU | 83 | 17.288 | 8.859 | 49.971 |
| 626 | CB | GLU | 83 | 18.859 | 11.256 | 51.500 |
| 627 | CG | GLU | 83 | 20.276 | 11.783 | 51.628 |
| 628 | CD | GLU | 83 | 21.227 | 10.691 | 51.166 |
| 629 | OE1 | GLU | 83 | 21.234 | 9.658 | 51.821 |
| 630 | OE2 | GLU | 83 | 21.696 | 10.801 | 50.038 |
| 631 | N | ASP | 84 | 16.136 | 10.777 | 49.801 |
| 632 | CA | ASP | 84 | 14.848 | 10.102 | 49.673 |
| 633 | C | ASP | 84 | 14.780 | 9.289 | 48.384 |
| 634 | O | ASP | 84 | 14.348 | 8.129 | 48.426 |
| 635 | CB | ASP | 84 | 13.769 | 11.174 | 49.640 |
| 636 | CG | ASP | 84 | 12.384 | 10.546 | 49.619 |
| 637 | OD1 | ASP | 84 | 11.468 | 11.207 | 49.149 |
| 638 | OD2 | ASP | 84 | 12.245 | 9.466 | 50.174 |
| 639 | N | LEU | 85 | 15.487 | 9.747 | 47.363 |
| 640 | CA | LEU | 85 | 15.479 | 9.038 | 46.085 |
| 641 | C | LEU | 85 | 16.428 | 7.845 | 46.100 |
| 642 | O | LEU | 85 | 16.073 | 6.794 | 45.554 |
| 643 | CB | LEU | 85 | 15.896 | 10.022 | 45.005 |
| 644 | CG | LEU | 85 | 14.951 | 11.215 | 44.972 |
| 645 | CD1 | LEU | 85 | 15.555 | 12.372 | 44.193 |
| 646 | CD2 | LEU | 85 | 13.583 | 10.830 | 44.419 |
| 647 | N | THR | 86 | 17.462 | 7.902 | 46.927 |
| 648 | CA | THR | 86 | 18.355 | 6.745 | 47.039 |
| 649 | C | THR | 86 | 17.735 | 5.678 | 47.935 |
| 650 | O | THR | 86 | 17.804 | 4.488 | 47.599 |
| 651 | CB | THR | 86 | 19.697 | 7.171 | 47.628 |
| 652 | OG1 | THR | 86 | 19.597 | 7.326 | 49.033 |
| 653 | CG2 | THR | 86 | 20.194 | 8.482 | 47.059 |
| 654 | N | GLU | 87 | 16.883 | 6.108 | 48.853 |
| 655 | CA | GLU | 87 | 16.237 | 5.172 | 49.767 |
| 656 | C | GLU | 87 | 15.080 | 4.460 | 49.072 |
| 657 | O | GLU | 87 | 14.964 | 3.235 | 49.200 |
| 658 | CB | GLU | 87 | 15.742 | 5.970 | 50.968 |
| 659 | CG | GLU | 87 | 15.376 | 5.081 | 52.149 |
| 660 | CD | GLU | 87 | 15.050 | 5.949 | 53.363 |
| 661 | OE1 | GLU | 87 | 13.933 | 5.852 | 53.852 |
| 662 | OE2 | GLU | 87 | 15.944 | 6.651 | 53.823 |
| 663 | N | ALA | 88 | 14.474 | 5.143 | 48.111 |
| 664 | CA | ALA | 88 | 13.410 | 4.536 | 47.300 |
| 665 | C | ALA | 88 | 13.956 | 3.640 | 46.186 |
| 666 | O | ALA | 88 | 13.228 | 2.800 | 45.647 |
| 667 | CB | ALA | 88 | 12.573 | 5.652 | 46.688 |
| 668 | N | GLU | 89 | 15.248 | 3.750 | 45.917 |
| 669 | CA | GLU | 89 | 15.908 | 2.851 | 44.967 |
| 670 | C | GLU | 89 | 16.651 | 1.713 | 45.674 |
| 671 | O | GLU | 89 | 17.522 | 1.092 | 45.052 |
| 672 | CB | GLU | 89 | 16.878 | 3.640 | 44.098 |
| 673 | CG | GLU | 89 | 16.191 | 4.738 | 43.292 |
| 674 | CD | GLU | 89 | 15.078 | 4.173 | 42.414 |
| 675 | OE1 | GLU | 89 | 13.932 | 4.499 | 42.692 |
| 676 | OE2 | GLU | 89 | 15.406 | 3.615 | 41.376 |
| 677 | N | TRP | 90 | 16.412 | 1.572 | 46.973 |
| 678 | CA | TRP | 90 | 16.915 | 0.463 | 47.808 |
| 679 | C | TRP | 90 | 18.333 | 0.676 | 48.332 |
| 680 | O | TRP | 90 | 19.130 | −0.268 | 48.389 |
| 681 | CB | TRP | 90 | 16.827 | −0.881 | 47.083 |
| 682 | CG | TRP | 90 | 15.427 | −1.450 | 46.948 |
| 683 | CD1 | TRP | 90 | 14.525 | −1.219 | 45.932 |
| 684 | CD2 | TRP | 90 | 14.785 | −2.359 | 47.868 |
| 685 | NE1 | TRP | 90 | 13.395 | −1.926 | 46.191 |
| 686 | CE2 | TRP | 90 | 13.508 | −2.623 | 47.338 |
| 687 | CE3 | TRP | 90 | 15.186 | −2.950 | 49.056 |
| 688 | CZ2 | TRP | 90 | 12.649 | −3.479 | 48.011 |
| 689 | CZ3 | TRP | 90 | 14.319 | −3.807 | 49.723 |
| 690 | CH2 | TRP | 90 | 13.056 | −4.070 | 49.202 |
| 691 | N | GLU | 91 | 18.637 | 1.896 | 48.740 |
| 692 | CA | GLU | 91 | 19.885 | 2.130 | 49.476 |
| 693 | C | GLU | 91 | 19.569 | 2.457 | 50.933 |
| 694 | O | GLU | 91 | 18.858 | 3.429 | 51.217 |
| 695 | CB | GLU | 91 | 20.676 | 3.279 | 48.855 |
| 696 | CG | GLU | 91 | 21.949 | 3.525 | 49.660 |
| 697 | CD | GLU | 91 | 22.763 | 4.691 | 49.116 |
| 698 | OE1 | GLU | 91 | 22.141 | 5.602 | 48.584 |
| 699 | OE2 | GLU | 91 | 23.907 | 4.806 | 49.540 |
| 700 | N | ASP | 92 | 20.112 | 1.661 | 51.842 |
| 701 | CA | ASP | 92 | 19.925 | 1.912 | 53.275 |
| 702 | C | ASP | 92 | 20.742 | 3.133 | 53.695 |
| 703 | O | ASP | 92 | 21.900 | 3.314 | 53.295 |
| 704 | CB | ASP | 92 | 20.371 | 0.675 | 54.046 |
| 705 | CG | ASP | 92 | 19.944 | 0.757 | 55.508 |
| 706 | OD1 | ASP | 92 | 18.920 | 1.376 | 55.763 |
| 707 | OD2 | ASP | 92 | 20.649 | 0.209 | 56.345 |
| 708 | N | LEU | 93 | 20.081 | 4.032 | 54.402 |
| 709 | CA | LEU | 93 | 20.722 | 5.288 | 54.802 |
| 710 | C | LEU | 93 | 20.498 | 5.582 | 56.278 |
| 711 | O | LEU | 93 | 19.358 | 5.824 | 56.699 |
| 712 | CB | LEU | 93 | 20.074 | 6.433 | 54.046 |
| 713 | CG | LEU | 93 | 19.938 | 6.228 | 52.549 |
| 714 | CD1 | LEU | 93 | 18.942 | 7.227 | 51.995 |
| 715 | CD2 | LEU | 93 | 21.274 | 6.346 | 51.841 |
| 716 | N | THR | 94 | 21.589 | 5.807 | 56.986 |
| 717 | CA | THR | 94 | 21.501 | 6.115 | 58.420 |
| 718 | C | THR | 94 | 21.434 | 7.629 | 58.636 |
| 719 | O | THR | 94 | 22.449 | 8.326 | 58.763 |
| 720 | CB | THR | 94 | 22.671 | 5.484 | 59.170 |
| 721 | OG1 | THR | 94 | 23.887 | 5.935 | 58.599 |
| 722 | CG2 | THR | 94 | 22.639 | 3.965 | 59.054 |
| 723 | N | GLN | 95 | 20.212 | 8.117 | 58.488 |

TABLE IV-continued

| Atom No. | Atom Type | Residue | Residue Position | X Coord. | Y Coord. | Z Coord. |
|---|---|---|---|---|---|---|
| 724 | CA | GLN | 95 | 19.888 | 9.536 | 58.646 |
| 725 | C | GLN | 95 | 18.390 | 9.757 | 58.850 |
| 726 | O | GLN | 95 | 18.018 | 10.683 | 59.578 |
| 727 | CB | GLN | 95 | 20.398 | 10.317 | 57.423 |
| 728 | CG | GLN | 95 | 20.200 | 9.628 | 56.065 |
| 729 | CD | GLN | 95 | 18.840 | 9.895 | 55.419 |
| 730 | OE1 | GLN | 95 | 18.474 | 11.042 | 55.144 |
| 731 | NE2 | GLN | 95 | 18.113 | 8.823 | 55.146 |
| 732 | N | GLN | 96 | 17.620 | 8.737 | 58.498 |
| 733 | CA | GLN | 96 | 16.165 | 8.849 | 58.278 |
| 734 | C | GLN | 96 | 15.707 | 10.274 | 57.957 |
| 735 | O | GLN | 96 | 15.362 | 11.048 | 58.858 |
| 736 | CB | GLN | 96 | 15.402 | 8.319 | 59.478 |
| 737 | CG | GLN | 96 | 14.458 | 7.181 | 59.086 |
| 738 | CD | GLN | 96 | 13.484 | 7.605 | 57.987 |
| 739 | OE1 | GLN | 96 | 13.045 | 8.760 | 57.922 |
| 740 | NE2 | GLN | 96 | 13.235 | 6.681 | 57.076 |
| 741 | N | TYR | 97 | 15.444 | 10.482 | 56.678 |
| 742 | CA | TYR | 97 | 15.101 | 11.800 | 56.131 |
| 743 | C | TYR | 97 | 13.760 | 12.337 | 56.623 |
| 744 | O | TYR | 97 | 13.700 | 13.484 | 57.088 |
| 745 | CB | TYR | 97 | 15.051 | 11.626 | 54.616 |
| 746 | CG | TYR | 97 | 14.305 | 12.705 | 53.838 |
| 747 | CD1 | TYR | 97 | 14.563 | 14.052 | 54.060 |
| 748 | CD2 | TYR | 97 | 13.350 | 12.329 | 52.902 |
| 749 | CE1 | TYR | 97 | 13.881 | 15.022 | 53.336 |
| 750 | CE2 | TYR | 97 | 12.668 | 13.296 | 52.179 |
| 751 | CZ | TYR | 97 | 12.940 | 14.639 | 52.393 |
| 752 | OH | TYR | 97 | 12.343 | 15.594 | 51.602 |
| 753 | N | TYR | 98 | 12.791 | 11.453 | 56.791 |
| 754 | CA | TYR | 98 | 11.466 | 11.905 | 57.201 |
| 755 | C | TYR | 98 | 11.449 | 12.142 | 58.700 |
| 756 | O | TYR | 98 | 10.900 | 13.153 | 59.143 |
| 757 | CB | TYR | 98 | 10.430 | 10.850 | 56.832 |
| 758 | CG | TYR | 98 | 10.248 | 10.639 | 55.332 |
| 759 | CD1 | TYR | 98 | 10.717 | 9.481 | 54.724 |
| 760 | CD2 | TYR | 98 | 9.599 | 11.608 | 54.576 |
| 761 | CE1 | TYR | 98 | 10.543 | 9.294 | 53.359 |
| 762 | CE2 | TYR | 98 | 9.424 | 11.422 | 53.212 |
| 763 | CZ | TYR | 98 | 9.895 | 10.265 | 52.608 |
| 764 | OH | TYR | 98 | 9.683 | 10.065 | 51.261 |
| 765 | N | SER | 99 | 12.348 | 11.463 | 59.388 |
| 766 | CA | SER | 99 | 12.456 | 11.632 | 60.831 |
| 767 | C | SER | 99 | 13.194 | 12.919 | 61.176 |
| 768 | O | SER | 99 | 12.724 | 13.664 | 62.045 |
| 769 | CB | SER | 99 | 13.221 | 10.442 | 61.373 |
| 770 | OG | SER | 99 | 12.546 | 9.274 | 60.929 |
| 771 | N | LEU | 100 | 14.131 | 13.313 | 60.328 |
| 772 | CA | LEU | 100 | 14.833 | 14.588 | 60.534 |
| 773 | C | LEU | 100 | 13.898 | 15.772 | 60.326 |
| 774 | O | LEU | 100 | 13.779 | 16.632 | 61.210 |
| 775 | CB | LEU | 100 | 15.959 | 14.717 | 59.514 |
| 776 | CG | LEU | 100 | 17.032 | 13.652 | 59.676 |
| 777 | CD1 | LEU | 100 | 18.076 | 13.774 | 58.571 |
| 778 | CD2 | LEU | 100 | 17.687 | 13.735 | 61.050 |
| 779 | N | VAL | 101 | 13.084 | 15.679 | 59.287 |
| 780 | CA | VAL | 101 | 12.186 | 16.780 | 58.927 |
| 781 | C | VAL | 101 | 10.908 | 16.814 | 59.772 |
| 782 | O | VAL | 101 | 10.275 | 17.870 | 59.893 |
| 783 | CB | VAL | 101 | 11.849 | 16.601 | 57.446 |
| 784 | CG1 | VAL | 101 | 10.853 | 17.638 | 56.937 |
| 785 | CG2 | VAL | 101 | 13.118 | 16.639 | 56.603 |
| 786 | N | HIS | 102 | 10.577 | 15.716 | 60.431 |
| 787 | CA | HIS | 102 | 9.362 | 15.708 | 61.251 |
| 788 | C | HIS | 102 | 9.651 | 15.792 | 62.749 |
| 789 | O | HIS | 102 | 8.717 | 15.982 | 63.535 |
| 790 | CB | HIS | 102 | 8.548 | 14.448 | 60.959 |
| 791 | CG | HIS | 102 | 8.044 | 14.309 | 59.530 |
| 792 | ND1 | HIS | 102 | 7.800 | 15.301 | 58.650 |
| 793 | CD2 | HIS | 102 | 7.744 | 13.129 | 58.891 |
| 794 | CE1 | HIS | 102 | 7.372 | 14.772 | 57.486 |
| 795 | NE2 | HIS | 102 | 7.338 | 13.429 | 57.636 |
| 796 | N | GLY | 103 | 10.910 | 15.689 | 63.143 |
| 797 | CA | GLY | 103 | 11.230 | 15.758 | 64.573 |
| 798 | C | GLY | 103 | 12.706 | 16.022 | 64.867 |
| 799 | O | GLY | 103 | 13.338 | 15.284 | 65.632 |
| 800 | N | ASP | 104 | 13.216 | 17.121 | 64.338 |
| 801 | CA | ASP | 104 | 14.588 | 17.563 | 64.646 |
| 802 | C | ASP | 104 | 14.754 | 17.927 | 66.126 |
| 803 | O | ASP | 104 | 13.760 | 18.018 | 66.857 |
| 804 | CB | ASP | 104 | 14.933 | 18.773 | 63.776 |
| 805 | CG | ASP | 104 | 13.954 | 19.921 | 64.008 |
| 806 | OD1 | ASP | 104 | 14.035 | 20.531 | 65.071 |
| 807 | OD2 | ASP | 104 | 13.055 | 20.072 | 63.195 |
| 808 | N | ALA | 105 | 15.984 | 18.270 | 66.490 |
| 809 | CA | ALA | 105 | 16.405 | 18.626 | 67.865 |
| 810 | C | ALA | 105 | 15.317 | 19.139 | 68.807 |
| 811 | O | ALA | 105 | 14.684 | 18.328 | 69.496 |
| 812 | CB | ALA | 105 | 17.516 | 19.664 | 67.766 |
| 813 | N | PHE | 106 | 14.964 | 20.410 | 68.703 |
| 814 | CA | PHE | 106 | 14.001 | 20.990 | 69.656 |
| 815 | C | PHE | 106 | 12.520 | 20.746 | 69.319 |
| 816 | O | PHE | 106 | 11.660 | 20.937 | 70.187 |
| 817 | CB | PHE | 106 | 14.262 | 22.492 | 69.751 |
| 818 | CG | PHE | 106 | 15.607 | 22.861 | 70.375 |
| 819 | CD1 | PHE | 106 | 16.583 | 23.494 | 69.615 |
| 820 | CD2 | PHE | 106 | 15.850 | 22.572 | 71.712 |
| 821 | CE1 | PHE | 106 | 17.803 | 23.829 | 70.190 |
| 822 | CE2 | PHE | 106 | 17.070 | 22.906 | 72.285 |
| 823 | CZ | PHE | 106 | 18.047 | 23.534 | 71.525 |
| 824 | N | ILE | 107 | 12.237 | 20.178 | 68.157 |
| 825 | CA | ILE | 107 | 10.843 | 19.964 | 67.745 |
| 826 | C | ILE | 107 | 10.362 | 18.541 | 68.050 |
| 827 | O | ILE | 107 | 9.158 | 18.323 | 68.254 |
| 828 | CB | ILE | 107 | 10.747 | 20.291 | 66.256 |
| 829 | CG1 | ILE | 107 | 11.068 | 21.766 | 66.035 |
| 830 | CG2 | ILE | 107 | 9.374 | 19.958 | 65.681 |
| 831 | CD1 | ILE | 107 | 10.889 | 22.173 | 64.577 |
| 832 | N | SER | 108 | 11.309 | 17.679 | 68.391 |
| 833 | CA | SER | 108 | 11.012 | 16.271 | 68.711 |
| 834 | C | SER | 108 | 10.370 | 16.073 | 70.086 |
| 835 | O | SER | 108 | 9.768 | 15.022 | 70.357 |
| 836 | CB | SER | 108 | 12.324 | 15.507 | 68.685 |
| 837 | OG | SER | 108 | 13.150 | 16.038 | 69.714 |
| 838 | N | ASN | 109 | 10.307 | 17.142 | 70.860 |
| 839 | CA | ASN | 109 | 9.642 | 17.091 | 72.153 |
| 840 | C | ASN | 109 | 8.141 | 17.325 | 72.090 |
| 841 | O | ASN | 109 | 7.448 | 17.029 | 73.069 |
| 842 | CB | ASN | 109 | 10.322 | 18.063 | 73.088 |
| 843 | CG | ASN | 109 | 11.292 | 17.196 | 73.858 |
| 844 | OD1 | ASN | 109 | 12.337 | 16.794 | 73.328 |
| 845 | ND2 | ASN | 109 | 10.741 | 16.643 | 74.917 |
| 846 | N | SER | 110 | 7.622 | 17.521 | 70.888 |
| 847 | CA | SER | 110 | 6.168 | 17.612 | 70.710 |
| 848 | C | SER | 110 | 5.468 | 16.252 | 70.864 |
| 849 | O | SER | 110 | 4.245 | 16.214 | 71.030 |
| 850 | CB | SER | 110 | 5.881 | 18.178 | 69.322 |
| 851 | OG | SER | 110 | 6.396 | 17.270 | 68.355 |
| 852 | N | ARG | 111 | 6.228 | 15.165 | 70.879 |
| 853 | CA | ARG | 111 | 5.659 | 13.846 | 71.186 |
| 854 | C | ARG | 111 | 5.987 | 13.407 | 72.619 |
| 855 | O | ARG | 111 | 5.313 | 12.538 | 73.182 |
| 856 | CB | ARG | 111 | 6.297 | 12.830 | 70.249 |
| 857 | CG | ARG | 111 | 6.351 | 13.311 | 68.806 |
| 858 | CD | ARG | 111 | 7.092 | 12.292 | 67.950 |
| 859 | NE | ARG | 111 | 8.407 | 11.989 | 68.541 |
| 860 | CZ | ARG | 111 | 8.973 | 10.781 | 68.489 |
| 861 | NH1 | ARG | 111 | 8.359 | 9.781 | 67.852 |
| 862 | NH2 | ARG | 111 | 10.161 | 10.575 | 69.062 |
| 863 | N | ASN | 112 | 6.915 | 14.115 | 73.242 |
| 864 | CA | ASN | 112 | 7.539 | 13.660 | 74.494 |
| 865 | C | ASN | 112 | 7.248 | 14.606 | 75.662 |
| 866 | O | ASN | 112 | 8.041 | 14.685 | 76.610 |
| 867 | CB | ASN | 112 | 9.056 | 13.580 | 74.285 |
| 868 | CG | ASN | 112 | 9.527 | 12.309 | 73.559 |
| 869 | OD1 | ASN | 112 | 10.046 | 11.384 | 74.203 |
| 870 | ND2 | ASN | 112 | 9.513 | 12.347 | 72.236 |
| 871 | N | TYR | 113 | 6.033 | 15.129 | 75.696 |
| 872 | CA | TYR | 113 | 5.677 | 16.187 | 76.656 |
| 873 | C | TYR | 113 | 5.409 | 15.729 | 78.095 |
| 874 | O | TYR | 113 | 5.533 | 16.554 | 79.005 |
| 875 | CB | TYR | 113 | 4.434 | 16.897 | 76.113 |

TABLE IV-continued

| Atom No. | Atom Type | Residue | Residue Position | X Coord. | Y Coord. | Z Coord. |
|---|---|---|---|---|---|---|
| 876 | CG | TYR | 113 | 3.776 | 17.888 | 77.076 |
| 877 | CD1 | TYR | 113 | 4.379 | 19.112 | 77.343 |
| 878 | CD2 | TYR | 113 | 2.576 | 17.556 | 77.695 |
| 879 | CE1 | TYR | 113 | 3.784 | 20.001 | 78.230 |
| 880 | CE2 | TYR | 113 | 1.980 | 18.444 | 78.582 |
| 881 | CZ | TYR | 113 | 2.588 | 19.663 | 78.848 |
| 882 | OH | TYR | 113 | 2.008 | 20.536 | 79.745 |
| 883 | N | PHE | 114 | 5.309 | 14.433 | 78.338 |
| 884 | CA | PHE | 114 | 4.803 | 13.977 | 79.641 |
| 885 | C | PHE | 114 | 5.804 | 13.981 | 80.803 |
| 886 | O | PHE | 114 | 5.367 | 13.788 | 81.943 |
| 887 | CB | PHE | 114 | 4.239 | 12.573 | 79.478 |
| 888 | CG | PHE | 114 | 3.091 | 12.459 | 78.481 |
| 889 | CD1 | PHE | 114 | 1.904 | 13.143 | 78.707 |
| 890 | CD2 | PHE | 114 | 3.231 | 11.666 | 77.350 |
| 891 | CE1 | PHE | 114 | 0.858 | 13.035 | 77.800 |
| 892 | CE2 | PHE | 114 | 2.186 | 11.557 | 76.443 |
| 893 | CZ | PHE | 114 | 0.999 | 12.242 | 76.668 |
| 894 | N | SER | 115 | 7.092 | 14.174 | 80.561 |
| 895 | CA | SER | 115 | 8.011 | 14.301 | 81.697 |
| 896 | C | SER | 115 | 9.059 | 15.372 | 81.457 |
| 897 | O | SER | 115 | 9.664 | 15.830 | 82.431 |
| 898 | CB | SER | 115 | 8.720 | 12.988 | 82.012 |
| 899 | OG | SER | 115 | 9.791 | 12.794 | 81.098 |
| 900 | N | GLN | 116 | 9.231 | 15.794 | 80.215 |
| 901 | CA | GLN | 116 | 10.215 | 16.833 | 79.883 |
| 902 | C | GLN | 116 | 9.997 | 18.117 | 80.674 |
| 903 | O | GLN | 116 | 8.913 | 18.358 | 81.221 |
| 904 | CB | GLN | 116 | 10.051 | 17.186 | 78.415 |
| 905 | CG | GLN | 116 | 8.647 | 17.726 | 78.172 |
| 906 | CD | GLN | 116 | 8.566 | 18.415 | 76.820 |
| 907 | OE1 | GLN | 116 | 8.245 | 17.792 | 75.801 |
| 908 | NE2 | GLN | 116 | 8.957 | 19.675 | 76.810 |
| 909 | N | CYS | 117 | 11.042 | 18.923 | 80.754 |
| 910 | CA | CYS | 117 | 10.891 | 20.261 | 81.327 |
| 911 | C | CYS | 117 | 9.927 | 21.044 | 80.447 |
| 912 | O | CYS | 117 | 9.909 | 20.843 | 79.226 |
| 913 | CB | CYS | 117 | 12.244 | 20.962 | 81.337 |
| 914 | SG | CYS | 117 | 13.552 | 20.152 | 82.284 |
| 915 | N | GLN | 118 | 9.069 | 21.843 | 81.061 |
| 916 | CA | GLN | 118 | 8.123 | 22.655 | 80.282 |
| 917 | C | GLN | 118 | 8.891 | 23.513 | 79.289 |
| 918 | O | GLN | 118 | 9.947 | 24.060 | 79.623 |
| 919 | CB | GLN | 118 | 7.320 | 23.557 | 81.209 |
| 920 | CG | GLN | 118 | 6.526 | 22.767 | 82.241 |
| 921 | CD | GLN | 118 | 5.740 | 23.741 | 83.113 |
| 922 | OE1 | GLN | 118 | 5.430 | 24.857 | 82.685 |
| 923 | NE2 | GLN | 118 | 5.442 | 23.316 | 84.328 |
| 924 | N | ALA | 119 | 8.421 | 23.516 | 78.054 |
| 925 | CA | ALA | 119 | 9.127 | 24.214 | 76.977 |
| 926 | C | ALA | 119 | 8.211 | 25.173 | 76.236 |
| 927 | O | ALA | 119 | 7.415 | 24.758 | 75.385 |
| 928 | CB | ALA | 119 | 9.658 | 23.178 | 75.996 |
| 929 | N | LEU | 120 | 8.383 | 26.454 | 76.502 |
| 930 | CA | LEU | 120 | 7.563 | 27.460 | 75.825 |
| 931 | C | LEU | 120 | 8.139 | 27.820 | 74.457 |
| 932 | O | LEU | 120 | 9.136 | 28.546 | 74.344 |
| 933 | CB | LEU | 120 | 7.462 | 28.703 | 76.701 |
| 934 | CG | LEU | 120 | 6.628 | 29.797 | 76.040 |
| 935 | CD1 | LEU | 120 | 5.192 | 29.334 | 75.816 |
| 936 | CD2 | LEU | 120 | 6.654 | 31.072 | 76.872 |
| 937 | N | LEU | 121 | 7.565 | 27.189 | 73.448 |
| 938 | CA | LEU | 121 | 7.826 | 27.543 | 72.052 |
| 939 | C | LEU | 121 | 7.051 | 28.824 | 71.754 |
| 940 | O | LEU | 121 | 5.823 | 28.856 | 71.911 |
| 941 | CB | LEU | 121 | 7.337 | 26.370 | 71.193 |
| 942 | CG | LEU | 121 | 7.667 | 26.452 | 69.699 |
| 943 | CD1 | LEU | 121 | 6.698 | 27.315 | 68.895 |
| 944 | CD2 | LEU | 121 | 9.118 | 26.837 | 69.444 |
| 945 | N | ASN | 122 | 7.766 | 29.890 | 71.433 |
| 946 | CA | ASN | 122 | 7.081 | 31.158 | 71.148 |
| 947 | C | ASN | 122 | 7.918 | 32.131 | 70.319 |
| 948 | O | ASN | 122 | 9.107 | 31.913 | 70.062 |
| 949 | CB | ASN | 122 | 6.696 | 31.816 | 72.469 |
| 950 | CG | ASN | 122 | 5.259 | 32.316 | 72.364 |
| 951 | OD1 | ASN | 122 | 5.020 | 33.441 | 71.906 |
| 952 | ND2 | ASN | 122 | 4.342 | 31.377 | 72.497 |
| 953 | N | ARG | 123 | 7.232 | 33.143 | 69.812 |
| 954 | CA | ARG | 123 | 7.870 | 34.242 | 69.082 |
| 955 | C | ARG | 123 | 7.602 | 35.564 | 69.792 |
| 956 | O | ARG | 123 | 8.383 | 36.518 | 69.692 |
| 957 | CB | ARG | 123 | 7.248 | 34.358 | 67.697 |
| 958 | CG | ARG | 123 | 7.446 | 33.131 | 66.822 |
| 959 | CD | ARG | 123 | 6.789 | 33.362 | 65.468 |
| 960 | NE | ARG | 123 | 7.067 | 32.263 | 64.535 |
| 961 | CZ | ARG | 123 | 6.774 | 32.330 | 63.235 |
| 962 | NH1 | ARG | 123 | 6.178 | 33.418 | 62.742 |
| 963 | NH2 | ARG | 123 | 7.065 | 31.306 | 62.431 |
| 964 | N | ILE | 124 | 6.498 | 35.591 | 70.520 |
| 965 | CA | ILE | 124 | 6.016 | 36.823 | 71.145 |
| 966 | C | ILE | 124 | 6.770 | 37.096 | 72.436 |
| 967 | O | ILE | 124 | 6.674 | 36.322 | 73.398 |
| 968 | CB | ILE | 124 | 4.529 | 36.633 | 71.432 |
| 969 | CG1 | ILE | 124 | 3.809 | 36.155 | 70.177 |
| 970 | CG2 | ILE | 124 | 3.888 | 37.919 | 71.942 |
| 971 | CD1 | ILE | 124 | 2.333 | 35.892 | 70.452 |
| 972 | N | THR | 125 | 7.309 | 38.301 | 72.525 |
| 973 | CA | THR | 125 | 8.147 | 38.698 | 73.664 |
| 974 | C | THR | 125 | 7.392 | 38.810 | 74.997 |
| 975 | O | THR | 125 | 7.977 | 38.463 | 76.030 |
| 976 | CB | THR | 125 | 8.787 | 40.038 | 73.304 |
| 977 | OG1 | THR | 125 | 9.638 | 39.824 | 72.184 |
| 978 | CG2 | THR | 125 | 9.637 | 40.611 | 74.434 |
| 979 | N | SER | 126 | 6.077 | 38.963 | 74.943 |
| 980 | CA | SER | 126 | 5.279 | 39.131 | 76.164 |
| 981 | C | SER | 126 | 4.724 | 37.828 | 76.747 |
| 982 | O | SER | 126 | 4.107 | 37.876 | 77.818 |
| 983 | CB | SER | 126 | 4.102 | 40.047 | 75.859 |
| 984 | OG | SER | 126 | 3.211 | 39.335 | 75.011 |
| 985 | N | VAL | 127 | 4.931 | 36.690 | 76.099 |
| 986 | CA | VAL | 127 | 4.397 | 35.441 | 76.664 |
| 987 | C | VAL | 127 | 5.414 | 34.816 | 77.613 |
| 988 | O | VAL | 127 | 5.080 | 34.385 | 78.729 |
| 989 | CB | VAL | 127 | 4.087 | 34.480 | 75.522 |
| 990 | CG1 | VAL | 127 | 3.589 | 33.140 | 76.051 |
| 991 | CG2 | VAL | 127 | 3.065 | 35.085 | 74.568 |
| 992 | N | ASN | 128 | 6.661 | 35.091 | 77.287 |
| 993 | CA | ASN | 128 | 7.806 | 34.602 | 78.057 |
| 994 | C | ASN | 128 | 7.881 | 35.094 | 79.511 |
| 995 | O | ASN | 128 | 8.038 | 34.212 | 80.362 |
| 996 | CB | ASN | 128 | 9.061 | 35.005 | 77.304 |
| 997 | CG | ASN | 128 | 8.864 | 34.685 | 75.828 |
| 998 | OD1 | ASN | 128 | 8.507 | 33.559 | 75.450 |
| 999 | ND2 | ASN | 128 | 9.110 | 35.687 | 75.007 |
| 1000 | N | PRO | 129 | 7.679 | 36.368 | 79.859 |
| 1001 | CA | PRO | 129 | 7.760 | 36.730 | 81.282 |
| 1002 | C | PRO | 129 | 6.658 | 36.144 | 82.176 |
| 1003 | O | PRO | 129 | 6.950 | 35.921 | 83.354 |
| 1004 | CB | PRO | 129 | 7.714 | 38.226 | 81.330 |
| 1005 | CG | PRO | 129 | 7.469 | 38.770 | 79.937 |
| 1006 | CD | PRO | 129 | 7.447 | 37.561 | 79.025 |
| 1007 | N | GLN | 130 | 5.564 | 35.646 | 81.618 |
| 1008 | CA | GLN | 130 | 4.513 | 35.056 | 82.455 |
| 1009 | C | GLN | 130 | 4.969 | 33.690 | 82.958 |
| 1010 | O | GLN | 130 | 5.108 | 33.479 | 84.172 |
| 1011 | CB | GLN | 130 | 3.271 | 34.880 | 81.592 |
| 1012 | CG | GLN | 130 | 2.915 | 36.176 | 80.874 |
| 1013 | CD | GLN | 130 | 1.683 | 35.964 | 80.001 |
| 1014 | OE1 | GLN | 130 | 0.784 | 35.188 | 80.346 |
| 1015 | NE2 | GLN | 130 | 1.674 | 36.628 | 78.859 |
| 1016 | N | THR | 131 | 5.545 | 32.945 | 82.030 |
| 1017 | CA | THR | 131 | 6.089 | 31.624 | 82.356 |
| 1018 | C | THR | 131 | 7.450 | 31.728 | 83.049 |
| 1019 | O | THR | 131 | 7.764 | 30.890 | 83.902 |
| 1020 | CB | THR | 131 | 6.207 | 30.818 | 81.068 |
| 1021 | OG1 | THR | 131 | 7.074 | 31.510 | 80.180 |
| 1022 | CG2 | THR | 131 | 4.852 | 30.671 | 80.386 |
| 1023 | N | ASP | 132 | 8.089 | 32.879 | 82.913 |
| 1024 | CA | ASP | 132 | 9.334 | 33.157 | 83.627 |
| 1025 | C | ASP | 132 | 9.069 | 33.515 | 85.089 |
| 1026 | O | ASP | 132 | 9.860 | 33.112 | 85.945 |
| 1027 | CB | ASP | 132 | 10.029 | 34.317 | 82.923 |

TABLE IV-continued

| Atom No. | Atom Type | Residue | Residue Position | X Coord. | Y Coord. | Z Coord. |
|---|---|---|---|---|---|---|
| 1028 | CG | ASP | 132 | 11.370 | 34.646 | 83.571 |
| 1029 | OD1 | ASP | 132 | 11.770 | 35.798 | 83.474 |
| 1030 | OD2 | ASP | 132 | 12.001 | 33.733 | 84.084 |
| 1031 | N | ILE | 133 | 7.873 | 33.988 | 85.404 |
| 1032 | CA | ILE | 133 | 7.507 | 34.216 | 86.807 |
| 1033 | C | ILE | 133 | 7.051 | 32.912 | 87.460 |
| 1034 | O | ILE | 133 | 7.287 | 32.698 | 88.654 |
| 1035 | CB | ILE | 133 | 6.387 | 35.253 | 86.859 |
| 1036 | CG1 | ILE | 133 | 6.881 | 36.603 | 86.356 |
| 1037 | CG2 | ILE | 133 | 5.824 | 35.397 | 88.269 |
| 1038 | CD1 | ILE | 133 | 5.758 | 37.633 | 86.344 |
| 1039 | N | ASP | 134 | 6.660 | 31.962 | 86.622 |
| 1040 | CA | ASP | 134 | 6.284 | 30.626 | 87.097 |
| 1041 | C | ASP | 134 | 7.503 | 29.723 | 87.309 |
| 1042 | O | ASP | 134 | 7.388 | 28.681 | 87.965 |
| 1043 | CB | ASP | 134 | 5.371 | 29.982 | 86.060 |
| 1044 | CG | ASP | 134 | 4.118 | 30.825 | 85.836 |
| 1045 | OD1 | ASP | 134 | 3.637 | 30.832 | 84.710 |
| 1046 | OD2 | ASP | 134 | 3.631 | 31.397 | 86.801 |
| 1047 | N | GLY | 135 | 8.653 | 30.134 | 86.800 |
| 1048 | CA | GLY | 135 | 9.895 | 29.400 | 87.050 |
| 1049 | C | GLY | 135 | 10.707 | 30.112 | 88.128 |
| 1050 | O | GLY | 135 | 11.212 | 29.479 | 89.065 |
| 1051 | N | LEU | 136 | 10.722 | 31.432 | 88.025 |
| 1052 | CA | LEU | 136 | 11.439 | 32.339 | 88.933 |
| 1053 | C | LEU | 136 | 12.843 | 31.827 | 89.247 |
| 1054 | O | LEU | 136 | 13.536 | 31.389 | 88.318 |
| 1055 | CB | LEU | 136 | 10.605 | 32.539 | 90.195 |
| 1056 | CG | LEU | 136 | 10.635 | 33.996 | 90.657 |
| 1057 | CD1 | LEU | 136 | 10.238 | 34.940 | 89.527 |
| 1058 | CD2 | LEU | 136 | 9.746 | 34.204 | 91.877 |
| 1059 | N | ARG | 137 | 13.177 | 31.763 | 90.532 |
| 1060 | CA | ARG | 137 | 14.527 | 31.448 | 91.056 |
| 1061 | C | ARG | 137 | 15.627 | 31.420 | 90.005 |
| 1062 | O | ARG | 137 | 15.952 | 32.453 | 89.418 |
| 1063 | CB | ARG | 137 | 14.473 | 30.112 | 91.781 |
| 1064 | CG | ARG | 137 | 13.800 | 30.287 | 93.135 |
| 1065 | CD | ARG | 137 | 14.574 | 31.310 | 93.957 |
| 1066 | NE | ARG | 137 | 13.944 | 31.555 | 95.261 |
| 1067 | CZ | ARG | 137 | 14.640 | 31.956 | 96.326 |
| 1068 | NH1 | ARG | 137 | 14.019 | 32.180 | 97.486 |
| 1069 | NH2 | ARG | 137 | 15.958 | 32.141 | 96.227 |
| 1070 | N | ASN | 138 | 16.197 | 30.258 | 89.764 |
| 1071 | CA | ASN | 138 | 17.203 | 30.133 | 88.703 |
| 1072 | C | ASN | 138 | 16.634 | 29.416 | 87.477 |
| 1073 | O | ASN | 138 | 17.366 | 29.112 | 86.527 |
| 1074 | CB | ASN | 138 | 18.396 | 29.365 | 89.262 |
| 1075 | CG | ASN | 138 | 19.003 | 30.121 | 90.443 |
| 1076 | OD1 | ASN | 138 | 19.492 | 31.245 | 90.288 |
| 1077 | ND2 | ASN | 138 | 18.918 | 29.524 | 91.621 |
| 1078 | N | ILE | 139 | 15.319 | 29.293 | 87.445 |
| 1079 | CA | ILE | 139 | 14.649 | 28.317 | 86.584 |
| 1080 | C | ILE | 139 | 14.132 | 28.887 | 85.254 |
| 1081 | O | ILE | 139 | 12.918 | 28.879 | 85.006 |
| 1082 | CB | ILE | 139 | 13.504 | 27.745 | 87.424 |
| 1083 | CG1 | ILE | 139 | 14.012 | 27.363 | 88.808 |
| 1084 | CG2 | ILE | 139 | 12.860 | 26.521 | 86.788 |
| 1085 | CD1 | ILE | 139 | 12.910 | 26.741 | 89.658 |
| 1086 | N | TRP | 140 | 15.035 | 29.307 | 84.377 |
| 1087 | CA | TRP | 140 | 14.600 | 29.663 | 83.015 |
| 1088 | C | TRP | 140 | 15.715 | 29.548 | 81.969 |
| 1089 | O | TRP | 140 | 16.650 | 30.357 | 81.924 |
| 1090 | CB | TRP | 140 | 14.028 | 31.074 | 83.019 |
| 1091 | CG | TRP | 140 | 12.980 | 31.302 | 81.947 |
| 1092 | CD1 | TRP | 140 | 12.913 | 32.358 | 81.065 |
| 1093 | CD2 | TRP | 140 | 11.853 | 30.447 | 81.648 |
| 1094 | NE1 | TRP | 140 | 11.818 | 32.195 | 80.280 |
| 1095 | CE2 | TRP | 140 | 11.153 | 31.070 | 80.601 |
| 1096 | CE3 | TRP | 140 | 11.392 | 29.251 | 82.181 |
| 1097 | CZ2 | TRP | 140 | 9.992 | 30.491 | 80.112 |
| 1098 | CZ3 | TRP | 140 | 10.235 | 28.673 | 81.675 |
| 1099 | CH2 | TRP | 140 | 9.536 | 29.292 | 80.645 |
| 1100 | N | ILE | 141 | 15.559 | 28.580 | 81.081 |
| 1101 | CA | ILE | 141 | 16.554 | 28.325 | 80.027 |
| 1102 | C | ILE | 141 | 16.111 | 28.871 | 78.672 |
| 1103 | O | ILE | 141 | 15.254 | 28.297 | 77.990 |
| 1104 | CB | ILE | 141 | 16.779 | 26.820 | 79.921 |
| 1105 | CG1 | ILE | 141 | 17.311 | 26.279 | 81.237 |
| 1106 | CG2 | ILE | 141 | 17.751 | 26.496 | 78.793 |
| 1107 | CD1 | ILE | 141 | 18.635 | 26.942 | 81.591 |
| 1108 | N | ILE | 142 | 16.799 | 29.915 | 78.250 |
| 1109 | CA | ILE | 142 | 16.498 | 30.617 | 77.002 |
| 1110 | C | ILE | 142 | 17.324 | 30.112 | 75.813 |
| 1111 | O | ILE | 142 | 18.535 | 30.344 | 75.749 |
| 1112 | CB | ILE | 142 | 16.824 | 32.077 | 77.282 |
| 1113 | CG1 | ILE | 142 | 15.925 | 32.643 | 78.371 |
| 1114 | CG2 | ILE | 142 | 16.736 | 32.928 | 76.034 |
| 1115 | CD1 | ILE | 142 | 16.210 | 34.125 | 78.585 |
| 1116 | N | LYS | 143 | 16.682 | 29.407 | 74.895 |
| 1117 | CA | LYS | 143 | 17.388 | 28.946 | 73.687 |
| 1118 | C | LYS | 143 | 16.501 | 28.997 | 72.437 |
| 1119 | O | LYS | 143 | 15.273 | 29.029 | 72.548 |
| 1120 | CB | LYS | 143 | 17.917 | 27.542 | 73.964 |
| 1121 | CG | LYS | 143 | 16.866 | 26.630 | 74.579 |
| 1122 | CD | LYS | 143 | 17.489 | 25.331 | 75.080 |
| 1123 | CE | LYS | 143 | 16.460 | 24.456 | 75.789 |
| 1124 | NZ | LYS | 143 | 17.088 | 23.245 | 76.340 |
| 1125 | N | PRO | 144 | 17.109 | 29.162 | 71.271 |
| 1126 | CA | PRO | 144 | 16.354 | 29.160 | 70.008 |
| 1127 | C | PRO | 144 | 15.836 | 27.765 | 69.663 |
| 1128 | O | PRO | 144 | 16.376 | 26.762 | 70.140 |
| 1129 | CB | PRO | 144 | 17.323 | 29.641 | 68.973 |
| 1130 | CG | PRO | 144 | 18.711 | 29.714 | 69.588 |
| 1131 | CD | PRO | 144 | 18.544 | 29.340 | 71.051 |
| 1132 | N | ALA | 145 | 14.816 | 27.709 | 68.820 |
| 1133 | CA | ALA | 145 | 14.230 | 26.423 | 68.407 |
| 1134 | C | ALA | 145 | 14.811 | 25.848 | 67.112 |
| 1135 | O | ALA | 145 | 14.335 | 24.808 | 66.641 |
| 1136 | CB | ALA | 145 | 12.732 | 26.613 | 68.215 |
| 1137 | N | ALA | 146 | 15.827 | 26.496 | 66.564 |
| 1138 | CA | ALA | 146 | 16.372 | 26.120 | 65.250 |
| 1139 | C | ALA | 146 | 17.078 | 24.765 | 65.254 |
| 1140 | O | ALA | 146 | 16.443 | 23.718 | 65.084 |
| 1141 | CB | ALA | 146 | 17.345 | 27.205 | 64.803 |
| 1142 | N | LYS | 147 | 18.395 | 24.801 | 65.319 |
| 1143 | CA | LYS | 147 | 19.152 | 23.551 | 65.355 |
| 1144 | C | LYS | 147 | 19.660 | 23.324 | 66.773 |
| 1145 | O | LYS | 147 | 18.990 | 22.655 | 67.568 |
| 1146 | CB | LYS | 147 | 20.286 | 23.608 | 64.324 |
| 1147 | CG | LYS | 147 | 21.099 | 22.312 | 64.241 |
| 1148 | CD | LYS | 147 | 20.217 | 21.084 | 64.052 |
| 1149 | CE | LYS | 147 | 21.048 | 19.809 | 64.121 |
| 1150 | NZ | LYS | 147 | 20.191 | 18.615 | 64.052 |
| 1151 | N | SER | 148 | 20.790 | 23.944 | 67.079 |
| 1152 | CA | SER | 148 | 21.483 | 23.768 | 68.359 |
| 1153 | C | SER | 148 | 22.855 | 24.430 | 68.300 |
| 1154 | O | SER | 148 | 22.985 | 25.636 | 68.047 |
| 1155 | CB | SER | 148 | 21.643 | 22.274 | 68.634 |
| 1156 | OG | SER | 148 | 22.028 | 21.613 | 67.434 |
| 1157 | N | ARG | 149 | 23.839 | 23.647 | 68.714 |
| 1158 | CA | ARG | 149 | 25.266 | 23.935 | 68.506 |
| 1159 | C | ARG | 149 | 25.727 | 25.182 | 69.250 |
| 1160 | O | ARG | 149 | 26.452 | 26.009 | 68.686 |
| 1161 | CB | ARG | 149 | 25.538 | 24.105 | 67.008 |
| 1162 | CG | ARG | 149 | 24.967 | 22.957 | 66.174 |
| 1163 | CD | ARG | 149 | 25.618 | 21.610 | 66.469 |
| 1164 | NE | ARG | 149 | 24.760 | 20.516 | 65.985 |
| 1165 | CZ | ARG | 149 | 24.787 | 19.289 | 66.510 |
| 1166 | NH1 | ARG | 149 | 25.757 | 18.955 | 67.363 |
| 1167 | NH2 | ARG | 149 | 23.934 | 18.357 | 66.079 |
| 1168 | N | GLY | 150 | 25.254 | 25.338 | 70.476 |
| 1169 | CA | GLY | 150 | 25.677 | 26.449 | 71.330 |
| 1170 | C | GLY | 150 | 25.073 | 27.822 | 71.069 |
| 1171 | O | GLY | 150 | 25.307 | 28.731 | 71.881 |
| 1172 | N | ARG | 151 | 24.322 | 27.982 | 69.990 |
| 1173 | CA | ARG | 151 | 23.797 | 29.302 | 69.635 |
| 1174 | C | ARG | 151 | 22.797 | 29.820 | 70.651 |
| 1175 | O | ARG | 151 | 21.683 | 29.309 | 70.793 |
| 1176 | CB | ARG | 151 | 23.168 | 29.262 | 68.249 |
| 1177 | CG | ARG | 151 | 24.189 | 29.657 | 67.188 |
| 1178 | CD | ARG | 151 | 23.565 | 29.711 | 65.797 |
| 1179 | NE | ARG | 151 | 24.439 | 30.427 | 64.850 |

TABLE IV-continued

| Atom No. | Atom Type | Residue | Residue Position | X Coord. | Y Coord. | Z Coord. |
|---|---|---|---|---|---|---|
| 1180 | CZ | ARG | 151 | 25.244 | 29.833 | 63.965 |
| 1181 | NH1 | ARG | 151 | 25.327 | 28.501 | 63.922 |
| 1182 | NH2 | ARG | 151 | 25.988 | 30.573 | 63.140 |
| 1183 | N | ASP | 152 | 23.267 | 30.823 | 71.377 |
| 1184 | CA | ASP | 152 | 22.486 | 31.557 | 72.373 |
| 1185 | C | ASP | 152 | 21.735 | 30.637 | 73.335 |
| 1186 | O | ASP | 152 | 20.509 | 30.521 | 73.262 |
| 1187 | CB | ASP | 152 | 21.508 | 32.459 | 71.627 |
| 1188 | CG | ASP | 152 | 22.246 | 33.420 | 70.700 |
| 1189 | OD1 | ASP | 152 | 22.794 | 34.388 | 71.206 |
| 1190 | OD2 | ASP | 152 | 22.332 | 33.115 | 69.518 |
| 1191 | N | ILE | 153 | 22.478 | 29.900 | 74.143 |
| 1192 | CA | ILE | 153 | 21.840 | 29.100 | 75.196 |
| 1193 | C | ILE | 153 | 22.045 | 29.831 | 76.522 |
| 1194 | O | ILE | 153 | 23.082 | 29.687 | 77.183 |
| 1195 | CB | ILE | 153 | 22.465 | 27.708 | 75.258 |
| 1196 | CG1 | ILE | 153 | 22.566 | 27.039 | 73.885 |
| 1197 | CG2 | ILE | 153 | 21.679 | 26.819 | 76.217 |
| 1198 | CD1 | ILE | 153 | 21.213 | 26.654 | 73.301 |
| 1199 | N | VAL | 154 | 21.076 | 30.662 | 76.862 |
| 1200 | CA | VAL | 154 | 21.191 | 31.562 | 78.015 |
| 1201 | C | VAL | 154 | 20.399 | 31.077 | 79.229 |
| 1202 | O | VAL | 154 | 19.165 | 31.142 | 79.258 |
| 1203 | CB | VAL | 154 | 20.664 | 32.931 | 77.587 |
| 1204 | CG1 | VAL | 154 | 20.786 | 33.956 | 78.710 |
| 1205 | CG2 | VAL | 154 | 21.376 | 33.429 | 76.334 |
| 1206 | N | CYS | 155 | 21.110 | 30.589 | 80.229 |
| 1207 | CA | CYS | 155 | 20.464 | 30.262 | 81.506 |
| 1208 | C | CYS | 155 | 20.258 | 31.532 | 82.328 |
| 1209 | O | CYS | 155 | 21.237 | 32.160 | 82.745 |
| 1210 | CB | CYS | 155 | 21.363 | 29.307 | 82.283 |
| 1211 | SG | CYS | 155 | 20.809 | 28.917 | 83.959 |
| 1212 | N | MET | 156 | 19.012 | 31.917 | 82.544 |
| 1213 | CA | MET | 156 | 18.772 | 33.138 | 83.314 |
| 1214 | C | MET | 156 | 18.043 | 32.869 | 84.628 |
| 1215 | O | MET | 156 | 17.166 | 32.003 | 84.756 |
| 1216 | CB | MET | 156 | 18.037 | 34.169 | 82.451 |
| 1217 | CG | MET | 156 | 16.564 | 33.865 | 82.186 |
| 1218 | SD | MET | 156 | 15.384 | 34.456 | 83.426 |
| 1219 | CE | MET | 156 | 15.826 | 36.208 | 83.431 |
| 1220 | N | ASP | 157 | 18.506 | 33.585 | 85.633 |
| 1221 | CA | ASP | 157 | 17.864 | 33.585 | 86.940 |
| 1222 | C | ASP | 157 | 17.211 | 34.930 | 87.246 |
| 1223 | O | ASP | 157 | 17.248 | 35.885 | 86.456 |
| 1224 | CB | ASP | 157 | 18.880 | 33.220 | 88.021 |
| 1225 | CG | ASP | 157 | 20.169 | 34.035 | 87.948 |
| 1226 | OD1 | ASP | 157 | 20.168 | 35.159 | 88.431 |
| 1227 | OD2 | ASP | 157 | 21.156 | 33.484 | 87.479 |
| 1228 | N | ARG | 158 | 16.562 | 34.941 | 88.396 |
| 1229 | CA | ARG | 158 | 15.856 | 36.094 | 88.961 |
| 1230 | C | ARG | 158 | 16.670 | 37.384 | 88.936 |
| 1231 | O | ARG | 158 | 17.900 | 37.380 | 88.816 |
| 1232 | CB | ARG | 158 | 15.494 | 35.721 | 90.394 |
| 1233 | CG | ARG | 158 | 16.726 | 35.230 | 91.148 |
| 1234 | CD | ARG | 158 | 16.358 | 34.543 | 92.458 |
| 1235 | NE | ARG | 158 | 15.669 | 35.456 | 93.380 |
| 1236 | CZ | ARG | 158 | 16.139 | 35.738 | 94.597 |
| 1237 | NH1 | ARG | 158 | 17.296 | 35.210 | 95.003 |
| 1238 | NH2 | ARG | 158 | 15.466 | 36.567 | 95.398 |
| 1239 | N | VAL | 159 | 15.913 | 38.473 | 88.900 |
| 1240 | CA | VAL | 159 | 16.377 | 39.878 | 88.809 |
| 1241 | C | VAL | 159 | 17.389 | 40.172 | 87.691 |
| 1242 | O | VAL | 159 | 18.208 | 41.092 | 87.813 |
| 1243 | CB | VAL | 159 | 16.883 | 40.389 | 90.168 |
| 1244 | CG1 | VAL | 159 | 15.803 | 40.242 | 91.235 |
| 1245 | CG2 | VAL | 159 | 18.188 | 39.759 | 90.653 |
| 1246 | N | GLU | 160 | 17.284 | 39.462 | 86.579 |
| 1247 | CA | GLU | 160 | 18.090 | 39.813 | 85.414 |
| 1248 | C | GLU | 160 | 17.270 | 40.638 | 84.437 |
| 1249 | O | GLU | 160 | 16.225 | 40.208 | 83.935 |
| 1250 | CB | GLU | 160 | 18.617 | 38.562 | 84.734 |
| 1251 | CG | GLU | 160 | 19.640 | 37.847 | 85.604 |
| 1252 | CD | GLU | 160 | 20.199 | 36.671 | 84.818 |
| 1253 | OE1 | GLU | 160 | 20.171 | 36.752 | 83.599 |
| 1254 | OE2 | GLU | 160 | 20.493 | 35.654 | 85.431 |
| 1255 | N | GLU | 161 | 17.858 | 41.756 | 84.049 |
| 1256 | CA | GLU | 161 | 17.188 | 42.710 | 83.159 |
| 1257 | C | GLU | 161 | 17.306 | 42.317 | 81.686 |
| 1258 | O | GLU | 161 | 16.519 | 42.784 | 80.853 |
| 1259 | CB | GLU | 161 | 17.829 | 44.070 | 83.394 |
| 1260 | CG | GLU | 161 | 17.657 | 44.500 | 84.847 |
| 1261 | CD | GLU | 161 | 18.509 | 45.733 | 85.129 |
| 1262 | OE1 | GLU | 161 | 18.088 | 46.551 | 85.933 |
| 1263 | OE2 | GLU | 161 | 19.598 | 45.795 | 84.576 |
| 1264 | N | ILE | 162 | 18.102 | 41.291 | 81.425 |
| 1265 | CA | ILE | 162 | 18.313 | 40.803 | 80.063 |
| 1266 | C | ILE | 162 | 17.230 | 39.837 | 79.580 |
| 1267 | O | ILE | 162 | 17.331 | 39.370 | 78.441 |
| 1268 | CB | ILE | 162 | 19.672 | 40.119 | 79.982 |
| 1269 | CG1 | ILE | 162 | 19.734 | 38.898 | 80.892 |
| 1270 | CG2 | ILE | 162 | 20.781 | 41.102 | 80.336 |
| 1271 | CD1 | ILE | 162 | 21.072 | 38.181 | 80.753 |
| 1272 | N | LEU | 163 | 16.157 | 39.651 | 80.337 |
| 1273 | CA | LEU | 163 | 15.071 | 38.771 | 79.889 |
| 1274 | C | LEU | 163 | 14.397 | 39.364 | 78.653 |
| 1275 | O | LEU | 163 | 14.324 | 38.679 | 77.625 |
| 1276 | CB | LEU | 163 | 14.070 | 38.617 | 81.039 |
| 1277 | CG | LEU | 163 | 12.989 | 37.552 | 80.810 |
| 1278 | CD1 | LEU | 163 | 11.768 | 38.052 | 80.040 |
| 1279 | CD2 | LEU | 163 | 13.554 | 36.270 | 80.209 |
| 1280 | N | GLU | 164 | 14.206 | 40.675 | 78.643 |
| 1281 | CA | GLU | 164 | 13.574 | 41.302 | 77.477 |
| 1282 | C | GLU | 164 | 14.581 | 41.541 | 76.350 |
| 1283 | O | GLU | 164 | 14.200 | 41.505 | 75.174 |
| 1284 | CB | GLU | 164 | 12.941 | 42.623 | 77.900 |
| 1285 | CG | GLU | 164 | 12.141 | 43.250 | 76.761 |
| 1286 | CD | GLU | 164 | 11.519 | 44.562 | 77.226 |
| 1287 | OE1 | GLU | 164 | 11.265 | 45.410 | 76.383 |
| 1288 | OE2 | GLU | 164 | 11.350 | 44.704 | 78.430 |
| 1289 | N | LEU | 165 | 15.861 | 41.509 | 76.684 |
| 1290 | CA | LEU | 165 | 16.895 | 41.657 | 75.664 |
| 1291 | C | LEU | 165 | 17.027 | 40.353 | 74.890 |
| 1292 | O | LEU | 165 | 16.863 | 40.359 | 73.663 |
| 1293 | CB | LEU | 165 | 18.215 | 41.992 | 76.349 |
| 1294 | CG | LEU | 165 | 19.345 | 42.167 | 75.341 |
| 1295 | CD1 | LEU | 165 | 19.026 | 43.276 | 74.344 |
| 1296 | CD2 | LEU | 165 | 20.665 | 42.446 | 76.051 |
| 1297 | N | ALA | 166 | 16.953 | 39.246 | 75.610 |
| 1298 | CA | ALA | 166 | 17.028 | 37.932 | 74.974 |
| 1299 | C | ALA | 166 | 15.740 | 37.591 | 74.232 |
| 1300 | O | ALA | 166 | 15.827 | 37.059 | 73.117 |
| 1301 | CB | ALA | 166 | 17.297 | 36.885 | 76.047 |
| 1302 | N | ALA | 167 | 14.625 | 38.147 | 74.684 |
| 1303 | CA | ALA | 167 | 13.340 | 37.960 | 74.001 |
| 1304 | C | ALA | 167 | 13.148 | 38.884 | 72.795 |
| 1305 | O | ALA | 167 | 12.249 | 38.657 | 71.979 |
| 1306 | CB | ALA | 167 | 12.220 | 38.184 | 75.009 |
| 1307 | N | ALA | 168 | 14.013 | 39.871 | 72.638 |
| 1308 | CA | ALA | 168 | 14.018 | 40.641 | 71.397 |
| 1309 | C | ALA | 168 | 15.080 | 40.104 | 70.441 |
| 1310 | O | ALA | 168 | 14.871 | 40.098 | 69.222 |
| 1311 | CB | ALA | 168 | 14.306 | 42.101 | 71.724 |
| 1312 | N | ASP | 169 | 16.103 | 39.480 | 71.001 |
| 1313 | CA | ASP | 169 | 17.201 | 38.928 | 70.197 |
| 1314 | C | ASP | 169 | 16.810 | 37.629 | 69.499 |
| 1315 | O | ASP | 169 | 16.684 | 37.606 | 68.268 |
| 1316 | CB | ASP | 169 | 18.397 | 38.644 | 71.106 |
| 1317 | CG | ASP | 169 | 18.972 | 39.917 | 71.726 |
| 1318 | OD1 | ASP | 169 | 19.555 | 39.802 | 72.799 |
| 1319 | OD2 | ASP | 169 | 18.909 | 40.956 | 71.083 |
| 1320 | N | HIS | 170 | 16.424 | 36.638 | 70.285 |
| 1321 | CA | HIS | 170 | 16.161 | 35.287 | 69.751 |
| 1322 | C | HIS | 170 | 14.990 | 35.251 | 68.759 |
| 1323 | O | HIS | 170 | 15.224 | 34.833 | 67.618 |
| 1324 | CB | HIS | 170 | 15.896 | 34.276 | 70.868 |
| 1325 | CG | HIS | 170 | 17.014 | 33.923 | 71.831 |
| 1326 | ND1 | HIS | 170 | 17.675 | 34.744 | 72.670 |
| 1327 | CD2 | HIS | 170 | 17.502 | 32.659 | 72.045 |
| 1328 | CE1 | HIS | 170 | 18.581 | 34.034 | 73.368 |
| 1329 | NE2 | HIS | 170 | 18.467 | 32.743 | 72.986 |
| 1330 | N | PRO | 171 | 13.777 | 35.670 | 69.119 |
| 1331 | CA | PRO | 171 | 12.717 | 35.738 | 68.113 |

TABLE IV-continued

| Atom No. | Atom Type | Residue | Residue Position | X Coord. | Y Coord. | Z Coord. |
|---|---|---|---|---|---|---|
| 1332 | C | PRO | 171 | 12.791 | 36.918 | 67.139 |
| 1333 | O | PRO | 171 | 11.867 | 37.031 | 66.325 |
| 1334 | CB | PRO | 171 | 11.442 | 35.830 | 68.891 |
| 1335 | CG | PRO | 171 | 11.758 | 36.089 | 70.348 |
| 1336 | CD | PRO | 171 | 13.272 | 36.104 | 70.435 |
| 1337 | N | LEU | 172 | 13.833 | 37.740 | 67.164 |
| 1338 | CA | LEU | 172 | 13.857 | 38.986 | 66.383 |
| 1339 | C | LEU | 172 | 12.535 | 39.720 | 66.592 |
| 1340 | O | LEU | 172 | 11.685 | 39.770 | 65.691 |
| 1341 | CB | LEU | 172 | 14.083 | 38.653 | 64.910 |
| 1342 | CG | LEU | 172 | 14.336 | 39.903 | 64.073 |
| 1343 | CD1 | LEU | 172 | 15.554 | 40.665 | 64.586 |
| 1344 | CD2 | LEU | 172 | 14.507 | 39.541 | 62.602 |
| 1345 | N | SER | 173 | 12.314 | 40.050 | 67.858 |
| 1346 | CA | SER | 173 | 11.094 | 40.669 | 68.423 |
| 1347 | C | SER | 173 | 9.763 | 39.882 | 68.367 |
| 1348 | O | SER | 173 | 8.976 | 40.007 | 69.316 |
| 1349 | CB | SER | 173 | 10.902 | 42.013 | 67.731 |
| 1350 | OG | SER | 173 | 12.087 | 42.769 | 67.939 |
| 1351 | N | ARG | 174 | 9.507 | 39.106 | 67.319 |
| 1352 | CA | ARG | 174 | 8.189 | 38.477 | 67.131 |
| 1353 | C | ARG | 174 | 8.115 | 37.518 | 65.933 |
| 1354 | O | ARG | 174 | 7.017 | 37.068 | 65.584 |
| 1355 | CB | ARG | 174 | 7.215 | 39.625 | 66.873 |
| 1356 | CG | ARG | 174 | 7.671 | 40.436 | 65.661 |
| 1357 | CD | ARG | 174 | 7.136 | 41.862 | 65.675 |
| 1358 | NE | ARG | 174 | 5.668 | 41.905 | 65.629 |
| 1359 | CZ | ARG | 174 | 5.001 | 42.998 | 65.254 |
| 1360 | NH1 | ARG | 174 | 3.667 | 43.001 | 65.252 |
| 1361 | NH2 | ARG | 174 | 5.672 | 44.097 | 64.898 |
| 1362 | N | ASP | 175 | 9.242 | 37.200 | 65.318 |
| 1363 | CA | ASP | 175 | 9.216 | 36.473 | 64.038 |
| 1364 | C | ASP | 175 | 9.816 | 35.060 | 64.077 |
| 1365 | O | ASP | 175 | 9.442 | 34.201 | 63.270 |
| 1366 | CB | ASP | 175 | 10.006 | 37.334 | 63.055 |
| 1367 | CG | ASP | 175 | 10.065 | 36.692 | 61.674 |
| 1368 | OD1 | ASP | 175 | 9.008 | 36.417 | 61.125 |
| 1369 | OD2 | ASP | 175 | 11.170 | 36.521 | 61.177 |
| 1370 | N | ASN | 176 | 10.741 | 34.825 | 64.988 |
| 1371 | CA | ASN | 176 | 11.434 | 33.530 | 65.061 |
| 1372 | C | ASN | 176 | 11.035 | 32.742 | 66.312 |
| 1373 | O | ASN | 176 | 10.750 | 33.324 | 67.363 |
| 1374 | CB | ASN | 176 | 12.937 | 33.818 | 65.045 |
| 1375 | CG | ASN | 176 | 13.766 | 32.537 | 65.043 |
| 1376 | OD1 | ASN | 176 | 13.465 | 31.587 | 64.310 |
| 1377 | ND2 | ASN | 176 | 14.789 | 32.524 | 65.878 |
| 1378 | N | LYS | 177 | 10.959 | 31.430 | 66.172 |
| 1379 | CA | LYS | 177 | 10.591 | 30.563 | 67.295 |
| 1380 | C | LYS | 177 | 11.763 | 30.244 | 68.223 |
| 1381 | O | LYS | 177 | 12.868 | 29.872 | 67.799 |
| 1382 | CB | LYS | 177 | 10.030 | 29.261 | 66.741 |
| 1383 | CG | LYS | 177 | 8.715 | 29.497 | 66.013 |
| 1384 | CD | LYS | 177 | 8.152 | 28.205 | 65.438 |
| 1385 | CE | LYS | 177 | 6.805 | 28.445 | 64.766 |
| 1386 | NZ | LYS | 177 | 6.273 | 27.202 | 64.187 |
| 1387 | N | TRP | 178 | 11.507 | 30.415 | 69.506 |
| 1388 | CA | TRP | 178 | 12.464 | 29.969 | 70.519 |
| 1389 | C | TRP | 178 | 11.800 | 28.972 | 71.470 |
| 1390 | O | TRP | 178 | 10.571 | 28.838 | 71.478 |
| 1391 | CB | TRP | 178 | 13.051 | 31.177 | 71.252 |
| 1392 | CG | TRP | 178 | 12.247 | 31.835 | 72.361 |
| 1393 | CD1 | TRP | 178 | 10.918 | 31.672 | 72.695 |
| 1394 | CD2 | TRP | 178 | 12.774 | 32.803 | 73.291 |
| 1395 | NE1 | TRP | 178 | 10.647 | 32.436 | 73.781 |
| 1396 | CE2 | TRP | 178 | 11.741 | 33.120 | 74.174 |
| 1397 | CE3 | TRP | 178 | 14.026 | 33.381 | 73.447 |
| 1398 | CZ2 | TRP | 178 | 11.977 | 33.980 | 75.238 |
| 1399 | CZ3 | TRP | 178 | 14.246 | 34.268 | 74.491 |
| 1400 | CH2 | TRP | 178 | 13.231 | 34.560 | 75.389 |
| 1401 | N | VAL | 179 | 12.619 | 28.226 | 72.189 |
| 1402 | CA | VAL | 179 | 12.135 | 27.251 | 73.172 |
| 1403 | C | VAL | 179 | 12.735 | 27.553 | 74.542 |
| 1404 | O | VAL | 179 | 13.920 | 27.305 | 74.791 |
| 1405 | CB | VAL | 179 | 12.547 | 25.842 | 72.745 |
| 1406 | CG1 | VAL | 179 | 12.237 | 24.816 | 73.829 |
| 1407 | CG2 | VAL | 179 | 11.886 | 25.429 | 71.439 |
| 1408 | N | VAL | 180 | 11.928 | 28.116 | 75.419 |
| 1409 | CA | VAL | 180 | 12.413 | 28.355 | 76.780 |
| 1410 | C | VAL | 180 | 11.946 | 27.269 | 77.751 |
| 1411 | O | VAL | 180 | 10.752 | 27.135 | 78.048 |
| 1412 | CB | VAL | 180 | 12.012 | 29.756 | 77.221 |
| 1413 | CG1 | VAL | 180 | 13.004 | 30.787 | 76.709 |
| 1414 | CG2 | VAL | 180 | 10.606 | 30.113 | 76.771 |
| 1415 | N | GLN | 181 | 12.906 | 26.470 | 78.191 |
| 1416 | CA | GLN | 181 | 12.617 | 25.338 | 79.083 |
| 1417 | C | GLN | 181 | 12.870 | 25.649 | 80.556 |
| 1418 | O | GLN | 181 | 13.510 | 26.644 | 80.918 |
| 1419 | CB | GLN | 181 | 13.419 | 24.098 | 78.687 |
| 1420 | CG | GLN | 181 | 12.956 | 23.514 | 77.354 |
| 1421 | CD | GLN | 181 | 13.411 | 22.060 | 77.205 |
| 1422 | OE1 | GLN | 181 | 13.459 | 21.309 | 78.187 |
| 1423 | NE2 | GLN | 181 | 13.688 | 21.668 | 75.971 |
| 1424 | N | LYS | 182 | 12.249 | 24.844 | 81.398 |
| 1425 | CA | LYS | 182 | 12.460 | 24.938 | 82.850 |
| 1426 | C | LYS | 182 | 13.832 | 24.403 | 83.252 |
| 1427 | O | LYS | 182 | 14.259 | 23.326 | 82.822 |
| 1428 | CB | LYS | 182 | 11.382 | 24.127 | 83.559 |
| 1429 | CG | LYS | 182 | 9.988 | 24.674 | 83.274 |
| 1430 | CD | LYS | 182 | 9.727 | 26.010 | 83.961 |
| 1431 | CE | LYS | 182 | 9.599 | 25.848 | 85.471 |
| 1432 | NZ | LYS | 182 | 8.465 | 24.976 | 85.815 |
| 1433 | N | TYR | 183 | 14.508 | 25.167 | 84.088 |
| 1434 | CA | TYR | 183 | 15.828 | 24.776 | 84.592 |
| 1435 | C | TYR | 183 | 15.746 | 24.009 | 85.910 |
| 1436 | O | TYR | 183 | 15.354 | 24.551 | 86.951 |
| 1437 | CB | TYR | 183 | 16.630 | 26.057 | 84.781 |
| 1438 | CG | TYR | 183 | 17.969 | 25.958 | 85.505 |
| 1439 | CD1 | TYR | 183 | 19.118 | 25.606 | 84.810 |
| 1440 | CD2 | TYR | 183 | 18.039 | 26.233 | 86.865 |
| 1441 | CE1 | TYR | 183 | 20.337 | 25.554 | 85.470 |
| 1442 | CE2 | TYR | 183 | 19.257 | 26.184 | 87.526 |
| 1443 | CZ | TYR | 183 | 20.405 | 25.854 | 86.823 |
| 1444 | OH | TYR | 183 | 21.630 | 25.936 | 87.447 |
| 1445 | N | ILE | 184 | 16.114 | 22.742 | 85.849 |
| 1446 | CA | ILE | 184 | 16.281 | 21.949 | 87.071 |
| 1447 | C | ILE | 184 | 17.529 | 22.440 | 87.801 |
| 1448 | O | ILE | 184 | 18.629 | 22.458 | 87.240 |
| 1449 | CB | ILE | 184 | 16.400 | 20.474 | 86.690 |
| 1450 | CG1 | ILE | 184 | 15.107 | 19.987 | 86.046 |
| 1451 | CG2 | ILE | 184 | 16.747 | 19.591 | 87.886 |
| 1452 | CD1 | ILE | 184 | 15.177 | 18.493 | 85.756 |
| 1453 | N | GLU | 185 | 17.364 | 22.738 | 89.080 |
| 1454 | CA | GLU | 185 | 18.420 | 23.390 | 89.870 |
| 1455 | C | GLU | 185 | 19.497 | 22.471 | 90.460 |
| 1456 | O | GLU | 185 | 20.215 | 22.890 | 91.375 |
| 1457 | CB | GLU | 185 | 17.761 | 24.213 | 90.967 |
| 1458 | CG | GLU | 185 | 16.949 | 25.344 | 90.347 |
| 1459 | CD | GLU | 185 | 16.406 | 26.270 | 91.428 |
| 1460 | OE1 | GLU | 185 | 16.539 | 27.478 | 91.258 |
| 1461 | OE2 | GLU | 185 | 15.920 | 25.762 | 92.428 |
| 1462 | N | THR | 186 | 19.631 | 21.255 | 89.953 |
| 1463 | CA | THR | 186 | 20.743 | 20.393 | 90.391 |
| 1464 | C | THR | 186 | 21.866 | 20.132 | 89.351 |
| 1465 | O | THR | 186 | 22.472 | 19.060 | 89.468 |
| 1466 | CB | THR | 186 | 20.152 | 19.042 | 90.777 |
| 1467 | OG1 | THR | 186 | 19.602 | 18.445 | 89.609 |
| 1468 | CG2 | THR | 186 | 19.051 | 19.171 | 91.822 |
| 1469 | N | PRO | 187 | 22.266 | 21.049 | 88.466 |
| 1470 | CA | PRO | 187 | 23.021 | 20.631 | 87.278 |
| 1471 | C | PRO | 187 | 24.545 | 20.716 | 87.427 |
| 1472 | O | PRO | 187 | 25.247 | 20.806 | 86.411 |
| 1473 | CB | PRO | 187 | 22.566 | 21.573 | 86.218 |
| 1474 | CG | PRO | 187 | 22.066 | 22.829 | 86.897 |
| 1475 | CD | PRO | 187 | 21.995 | 22.492 | 88.374 |
| 1476 | N | LEU | 188 | 25.046 | 20.613 | 88.649 |
| 1477 | CA | LEU | 188 | 26.482 | 20.774 | 88.913 |
| 1478 | C | LEU | 188 | 27.239 | 19.448 | 88.780 |
| 1479 | O | LEU | 188 | 28.469 | 19.417 | 88.649 |
| 1480 | CB | LEU | 188 | 26.629 | 21.307 | 90.335 |
| 1481 | CG | LEU | 188 | 28.018 | 21.878 | 90.587 |
| 1482 | CD1 | LEU | 188 | 28.256 | 23.095 | 89.699 |
| 1483 | CD2 | LEU | 188 | 28.192 | 22.251 | 92.055 |

TABLE IV-continued

| Atom No. | Atom Type | Residue | Residue Position | X Coord. | Y Coord. | Z Coord. |
|---|---|---|---|---|---|---|
| 1484 | N | LEU | 189 | 26.490 | 18.363 | 88.674 |
| 1485 | CA | LEU | 189 | 27.101 | 17.033 | 88.529 |
| 1486 | C | LEU | 189 | 27.239 | 16.592 | 87.068 |
| 1487 | O | LEU | 189 | 27.461 | 15.406 | 86.795 |
| 1488 | CB | LEU | 189 | 26.319 | 15.997 | 89.334 |
| 1489 | CG | LEU | 189 | 26.951 | 15.724 | 90.703 |
| 1490 | CD1 | LEU | 189 | 28.420 | 15.346 | 90.551 |
| 1491 | CD2 | LEU | 189 | 26.819 | 16.893 | 91.677 |
| 1492 | N | ILE | 190 | 27.054 | 17.527 | 86.151 |
| 1493 | CA | ILE | 190 | 27.236 | 17.253 | 84.724 |
| 1494 | C | ILE | 190 | 28.206 | 18.242 | 84.092 |
| 1495 | O | ILE | 190 | 28.659 | 18.018 | 82.965 |
| 1496 | CB | ILE | 190 | 25.875 | 17.353 | 84.057 |
| 1497 | CG1 | ILE | 190 | 24.976 | 18.280 | 84.855 |
| 1498 | CG2 | ILE | 190 | 25.240 | 15.990 | 83.913 |
| 1499 | CD1 | ILE | 190 | 23.514 | 18.142 | 84.467 |
| 1500 | N | CYS | 191 | 28.340 | 19.373 | 84.771 |
| 1501 | CA | CYS | 191 | 29.255 | 20.487 | 84.468 |
| 1502 | C | CYS | 191 | 28.779 | 21.644 | 85.337 |
| 1503 | O | CYS | 191 | 28.156 | 21.397 | 86.375 |
| 1504 | CB | CYS | 191 | 29.300 | 20.872 | 82.987 |
| 1505 | SG | CYS | 191 | 27.733 | 21.239 | 82.172 |
| 1506 | N | ASP | 192 | 28.994 | 22.878 | 84.913 |
| 1507 | CA | ASP | 192 | 28.500 | 24.007 | 85.710 |
| 1508 | C | ASP | 192 | 26.989 | 24.136 | 85.559 |
| 1509 | O | ASP | 192 | 26.262 | 24.276 | 86.552 |
| 1510 | CB | ASP | 192 | 29.168 | 25.298 | 85.245 |
| 1511 | CG | ASP | 192 | 28.651 | 26.480 | 86.063 |
| 1512 | OD1 | ASP | 192 | 28.974 | 26.513 | 87.242 |
| 1513 | OD2 | ASP | 192 | 27.783 | 27.180 | 85.560 |
| 1514 | N | THR | 193 | 26.520 | 24.013 | 84.328 |
| 1515 | CA | THR | 193 | 25.083 | 24.098 | 84.071 |
| 1516 | C | THR | 193 | 24.697 | 23.173 | 82.927 |
| 1517 | O | THR | 193 | 24.786 | 23.556 | 81.755 |
| 1518 | CB | THR | 193 | 24.714 | 25.536 | 83.730 |
| 1519 | OG1 | THR | 193 | 25.101 | 26.369 | 84.814 |
| 1520 | CG2 | THR | 193 | 23.219 | 25.718 | 83.504 |
| 1521 | N | LYS | 194 | 24.271 | 21.979 | 83.323 |
| 1522 | CA | LYS | 194 | 23.742 | 20.875 | 82.483 |
| 1523 | C | LYS | 194 | 24.463 | 20.569 | 81.166 |
| 1524 | O | LYS | 194 | 24.730 | 21.439 | 80.337 |
| 1525 | CB | LYS | 194 | 22.223 | 21.004 | 82.318 |
| 1526 | CG | LYS | 194 | 21.682 | 22.385 | 81.949 |
| 1527 | CD | LYS | 194 | 21.977 | 22.783 | 80.511 |
| 1528 | CE | LYS | 194 | 21.331 | 24.112 | 80.169 |
| 1529 | NZ | LYS | 194 | 19.875 | 23.968 | 80.175 |
| 1530 | N | PHE | 195 | 24.811 | 19.304 | 81.002 |
| 1531 | CA | PHE | 195 | 25.551 | 18.901 | 79.804 |
| 1532 | C | PHE | 195 | 24.770 | 17.961 | 78.892 |
| 1533 | O | PHE | 195 | 24.930 | 18.055 | 77.669 |
| 1534 | CB | PHE | 195 | 26.814 | 18.173 | 80.267 |
| 1535 | CG | PHE | 195 | 27.777 | 17.742 | 79.158 |
| 1536 | CD1 | PHE | 195 | 27.475 | 16.671 | 78.324 |
| 1537 | CD2 | PHE | 195 | 28.980 | 18.406 | 78.998 |
| 1538 | CE1 | PHE | 195 | 28.337 | 16.290 | 77.308 |
| 1539 | CE2 | PHE | 195 | 29.847 | 18.019 | 77.989 |
| 1540 | CZ | PHE | 195 | 29.527 | 16.974 | 77.136 |
| 1541 | N | ASP | 196 | 23.881 | 17.162 | 79.475 |
| 1542 | CA | ASP | 196 | 23.356 | 15.944 | 78.818 |
| 1543 | C | ASP | 196 | 24.576 | 15.042 | 78.626 |
| 1544 | O | ASP | 196 | 25.444 | 15.111 | 79.500 |
| 1545 | CB | ASP | 196 | 22.684 | 16.309 | 77.495 |
| 1546 | CG | ASP | 196 | 21.517 | 15.411 | 77.099 |
| 1547 | OD1 | ASP | 196 | 21.741 | 14.212 | 76.993 |
| 1548 | OD2 | ASP | 196 | 20.585 | 15.969 | 76.543 |
| 1549 | N | ILE | 197 | 24.488 | 14.022 | 77.784 |
| 1550 | CA | ILE | 197 | 25.659 | 13.271 | 77.267 |
| 1551 | C | ILE | 197 | 25.279 | 12.821 | 75.865 |
| 1552 | O | ILE | 197 | 24.134 | 12.398 | 75.694 |
| 1553 | CB | ILE | 197 | 25.998 | 12.024 | 78.095 |
| 1554 | CG1 | ILE | 197 | 26.420 | 12.354 | 79.510 |
| 1555 | CG2 | ILE | 197 | 27.144 | 11.240 | 77.458 |
| 1556 | CD1 | ILE | 197 | 27.749 | 13.096 | 79.506 |
| 1557 | N | ARG | 198 | 26.183 | 12.923 | 74.899 |
| 1558 | CA | ARG | 198 | 25.862 | 12.535 | 73.523 |
| 1559 | C | ARG | 198 | 25.479 | 11.064 | 73.441 |
| 1560 | O | ARG | 198 | 26.242 | 10.161 | 73.808 |
| 1561 | CB | ARG | 198 | 27.056 | 12.831 | 72.622 |
| 1562 | CG | ARG | 198 | 26.689 | 12.644 | 71.155 |
| 1563 | CD | ARG | 198 | 25.500 | 13.514 | 70.751 |
| 1564 | NE | ARG | 198 | 25.764 | 14.948 | 70.943 |
| 1565 | CZ | ARG | 198 | 25.356 | 15.898 | 70.100 |
| 1566 | NH1 | ARG | 198 | 24.809 | 15.563 | 68.930 |
| 1567 | NH2 | ARG | 198 | 25.581 | 17.182 | 70.387 |
| 1568 | N | GLN | 199 | 24.242 | 10.872 | 73.017 |
| 1569 | CA | GLN | 199 | 23.637 | 9.547 | 72.950 |
| 1570 | C | GLN | 199 | 23.805 | 8.938 | 71.566 |
| 1571 | O | GLN | 199 | 24.034 | 9.659 | 70.585 |
| 1572 | CB | GLN | 199 | 22.151 | 9.707 | 73.261 |
| 1573 | CG | GLN | 199 | 21.936 | 10.696 | 74.405 |
| 1574 | CD | GLN | 199 | 21.540 | 10.019 | 75.712 |
| 1575 | OE1 | GLN | 199 | 20.423 | 9.500 | 75.818 |
| 1576 | NE2 | GLN | 199 | 22.339 | 10.239 | 76.739 |
| 1577 | N | TRP | 200 | 23.797 | 7.617 | 71.518 |
| 1578 | CA | TRP | 200 | 23.790 | 6.907 | 70.229 |
| 1579 | C | TRP | 200 | 23.221 | 5.491 | 70.356 |
| 1580 | O | TRP | 200 | 23.968 | 4.530 | 70.591 |
| 1581 | CB | TRP | 200 | 25.218 | 6.841 | 69.701 |
| 1582 | CG | TRP | 200 | 25.359 | 6.237 | 68.316 |
| 1583 | CD1 | TRP | 200 | 26.122 | 5.144 | 67.970 |
| 1584 | CD2 | TRP | 200 | 24.731 | 6.702 | 67.103 |
| 1585 | NE1 | TRP | 200 | 25.990 | 4.934 | 66.638 |
| 1586 | CE2 | TRP | 200 | 25.171 | 5.841 | 66.077 |
| 1587 | CE3 | TRP | 200 | 23.867 | 7.746 | 66.814 |
| 1588 | CZ2 | TRP | 200 | 24.735 | 6.044 | 64.777 |
| 1589 | CZ3 | TRP | 200 | 23.434 | 7.940 | 65.508 |
| 1590 | CH2 | TRP | 200 | 23.867 | 7.092 | 64.493 |
| 1591 | N | PHE | 201 | 21.913 | 5.359 | 70.182 |
| 1592 | CA | PHE | 201 | 21.301 | 4.024 | 70.300 |
| 1593 | C | PHE | 201 | 21.163 | 3.327 | 68.960 |
| 1594 | O | PHE | 201 | 20.784 | 3.920 | 67.943 |
| 1595 | CB | PHE | 201 | 19.970 | 4.036 | 71.054 |
| 1596 | CG | PHE | 201 | 18.855 | 4.956 | 70.570 |
| 1597 | CD1 | PHE | 201 | 18.049 | 4.583 | 69.502 |
| 1598 | CD2 | PHE | 201 | 18.623 | 6.156 | 71.230 |
| 1599 | CE1 | PHE | 201 | 17.020 | 5.418 | 69.088 |
| 1600 | CE2 | PHE | 201 | 17.592 | 6.987 | 70.819 |
| 1601 | CZ | PHE | 201 | 16.792 | 6.617 | 69.748 |
| 1602 | N | LEU | 202 | 21.338 | 2.022 | 69.018 |
| 1603 | CA | LEU | 202 | 21.421 | 1.218 | 67.799 |
| 1604 | C | LEU | 202 | 20.087 | 0.538 | 67.506 |
| 1605 | O | LEU | 202 | 19.979 | −0.692 | 67.610 |
| 1606 | CB | LEU | 202 | 22.529 | 0.162 | 67.932 |
| 1607 | CG | LEU | 202 | 23.967 | 0.705 | 67.955 |
| 1608 | CD1 | LEU | 202 | 24.162 | 1.819 | 66.940 |
| 1609 | CD2 | LEU | 202 | 24.449 | 1.163 | 69.331 |
| 1610 | N | VAL | 203 | 19.101 | 1.349 | 67.140 |
| 1611 | CA | VAL | 203 | 17.736 | 0.888 | 66.815 |
| 1612 | C | VAL | 203 | 17.208 | −0.058 | 67.892 |
| 1613 | O | VAL | 203 | 17.353 | −1.284 | 67.784 |
| 1614 | CB | VAL | 203 | 17.785 | 0.204 | 65.450 |
| 1615 | CG1 | VAL | 203 | 16.421 | −0.319 | 65.014 |
| 1616 | CG2 | VAL | 203 | 18.335 | 1.159 | 64.398 |
| 1617 | N | THR | 204 | 16.773 | 0.540 | 68.995 |
| 1618 | CA | THR | 204 | 16.378 | −0.163 | 70.241 |
| 1619 | C | THR | 204 | 17.535 | −0.822 | 71.031 |
| 1620 | O | THR | 204 | 17.454 | −0.883 | 72.263 |
| 1621 | CB | THR | 204 | 15.271 | −1.174 | 69.919 |
| 1622 | OG1 | THR | 204 | 14.078 | −0.433 | 69.704 |
| 1623 | CG2 | THR | 204 | 14.989 | −2.150 | 71.058 |
| 1624 | N | ASP | 205 | 18.637 | −1.175 | 70.382 |
| 1625 | CA | ASP | 205 | 19.786 | −1.756 | 71.086 |
| 1626 | C | ASP | 205 | 20.497 | −0.727 | 71.960 |
| 1627 | O | ASP | 205 | 20.904 | 0.354 | 71.506 |
| 1628 | CB | ASP | 205 | 20.781 | −2.317 | 70.074 |
| 1629 | CG | ASP | 205 | 20.187 | −3.460 | 69.254 |
| 1630 | OD1 | ASP | 205 | 20.841 | −3.845 | 68.294 |
| 1631 | OD2 | ASP | 205 | 19.303 | −4.117 | 69.788 |
| 1632 | N | TRP | 206 | 20.602 | −1.080 | 73.229 |
| 1633 | CA | TRP | 206 | 21.315 | −0.260 | 74.210 |
| 1634 | C | TRP | 206 | 22.788 | −0.650 | 74.303 |
| 1635 | O | TRP | 206 | 23.140 | −1.737 | 74.772 |

TABLE IV-continued

| Atom No. | Atom Type | Residue | Residue Position | X Coord. | Y Coord. | Z Coord. |
|---|---|---|---|---|---|---|
| 1636 | CB | TRP | 206 | 20.625 | −0.443 | 75.562 |
| 1637 | CG | TRP | 206 | 21.440 | −0.056 | 76.784 |
| 1638 | CD1 | TRP | 206 | 21.855 | 1.206 | 77.159 |
| 1639 | CD2 | TRP | 206 | 21.933 | −0.965 | 77.791 |
| 1640 | NE1 | TRP | 206 | 22.566 | 1.098 | 78.314 |
| 1641 | CE2 | TRP | 206 | 22.633 | −0.182 | 78.725 |
| 1642 | CE3 | TRP | 206 | 21.839 | −2.337 | 77.957 |
| 1643 | CZ2 | TRP | 206 | 23.232 | −0.789 | 79.820 |
| 1644 | CZ3 | TRP | 206 | 22.446 | −2.940 | 79.053 |
| 1645 | CH2 | TRP | 206 | 23.138 | −2.169 | 79.981 |
| 1646 | N | ASN | 207 | 23.632 | 0.223 | 73.779 |
| 1647 | CA | ASN | 207 | 25.082 | 0.083 | 73.944 |
| 1648 | C | ASN | 207 | 25.456 | 0.542 | 75.351 |
| 1649 | O | ASN | 207 | 25.306 | 1.722 | 75.693 |
| 1650 | CB | ASN | 207 | 25.773 | 0.940 | 72.886 |
| 1651 | CG | ASN | 207 | 27.284 | 0.711 | 72.885 |
| 1652 | OD1 | ASN | 207 | 27.785 | −0.259 | 72.307 |
| 1653 | ND2 | ASN | 207 | 28.000 | 1.658 | 73.461 |
| 1654 | N | PRO | 208 | 26.058 | −0.369 | 76.102 |
| 1655 | CA | PRO | 208 | 25.981 | −0.344 | 77.575 |
| 1656 | C | PRO | 208 | 26.917 | 0.620 | 78.320 |
| 1657 | O | PRO | 208 | 26.930 | 0.587 | 79.555 |
| 1658 | CB | PRO | 208 | 26.307 | −1.744 | 78.000 |
| 1659 | CG | PRO | 208 | 26.735 | −2.563 | 76.797 |
| 1660 | CD | PRO | 208 | 26.542 | −1.657 | 75.595 |
| 1661 | N | LEU | 209 | 27.643 | 1.486 | 77.634 |
| 1662 | CA | LEU | 209 | 28.696 | 2.230 | 78.338 |
| 1663 | C | LEU | 209 | 28.286 | 3.636 | 78.799 |
| 1664 | O | LEU | 209 | 27.103 | 3.934 | 79.005 |
| 1665 | CB | LEU | 209 | 29.950 | 2.278 | 77.483 |
| 1666 | CG | LEU | 209 | 31.177 | 1.775 | 78.241 |
| 1667 | CD1 | LEU | 209 | 31.024 | 0.315 | 78.647 |
| 1668 | CD2 | LEU | 209 | 32.441 | 1.972 | 77.414 |
| 1669 | N | THR | 210 | 29.300 | 4.471 | 78.970 |
| 1670 | CA | THR | 210 | 29.176 | 5.698 | 79.751 |
| 1671 | C | THR | 210 | 30.256 | 6.760 | 79.455 |
| 1672 | O | THR | 210 | 31.331 | 6.450 | 78.935 |
| 1673 | CB | THR | 210 | 29.317 | 5.195 | 81.174 |
| 1674 | OG1 | THR | 210 | 29.616 | 6.282 | 82.030 |
| 1675 | CG2 | THR | 210 | 30.445 | 4.182 | 81.264 |
| 1676 | N | ILE | 211 | 29.937 | 8.008 | 79.779 |
| 1677 | CA | ILE | 211 | 30.884 | 9.134 | 79.730 |
| 1678 | C | ILE | 211 | 30.384 | 10.318 | 80.572 |
| 1679 | O | ILE | 211 | 29.178 | 10.593 | 80.582 |
| 1680 | CB | ILE | 211 | 31.084 | 9.508 | 78.263 |
| 1681 | CG1 | ILE | 211 | 32.522 | 9.249 | 77.852 |
| 1682 | CG2 | ILE | 211 | 30.704 | 10.953 | 77.970 |
| 1683 | CD1 | ILE | 211 | 33.485 | 10.145 | 78.617 |
| 1684 | N | TRP | 212 | 31.265 | 10.865 | 81.402 |
| 1685 | CA | TRP | 212 | 30.932 | 12.008 | 82.271 |
| 1686 | C | TRP | 212 | 31.738 | 13.277 | 82.063 |
| 1687 | O | TRP | 212 | 32.701 | 13.288 | 81.296 |
| 1688 | CB | TRP | 212 | 30.968 | 11.549 | 83.722 |
| 1689 | CG | TRP | 212 | 29.622 | 10.906 | 83.891 |
| 1690 | CD1 | TRP | 212 | 29.285 | 9.615 | 84.207 |
| 1691 | CD2 | TRP | 212 | 28.400 | 11.628 | 83.730 |
| 1692 | NE1 | TRP | 212 | 27.948 | 9.493 | 84.035 |
| 1693 | CE2 | TRP | 212 | 27.400 | 10.662 | 83.650 |
| 1694 | CE3 | TRP | 212 | 28.123 | 12.964 | 83.424 |
| 1695 | CZ2 | TRP | 212 | 26.169 | 11.000 | 83.100 |
| 1696 | CZ3 | TRP | 212 | 26.867 | 13.303 | 82.961 |
| 1697 | CH2 | TRP | 212 | 25.910 | 12.330 | 82.777 |
| 1698 | N | PHE | 213 | 31.185 | 14.371 | 82.576 |
| 1699 | CA | PHE | 213 | 31.766 | 15.722 | 82.432 |
| 1700 | C | PHE | 213 | 31.444 | 16.584 | 83.655 |
| 1701 | O | PHE | 213 | 31.410 | 17.816 | 83.560 |
| 1702 | CB | PHE | 213 | 31.151 | 16.387 | 81.199 |
| 1703 | CG | PHE | 213 | 31.538 | 15.794 | 79.850 |
| 1704 | CD1 | PHE | 213 | 30.801 | 14.751 | 79.301 |
| 1705 | CD2 | PHE | 213 | 32.606 | 16.326 | 79.147 |
| 1706 | CE1 | PHE | 213 | 31.166 | 14.217 | 78.070 |
| 1707 | CE2 | PHE | 213 | 32.969 | 15.795 | 77.923 |
| 1708 | CZ | PHE | 213 | 32.254 | 14.739 | 77.386 |
| 1709 | N | TYR | 214 | 31.342 | 15.925 | 84.799 |
| 1710 | CA | TYR | 214 | 30.822 | 16.510 | 86.052 |
| 1711 | C | TYR | 214 | 31.707 | 17.598 | 86.670 |
| 1712 | O | TYR | 214 | 32.231 | 18.443 | 85.941 |
| 1713 | CB | TYR | 214 | 30.541 | 15.373 | 87.046 |
| 1714 | CG | TYR | 214 | 31.679 | 14.448 | 87.518 |
| 1715 | CD1 | TYR | 214 | 32.041 | 14.475 | 88.859 |
| 1716 | CD2 | TYR | 214 | 32.293 | 13.549 | 86.652 |
| 1717 | CE1 | TYR | 214 | 33.049 | 13.642 | 89.325 |
| 1718 | CE2 | TYR | 214 | 33.303 | 12.716 | 87.114 |
| 1719 | CZ | TYR | 214 | 33.681 | 12.767 | 88.450 |
| 1720 | OH | TYR | 214 | 34.685 | 11.950 | 88.909 |
| 1721 | N | LYS | 215 | 31.645 | 17.756 | 87.978 |
| 1722 | CA | LYS | 215 | 32.567 | 18.693 | 88.630 |
| 1723 | C | LYS | 215 | 33.276 | 18.063 | 89.825 |
| 1724 | O | LYS | 215 | 32.659 | 17.606 | 90.795 |
| 1725 | CB | LYS | 215 | 31.845 | 19.980 | 88.997 |
| 1726 | CG | LYS | 215 | 32.275 | 21.074 | 88.028 |
| 1727 | CD | LYS | 215 | 31.487 | 22.359 | 88.204 |
| 1728 | CE | LYS | 215 | 32.103 | 23.477 | 87.379 |
| 1729 | NZ | LYS | 215 | 32.300 | 23.069 | 85.982 |
| 1730 | N | THR | 263 | 36.916 | 26.099 | 84.721 |
| 1731 | CA | THR | 263 | 36.173 | 26.956 | 83.787 |
| 1732 | C | THR | 263 | 34.709 | 27.074 | 84.203 |
| 1733 | O | THR | 263 | 33.842 | 27.322 | 83.353 |
| 1734 | CB | THR | 263 | 36.230 | 26.367 | 82.387 |
| 1735 | OG1 | THR | 263 | 35.590 | 25.100 | 82.431 |
| 1736 | CG2 | THR | 263 | 37.661 | 26.185 | 81.893 |
| 1737 | N | SER | 264 | 34.488 | 27.138 | 85.508 |
| 1738 | CA | SER | 264 | 33.128 | 27.122 | 86.088 |
| 1739 | C | SER | 264 | 32.314 | 28.415 | 85.933 |
| 1740 | O | SER | 264 | 31.167 | 28.460 | 86.386 |
| 1741 | CB | SER | 264 | 33.245 | 26.816 | 87.577 |
| 1742 | OG | SER | 264 | 33.957 | 27.880 | 88.191 |
| 1743 | N | THR | 265 | 32.840 | 29.403 | 85.225 |
| 1744 | CA | THR | 265 | 32.115 | 30.660 | 85.014 |
| 1745 | C | THR | 265 | 31.146 | 30.573 | 83.834 |
| 1746 | O | THR | 265 | 30.357 | 31.499 | 83.619 |
| 1747 | CB | THR | 265 | 33.122 | 31.766 | 84.727 |
| 1748 | OG1 | THR | 265 | 33.709 | 31.516 | 83.457 |
| 1749 | CG2 | THR | 265 | 34.223 | 31.814 | 85.780 |
| 1750 | N | ARG | 266 | 31.222 | 29.501 | 83.059 |
| 1751 | CA | ARG | 266 | 30.264 | 29.332 | 81.962 |
| 1752 | C | ARG | 266 | 29.095 | 28.425 | 82.334 |
| 1753 | O | ARG | 266 | 29.258 | 27.237 | 82.643 |
| 1754 | CB | ARG | 266 | 30.982 | 28.818 | 80.725 |
| 1755 | CG | ARG | 266 | 31.777 | 29.945 | 80.081 |
| 1756 | CD | ARG | 266 | 32.570 | 29.457 | 78.880 |
| 1757 | NE | ARG | 266 | 33.633 | 28.544 | 79.315 |
| 1758 | CZ | ARG | 266 | 34.507 | 27.983 | 78.478 |
| 1759 | NH1 | ARG | 266 | 34.399 | 28.187 | 77.163 |
| 1760 | NH2 | ARG | 266 | 35.463 | 27.186 | 78.956 |
| 1761 | N | PHE | 267 | 27.913 | 28.969 | 82.100 |
| 1762 | CA | PHE | 267 | 26.638 | 28.301 | 82.399 |
| 1763 | C | PHE | 267 | 26.120 | 27.416 | 81.259 |
| 1764 | O | PHE | 267 | 24.926 | 27.457 | 80.942 |
| 1765 | CB | PHE | 267 | 25.600 | 29.381 | 82.724 |
| 1766 | CG | PHE | 267 | 25.509 | 30.561 | 81.745 |
| 1767 | CD1 | PHE | 267 | 24.863 | 30.422 | 80.522 |
| 1768 | CD2 | PHE | 267 | 26.058 | 31.790 | 82.096 |
| 1769 | CE1 | PHE | 267 | 24.785 | 31.496 | 79.645 |
| 1770 | CE2 | PHE | 267 | 25.980 | 32.865 | 81.220 |
| 1771 | CZ | PHE | 267 | 25.346 | 32.718 | 79.993 |
| 1772 | N | GLN | 268 | 26.982 | 26.594 | 80.688 |
| 1773 | CA | GLN | 268 | 26.590 | 25.847 | 79.494 |
| 1774 | C | GLN | 268 | 27.075 | 24.393 | 79.455 |
| 1775 | O | GLN | 268 | 27.784 | 23.909 | 80.347 |
| 1776 | CB | GLN | 268 | 27.077 | 26.629 | 78.286 |
| 1777 | CG | GLN | 268 | 25.937 | 27.324 | 77.550 |
| 1778 | CD | GLN | 268 | 25.853 | 26.690 | 76.169 |
| 1779 | OE1 | GLN | 268 | 25.869 | 25.453 | 76.058 |
| 1780 | NE2 | GLN | 268 | 25.892 | 27.533 | 75.152 |
| 1781 | N | GLU | 269 | 26.843 | 23.808 | 78.288 |
| 1782 | CA | GLU | 269 | 26.862 | 22.355 | 78.078 |
| 1783 | C | GLU | 269 | 28.123 | 21.792 | 77.397 |
| 1784 | O | GLU | 269 | 29.249 | 22.191 | 77.713 |
| 1785 | CB | GLU | 269 | 25.615 | 22.140 | 77.227 |
| 1786 | CG | GLU | 269 | 24.486 | 22.975 | 77.843 |
| 1787 | CD | GLU | 269 | 23.397 | 23.320 | 76.845 |

TABLE IV-continued

| Atom No. | Atom Type | Residue | Residue Position | X Coord. | Y Coord. | Z Coord. |
|---|---|---|---|---|---|---|
| 1788 | OE1 | GLU | 269 | 23.710 | 23.280 | 75.666 |
| 1789 | OE2 | GLU | 269 | 22.244 | 23.400 | 77.243 |
| 1790 | N | TYR | 270 | 27.884 | 20.878 | 76.460 |
| 1791 | CA | TYR | 270 | 28.895 | 20.054 | 75.737 |
| 1792 | C | TYR | 270 | 30.297 | 20.611 | 75.493 |
| 1793 | O | TYR | 270 | 30.462 | 21.794 | 75.181 |
| 1794 | CB | TYR | 270 | 28.360 | 19.602 | 74.388 |
| 1795 | CG | TYR | 270 | 27.349 | 18.465 | 74.383 |
| 1796 | CD1 | TYR | 270 | 26.027 | 18.716 | 74.714 |
| 1797 | CD2 | TYR | 270 | 27.741 | 17.183 | 74.018 |
| 1798 | CE1 | TYR | 270 | 25.100 | 17.688 | 74.697 |
| 1799 | CE2 | TYR | 270 | 26.810 | 16.152 | 74.007 |
| 1800 | CZ | TYR | 270 | 25.490 | 16.411 | 74.349 |
| 1801 | OH | TYR | 270 | 24.545 | 15.410 | 74.343 |
| 1802 | N | LEU | 271 | 31.140 | 19.633 | 75.190 |
| 1803 | CA | LEU | 271 | 32.612 | 19.726 | 75.218 |
| 1804 | C | LEU | 271 | 33.330 | 20.217 | 73.966 |
| 1805 | O | LEU | 271 | 34.568 | 20.213 | 73.948 |
| 1806 | CB | LEU | 271 | 33.179 | 18.337 | 75.540 |
| 1807 | CG | LEU | 271 | 33.191 | 17.350 | 74.363 |
| 1808 | CD1 | LEU | 271 | 34.374 | 16.395 | 74.483 |
| 1809 | CD2 | LEU | 271 | 31.882 | 16.579 | 74.182 |
| 1810 | N | GLN | 272 | 32.619 | 20.693 | 72.961 |
| 1811 | CA | GLN | 272 | 33.300 | 20.916 | 71.681 |
| 1812 | C | GLN | 272 | 34.090 | 22.217 | 71.637 |
| 1813 | O | GLN | 272 | 35.085 | 22.296 | 70.905 |
| 1814 | CB | GLN | 272 | 32.254 | 20.909 | 70.574 |
| 1815 | CG | GLN | 272 | 32.874 | 21.007 | 69.188 |
| 1816 | CD | GLN | 272 | 31.769 | 21.016 | 68.146 |
| 1817 | OE1 | GLN | 272 | 30.621 | 21.359 | 68.448 |
| 1818 | NE2 | GLN | 272 | 32.132 | 20.658 | 66.928 |
| 1819 | N | ARG | 273 | 33.742 | 23.184 | 72.469 |
| 1820 | CA | ARG | 273 | 34.474 | 24.443 | 72.419 |
| 1821 | C | ARG | 273 | 35.527 | 24.495 | 73.523 |
| 1822 | O | ARG | 273 | 36.609 | 25.056 | 73.295 |
| 1823 | CB | ARG | 273 | 33.444 | 25.570 | 72.482 |
| 1824 | CG | ARG | 273 | 32.416 | 25.302 | 71.375 |
| 1825 | CD | ARG | 273 | 31.165 | 26.163 | 71.446 |
| 1826 | NE | ARG | 273 | 31.428 | 27.556 | 71.060 |
| 1827 | CZ | ARG | 273 | 30.458 | 28.470 | 70.983 |
| 1828 | NH1 | ARG | 273 | 30.753 | 29.730 | 70.657 |
| 1829 | NH2 | ARG | 273 | 29.197 | 28.129 | 71.260 |
| 1830 | N | GLN | 274 | 35.281 | 23.771 | 74.609 |
| 1831 | CA | GLN | 274 | 36.265 | 23.595 | 75.702 |
| 1832 | C | GLN | 274 | 35.825 | 22.531 | 76.693 |
| 1833 | O | GLN | 274 | 35.372 | 22.928 | 77.772 |
| 1834 | CB | GLN | 274 | 36.373 | 24.881 | 76.529 |
| 1835 | CG | GLN | 274 | 37.398 | 25.889 | 76.030 |
| 1836 | CD | GLN | 274 | 38.778 | 25.265 | 76.001 |
| 1837 | OE1 | GLN | 274 | 39.326 | 24.872 | 77.039 |
| 1838 | NE2 | GLN | 274 | 39.279 | 25.113 | 74.790 |
| 1839 | N | GLY | 275 | 36.071 | 21.254 | 76.436 |
| 1840 | CA | GLY | 275 | 35.565 | 20.212 | 77.349 |
| 1841 | C | GLY | 275 | 36.568 | 19.176 | 77.871 |
| 1842 | O | GLY | 275 | 37.733 | 19.130 | 77.464 |
| 1843 | N | ARG | 276 | 36.090 | 18.407 | 78.841 |
| 1844 | CA | ARG | 276 | 36.853 | 17.313 | 79.479 |
| 1845 | C | ARG | 276 | 35.913 | 16.208 | 80.000 |
| 1846 | O | ARG | 276 | 34.974 | 16.515 | 80.741 |
| 1847 | CB | ARG | 276 | 37.674 | 17.950 | 80.613 |
| 1848 | CG | ARG | 276 | 38.069 | 16.973 | 81.720 |
| 1849 | CD | ARG | 276 | 37.046 | 16.965 | 82.851 |
| 1850 | NE | ARG | 276 | 37.202 | 15.762 | 83.664 |
| 1851 | CZ | ARG | 276 | 36.214 | 15.000 | 84.130 |
| 1852 | NH1 | ARG | 276 | 34.945 | 15.257 | 83.809 |
| 1853 | NH2 | ARG | 276 | 36.509 | 13.966 | 84.917 |
| 1854 | N | GLY | 277 | 36.227 | 14.946 | 79.736 |
| 1855 | CA | GLY | 277 | 35.329 | 13.852 | 80.149 |
| 1856 | C | GLY | 277 | 35.904 | 12.839 | 81.142 |
| 1857 | O | GLY | 277 | 36.959 | 13.051 | 81.749 |
| 1858 | N | ALA | 278 | 35.128 | 11.787 | 81.370 |
| 1859 | CA | ALA | 278 | 35.488 | 10.667 | 82.266 |
| 1860 | C | ALA | 278 | 34.484 | 9.517 | 82.209 |
| 1861 | O | ALA | 278 | 33.380 | 9.635 | 82.746 |
| 1862 | CB | ALA | 278 | 35.460 | 11.135 | 83.711 |
| 1863 | N | VAL | 279 | 34.884 | 8.390 | 81.652 |
| 1864 | CA | VAL | 279 | 33.983 | 7.230 | 81.579 |
| 1865 | C | VAL | 279 | 33.850 | 6.557 | 82.950 |
| 1866 | O | VAL | 279 | 34.852 | 6.317 | 83.635 |
| 1867 | CB | VAL | 279 | 34.567 | 6.241 | 80.577 |
| 1868 | CG1 | VAL | 279 | 33.615 | 5.096 | 80.286 |
| 1869 | CG2 | VAL | 279 | 34.918 | 6.945 | 79.284 |
| 1870 | N | TRP | 280 | 32.615 | 6.329 | 83.366 |
| 1871 | CA | TRP | 280 | 32.362 | 5.680 | 84.654 |
| 1872 | C | TRP | 280 | 31.191 | 4.700 | 84.537 |
| 1873 | O | TRP | 280 | 31.386 | 3.521 | 84.208 |
| 1874 | CB | TRP | 280 | 32.064 | 6.747 | 85.703 |
| 1875 | CG | TRP | 280 | 32.847 | 6.545 | 86.981 |
| 1876 | CD1 | TRP | 280 | 33.985 | 7.224 | 87.357 |
| 1877 | CD2 | TRP | 280 | 32.557 | 5.603 | 88.037 |
| 1878 | NE1 | TRP | 280 | 34.392 | 6.742 | 88.558 |
| 1879 | CE2 | TRP | 280 | 33.573 | 5.768 | 88.996 |
| 1880 | CE3 | TRP | 280 | 31.559 | 4.661 | 88.227 |
| 1881 | CZ2 | TRP | 280 | 33.585 | 4.967 | 90.126 |
| 1882 | CZ3 | TRP | 280 | 31.571 | 3.871 | 89.372 |
| 1883 | CH2 | TRP | 280 | 32.582 | 4.020 | 90.314 |
| 1884 | N | GLY | 281 | 29.993 | 5.179 | 84.844 |
| 1885 | CA | GLY | 281 | 28.784 | 4.362 | 84.666 |
| 1886 | C | GLY | 281 | 27.594 | 5.213 | 84.226 |
| 1887 | O | GLY | 281 | 27.708 | 6.436 | 84.075 |
| 1888 | N | SER | 282 | 26.440 | 4.567 | 84.130 |
| 1889 | CA | SER | 282 | 25.162 | 5.232 | 83.779 |
| 1890 | C | SER | 282 | 24.367 | 5.610 | 85.025 |
| 1891 | O | SER | 282 | 23.137 | 5.603 | 85.049 |
| 1892 | CB | SER | 282 | 24.373 | 4.269 | 82.904 |
| 1893 | OG | SER | 282 | 25.149 | 3.995 | 81.748 |
| 1894 | N | VAL | 283 | 25.108 | 6.198 | 85.936 |
| 1895 | CA | VAL | 283 | 24.798 | 6.259 | 87.359 |
| 1896 | C | VAL | 283 | 23.789 | 7.309 | 87.865 |
| 1897 | O | VAL | 283 | 22.854 | 7.680 | 87.146 |
| 1898 | CB | VAL | 283 | 26.180 | 6.391 | 87.944 |
| 1899 | CG1 | VAL | 283 | 26.851 | 5.026 | 87.945 |
| 1900 | CG2 | VAL | 283 | 26.987 | 7.330 | 87.056 |
| 1901 | N | ILE | 284 | 23.872 | 7.601 | 89.158 |
| 1902 | CA | ILE | 284 | 22.805 | 8.318 | 89.882 |
| 1903 | C | ILE | 284 | 23.179 | 9.781 | 90.210 |
| 1904 | O | ILE | 284 | 23.313 | 10.582 | 89.276 |
| 1905 | CB | ILE | 284 | 22.478 | 7.503 | 91.131 |
| 1906 | CG1 | ILE | 284 | 22.653 | 6.016 | 90.847 |
| 1907 | CG2 | ILE | 284 | 21.035 | 7.721 | 91.606 |
| 1908 | CD1 | ILE | 284 | 22.223 | 5.150 | 92.023 |
| 1909 | N | TYR | 285 | 23.248 | 10.135 | 91.494 |
| 1910 | CA | TYR | 285 | 23.580 | 11.504 | 91.980 |
| 1911 | C | TYR | 285 | 22.560 | 12.583 | 91.540 |
| 1912 | O | TYR | 285 | 21.772 | 12.317 | 90.628 |
| 1913 | CB | TYR | 285 | 25.020 | 11.816 | 91.582 |
| 1914 | CG | TYR | 285 | 26.090 | 11.349 | 92.573 |
| 1915 | CD1 | TYR | 285 | 25.762 | 10.515 | 93.636 |
| 1916 | CD2 | TYR | 285 | 27.400 | 11.791 | 92.422 |
| 1917 | CE1 | TYR | 285 | 26.745 | 10.098 | 94.522 |
| 1918 | CE2 | TYR | 285 | 28.386 | 11.372 | 93.305 |
| 1919 | CZ | TYR | 285 | 28.055 | 10.520 | 94.349 |
| 1920 | OH | TYR | 285 | 29.044 | 10.043 | 95.183 |
| 1921 | N | PRO | 286 | 22.557 | 13.793 | 92.106 |
| 1922 | CA | PRO | 286 | 23.764 | 14.565 | 92.505 |
| 1923 | C | PRO | 286 | 24.390 | 14.143 | 93.835 |
| 1924 | O | PRO | 286 | 25.616 | 14.182 | 93.989 |
| 1925 | CB | PRO | 286 | 23.328 | 15.995 | 92.590 |
| 1926 | CG | PRO | 286 | 21.841 | 16.088 | 92.332 |
| 1927 | CD | PRO | 286 | 21.400 | 14.687 | 91.951 |
| 1928 | N | SER | 287 | 23.552 | 13.778 | 94.786 |
| 1929 | CA | SER | 287 | 24.020 | 13.201 | 96.048 |
| 1930 | C | SER | 287 | 22.937 | 12.269 | 96.558 |
| 1931 | O | SER | 287 | 23.183 | 11.300 | 97.285 |
| 1932 | CB | SER | 287 | 24.258 | 14.300 | 97.081 |
| 1933 | OG | SER | 287 | 25.335 | 15.121 | 96.661 |
| 1934 | N | MET | 288 | 21.727 | 12.602 | 96.148 |
| 1935 | CA | MET | 288 | 20.536 | 11.884 | 96.590 |
| 1936 | C | MET | 288 | 20.171 | 10.737 | 95.661 |
| 1937 | O | MET | 288 | 20.659 | 10.632 | 94.529 |
| 1938 | CB | MET | 288 | 19.376 | 12.866 | 96.699 |
| 1939 | CG | MET | 288 | 19.177 | 13.429 | 98.111 |

TABLE IV-continued

| Atom No. | Atom Type | Residue | Residue Position | X Coord. | Y Coord. | Z Coord. |
|---|---|---|---|---|---|---|
| 1940 | SD | MET | 288 | 20.515 | 14.389 | 98.870 |
| 1941 | CE | MET | 288 | 21.344 | 13.099 | 99.832 |
| 1942 | N | LYS | 289 | 19.346 | 9.860 | 96.204 |
| 1943 | CA | LYS | 289 | 18.858 | 8.682 | 95.484 |
| 1944 | C | LYS | 289 | 17.475 | 8.943 | 94.894 |
| 1945 | O | LYS | 289 | 17.365 | 9.159 | 93.681 |
| 1946 | CB | LYS | 289 | 18.783 | 7.551 | 96.508 |
| 1947 | CG | LYS | 289 | 18.269 | 6.235 | 95.932 |
| 1948 | CD | LYS | 289 | 18.028 | 5.241 | 97.063 |
| 1949 | CE | LYS | 289 | 17.433 | 3.931 | 96.562 |
| 1950 | NZ | LYS | 289 | 17.166 | 3.020 | 97.687 |
| 1951 | N | LYS | 290 | 16.542 | 9.257 | 95.788 |
| 1952 | CA | LYS | 290 | 15.095 | 9.383 | 95.497 |
| 1953 | C | LYS | 290 | 14.651 | 8.816 | 94.140 |
| 1954 | O | LYS | 290 | 14.882 | 7.638 | 93.851 |
| 1955 | CB | LYS | 290 | 14.673 | 10.844 | 95.684 |
| 1956 | CG | LYS | 290 | 15.700 | 11.857 | 95.167 |
| 1957 | CD | LYS | 290 | 15.222 | 13.289 | 95.384 |
| 1958 | CE | LYS | 290 | 13.900 | 13.560 | 94.670 |
| 1959 | NZ | LYS | 290 | 14.031 | 13.416 | 93.212 |
| 1960 | N | ALA | 291 | 13.998 | 9.636 | 93.333 |
| 1961 | CA | ALA | 291 | 13.525 | 9.202 | 92.012 |
| 1962 | C | ALA | 291 | 14.541 | 9.450 | 90.893 |
| 1963 | O | ALA | 291 | 14.182 | 9.403 | 89.710 |
| 1964 | CB | ALA | 291 | 12.234 | 9.947 | 91.693 |
| 1965 | N | ILE | 292 | 15.779 | 9.741 | 91.254 |
| 1966 | CA | ILE | 292 | 16.765 | 10.170 | 90.263 |
| 1967 | C | ILE | 292 | 17.585 | 9.001 | 89.722 |
| 1968 | O | ILE | 292 | 18.076 | 8.158 | 90.482 |
| 1969 | CB | ILE | 292 | 17.696 | 11.182 | 90.939 |
| 1970 | CG1 | ILE | 292 | 16.913 | 12.361 | 91.497 |
| 1971 | CG2 | ILE | 292 | 18.748 | 11.705 | 89.969 |
| 1972 | CD1 | ILE | 292 | 16.287 | 13.188 | 90.377 |
| 1973 | N | ALA | 293 | 17.598 | 8.894 | 88.404 |
| 1974 | CA | ALA | 293 | 18.621 | 8.110 | 87.709 |
| 1975 | C | ALA | 293 | 18.570 | 6.582 | 87.793 |
| 1976 | O | ALA | 293 | 17.622 | 5.994 | 88.328 |
| 1977 | CB | ALA | 293 | 19.983 | 8.631 | 88.135 |
| 1978 | N | HIS | 294 | 19.680 | 5.998 | 87.353 |
| 1979 | CA | HIS | 294 | 19.873 | 4.576 | 86.992 |
| 1980 | C | HIS | 294 | 18.626 | 3.708 | 86.806 |
| 1981 | O | HIS | 294 | 18.082 | 3.653 | 85.695 |
| 1982 | CB | HIS | 294 | 20.812 | 3.953 | 88.003 |
| 1983 | CG | HIS | 294 | 22.051 | 3.422 | 87.323 |
| 1984 | ND1 | HIS | 294 | 22.110 | 2.877 | 86.095 |
| 1985 | CD2 | HIS | 294 | 23.329 | 3.423 | 87.818 |
| 1986 | CE1 | HIS | 294 | 23.379 | 2.507 | 85.831 |
| 1987 | NE2 | HIS | 294 | 24.133 | 2.844 | 86.898 |
| 1988 | N | ALA | 295 | 18.090 | 3.151 | 87.883 |
| 1989 | CA | ALA | 295 | 16.939 | 2.233 | 87.779 |
| 1990 | C | ALA | 295 | 15.670 | 2.857 | 87.185 |
| 1991 | O | ALA | 295 | 14.946 | 2.176 | 86.447 |
| 1992 | CB | ALA | 295 | 16.606 | 1.736 | 89.180 |
| 1993 | N | MET | 296 | 15.542 | 4.171 | 87.284 |
| 1994 | CA | MET | 296 | 14.376 | 4.866 | 86.734 |
| 1995 | C | MET | 296 | 14.478 | 5.083 | 85.218 |
| 1996 | O | MET | 296 | 13.447 | 5.121 | 84.535 |
| 1997 | CB | MET | 296 | 14.299 | 6.222 | 87.431 |
| 1998 | CG | MET | 296 | 13.028 | 6.981 | 87.072 |
| 1999 | SD | MET | 296 | 11.494 | 6.205 | 87.625 |
| 2000 | CE | MET | 296 | 11.815 | 6.216 | 89.405 |
| 2001 | N | LYS | 297 | 15.678 | 4.948 | 84.675 |
| 2002 | CA | LYS | 297 | 15.918 | 5.255 | 83.262 |
| 2003 | C | LYS | 297 | 15.701 | 4.080 | 82.340 |
| 2004 | O | LYS | 297 | 15.696 | 4.234 | 81.109 |
| 2005 | CB | LYS | 297 | 17.356 | 5.645 | 83.125 |
| 2006 | CG | LYS | 297 | 17.700 | 6.765 | 84.068 |
| 2007 | CD | LYS | 297 | 19.200 | 6.840 | 84.062 |
| 2008 | CE | LYS | 297 | 19.733 | 8.109 | 84.661 |
| 2009 | NZ | LYS | 297 | 21.174 | 7.974 | 84.702 |
| 2010 | N | VAL | 298 | 15.372 | 2.947 | 82.931 |
| 2011 | CA | VAL | 298 | 15.039 | 1.764 | 82.151 |
| 2012 | C | VAL | 298 | 13.695 | 1.957 | 81.436 |
| 2013 | O | VAL | 298 | 13.554 | 1.511 | 80.292 |
| 2014 | CB | VAL | 298 | 15.008 | 0.602 | 83.139 |
| 2015 | CG1 | VAL | 298 | 14.678 | −0.715 | 82.462 |
| 2016 | CG2 | VAL | 298 | 16.341 | 0.495 | 83.873 |
| 2017 | N | ALA | 299 | 12.893 | 2.890 | 81.933 |
| 2018 | CA | ALA | 299 | 11.633 | 3.240 | 81.277 |
| 2019 | C | ALA | 299 | 11.813 | 4.184 | 80.081 |
| 2020 | O | ALA | 299 | 11.076 | 4.059 | 79.093 |
| 2021 | CB | ALA | 299 | 10.760 | 3.905 | 82.329 |
| 2022 | N | GLN | 300 | 12.885 | 4.965 | 80.075 |
| 2023 | CA | GLN | 300 | 13.200 | 5.793 | 78.903 |
| 2024 | C | GLN | 300 | 13.700 | 4.903 | 77.781 |
| 2025 | O | GLN | 300 | 13.013 | 4.752 | 76.760 |
| 2026 | CB | GLN | 300 | 14.328 | 6.770 | 79.238 |
| 2027 | CG | GLN | 300 | 13.901 | 7.960 | 80.088 |
| 2028 | CD | GLN | 300 | 13.602 | 9.187 | 79.225 |
| 2029 | OE1 | GLN | 300 | 13.397 | 9.072 | 78.008 |
| 2030 | NE2 | GLN | 300 | 13.762 | 10.354 | 79.822 |
| 2031 | N | ASP | 301 | 14.644 | 4.055 | 78.164 |
| 2032 | CA | ASP | 301 | 15.382 | 3.209 | 77.222 |
| 2033 | C | ASP | 301 | 14.614 | 1.983 | 76.719 |
| 2034 | O | ASP | 301 | 15.062 | 1.343 | 75.762 |
| 2035 | CB | ASP | 301 | 16.649 | 2.767 | 77.949 |
| 2036 | CG | ASP | 301 | 17.689 | 2.175 | 77.001 |
| 2037 | OD1 | ASP | 301 | 18.350 | 1.230 | 77.409 |
| 2038 | OD2 | ASP | 301 | 17.839 | 2.702 | 75.907 |
| 2039 | N | HIS | 302 | 13.470 | 1.668 | 77.301 |
| 2040 | CA | HIS | 302 | 12.664 | 0.593 | 76.721 |
| 2041 | C | HIS | 302 | 11.460 | 1.077 | 75.922 |
| 2042 | O | HIS | 302 | 10.935 | 0.299 | 75.122 |
| 2043 | CB | HIS | 302 | 12.193 | −0.352 | 77.816 |
| 2044 | CG | HIS | 302 | 13.272 | −1.295 | 78.302 |
| 2045 | ND1 | HIS | 302 | 13.304 | −1.926 | 79.488 |
| 2046 | CD2 | HIS | 302 | 14.395 | −1.686 | 77.610 |
| 2047 | CE1 | HIS | 302 | 14.415 | −2.687 | 79.560 |
| 2048 | NE2 | HIS | 302 | 15.090 | −2.536 | 78.398 |
| 2049 | N | VAL | 303 | 11.052 | 2.327 | 76.068 |
| 2050 | CA | VAL | 303 | 9.872 | 2.760 | 75.313 |
| 2051 | C | VAL | 303 | 10.228 | 3.737 | 74.194 |
| 2052 | O | VAL | 303 | 9.809 | 3.556 | 73.040 |
| 2053 | CB | VAL | 303 | 8.876 | 3.391 | 76.280 |
| 2054 | CG1 | VAL | 303 | 7.617 | 3.852 | 75.553 |
| 2055 | CG2 | VAL | 303 | 8.513 | 2.431 | 77.406 |
| 2056 | N | GLU | 304 | 11.145 | 4.642 | 74.485 |
| 2057 | CA | GLU | 304 | 11.525 | 5.670 | 73.503 |
| 2058 | C | GLU | 304 | 12.277 | 5.126 | 72.264 |
| 2059 | O | GLU | 304 | 11.820 | 5.466 | 71.163 |
| 2060 | CB | GLU | 304 | 12.332 | 6.755 | 74.218 |
| 2061 | CG | GLU | 304 | 12.033 | 8.167 | 73.703 |
| 2062 | CD | GLU | 304 | 12.718 | 8.450 | 72.375 |
| 2063 | OE1 | GLU | 304 | 13.748 | 7.828 | 72.133 |
| 2064 | OE2 | GLU | 304 | 12.292 | 9.370 | 71.684 |
| 2065 | N | PRO | 305 | 13.301 | 4.272 | 72.362 |
| 2066 | CA | PRO | 305 | 13.986 | 3.827 | 71.138 |
| 2067 | C | PRO | 305 | 13.201 | 2.863 | 70.238 |
| 2068 | O | PRO | 305 | 13.701 | 2.557 | 69.153 |
| 2069 | CB | PRO | 305 | 15.249 | 3.164 | 71.589 |
| 2070 | CG | PRO | 305 | 15.228 | 3.019 | 73.095 |
| 2071 | CD | PRO | 305 | 13.966 | 3.720 | 73.557 |
| 2072 | N | ARG | 306 | 11.990 | 2.461 | 70.603 |
| 2073 | CA | ARG | 306 | 11.194 | 1.629 | 69.702 |
| 2074 | C | ARG | 306 | 10.495 | 2.492 | 68.656 |
| 2075 | O | ARG | 306 | 10.490 | 2.124 | 67.474 |
| 2076 | CB | ARG | 306 | 10.148 | 0.874 | 70.508 |
| 2077 | CG | ARG | 306 | 10.782 | 0.029 | 71.603 |
| 2078 | CD | ARG | 306 | 9.725 | −0.825 | 72.289 |
| 2079 | NE | ARG | 306 | 8.612 | 0.012 | 72.766 |
| 2080 | CZ | ARG | 306 | 7.880 | −0.289 | 73.840 |
| 2081 | NH1 | ARG | 306 | 6.855 | 0.491 | 74.188 |
| 2082 | NH2 | ARG | 306 | 8.150 | −1.390 | 74.545 |
| 2083 | N | LYS | 307 | 10.211 | 3.737 | 69.019 |
| 2084 | CA | LYS | 307 | 9.608 | 4.672 | 68.061 |
| 2085 | C | LYS | 307 | 10.672 | 5.130 | 67.075 |
| 2086 | O | LYS | 307 | 10.476 | 5.071 | 65.853 |
| 2087 | CB | LYS | 307 | 9.092 | 5.893 | 68.813 |
| 2088 | CG | LYS | 307 | 8.117 | 5.517 | 69.921 |
| 2089 | CD | LYS | 307 | 7.575 | 6.766 | 70.609 |
| 2090 | CE | LYS | 307 | 8.699 | 7.614 | 71.196 |
| 2091 | NZ | LYS | 307 | 8.166 | 8.840 | 71.812 |

TABLE IV-continued

| Atom No. | Atom Type | Residue | Residue Position | X Coord. | Y Coord. | Z Coord. |
|---|---|---|---|---|---|---|
| 2092 | N | ASN | 308 | 11.880 | 5.223 | 67.603 |
| 2093 | CA | ASN | 308 | 13.041 | 5.580 | 66.796 |
| 2094 | C | ASN | 308 | 13.749 | 4.373 | 66.178 |
| 2095 | O | ASN | 308 | 14.868 | 4.506 | 65.671 |
| 2096 | CB | ASN | 308 | 13.979 | 6.421 | 67.633 |
| 2097 | CG | ASN | 308 | 13.300 | 7.745 | 67.970 |
| 2098 | OD1 | ASN | 308 | 12.343 | 8.167 | 67.307 |
| 2099 | ND2 | ASN | 308 | 13.811 | 8.388 | 69.001 |
| 2100 | N | SER | 309 | 13.092 | 3.223 | 66.187 |
| 2101 | CA | SER | 309 | 13.511 | 2.113 | 65.336 |
| 2102 | C | SER | 309 | 12.789 | 2.221 | 64.001 |
| 2103 | O | SER | 309 | 13.301 | 1.767 | 62.972 |
| 2104 | CB | SER | 309 | 13.152 | 0.790 | 65.997 |
| 2105 | OG | SER | 309 | 13.971 | 0.656 | 67.146 |
| 2106 | N | PHE | 310 | 11.686 | 2.953 | 64.002 |
| 2107 | CA | PHE | 310 | 10.999 | 3.266 | 62.747 |
| 2108 | C | PHE | 310 | 11.547 | 4.587 | 62.219 |
| 2109 | O | PHE | 310 | 11.749 | 4.769 | 61.014 |
| 2110 | CB | PHE | 310 | 9.507 | 3.433 | 63.024 |
| 2111 | CG | PHE | 310 | 8.858 | 2.302 | 63.818 |
| 2112 | CD1 | PHE | 310 | 8.222 | 2.586 | 65.020 |
| 2113 | CD2 | PHE | 310 | 8.891 | 0.996 | 63.343 |
| 2114 | CE1 | PHE | 310 | 7.630 | 1.566 | 65.753 |
| 2115 | CE2 | PHE | 310 | 8.300 | −0.024 | 64.076 |
| 2116 | CZ | PHE | 310 | 7.671 | 0.260 | 65.282 |
| 2117 | N | GLU | 311 | 11.925 | 5.433 | 63.165 |
| 2118 | CA | GLU | 311 | 12.505 | 6.744 | 62.849 |
| 2119 | C | GLU | 311 | 14.033 | 6.753 | 62.710 |
| 2120 | O | GLU | 311 | 14.591 | 7.803 | 62.383 |
| 2121 | CB | GLU | 311 | 12.096 | 7.722 | 63.943 |
| 2122 | CG | GLU | 311 | 10.585 | 7.914 | 64.021 |
| 2123 | CD | GLU | 311 | 10.045 | 8.463 | 62.703 |
| 2124 | OE1 | GLU | 311 | 9.522 | 7.669 | 61.933 |
| 2125 | OE2 | GLU | 311 | 10.125 | 9.666 | 62.509 |
| 2126 | N | LEU | 312 | 14.673 | 5.609 | 62.913 |
| 2127 | CA | LEU | 312 | 16.139 | 5.410 | 62.804 |
| 2128 | C | LEU | 312 | 17.033 | 6.607 | 63.165 |
| 2129 | O | LEU | 312 | 17.841 | 7.028 | 62.326 |
| 2130 | CB | LEU | 312 | 16.433 | 5.004 | 61.365 |
| 2131 | CG | LEU | 312 | 15.697 | 3.727 | 60.972 |
| 2132 | CD1 | LEU | 312 | 15.764 | 3.496 | 59.467 |
| 2133 | CD2 | LEU | 312 | 16.237 | 2.520 | 61.730 |
| 2134 | N | TYR | 313 | 16.952 | 7.067 | 64.410 |
| 2135 | CA | TYR | 313 | 17.764 | 8.212 | 64.895 |
| 2136 | C | TYR | 313 | 17.453 | 8.514 | 66.367 |
| 2137 | O | TYR | 313 | 16.573 | 7.872 | 66.949 |
| 2138 | CB | TYR | 313 | 17.521 | 9.465 | 64.036 |
| 2139 | CG | TYR | 313 | 16.247 | 10.300 | 64.246 |
| 2140 | CD1 | TYR | 313 | 15.074 | 9.748 | 64.747 |
| 2141 | CD2 | TYR | 313 | 16.290 | 11.650 | 63.922 |
| 2142 | CE1 | TYR | 313 | 13.950 | 10.542 | 64.928 |
| 2143 | CE2 | TYR | 313 | 15.166 | 12.446 | 64.097 |
| 2144 | CZ | TYR | 313 | 13.997 | 11.889 | 64.600 |
| 2145 | OH | TYR | 313 | 12.862 | 12.655 | 64.716 |
| 2146 | N | GLY | 314 | 18.149 | 9.468 | 66.966 |
| 2147 | CA | GLY | 314 | 17.768 | 9.882 | 68.324 |
| 2148 | C | GLY | 314 | 18.922 | 10.054 | 69.306 |
| 2149 | O | GLY | 314 | 19.587 | 9.076 | 69.678 |
| 2150 | N | ALA | 315 | 19.063 | 11.273 | 69.808 |
| 2151 | CA | ALA | 315 | 20.085 | 11.542 | 70.826 |
| 2152 | C | ALA | 315 | 19.905 | 12.831 | 71.636 |
| 2153 | O | ALA | 315 | 20.075 | 13.922 | 71.073 |
| 2154 | CB | ALA | 315 | 21.434 | 11.607 | 70.123 |
| 2155 | N | ASP | 316 | 19.530 | 12.674 | 72.907 |
| 2156 | CA | ASP | 316 | 19.681 | 13.679 | 74.014 |
| 2157 | C | ASP | 316 | 18.537 | 13.661 | 75.037 |
| 2158 | O | ASP | 316 | 17.411 | 14.138 | 74.804 |
| 2159 | CB | ASP | 316 | 19.997 | 15.109 | 73.586 |
| 2160 | CG | ASP | 316 | 21.507 | 15.237 | 73.351 |
| 2161 | OD1 | ASP | 316 | 22.163 | 14.220 | 73.214 |
| 2162 | OD2 | ASP | 316 | 22.002 | 16.356 | 73.434 |
| 2163 | N | PHE | 317 | 18.888 | 13.152 | 76.210 |
| 2164 | CA | PHE | 317 | 17.938 | 12.996 | 77.318 |
| 2165 | C | PHE | 317 | 18.437 | 13.647 | 78.623 |
| 2166 | O | PHE | 317 | 19.633 | 13.662 | 78.942 |
| 2167 | CB | PHE | 317 | 17.674 | 11.509 | 77.532 |
| 2168 | CG | PHE | 317 | 16.927 | 10.791 | 76.402 |
| 2169 | CD1 | PHE | 317 | 17.606 | 10.279 | 75.302 |
| 2170 | CD2 | PHE | 317 | 15.550 | 10.642 | 76.488 |
| 2171 | CE1 | PHE | 317 | 16.915 | 9.624 | 74.292 |
| 2172 | CE2 | PHE | 317 | 14.857 | 9.982 | 75.480 |
| 2173 | CZ | PHE | 317 | 15.539 | 9.473 | 74.383 |
| 2174 | N | VAL | 318 | 17.456 | 14.039 | 79.418 |
| 2175 | CA | VAL | 318 | 17.640 | 14.825 | 80.648 |
| 2176 | C | VAL | 318 | 17.956 | 13.924 | 81.859 |
| 2177 | O | VAL | 318 | 18.158 | 12.723 | 81.678 |
| 2178 | CB | VAL | 318 | 16.307 | 15.558 | 80.759 |
| 2179 | CG1 | VAL | 318 | 15.182 | 14.547 | 80.920 |
| 2180 | CG2 | VAL | 318 | 16.228 | 16.693 | 81.779 |
| 2181 | N | LEU | 319 | 18.173 | 14.513 | 83.029 |
| 2182 | CA | LEU | 319 | 18.519 | 13.764 | 84.250 |
| 2183 | C | LEU | 319 | 17.325 | 13.121 | 84.950 |
| 2184 | O | LEU | 319 | 17.226 | 11.889 | 85.022 |
| 2185 | CB | LEU | 319 | 19.155 | 14.751 | 85.232 |
| 2186 | CG | LEU | 319 | 19.538 | 14.140 | 86.584 |
| 2187 | CD1 | LEU | 319 | 20.371 | 12.874 | 86.435 |
| 2188 | CD2 | LEU | 319 | 20.254 | 15.166 | 87.455 |
| 2189 | N | GLY | 320 | 16.411 | 13.951 | 85.423 |
| 2190 | CA | GLY | 320 | 15.371 | 13.460 | 86.333 |
| 2191 | C | GLY | 320 | 13.961 | 13.514 | 85.762 |
| 2192 | O | GLY | 320 | 13.016 | 13.013 | 86.388 |
| 2193 | N | ARG | 321 | 13.830 | 14.071 | 84.571 |
| 2194 | CA | ARG | 321 | 12.535 | 14.095 | 83.886 |
| 2195 | C | ARG | 321 | 12.339 | 12.772 | 83.150 |
| 2196 | O | ARG | 321 | 12.595 | 12.652 | 81.947 |
| 2197 | CB | ARG | 321 | 12.547 | 15.269 | 82.916 |
| 2198 | CG | ARG | 321 | 12.932 | 16.602 | 83.561 |
| 2199 | CD | ARG | 321 | 11.781 | 17.348 | 84.238 |
| 2200 | NE | ARG | 321 | 11.328 | 16.718 | 85.489 |
| 2201 | CZ | ARG | 321 | 10.072 | 16.796 | 85.934 |
| 2202 | NH1 | ARG | 321 | 9.171 | 17.523 | 85.268 |
| 2203 | NH2 | ARG | 321 | 9.726 | 16.174 | 87.063 |
| 2204 | N | ASP | 322 | 11.940 | 11.770 | 83.914 |
| 2205 | CA | ASP | 322 | 11.892 | 10.399 | 83.414 |
| 2206 | C | ASP | 322 | 10.524 | 9.768 | 83.665 |
| 2207 | O | ASP | 322 | 9.543 | 10.163 | 83.020 |
| 2208 | CB | ASP | 322 | 13.003 | 9.633 | 84.138 |
| 2209 | CG | ASP | 322 | 13.435 | 8.322 | 83.471 |
| 2210 | OD1 | ASP | 322 | 14.604 | 8.012 | 83.646 |
| 2211 | OD2 | ASP | 322 | 12.571 | 7.533 | 83.136 |
| 2212 | N | PHE | 323 | 10.433 | 9.011 | 84.757 |
| 2213 | CA | PHE | 323 | 9.428 | 7.940 | 85.049 |
| 2214 | C | PHE | 323 | 9.079 | 6.962 | 83.895 |
| 2215 | O | PHE | 323 | 8.923 | 5.764 | 84.152 |
| 2216 | CB | PHE | 323 | 8.168 | 8.497 | 85.735 |
| 2217 | CG | PHE | 323 | 7.224 | 9.441 | 84.988 |
| 2218 | CD1 | PHE | 323 | 7.310 | 10.815 | 85.180 |
| 2219 | CD2 | PHE | 323 | 6.234 | 8.921 | 84.163 |
| 2220 | CE1 | PHE | 323 | 6.439 | 11.665 | 84.513 |
| 2221 | CE2 | PHE | 323 | 5.365 | 9.771 | 83.493 |
| 2222 | CZ | PHE | 323 | 5.470 | 11.144 | 83.666 |
| 2223 | N | ARG | 324 | 8.886 | 7.470 | 82.691 |
| 2224 | CA | ARG | 324 | 8.779 | 6.715 | 81.450 |
| 2225 | C | ARG | 324 | 9.759 | 7.430 | 80.499 |
| 2226 | O | ARG | 324 | 10.751 | 7.927 | 81.049 |
| 2227 | CB | ARG | 324 | 7.302 | 6.700 | 81.065 |
| 2228 | CG | ARG | 324 | 6.590 | 5.553 | 81.768 |
| 2229 | CD | ARG | 324 | 7.204 | 4.226 | 81.335 |
| 2230 | NE | ARG | 324 | 6.693 | 3.103 | 82.133 |
| 2231 | CZ | ARG | 324 | 7.194 | 1.868 | 82.053 |
| 2232 | NH1 | ARG | 324 | 8.165 | 1.596 | 81.178 |
| 2233 | NH2 | ARG | 324 | 6.696 | 0.896 | 82.820 |
| 2234 | N | PRO | 325 | 9.665 | 7.368 | 79.175 |
| 2235 | CA | PRO | 325 | 10.573 | 8.193 | 78.366 |
| 2236 | C | PRO | 325 | 10.425 | 9.699 | 78.597 |
| 2237 | O | PRO | 325 | 10.663 | 10.219 | 79.698 |
| 2238 | CB | PRO | 325 | 10.266 | 7.866 | 76.942 |
| 2239 | CG | PRO | 325 | 9.116 | 6.883 | 76.889 |
| 2240 | CD | PRO | 325 | 8.769 | 6.567 | 78.330 |

TABLE IV-continued

| Atom No. | Atom Type | Residue | Residue Position | X Coord. | Y Coord. | Z Coord. |
|---|---|---|---|---|---|---|
| 2241 | N | TRP | 326 | 10.319 | 10.382 | 77.467 |
| 2242 | CA | TRP | 326 | 9.917 | 11.796 | 77.360 |
| 2243 | C | TRP | 326 | 11.095 | 12.786 | 77.415 |
| 2244 | O | TRP | 326 | 11.124 | 13.684 | 78.268 |
| 2245 | CB | TRP | 326 | 8.831 | 12.154 | 78.372 |
| 2246 | CG | TRP | 326 | 7.735 | 11.122 | 78.634 |
| 2247 | CD1 | TRP | 326 | 7.336 | 10.694 | 79.877 |
| 2248 | CD2 | TRP | 326 | 6.942 | 10.378 | 77.678 |
| 2249 | NE1 | TRP | 326 | 6.380 | 9.754 | 79.731 |
| 2250 | CE2 | TRP | 326 | 6.123 | 9.518 | 78.433 |
| 2251 | CE3 | TRP | 326 | 6.890 | 10.353 | 76.290 |
| 2252 | CZ2 | TRP | 326 | 5.272 | 8.632 | 77.787 |
| 2253 | CZ3 | TRP | 326 | 6.033 | 9.463 | 75.655 |
| 2254 | CH2 | TRP | 326 | 5.228 | 8.610 | 76.395 |
| 2255 | N | LEU | 327 | 12.114 | 12.420 | 76.643 |
| 2256 | CA | LEU | 327 | 13.174 | 13.252 | 75.991 |
| 2257 | C | LEU | 327 | 13.300 | 14.769 | 76.286 |
| 2258 | O | LEU | 327 | 12.377 | 15.400 | 76.811 |
| 2259 | CB | LEU | 327 | 12.716 | 13.079 | 74.540 |
| 2260 | CG | LEU | 327 | 13.584 | 13.628 | 73.425 |
| 2261 | CD1 | LEU | 327 | 14.809 | 12.752 | 73.208 |
| 2262 | CD2 | LEU | 327 | 12.760 | 13.728 | 72.151 |
| 2263 | N | ILE | 328 | 14.461 | 15.351 | 75.983 |
| 2264 | CA | ILE | 328 | 14.535 | 16.826 | 75.909 |
| 2265 | C | ILE | 328 | 14.959 | 17.365 | 74.525 |
| 2266 | O | ILE | 328 | 14.852 | 18.583 | 74.319 |
| 2267 | CB | ILE | 328 | 15.380 | 17.426 | 77.037 |
| 2268 | CG1 | ILE | 328 | 16.744 | 16.768 | 77.218 |
| 2269 | CG2 | ILE | 328 | 14.591 | 17.446 | 78.342 |
| 2270 | CD1 | ILE | 328 | 17.809 | 17.384 | 76.321 |
| 2271 | N | GLU | 329 | 15.495 | 16.507 | 73.656 |
| 2272 | CA | GLU | 329 | 15.757 | 16.843 | 72.229 |
| 2273 | C | GLU | 329 | 16.406 | 15.683 | 71.456 |
| 2274 | O | GLU | 329 | 17.395 | 15.097 | 71.912 |
| 2275 | CB | GLU | 329 | 16.658 | 18.075 | 72.065 |
| 2276 | CG | GLU | 329 | 18.032 | 17.917 | 72.704 |
| 2277 | CD | GLU | 329 | 18.999 | 18.977 | 72.187 |
| 2278 | OE1 | GLU | 329 | 18.534 | 19.970 | 71.649 |
| 2279 | OE2 | GLU | 329 | 20.198 | 18.737 | 72.288 |
| 2280 | N | ILE | 330 | 15.850 | 15.340 | 70.304 |
| 2281 | CA | ILE | 330 | 16.503 | 14.354 | 69.427 |
| 2282 | C | ILE | 330 | 17.438 | 15.000 | 68.407 |
| 2283 | O | ILE | 330 | 17.009 | 15.540 | 67.380 |
| 2284 | CB | ILE | 330 | 15.442 | 13.557 | 68.672 |
| 2285 | CG1 | ILE | 330 | 14.670 | 12.637 | 69.595 |
| 2286 | CG2 | ILE | 330 | 16.047 | 12.737 | 67.542 |
| 2287 | CD1 | ILE | 330 | 13.565 | 11.922 | 68.831 |
| 2288 | N | ASN | 331 | 18.726 | 14.899 | 68.675 |
| 2289 | CA | ASN | 331 | 19.709 | 15.292 | 67.672 |
| 2290 | C | ASN | 331 | 19.815 | 14.239 | 66.576 |
| 2291 | O | ASN | 331 | 19.484 | 13.057 | 66.757 |
| 2292 | CB | ASN | 331 | 21.053 | 15.547 | 68.337 |
| 2293 | CG | ASN | 331 | 20.930 | 16.806 | 69.188 |
| 2294 | OD1 | ASN | 331 | 20.186 | 17.733 | 68.839 |
| 2295 | ND2 | ASN | 331 | 21.655 | 16.827 | 70.291 |
| 2296 | N | SER | 332 | 20.156 | 14.748 | 65.406 |
| 2297 | CA | SER | 332 | 20.239 | 13.966 | 64.163 |
| 2298 | C | SER | 332 | 21.281 | 12.852 | 64.208 |
| 2299 | O | SER | 332 | 21.961 | 12.634 | 65.216 |
| 2300 | CB | SER | 332 | 20.588 | 14.924 | 63.030 |
| 2301 | OG | SER | 332 | 21.866 | 15.483 | 63.310 |
| 2302 | N | SER | 333 | 21.392 | 12.153 | 63.090 |
| 2303 | CA | SER | 333 | 22.332 | 11.023 | 62.981 |
| 2304 | C | SER | 333 | 23.841 | 11.342 | 63.121 |
| 2305 | O | SER | 333 | 24.512 | 10.468 | 63.684 |
| 2306 | CB | SER | 333 | 22.080 | 10.269 | 61.673 |
| 2307 | OG | SER | 333 | 22.403 | 11.096 | 60.561 |
| 2308 | N | PRO | 334 | 24.409 | 12.472 | 62.687 |
| 2309 | CA | PRO | 334 | 25.787 | 12.781 | 63.105 |
| 2310 | C | PRO | 334 | 25.899 | 13.269 | 64.552 |
| 2311 | O | PRO | 334 | 26.039 | 14.474 | 64.796 |
| 2312 | CB | PRO | 334 | 26.247 | 13.870 | 62.191 |
| 2313 | CG | PRO | 334 | 25.039 | 14.451 | 61.484 |
| 2314 | CD | PRO | 334 | 23.872 | 13.562 | 61.856 |
| 2315 | N | THR | 335 | 25.847 | 12.345 | 65.492 |
| 2316 | CA | THR | 335 | 26.129 | 12.675 | 66.892 |
| 2317 | C | THR | 335 | 27.637 | 12.610 | 67.123 |
| 2318 | O | THR | 335 | 28.315 | 11.808 | 66.479 |
| 2319 | CB | THR | 335 | 25.399 | 11.689 | 67.795 |
| 2320 | OG1 | THR | 335 | 25.927 | 10.388 | 67.591 |
| 2321 | CG2 | THR | 335 | 23.911 | 11.660 | 67.484 |
| 2322 | N | MET | 336 | 28.163 | 13.538 | 67.906 |
| 2323 | CA | MET | 336 | 29.613 | 13.569 | 68.183 |
| 2324 | C | MET | 336 | 30.016 | 12.792 | 69.429 |
| 2325 | O | MET | 336 | 29.833 | 13.260 | 70.559 |
| 2326 | CB | MET | 336 | 30.084 | 15.010 | 68.350 |
| 2327 | CG | MET | 336 | 30.195 | 15.773 | 67.033 |
| 2328 | SD | MET | 336 | 31.506 | 15.261 | 65.891 |
| 2329 | CE | MET | 336 | 30.663 | 13.980 | 64.934 |
| 2330 | N | HIS | 337 | 30.642 | 11.652 | 69.193 |
| 2331 | CA | HIS | 337 | 31.210 | 10.823 | 70.243 |
| 2332 | C | HIS | 337 | 32.481 | 10.123 | 69.722 |
| 2333 | O | HIS | 337 | 32.408 | 9.203 | 68.899 |
| 2334 | CB | HIS | 337 | 30.130 | 9.826 | 70.684 |
| 2335 | CG | HIS | 337 | 29.545 | 8.914 | 69.618 |
| 2336 | ND1 | HIS | 337 | 29.928 | 7.653 | 69.341 |
| 2337 | CD2 | HIS | 337 | 28.507 | 9.210 | 68.766 |
| 2338 | CE1 | HIS | 337 | 29.178 | 7.169 | 68.331 |
| 2339 | NE2 | HIS | 337 | 28.303 | 8.135 | 67.973 |
| 2340 | N | PRO | 338 | 33.631 | 10.674 | 70.080 |
| 2341 | CA | PRO | 338 | 34.941 | 10.135 | 69.681 |
| 2342 | C | PRO | 338 | 35.190 | 8.690 | 70.107 |
| 2343 | O | PRO | 338 | 34.277 | 7.941 | 70.475 |
| 2344 | CB | PRO | 338 | 35.959 | 11.036 | 70.308 |
| 2345 | CG | PRO | 338 | 35.252 | 12.158 | 71.039 |
| 2346 | CD | PRO | 338 | 33.767 | 11.913 | 70.843 |
| 2347 | N | SER | 339 | 36.473 | 8.362 | 70.165 |
| 2348 | CA | SER | 339 | 36.975 | 6.984 | 70.362 |
| 2349 | C | SER | 339 | 36.921 | 6.455 | 71.802 |
| 2350 | O | SER | 339 | 37.359 | 5.328 | 72.078 |
| 2351 | CB | SER | 339 | 38.427 | 6.959 | 69.896 |
| 2352 | OG | SER | 339 | 38.468 | 7.357 | 68.530 |
| 2353 | N | THR | 340 | 36.221 | 7.168 | 72.661 |
| 2354 | CA | THR | 340 | 36.253 | 6.848 | 74.083 |
| 2355 | C | THR | 340 | 35.607 | 5.503 | 74.535 |
| 2356 | O | THR | 340 | 36.196 | 4.938 | 75.467 |
| 2357 | CB | THR | 340 | 35.628 | 8.024 | 74.820 |
| 2358 | OG1 | THR | 340 | 36.060 | 9.234 | 74.207 |
| 2359 | CG2 | THR | 340 | 36.071 | 8.054 | 76.272 |
| 2360 | N | PRO | 341 | 34.618 | 4.873 | 73.881 |
| 2361 | CA | PRO | 341 | 34.101 | 3.619 | 74.460 |
| 2362 | C | PRO | 341 | 35.125 | 2.483 | 74.489 |
| 2363 | O | PRO | 341 | 35.350 | 1.923 | 75.570 |
| 2364 | CB | PRO | 341 | 32.927 | 3.225 | 73.620 |
| 2365 | CG | PRO | 341 | 32.776 | 4.190 | 72.466 |
| 2366 | CD | PRO | 341 | 33.856 | 5.231 | 72.664 |
| 2367 | N | VAL | 342 | 35.936 | 2.389 | 73.445 |
| 2368 | CA | VAL | 342 | 36.922 | 1.310 | 73.329 |
| 2369 | C | VAL | 342 | 38.249 | 1.671 | 74.007 |
| 2370 | O | VAL | 342 | 39.095 | 0.803 | 74.244 |
| 2371 | CB | VAL | 342 | 37.151 | 1.074 | 71.839 |
| 2372 | CG1 | VAL | 342 | 35.930 | −0.211 | 71.581 |
| 2373 | CG2 | VAL | 342 | 35.823 | 1.031 | 71.095 |
| 2374 | N | THR | 343 | 38.404 | 2.937 | 74.363 |
| 2375 | CA | THR | 343 | 39.615 | 3.368 | 75.069 |
| 2376 | C | THR | 343 | 39.413 | 3.427 | 76.582 |
| 2377 | O | THR | 343 | 40.337 | 3.819 | 77.305 |
| 2378 | CB | THR | 343 | 40.064 | 4.734 | 74.563 |
| 2379 | OG1 | THR | 343 | 39.033 | 5.675 | 74.827 |
| 2380 | CG2 | THR | 343 | 40.346 | 4.723 | 73.065 |
| 2381 | N | ALA | 344 | 38.215 | 3.116 | 77.049 |
| 2382 | CA | ALA | 344 | 37.975 | 3.074 | 78.493 |
| 2383 | C | ALA | 344 | 37.489 | 1.697 | 78.928 |
| 2384 | O | ALA | 344 | 38.005 | 1.117 | 79.893 |
| 2385 | CB | ALA | 344 | 36.939 | 4.125 | 78.844 |
| 2386 | N | GLN | 345 | 36.506 | 1.183 | 78.208 |
| 2387 | CA | GLN | 345 | 36.038 | −0.185 | 78.440 |
| 2388 | C | GLN | 345 | 36.031 | −0.987 | 77.146 |
| 2389 | O | GLN | 345 | 36.742 | −0.688 | 76.181 |
| 2390 | CB | GLN | 345 | 34.653 | −0.233 | 79.081 |

TABLE IV-continued

| Atom No. | Atom Type | Residue | Residue Position | X Coord. | Y Coord. | Z Coord. |
|---|---|---|---|---|---|---|
| 2391 | CG | GLN | 345 | 34.682 | −0.143 | 80.607 |
| 2392 | CD | GLN | 345 | 34.094 | 1.187 | 81.069 |
| 2393 | OE1 | GLN | 345 | 34.427 | 2.234 | 80.506 |
| 2394 | NE2 | GLN | 345 | 33.137 | 1.114 | 81.981 |
| 2395 | N | LEU | 346 | 35.168 | −1.987 | 77.140 |
| 2396 | CA | LEU | 346 | 35.212 | −3.044 | 76.123 |
| 2397 | C | LEU | 346 | 34.089 | −3.014 | 75.080 |
| 2398 | O | LEU | 346 | 33.690 | −4.089 | 74.618 |
| 2399 | CB | LEU | 346 | 35.151 | −4.375 | 76.866 |
| 2400 | CG | LEU | 346 | 36.300 | −4.523 | 77.862 |
| 2401 | CD1 | LEU | 346 | 36.084 | −5.721 | 78.780 |
| 2402 | CD2 | LEU | 346 | 37.647 | −4.616 | 77.152 |
| 2403 | N | CYS | 347 | 33.546 | −1.859 | 74.733 |
| 2404 | CA | CYS | 347 | 32.458 | −1.897 | 73.740 |
| 2405 | C | CYS | 347 | 32.633 | −0.896 | 72.599 |
| 2406 | O | CYS | 347 | 33.133 | 0.222 | 72.776 |
| 2407 | CB | CYS | 347 | 31.111 | −1.670 | 74.414 |
| 2408 | SG | CYS | 347 | 30.751 | 0.024 | 74.906 |
| 2409 | N | ALA | 348 | 32.171 | −1.314 | 71.432 |
| 2410 | CA | ALA | 348 | 32.212 | −0.460 | 70.242 |
| 2411 | C | ALA | 348 | 30.833 | −0.331 | 69.598 |
| 2412 | O | ALA | 348 | 30.452 | −1.160 | 68.760 |
| 2413 | CB | ALA | 348 | 33.191 | −1.059 | 69.238 |
| 2414 | N | GLN | 349 | 30.240 | 0.841 | 69.763 |
| 2415 | CA | GLN | 349 | 28.895 | 1.084 | 69.222 |
| 2416 | C | GLN | 349 | 28.875 | 1.287 | 67.706 |
| 2417 | O | GLN | 349 | 27.894 | 0.889 | 67.067 |
| 2418 | CB | GLN | 349 | 28.285 | 2.285 | 69.937 |
| 2419 | CG | GLN | 349 | 29.212 | 3.493 | 69.966 |
| 2420 | CD | GLN | 349 | 28.675 | 4.535 | 70.943 |
| 2421 | OE1 | GLN | 349 | 29.444 | 5.336 | 71.491 |
| 2422 | NE2 | GLN | 349 | 27.378 | 4.476 | 71.190 |
| 2423 | N | VAL | 350 | 30.032 | 1.561 | 67.122 |
| 2424 | CA | VAL | 350 | 30.125 | 1.665 | 65.665 |
| 2425 | C | VAL | 350 | 30.313 | 0.289 | 65.011 |
| 2426 | O | VAL | 350 | 29.847 | 0.074 | 63.884 |
| 2427 | CB | VAL | 350 | 31.253 | 2.634 | 65.327 |
| 2428 | CG1 | VAL | 350 | 32.529 | 2.327 | 66.102 |
| 2429 | CG2 | VAL | 350 | 31.506 | 2.700 | 63.828 |
| 2430 | N | GLN | 351 | 30.659 | −0.697 | 65.824 |
| 2431 | CA | GLN | 351 | 30.724 | −2.071 | 65.338 |
| 2432 | C | GLN | 351 | 29.356 | −2.721 | 65.517 |
| 2433 | O | GLN | 351 | 28.942 | −3.534 | 64.683 |
| 2434 | CB | GLN | 351 | 31.794 | −2.813 | 66.124 |
| 2435 | CG | GLN | 351 | 31.962 | −4.246 | 65.641 |
| 2436 | CD | GLN | 351 | 33.177 | −4.856 | 66.327 |
| 2437 | OE1 | GLN | 351 | 33.108 | −5.294 | 67.481 |
| 2438 | NE2 | GLN | 351 | 34.298 | −4.803 | 65.629 |
| 2439 | N | GLU | 352 | 28.559 | −2.118 | 66.385 |
| 2440 | CA | GLU | 352 | 27.157 | −2.516 | 66.514 |
| 2441 | C | GLU | 352 | 26.315 | −1.836 | 65.425 |
| 2442 | O | GLU | 352 | 25.337 | −2.430 | 64.957 |
| 2443 | CB | GLU | 352 | 26.677 | −2.163 | 67.919 |
| 2444 | CG | GLU | 352 | 25.332 | −2.808 | 68.240 |
| 2445 | CD | GLU | 352 | 25.020 | −2.664 | 69.728 |
| 2446 | OE1 | GLU | 352 | 25.757 | −3.237 | 70.519 |
| 2447 | OE2 | GLU | 352 | 24.031 | −2.019 | 70.052 |
| 2448 | N | ASP | 353 | 26.857 | −0.776 | 64.837 |
| 2449 | CA | ASP | 353 | 26.287 | −0.198 | 63.609 |
| 2450 | C | ASP | 353 | 26.582 | −1.083 | 62.404 |
| 2451 | O | ASP | 353 | 25.725 | −1.228 | 61.524 |
| 2452 | CB | ASP | 353 | 26.920 | 1.161 | 63.316 |
| 2453 | CG | ASP | 353 | 26.445 | 2.246 | 64.268 |
| 2454 | OD1 | ASP | 353 | 25.317 | 2.682 | 64.103 |
| 2455 | OD2 | ASP | 353 | 27.267 | 2.752 | 65.021 |
| 2456 | N | THR | 354 | 27.652 | −1.856 | 62.498 |
| 2457 | CA | THR | 354 | 28.018 | −2.786 | 61.429 |
| 2458 | C | THR | 354 | 27.180 | −4.061 | 61.516 |
| 2459 | O | THR | 354 | 26.836 | −4.647 | 60.482 |
| 2460 | CB | THR | 354 | 29.498 | −3.124 | 61.579 |
| 2461 | OG1 | THR | 354 | 30.230 | −1.907 | 61.637 |
| 2462 | CG2 | THR | 354 | 30.017 | −3.950 | 60.409 |
| 2463 | N | ILE | 355 | 26.629 | −4.313 | 62.693 |
| 2464 | CA | ILE | 355 | 25.691 | −5.425 | 62.868 |
| 2465 | C | ILE | 355 | 24.300 | −5.052 | 62.350 |
| 2466 | O | ILE | 355 | 23.596 | −5.909 | 61.797 |
| 2467 | CB | ILE | 355 | 25.634 | −5.757 | 64.356 |
| 2468 | CG1 | ILE | 355 | 27.017 | −6.143 | 64.865 |
| 2469 | CG2 | ILE | 355 | 24.636 | −6.875 | 64.635 |
| 2470 | CD1 | ILE | 355 | 26.998 | −6.447 | 66.358 |
| 2471 | N | LYS | 356 | 24.047 | −3.756 | 62.249 |
| 2472 | CA | LYS | 356 | 22.788 | −3.268 | 61.679 |
| 2473 | C | LYS | 356 | 22.812 | −3.191 | 60.150 |
| 2474 | O | LYS | 356 | 21.759 | −2.975 | 59.538 |
| 2475 | CB | LYS | 356 | 22.466 | −1.898 | 62.253 |
| 2476 | CG | LYS | 356 | 22.311 | −1.948 | 63.767 |
| 2477 | CD | LYS | 356 | 21.764 | −0.623 | 64.272 |
| 2478 | CE | LYS | 356 | 22.616 | 0.538 | 63.776 |
| 2479 | NZ | LYS | 356 | 21.991 | 1.830 | 64.100 |
| 2480 | N | VAL | 357 | 23.923 | −3.582 | 59.537 |
| 2481 | CA | VAL | 357 | 24.013 | −3.651 | 58.069 |
| 2482 | C | VAL | 357 | 23.321 | −4.910 | 57.513 |
| 2483 | O | VAL | 357 | 22.993 | −4.963 | 56.319 |
| 2484 | CB | VAL | 357 | 25.493 | −3.609 | 57.687 |
| 2485 | CG1 | VAL | 357 | 25.719 | −3.737 | 56.184 |
| 2486 | CG2 | VAL | 357 | 26.135 | −2.324 | 58.198 |
| 2487 | N | ALA | 358 | 22.844 | −5.759 | 58.416 |
| 2488 | CA | ALA | 358 | 22.034 | −6.927 | 58.043 |
| 2489 | C | ALA | 358 | 20.614 | −6.565 | 57.581 |
| 2490 | O | ALA | 358 | 19.973 | −7.382 | 56.910 |
| 2491 | CB | ALA | 358 | 21.950 | −7.852 | 59.252 |
| 2492 | N | VAL | 359 | 20.236 | −5.298 | 57.713 |
| 2493 | CA | VAL | 359 | 18.957 | −4.804 | 57.182 |
| 2494 | C | VAL | 359 | 19.015 | −4.598 | 55.656 |
| 2495 | O | VAL | 359 | 17.977 | −4.491 | 54.996 |
| 2496 | CB | VAL | 359 | 18.652 | −3.488 | 57.899 |
| 2497 | CG1 | VAL | 359 | 17.348 | −2.850 | 57.431 |
| 2498 | CG2 | VAL | 359 | 18.612 | −3.701 | 59.409 |
| 2499 | N | ASP | 360 | 20.206 | −4.720 | 55.085 |
| 2500 | CA | ASP | 360 | 20.381 | −4.668 | 53.627 |
| 2501 | C | ASP | 360 | 20.198 | −6.020 | 52.929 |
| 2502 | O | ASP | 360 | 20.471 | −6.117 | 51.725 |
| 2503 | CB | ASP | 360 | 21.769 | −4.126 | 53.312 |
| 2504 | CG | ASP | 360 | 21.791 | −2.621 | 53.541 |
| 2505 | OD1 | ASP | 360 | 21.997 | −2.212 | 54.676 |
| 2506 | OD2 | ASP | 360 | 21.442 | −1.914 | 52.606 |
| 2507 | N | ARG | 361 | 19.776 | −7.044 | 53.658 |
| 2508 | CA | ARG | 361 | 19.529 | −8.365 | 53.061 |
| 2509 | C | ARG | 361 | 18.211 | −8.398 | 52.275 |
| 2510 | O | ARG | 361 | 17.150 | −8.746 | 52.808 |
| 2511 | CB | ARG | 361 | 19.479 | −9.373 | 54.203 |
| 2512 | CG | ARG | 361 | 19.349 | −10.811 | 53.717 |
| 2513 | CD | ARG | 361 | 19.255 | −11.771 | 54.899 |
| 2514 | NE | ARG | 361 | 20.449 | −11.670 | 55.754 |
| 2515 | CZ | ARG | 361 | 20.405 | −11.368 | 57.054 |
| 2516 | NH1 | ARG | 361 | 19.235 | −11.106 | 57.642 |
| 2517 | NH2 | ARG | 361 | 21.536 | −11.299 | 57.760 |

What is claimed is:

1. An isolated polypeptide comprising a polypeptide sequence selected from the group consisting of:
   (a) an isolated polypeptide comprising amino acids 1 to 541 of SEQ ID NO:2; and
   (b) an isolated polypeptide comprising amino acids 2 to 541 of SEQ ID NO:2.

2. The isolated polypeptide of claim 1, wherein said polypeptide is (a).

3. The isolated polypeptide of claim 1, wherein said polypeptide is (b).

4. An isolated polypeptide produced by a method comprising:
   (a) culturing an isolated recombinant host cell comprising a vector that comprises the coding region encoding the polypeptide of claim 1 under conditions such that the polypeptide of claim 1 is expressed; and
   (b) recovering said polypeptide.

5. The isolated polypeptide of claim 1 wherein said polypeptide sequence further comprises a heterologous polypeptide sequence.

6. The isolated polypeptide of claim 5 wherein said heterologous polypeptide is the Fc domain of an immunoglobulin.

7. An isolated polypeptide comprising the polypeptide encoded by the BGS-42 cDNA clone A in ATCC Deposit No. PTA-4454.

8. An isolated polypeptide comprising the polypeptide encoded by the BGS-42 cDNA clone B in ATCC Deposit No. PTA-4454.

9. An isolated polypeptide comprising the polypeptide encoded by the BGS-42 cDNA clone C in ATCC Deposit No. PTA-4454.

10. An isolated polypeptide comprising a polypeptide sequence that is at least 95.0% identical to amino acids 2 to 541 of SEQ ID NO:2, wherein percent identity is calculated using CLUSTALW global sequence alignment using default parameters, and wherein said polypeptide has tubulin tyrosine ligase activity.

11. An isolated polypeptide consisting of at least 50 contiguous amino acids of SEQ ID NO:2.

12. An isolated polypeptide comprising amino acids 73 to 365 of SEQ ID NO:2.

13. An isolated polypeptide comprising amino acids 133 to 374 of SEQ ID NO:2.

14. An isolated polypeptide comprising amino acids 2 to 541 of SEQ ID NO:2, wherein the amino acid located at amino acid position 515 is a glutamie acid.

15. An isolated polypeptide comprising amino acids 2 to 541 of SEQ ID NO:2, wherein the amino acid located at amino acid position 524 is a serin.

16. An isolated polypeptide comprising at least 394 contiguous amino acids of SEQ ID NO:2, wherein said polypeptide has tubulin tyrosine ligase activity.

17. The isolated polypeptide of claim 1(a) or (b), wherein said encoded polypeptide has one amino acid substitution and has tubulin tyrosine ligase activity.

18. An isolated polypeptide comprising a polypeptide encoded by a polynucleotide that hybridizes under stringent conditions to the polynucleotide encoding amino acids 2 to 541 of SEQ ID NO:2, wherein said stringent conditions are as follows: an overnight incubation at 42 degree C in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65 degree C, wherein said polynucleotide encodes a polypeptide that has tubulin tyrosine ligase activity.

19. An isolated polypeptide produced by a method comprising:
   (a) culturing an isolated recombinant host cell comprising a vector that comprises a coding region operatively linked to nucleotides −2057 to −1 of the sequence provided in FIGS. 7A–B (nucleotides 1 to 2058 of SEQ ID NO:27) under conditions such that a polypeptide is expressed; and
   (b) recovering said polypeptide.

* * * * *

UNITED STATES PATENT AND TRADEMARK OFFICE
CERTIFICATE OF CORRECTION

PATENT NO.        : 7,122,358 B2                                           Page 1 of 1
APPLICATION NO.   : 10/635977
DATED             : October 17, 2006
INVENTOR(S)       : John N. Feder, Thomas C. Nelson and Shujian Wu It is certified that error appears in the above-identified patent and that said Letters Patent is hereby corrected as shown below:

Item (75) Inventors: Add "Liana M. Lee"

Column 323 - What is claimed is:

Claim 10, line 46, second word on this line should be --a--

Claim 10, line 46, should now read --using a CLUSTALWglobal sequence alignment using default--

Column 324

Claim 14, line 16, "glutamie" should read --glutamic--

Claim 15, line 19, "serin" should read --serine--

Claim 17, line 25, delete "encoded"

Claim 18, line 37, delete "polynucleotide encodes a" and delete "that" after "polypeptide"
Claim 18 line 37 and 38 should now read --wherein said polypeptide has tubulin tyrosine ligase activity.--

Signed and Sealed this

Ninth Day of January, 2007

JON W. DUDAS
*Director of the United States Patent and Trademark Office*